US012491251B2

(12) United States Patent
Gray et al.

(10) Patent No.: US 12,491,251 B2
(45) Date of Patent: Dec. 9, 2025

(54) DEGRADERS OF CYCLIN-DEPENDENT KINASE 7 (CDK7) AND USES THEREOF

(71) Applicant: DANA-FARBER CANCER INSTITUTE, INC., Boston, MA (US)

(72) Inventors: Nathanael S. Gray, Boston, MA (US); Guangyan Du, Jamaica Plain, MA (US); Tinghu Zhang, Brookline, MA (US); Zhixiang He, Brookline, MA (US); Nicholas Kwiatkowski, Brookline, MA (US); Jie Jiang, Brookline, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 850 days.

(21) Appl. No.: 17/631,774

(22) PCT Filed: Aug. 4, 2020

(86) PCT No.: PCT/US2020/044815

§ 371 (c)(1),
(2) Date: Jan. 31, 2022

(87) PCT Pub. No.: WO2021/026109

PCT Pub. Date: Feb. 11, 2021

(65) Prior Publication Data

US 2022/0280649 A1 Sep. 8, 2022

Related U.S. Application Data

(60) Provisional application No. 62/882,958, filed on Aug. 5, 2019.

(51) Int. Cl.
*A61K 47/55* (2017.01)
*A61K 47/54* (2017.01)

(52) U.S. Cl.
CPC .............. *A61K 47/55* (2017.08); *A61K 47/54* (2017.08); *A61K 47/545* (2017.08)

(58) Field of Classification Search
CPC ....... A61K 47/55; A61K 47/545; A61K 47/54
See application file for complete search history.

(56) References Cited

U.S. PATENT DOCUMENTS

2016/0272639 A1* 9/2016 Crew ........................ A61P 7/04
2017/0121321 A1 5/2017 Crews et al.
2018/0186818 A1 7/2018 Iwase et al.
2019/0055248 A1 2/2019 Gray et al.
2019/0076539 A1 3/2019 Phillips et al.
2019/0111143 A1 4/2019 Gray et al.
2020/0216450 A1 7/2020 Shu

FOREIGN PATENT DOCUMENTS

| | | | | |
|---|---|---|---|---|
| CN | 104736569 | A | 6/2015 | |
| CN | 107735401 | A | 2/2018 | |
| CN | 108366992 | A | 8/2018 | |
| CN | 109153675 | A | 1/2019 | |
| CN | 109516989 | A | 3/2019 | |
| JP | 2004-505977 | A | 2/2004 | |
| JP | 2018-502098 | A | 1/2018 | |
| JP | 2018-531983 | A | 1/2018 | |
| JP | 2019-514882 | A | 6/2019 | |
| WO | 2002012242 | A2 | 2/2002 | |
| WO | 2013070688 | A1 | 5/2013 | |
| WO | 2013106643 | A2 | 7/2013 | |
| WO | 2016105528 | A2 | 6/2016 | |
| WO | 2017079267 | A1 | 5/2017 | |
| WO | 2017185023 | A1 | 10/2017 | |
| WO | WO-2018106870 | A1 * | 6/2018 | .............. A61P 35/00 |

OTHER PUBLICATIONS

Olson, et al., "Development of a Selective CDK7 Covalent Inhibitor Reveals Predominant Cell-Cycle Phenotype," Cell Chemical Biology, Jun. 20, 2019, vol. 26, pp. 792-803.
Huang et al., "A Chemoproteomic Approach to Query the Degradable Kinome Using a Multi-kinase Degrader," Cell Chem. Biol., vol. 25, No. 1, pp. 88-99, 2018.
Bekes, M., et al. "PROTAC targeted protein degraders: the past is prologue", Nature Reviews Drug Discovery, 2022, vol. 21, pp. 181-200.
Bondeson, D. P., et al., "Lesson in PROTAC design from selective degradation with a promiscuous warhead", Cell Chem. Biol., 2018, vol. 25, No. 1, pp. 78-87.
Li, X., et al., "Proteolysis-targeting chimera (PROTAC) for targeted protein degradation and cancer therapy", Journal of Hematology & Oncology, 2020, vol. 13, No. 50, 14 pages.
Tan, L. et al., "Wehn Kinases Meet PROTACs", Chin. J. Chem., 2018, vol. 36, pp. 971-977.

* cited by examiner

*Primary Examiner* — Andrew D Kosar
*Assistant Examiner* — Phillip Matthew Rzeczycki
(74) *Attorney, Agent, or Firm* — ArentFox Schiff LLP; Daniel W. Clarke; Shawn P. Foley

(57) ABSTRACT

Disclosed are bispecific compounds (degraders) that target CDK7 for degradation. Also disclosed are pharmaceutical compositions containing the degraders and methods of using the compounds to treat disease.

25 Claims, 3 Drawing Sheets

DEGRADERS OF CYCLIN-DEPENDENT KINASE 7 (CDK7) AND USES THEREOF

RELATED APPLICATIONS

The present application is a national stage application, filed under 35 U.S.C. § 371, of International Application No. PCT/US2020/044815, filed Aug. 4, 2020, which claims the benefit of priority under 35 U.S.C. § 119 (e) to U.S. Provisional Application No. 62/882,958, filed on Aug. 5, 2019, each of which is incorporated herein by reference in its entirety.

GOVERNMENT LICENSE RIGHTS

This invention was made with government support under grant number W81XWH-16-1-0252 awarded by the U.S. Army Medical Research and Development Command. The government has certain rights in the invention.

BACKGROUND OF THE INVENTION

Cyclin-dependent kinase 7 (CDK7) is a master regulator of cell cycle progression and gene transcription. It has been reported CDK7 inhibition decreases the proliferation and increases cell death in different tumor models (Kwiatkowski et al., Nature 511(7511):616-620 (2014); Olson et al., Cell Chem. Biol. 26(6):792-803.e10 (2019).

SUMMARY OF THE INVENTION

A first aspect of the present invention is directed to a bispecific compound, comprising a targeting ligand that binds cyclin-dependent kinase 7 (CDK7) and a degron covalently attached to each other by a linker, wherein the compound has a structure represented by formula (I):

(I)

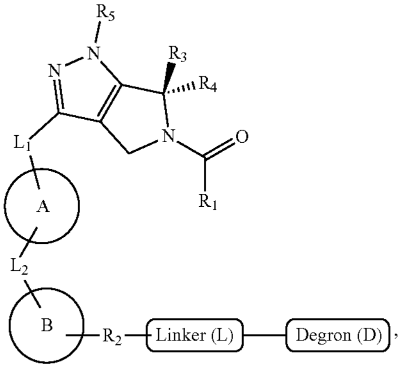

wherein $R_1$, $R_2$, $R_3$, $R_4$, $R_5$, $L_1$, $L_2$, A, and B are as defined herein, and the degron represents a moiety that binds an E3 ubiquitin ligase;

or a pharmaceutically acceptable salt or stereoisomer thereof. The targeting ligand (TL) is attached to the Linker (L) via the $R_2$ group of the TL.

Another aspect of the present invention is directed to a pharmaceutical composition that includes a therapeutically effective amount of the bispecific compound of formula (I) or a pharmaceutically acceptable salt or stereoisomer thereof, and a pharmaceutically acceptable carrier.

A further aspect of the present invention is directed to methods for making bispecific compounds of formula (I) or pharmaceutically acceptable salts or stereoisomers thereof.

Further aspects of the present invention are directed to methods of treating diseases or disorders involving aberrant (e.g., dysfunctional or dysregulated) CDK7 activity, that entails administration of a therapeutically effective amount of a bispecific compound of formula (I) or a pharmaceutically acceptable salt or stereoisomer thereof, to a subject in need thereof.

In some embodiments, the disease or disorder is a cancer.

In some embodiments, the cancer is a solid tumor. In some embodiments, the solid tumor is breast cancer, brain cancer, lung cancer, colorectal cancer, neuroblastoma, osteosarcoma or lymphoma.

In some embodiments, the cancer is a hematologic cancer. In some embodiments, the hematologic cancer is leukemia, lymphoma or multiple myeloma.

In some embodiments, the disease or disorder is an autoimmune disease or disorder.

Without intending to be bound by any particular theory of operation, the bispecific compounds of formula (I) of the present invention are believed to cause degradation of CDK7 by recruitment of cells' Ubiquitin/Proteasome System, whose function is to routinely identify and remove damaged proteins, into close proximity with CDK7 as a result of binding between CDK7, and the targeting ligand. After destruction of a CDK7 protein, the degrader is released and continues to be active. Applicant has recently identified a CDK7 inhibitor with low nanomolar potency. By conjugating this potent CDK7 ligand with an E3 ligase binder, bispecific degrader molecules of the present invention were found to be able to recruit the E3 ligase, and therefore promote the degradation of CDK7. Thus, by engaging and exploiting the body's own natural protein disposal system, the bispecific compounds of the present invention may represent a potential improvement over current small molecule inhibitors of CDK7 and may overcome one or more limitations regarding their use. Thus, effective intracellular concentrations of the degraders may be significantly lower than for small molecule CDK7 inhibitors. Collectively, the present bispecific compounds may represent a set of new chemical tools for CDK7 knockdown and may provide a potential treatment modality for CDK7-associated cancers and autoimmune disorders.

DETAILED DESCRIPTION OF THE INVENTION

Figure 1A:
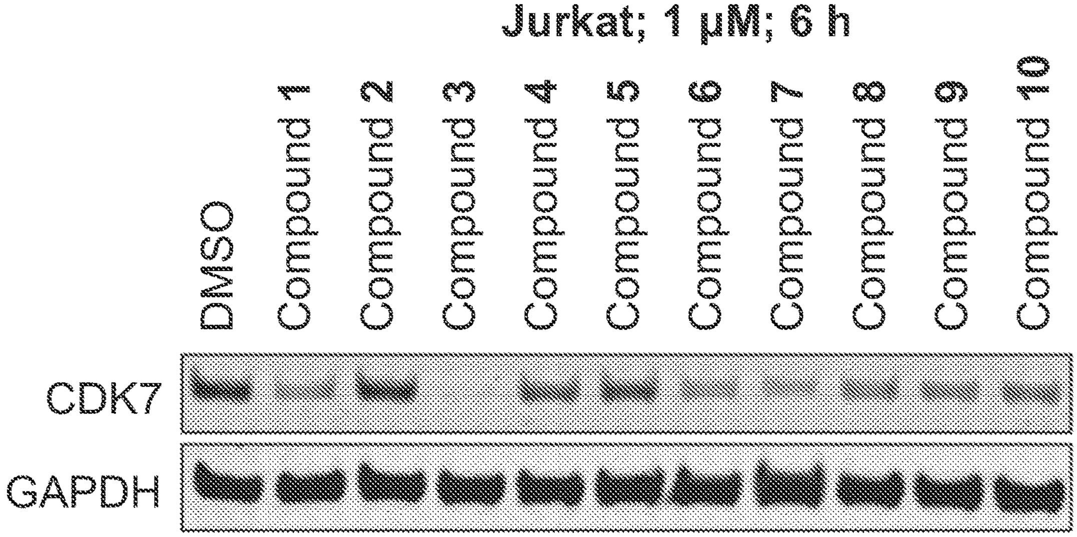
FIG. 1A is an immunoblot that shows CDK7 degradation after treating Jurkat cells with inventive bispecific compounds 1-10 and DMSO (negative control) at 6 hours.
Figure 1B:
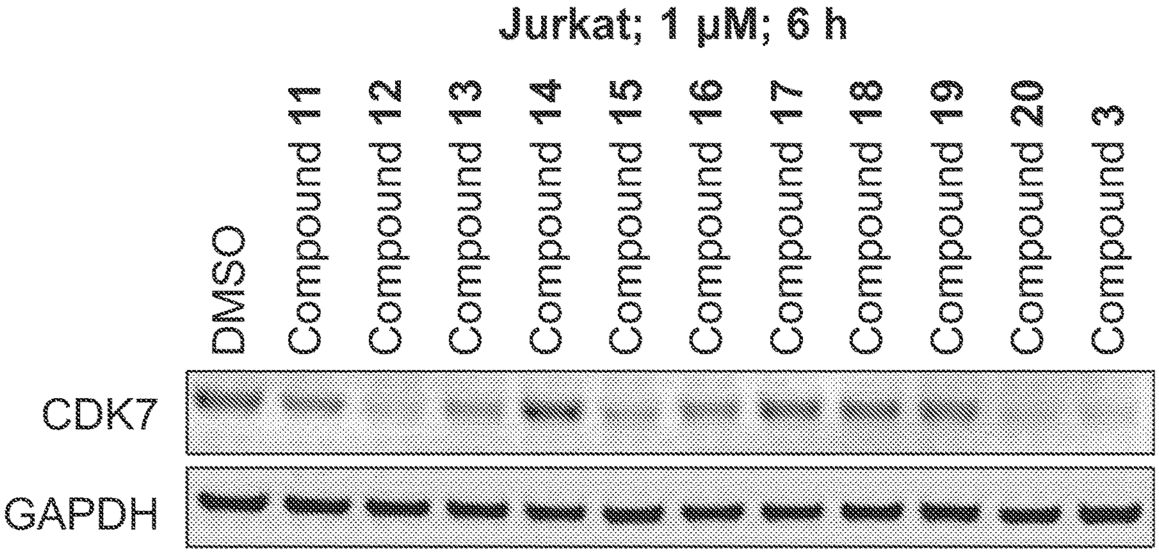
FIG. 1B is an immunoblot that shows CDK7 degradation after treating Jurkat cells with inventive bispecific compounds 11-20, 3 (positive control) and DMSO (negative control) at 6 hours.

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms “a”, “an”, and “the” include plural referents unless the context clearly dictates otherwise. Thus, for example, reference to “a composition” includes mixtures of two or more such compositions, reference to “an inhibitor” includes mixtures of two or more such inhibitors, and the like.

Unless stated otherwise, the term “about” means within 10% (e.g., within 5%, 2% or 1%) of the particular value modified by the term “about.”

The transitional term “comprising,” which is synonymous with “including,” “containing,” or “characterized by,” is inclusive or open-ended and does not exclude additional, unrecited elements or method steps. By contrast, the transitional phrase “consisting of” excludes any element, step, or ingredient not specified in the claim. The transitional phrase “consisting essentially of” limits the scope of a claim to the specified materials or steps “and those that do not materially affect the basic and novel characteristic(s)” of the claimed invention.

With respect to compounds of the present invention, and to the extent the following terms are used herein to further describe them, the following definitions apply.

As used herein, the term “alkyl” refers to a saturated linear or branched-chain monovalent hydrocarbon radical. In one embodiment, the alkyl radical is a $C_1$-$C_{18}$ group. In other embodiments, the alkyl radical is a $C_0$-$C_6$, $C_0$-$C_5$, $C_0$-$C_3$, $C_1$-$C_{12}$, $C_1$-$C_8$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group. In some embodiments, an alkyl group is a $C_1$-$C_2$ alkyl group.

As used herein, the term “alkylene” refers to a straight or branched divalent hydrocarbon chain linking the rest of the molecule to a radical group, consisting solely of carbon and hydrogen, containing no unsaturation and having from one to 12 carbon atoms, for example, methylene, ethylene, propylene, n-butylene, and the like. The alkylene chain may be attached to the rest of the molecule through a single bond and to the radical group through a single bond. In some embodiments, the alkylene group contains one to 8 carbon atoms ($C_1$-$C_8$ alkylene). In other embodiments, an alkylene group contains one to 5 carbon atoms ($C_1$-$C_5$ alkylene). In other embodiments, an alkylene group contains one to 4 carbon atoms ($C_1$-$C_4$ alkylene). In other embodiments, an alkylene contains one to three carbon atoms ($C_1$-$C_3$ alkylene). In other embodiments, an alkylene group contains one to two carbon atoms ($C_1$-$C_2$ alkylene). In other embodiments, an alkylene group contains one carbon atom ($C_1$ alkylene).

As used herein, the term “haloalkyl” refers to an alkyl group as defined herein that is substituted with one or more (e.g., 1, 2, 3, or 4) halo groups.

As used herein, the term “alkenyl” refers to a linear or branched-chain monovalent hydrocarbon radical with at least one carbon-carbon double bond. An alkenyl includes radicals having “cis” and “trans” orientations, or alternatively, “E” and “Z” orientations. In one example, the alkenyl radical is a $C_2$-$C_{18}$ group. In other embodiments, the alkenyl radical is a $C_2$-$C_{12}$, $C_2$-$C_{10}$, $C_2$-$C_8$, $C_2$-$C_6$ or $C_2$-$C_3$ group. Examples include ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

As used herein, the term “alkynyl” refers to a linear or branched monovalent hydrocarbon radical with at least one carbon-carbon triple bond. In one example, the alkynyl radical is a $C_2$-$C_{18}$ group. In other examples, the alkynyl radical is $C_2$-$C_{12}$, $C_2$-$C_{10}$, $C_2$-$C_8$, $C_2$-$C_6$ or $C_2$-$C_3$. Examples include ethynyl prop-1-ynyl, prop-2-ynyl, but-1-ynyl, but-2-ynyl and but-3-ynyl.

The terms “alkoxyl” or “alkoxy” as used herein refer to an alkyl group, as defined above, having an oxygen radical attached thereto. Representative alkoxyl groups include methoxy, ethoxy, propyloxy, tert-butoxy and the like. An “ether” is two hydrocarbyl groups covalently linked by an oxygen. Accordingly, the substituent of an alkyl that renders that alkyl an ether is or resembles an alkoxyl, such as can be represented by one of —O-alkyl, —O-alkenyl, and —O-alkynyl.

As used herein, the term “halogen” (or “halo” or “halide”) refers to fluorine, chlorine, bromine, or iodine.

As used herein, the term “carbocyclic” (also “carbocyclyl”) refers to a group that used alone or as part of a larger moiety, contains a saturated, partially unsaturated, or aromatic ring system having 3 to 20 carbon atoms, that is alone or part of a larger moiety (e.g., an alkcarbocyclic group). The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In another embodiment, carbocyclyl, as a monocycle, includes $C_3$-$C_8$, $C_3$-$C_6$ or $C_5$-$C_6$. In some embodiments, carbocyclyl, as a bicycle, includes $C_7$-$C_{12}$. In another embodiment, carbocyclyl, as a spiro system, includes $C_5$-$C_{12}$. Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, such as for example bicyclo[2.2.1]heptane, bicyclo[2.2.2]octane, naphthalene, and bicyclo[3.2.2]nonane. Representative examples of spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

Thus, the term carbocyclic also embraces carbocyclylalkyl groups which as used herein refer to a group of the formula —$R^c$-carbocyclyl where $R^c$ is an alkylene chain. The term carbocyclic also embraces carbocyclylalkoxy groups which as used herein refer to a group bonded through an oxygen atom of the formula —O—$R^c$-carbocyclyl where $R^c$ is an alkylene chain.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or $S(O)_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and Spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur or oxygen. In some embodiments, heterocyclyl includes 4- to 6-membered monocycles having one or more heteroatoms selected from nitrogen, sulfur or oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, thiophenyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups. In some embodiments, a heterocyclic group includes a heterocyclic ring fused to one or more (e.g., 1, 2 or 3) different cyclic groups (e.g., carbocyclic rings or heterocyclic rings), where the radical or point of attachment is on the heterocyclic ring, and in some embodiments wherein the point of attachment is a heteroatom contained in the heterocyclic ring.

Thus, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —$R^c$-heterocyclyl where $R^c$ is an alkylene chain. The term heterocyclic also embraces heterocyclylalkoxy groups which as used herein refer to a radical bonded through an oxygen atom of the formula —O—$R^c$-heterocyclyl where $R^c$ is an alkylene chain.

As used herein, the term "aryl" used alone or as part of a larger moiety (e.g., "aralkyl", wherein the terminal carbon atom on the alkyl group is the point of attachment, e.g., a benzyl group), "aralkoxy" wherein the oxygen atom is the point of attachment, or "aroxyalkyl" wherein the point of attachment is on the aryl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, naphthyridinyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Thus, the term aryl embraces aralkyl groups (e.g., benzyl) which as disclosed above refer to a group of the formula —$R^c$-aryl where $R^c$ is an alkylene chain such as methylene or ethylene. In some embodiments, the aralkyl group is an optionally substituted benzyl group. The term aryl also embraces aralkoxy groups which as used herein refer to a group bonded through an oxygen atom of the formula —O—$R^c$-aryl where $R^c$ is an alkylene chain such as methylene or ethylene.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, imidazopyridyl, pyrazinyl, pyridazinyl, triazinyl, tetrazinyl, tetrazolo[1,5-b]pyridazinyl, purinyl, deazapurinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, indolizinyl, isoindolyl, benzothienyl, benzothiophenyl, methylenedioxyphenyl, benzofuranyl, dibenzofuranyl, indazolyl, benzimidazolyl, benzodioxazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tri-cyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring.

The term heteroaryl also embraces N-heteroaryl groups which as used herein refers to a heteroaryl group, as defined above, and which contains at least one nitrogen atom and where the point of attachment of the N-heteroaryl group to the rest of the molecule is through a nitrogen atom in the heteroaryl group. The term heteroaryl further embraces C-heteroaryl groups which as used herein refer to a heteroaryl group as defined above and where the point of attachment of the heteroaryl group to the rest of the molecule is through a carbon atom in the heteroaryl group. The term heteroaryl further embraces heteroarylalkyl groups which as disclosed above refer to a group of the formula —Rc-heteroaryl, wherein Rc is an alkylene chain as defined above. The term heteroaryl further embraces heteroaralkoxy (or heteroarylalkoxy) groups which as used herein refer to a group bonded through an oxygen atom of the formula —O—Rc-heteroaryl, where Rc is an alkylene group as defined above.

Unless stated otherwise, and to the extent not further defined for any particular group(s), any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1, 2, 3, or 4) heteroatoms such as oxygen, sulfur, and nitrogen grouped in a linear, branched, or cyclic structural format.

To the extent not disclosed otherwise for any particular group(s), representative examples of substituents may thus include alkyl, substituted alkyl (e.g., $C_1$-$C_6$, $C_1$-$C_5$, $C_1$-$C_4$, $C_1$-$C_3$, $C_1$-$C_2$, alkoxy (e.g., $C_1$-$C_6$, $C_1$-$C_5$, $C_1$-$C_4$, $C_1$-$C_3$, $C_1$-$C_2$, $C_1$), substituted alkoxy (e.g., $C_1$-$C_6$, $C_1$-$C_5$, $C_1$-$C_4$, $C_1$-$C_3$, $C_1$-$C_2$, haloalkyl (e.g., $CF_3$), alkenyl (e.g., $C_2$-$C_6$, $C_2$-$C_5$, $C_2$-$C_4$, $C_2$-$C_3$, $C_2$), substituted alkenyl (e.g., $C_2$-$C_6$, $C_2$-$C_5$, $C_2$-$C_4$, $C_2$-$C_3$, $C_2$), alkynyl (e.g., $C_2$-$C_6$, $C_2$-$C_5$, $C_2$-$C_4$, $C_2$-$C_3$, $C_2$), substituted alkynyl (e.g., $C_2$-$C_6$, $C_2$-$C_5$, $C_2$-$C_4$, $C_2$-$C_3$, $C_2$), cyclic (e.g., $C_3$-$C_{12}$, $C_5$-$C_6$), substituted cyclic (e.g., $C_3$-$C_{12}$, $C_5$-$C_6$), carbocyclic (e.g., $C_3$-$C_{12}$, $C_5$-$C_6$), substituted carbocyclic (e.g., $C_3$-$C_{12}$, $C_5$-$C_6$), heterocyclic (e.g., $C_3$-$C_{12}$, $C_5$-$C_6$), substituted heterocyclic (e.g., $C_3$-$C_{12}$, $C_5$-$C_6$), aryl (e.g., benzyl and phenyl), substituted aryl (e.g., substituted benzyl or phenyl), heteroaryl (e.g., pyridyl or pyrimidyl), substituted heteroaryl (e.g., substituted pyridyl or pyrimidyl), aralkyl (e.g., benzyl), substituted aralkyl (e.g., substituted benzyl), halo, hydroxyl, aryloxy (e.g., $C_6$-$C_{12}$, $C_6$), substituted aryloxy (e.g., $C_6$-$C_{12}$, $C_6$), alkylthio (e.g., $C_1$-$C_6$), substituted alkylthio (e.g., $C_1$-$C_6$), arylthio (e.g., $C_6$-$C_{12}$, $C_6$), substituted arylthio (e.g., $C_6$-$C_{12}$, $C_6$), cyano, carbonyl, substituted carbonyl, carboxyl, substituted carboxyl, amino, substituted amino, amido, substituted amido, thio, substituted thio, sulfinyl, substituted sulfinyl, sulfonyl, substituted sulfonyl, sulfinamide, substituted sulfinamide, sulfonamide, substituted sulfonamide, urea, substituted urea, carbamate, substituted carbamate, amino acid, and peptide groups.

The substituent may be "a nitrogen protecting group" (also referred to as an amino protecting group). Nitrogen protecting groups include, but are not limited to, —OH, —$OR^{aa}$, —$N(R^{bb})_2$, —$C(=O)R^{aa}$, —$C(=O)N(R^{bb})_2$, —$CO_2R^{aa}$, —$SO_2R^{aa}$, —$C(=NR^{bb})R^{aa}$, —$C(=NR^{bb})OR^{aa}$, —$C(=NR^{bb})N(R^{bb})_2$, —$SO_2N(R^{bb})_2$, —$SO_2R^{bb}$, —$SO_2OR^{bb}$, —$SOR^{aa}$, —$C(=S)N(R^{bb})_2$, —$C(=O)SR^{bb}$, —$C(=S)SR^{bb}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-4}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{cc}$ groups, and wherein $R^{aa}$, $R^{bb}$ and $R^{cc}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999.

Representative examples of protecting groups such as amide groups (e.g., —$C(=O)R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —$C(=O)OR^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Trot), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-0,3-dithianylAmethyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methy 1-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —$S(=O)_2R^{aa}$) include, but are not limited to, p-toluenesulfonamide (Ts), benzenesulfonamide, 2,3,6, -trimethyl-4-methoxybenzenesulfonamide (Mtr), 2,4,6-trimethoxybenzenesulfonamide (Mtb), 2,6-dimethyi-4-methoxybenzenesuifonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 13-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N-dimethylaminomethylene)amine, N,N'-isopropydenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinifrobenzencsulfenamide, pentachlorobenzenesulfenamide, 2-nitro-4-methoxybenzenesulfenamide, triphenylmethylsulfenamide, and 3-nitropyridinesulfenamide (NPYs).

The substituent may be "an oxygen protecting group" (also referred to as a hydroxyl protecting group). Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl(CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxy ethyl, 1-(2-chloroethoxy)ethyl, 1-methyl-1-methoxy ethyl, 1-methyl-1-benzyloxy ethyl, 1-methy 1-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl) methyl, 4-(4'-bromophenacyloxyphenyl)diphenylmethyl, 4,4',4"-tris(4,5-dichlorophthalimidophenyl)methyl. 4,4',4"-tris(levulinoyloxyphenyl)methyl, 4,4',4"-tris(benzoyloxyphenyemethyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DRIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Trot), 2-(trimethylsilyl) ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

The term "leaving group" is given its ordinary meaning in the art of synthetic organic chemistry and refers to an atom or a group capable of being displaced by a nucleophile. See, for example, *Smith, March Advanced Organic Chemistry 6th ed.* (501-502). Examples of suitable leaving groups include, but are not limited to, halogen (such as F, Cl, Br, or I), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. Exemplary leaving groups include, but are not limited to, activated substituted hydroxyl groups (e.g., $-OC(=O)SR^{aa}$, $-OC(=O)R^{aa}$, $-OCO_2R^{aa}$, $-OC(=O)N(R^{bb})_2$, $-OC(=NR^{bb})R^{aa}$, $-OC(=NR^{bb})OR^{aa}$, $-OC(=NR^{bb})N(R^{bb})_2$, $-OS(=O)R^{aa}$, $-OSO_2R^{aa}$, $-OP(R^{cc})_2$, $-OP(R^{cc})_3$, $-OP(=O)_2R^{aa}$, $-OP(=O)(R^{aa})_2$, $-OP(=O)(OR^{cc})_2$, $-OP(=O)_2N(R^{bb})_2$, and $-OP(=O)(NR^{bb})_2$, wherein $R^{aa}$, $R^{bb}$, and $R^{cc}$ are as defined herein). In some cases, the leaving group is a sulfonic acid ester, such as toluenesulfonate (tosylate, —OTs), methanesulfonate (mesylate, —OMs), p-bromobenzenesulfonyloxy (brosylate, —OBs), $-OS(=O)_2(CF_2)_3CF_3$ (nonaflate, —ONf, or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

The term "binding" as it relates to interaction between the targeting ligand and the targeted proteins, which for purposes of this invention is CDK7 and mutant forms thereof (collectively "CDK7"), typically refers to an inter-molecular interaction that may be preferential or substantially specific (also referred to herein as "selective") in that binding of the targeting ligand with other proteinaceous entities present in the cell is functionally insignificant. The present bispecific compounds may preferentially bind and recruit CDK7, and mutant forms thereof, for targeted degradation.

The term "binding" as it relates to interaction between the degron and the E3 ubiquitin ligase, typically refers to an inter-molecular interaction that may or may not exhibit an affinity level that equals or exceeds that affinity between the targeting ligand and the target protein, but nonetheless wherein the affinity is sufficient to achieve recruitment of the ligase to the targeted degradation and the selective degradation of the targeted protein.

Broadly, the bispecific compound includes one moiety (referred to herein as a targeting ligand) that binds cyclin-dependent kinase 7 (CDK7)) and a second moiety, referred to as a "degron" that binds an E3 ubiquitin ligase, that are joined together via a linker. The compound has a structure represented by formula (I):

(I)

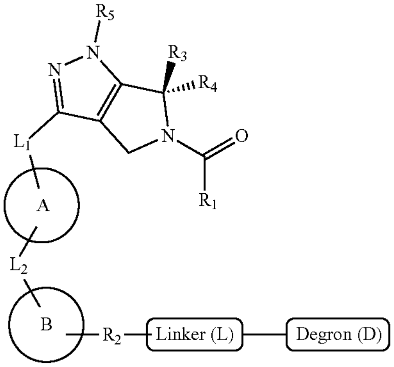

or a pharmaceutically acceptable salt or stereoisomer thereof, wherein

- $R_1$ represents —$NR^aR^b$, —$CHR^aR^b$ or —$OR^a$, wherein each of Ra and Rb is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, or an oxygen protecting group when attached to an oxygen atom, or $R^a$ and $R^b$ together with the atoms to which they are bound form an optionally substituted carbocyclic, optionally substituted heterocyclic, optionally substituted aryl, or optionally substituted heteroaryl ring;
- each of $R_3$ and $R_4$ independently represents hydrogen, halogen, optionally substituted $C_1$-$C_6$ alkyl, or optionally substituted aryl, or $R_3$ and $R_4$ together with the atoms to which they are bound form an optionally substituted $C_3$-$C_6$ carbocyclyl ring;
- $R_5$ independently represents hydrogen, optionally substituted $C_1$-$C_6$ alkyl, or a nitrogen protecting group;
- $L_1$ represents —$NR^{L1}$—, —$NR^{L1}C$(═O)—, —C(═O)$NR^{L1}$—, —O—, or —S—, wherein $R^{L1}$ is hydrogen, optionally substituted $C_1$-$C_6$ alkyl, or a nitrogen protecting group;
- A represents optionally substituted carbocyclyl, optionally substituted heterocyclyl, optionally substituted aryl, or optionally substituted heteroaryl;
- $L_2$ represents a bond or absent, —C(═O)—, —C(—O)$NR^{L2}$—, —$NR^{L2}C$(═O)—, —O—, or —S—, wherein $R^{L2}$ is hydrogen, optionally substituted $C_1$-$C_6$ alkyl, or a nitrogen protecting group;
- B is a bond or absent, optionally substituted carbocyclyl, optionally substituted heterocyclyl, optionally substituted aryl, or optionally substituted heteroaryl; and $R_2$ is absent, or any one of the following structures:

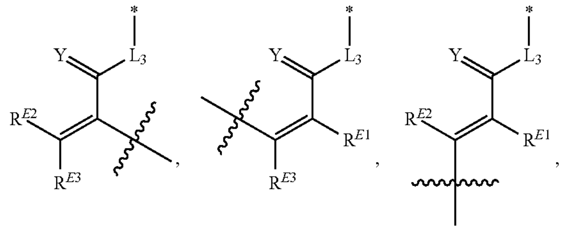

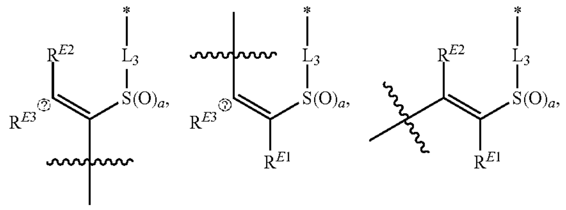

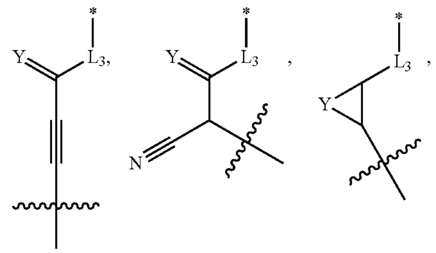

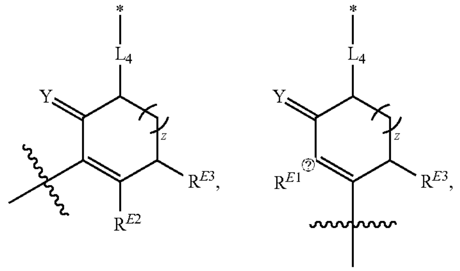

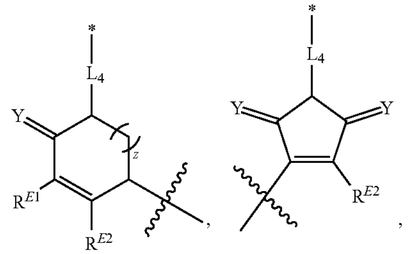

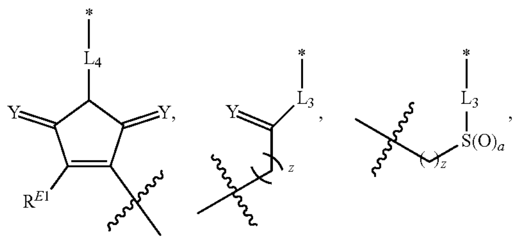

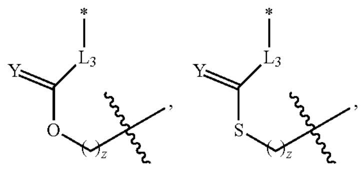

-continued
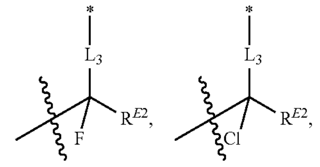
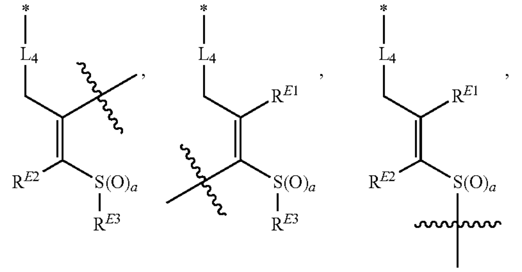
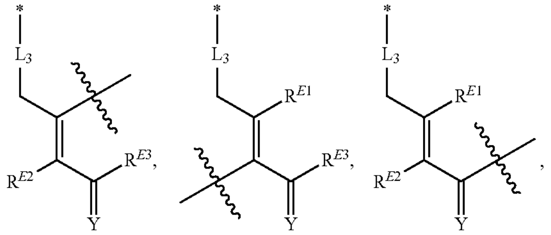
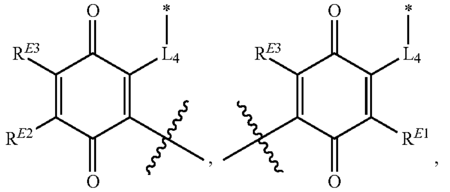
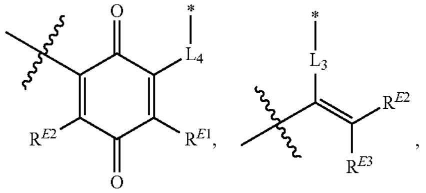
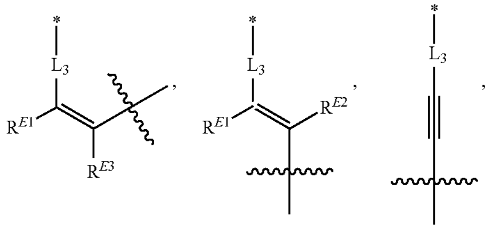
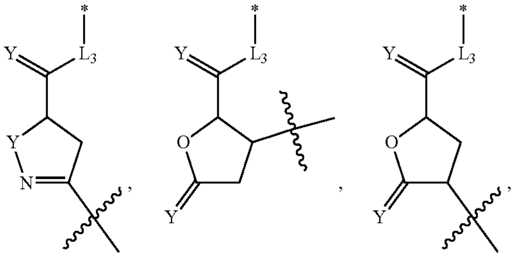
-continued
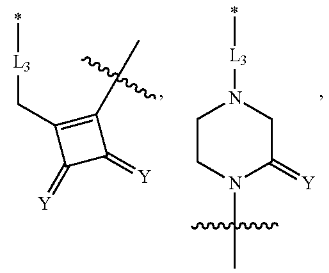
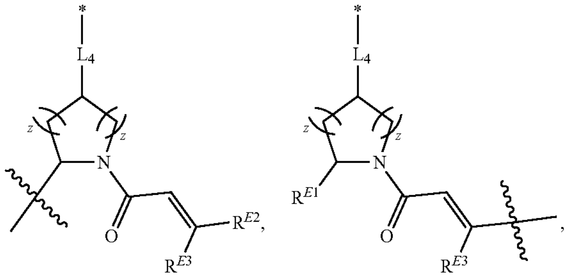
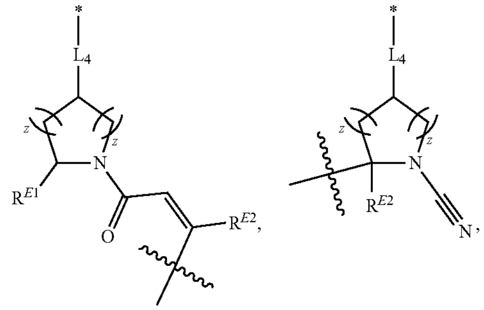
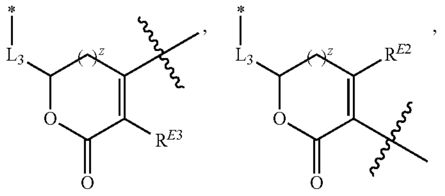
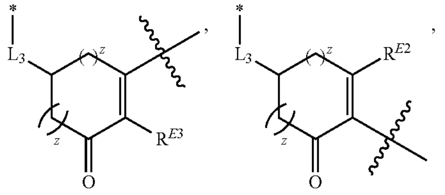
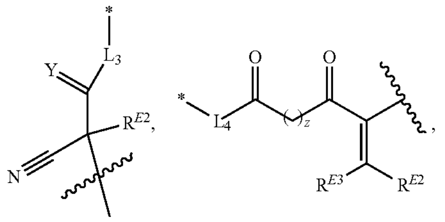
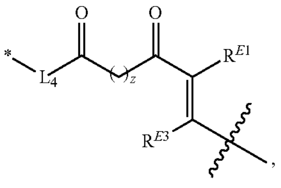

-continued

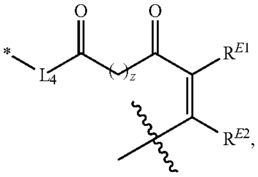,

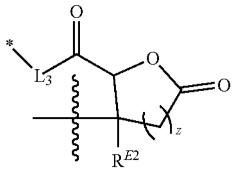,

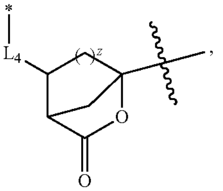,

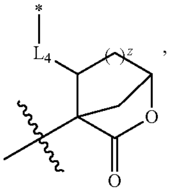,

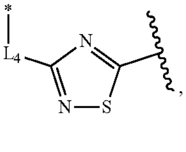,

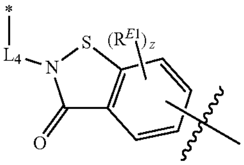,

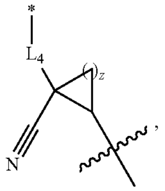,

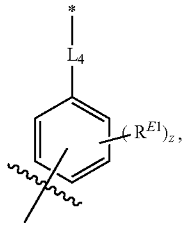,

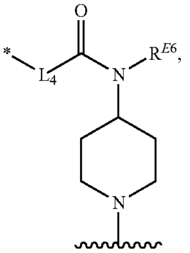,

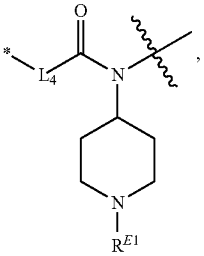, or

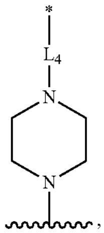, wherein the asterisk (*) represents the point of attachment to B and the squiggle represents the point of attachment to

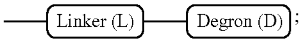

;

$L_3$ is a bond or absent or an optionally substituted $C_{1-4}$ hydrocarbon chain, optionally wherein one or more carbon units of the hydrocarbon chain are independently replaced with —C(=O)—, —O—, —S—, —NR$^{L3a}$, —NR$^{L3a}$C(=O)—, —C(=O) NR$^{L3a}$, —SC(=O)—, —C(=O)S—, —OC(=O)—, —C(=O)O—, —NR$^{L3a}$C(=S)—, —C(=S) NR$^{L3a}$—, trans-CR$^{L3b}$=CR$^{L3b}$—, cis-CR$^{L3b}$—CR$^{L3b}$—C—S(=O)—, —C=C—, —S(=O)—, —S(=O)O—, —OS(=O)—, —S(=O) NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups together with the atoms to which they are bound form an optionally substituted carbocyclic or optionally substituted heterocyclic ring;

$L_4$ is a bond or an optionally substituted, branched or unbranched $C_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(REE)$_2$, —CH$_2$SREE, —OR$^{EE}$, —N(REE)$_2$, —Si(REE)$_3$, and —SR$^{EE}$ wherein each occurrence of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two REE groups together with the atoms to which they are bound form an optionally substituted heterocyclic ring; or R$^{E1}$ and R$^{E3}$, or R$^{E2}$ and R$^{E3}$, or R$^{E1}$ and R$^{E2}$ together with the atoms to which they are bound form an optionally substituted carbocyclic or optionally substituted heterocyclic ring;

R$^{E4}$ is a leaving group;

R$^{E6}$ is hydrogen, substituted or unsubstituted $C_{1-6}$ alkyl, or a nitrogen protecting group;

each instance of Y is independently O, S, or NR$^{E7}$, wherein R$^{E7}$ is hydrogen, substituted or unsubstituted $C_{1-6}$ alkyl, or a nitrogen protecting group;

a is 1 or 2; and each instance of z is independently 0, 1, 2, 3, 4, 5, or 6, as valency permits.

With respect to compounds of the present invention, the targeting ligand is represented by the following structure:

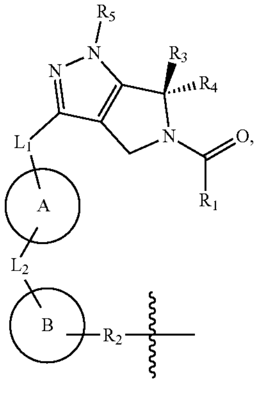

wherein the squiggle represents the squiggle represents the point of attachment to

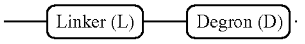

In some embodiments, $R_1$ is

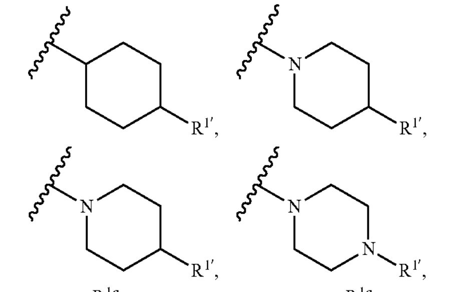

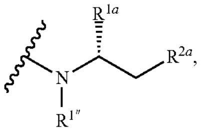

or

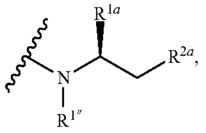

wherein each of $R^{1'}$ is $R^{1''}$ are independently hydrogen, optionally substituted $C_1$-$C_6$ alkyl, or a nitrogen protecting group, $R^{1a}$ is hydrogen, $C_1$-$C_6$ alkyl, or optionally substituted aryl, and $R^{2a}$ is hydrogen, —$OR^{1N}$, or —$NR^{1N}R^{2N}$, wherein each of $R^{1N}$ and $R^{2N}$ is independently hydrogen, $C_1$-$C_6$ alkyl or a nitrogen protecting group when attached to a nitrogen or an oxygen protecting group when attached to an oxygen atom.

In some embodiments, $R^{1''}$ is hydrogen, Bn, BOC, Cbz, Fmoc, trifluoroacetyl, triphenylmethyl, acetyl, or Ts.

In some embodiments, $R_1$ is

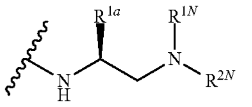

or

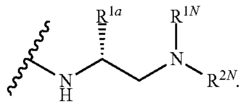

In some embodiments, $R_1$ is

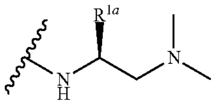

or

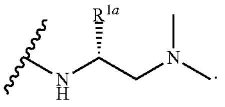

In some embodiments, $R^{1a}$ is hydrogen, methyl, ethyl, propyl or phenyl.

In certain embodiments, $R^{2a}$ is hydrogen. In some embodiments, $R^{2a}$ is —$OR^{1N}$, wherein $R^{1N}$ is hydrogen, $C_1$-$C_6$ alkyl, or an oxygen protecting group. In some embodiments, $R^{2a}$ is —OH. In certain embodiments, $R^{2a}$ is —$NR^{1N}R^{2N}$ wherein each of $R^{1N}$ and $R^{2N}$ is independently hydrogen, $C_1$-$C_6$ alkyl, or a nitrogen protecting group. In some embodiments, both $R^{1N}$ and $R^{2N}$ are hydrogen, methyl, ethyl, propyl or nitrogen protecting group. In some embodiments, at least one of $R^{1N}$ and $R^{2N}$ is hydrogen, methyl, ethyl, propyl or nitrogen protecting group. In some embodiments, $R^{1N}$ is methyl, and $R^{2N}$ is hydrogen. In some embodiments, $R^{1N}$ is ethyl, and $R^{2N}$ is hydrogen. In some embodiments, $R^{1N}$ is propyl, and $R^{2N}$ is hydrogen. In some embodiments, $R^{1N}$ is a nitrogen protecting group, and $R^{2N}$ is hydrogen. In some embodiments, $R^{1N}$ is methyl, and $R^{2N}$ is a nitrogen protecting group. In some embodiments, $R^{1N}$ is ethyl, and $R^{2N}$ is a nitrogen protecting group. In some embodiments, $R^{1N}$ is propyl, and $R^{2N}$ is a nitrogen protecting group.

In some embodiments, $R_1$ is

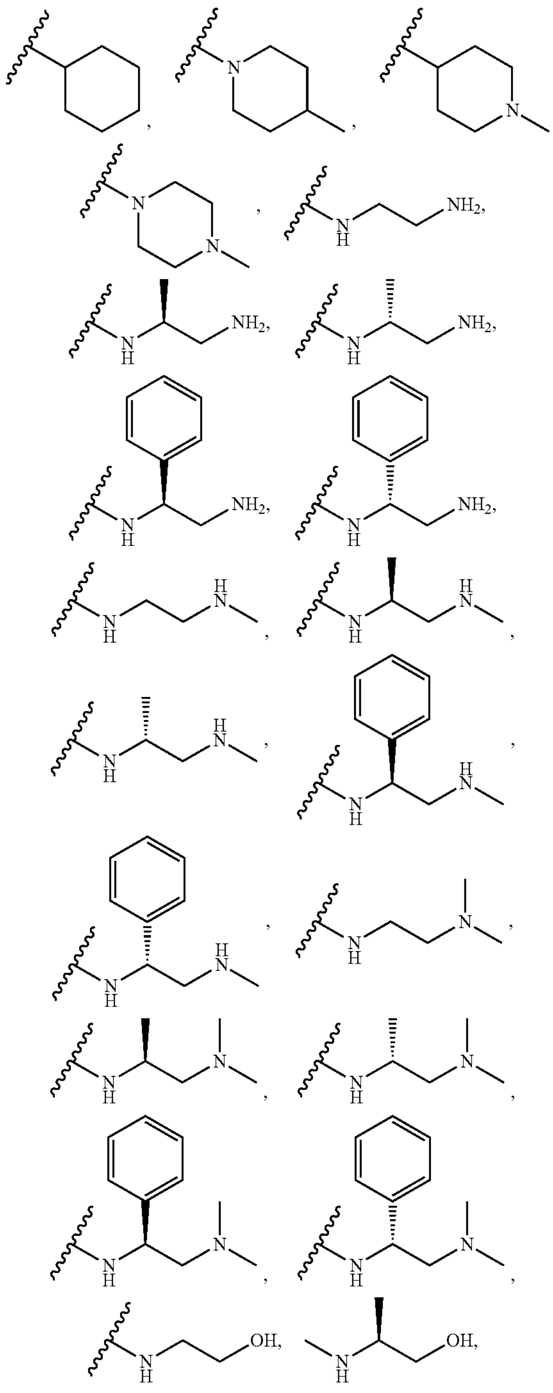

-continued

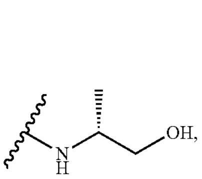

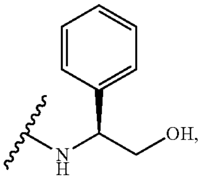

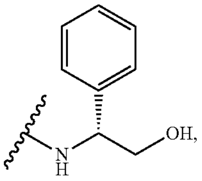

or

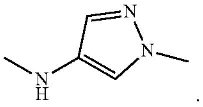

In some embodiments, $R_2$ is a bond,

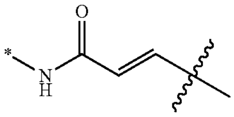

or

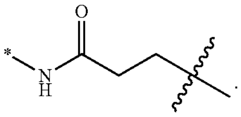

In some embodiments, $R_3$ and $R_4$ are independently methyl, isopropyl, or phenyl, or $R_3$ and $R_4$ together with the atoms to which they are bound form an optionally substituted $C_3$-$C_6$ carbocyclyl ring. In some embodiments, $R_3$ and $R_4$ are both methyl.

In some embodiments, $R_5$ is hydrogen or methyl.

In some embodiments, A is 6-membered carbocyclyl or 6-membered heterocyclyl.

In some embodiments, B is a bond, 6-membered carbocyclyl or 6-membered heterocyclyl.

In some embodiments, $L_1$ is $L_1$ is NH or —NHC(O)—.

In some embodiments, $L_2$ is a bond, NH or —NHC(O)—.

In some embodiments, wherein $L_1$ is NH or —NHC(O)—, $R_3$ and $R_4$ are methyl, and $R_5$ is H, the compounds of formula (I) have a structure represented by any one of formulas (I-1a) and (I-1b):

(I-1a)

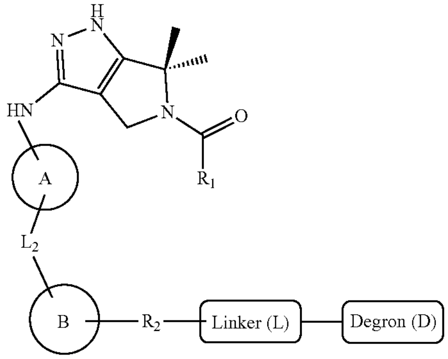

and

-continued (I-1b)

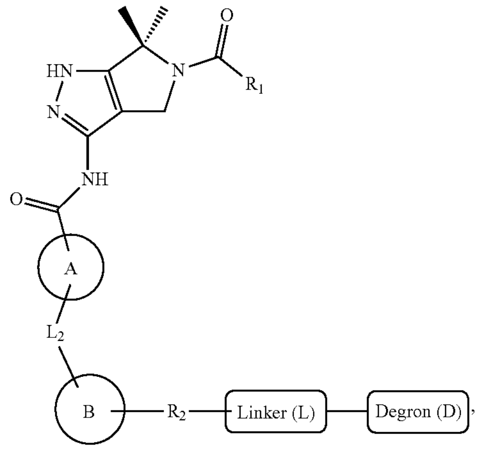

or a pharmaceutically acceptable salt or stereoisomer thereof.

In some embodiments, wherein A is 6-membered carbocyclyl, $R_3$ and $R_4$ are methyl and $R_5$ is H, the compounds of formula (I) have a structure represented by any one of formulas (I-2a) to (I-2f):

(I-2a)

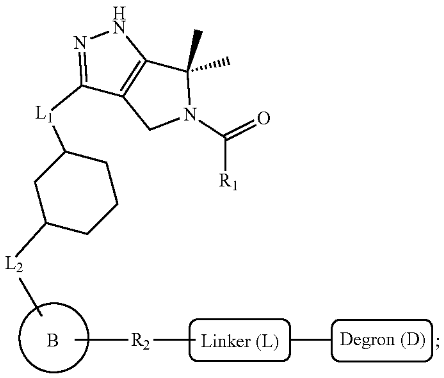

(I-2b)

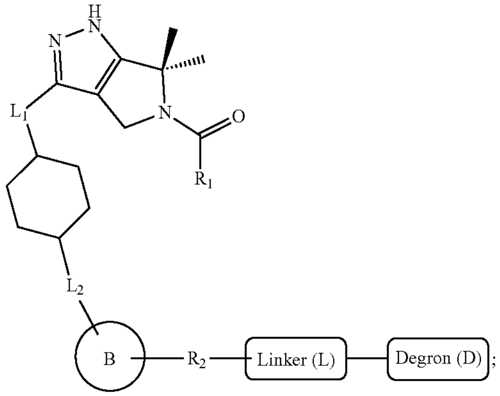

-continued
(I-2c)
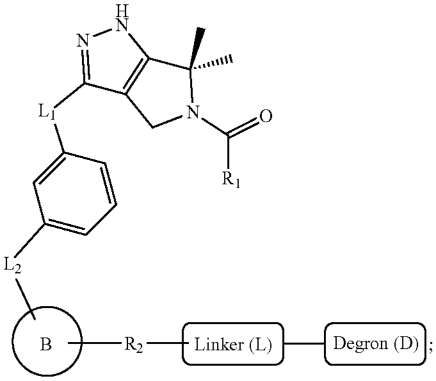
(I-2d)
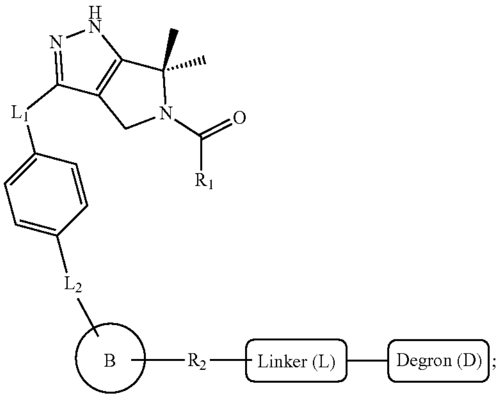
(I-2e)
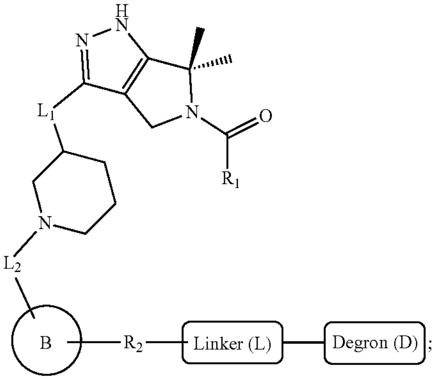
and
(I-2f)
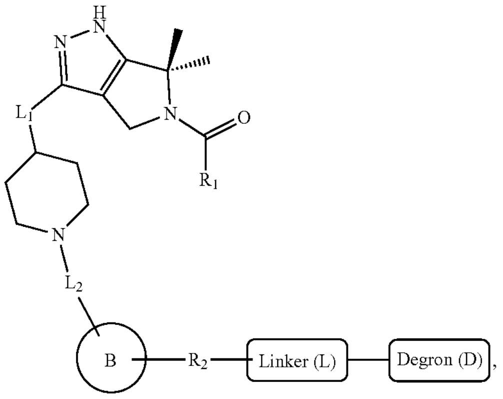
or a pharmaceutically acceptable salt or stereoisomer thereof.
In some embodiments, wherein $L_1$ is NH or —NHC(O)—, $R_1$ is
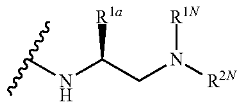
or
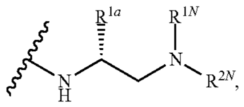
$R_3$ and $R_4$ are methyl and $R_5$ is H, the compounds of formula (I) have a structure represented by any one of formulas (I-3a) to (I-3d):
(I-3a)
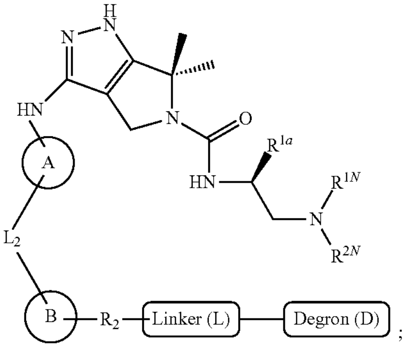
(I-3b)
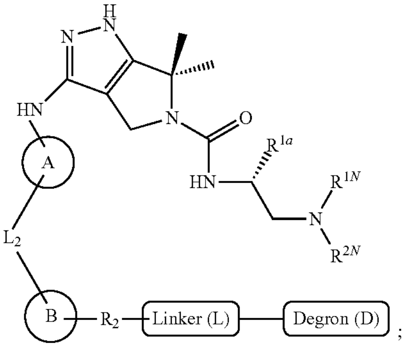
(I-3c)
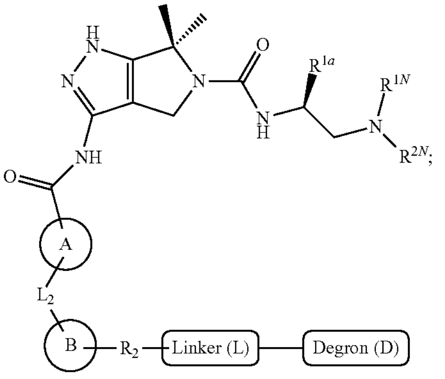
and -continued
(I-3d)
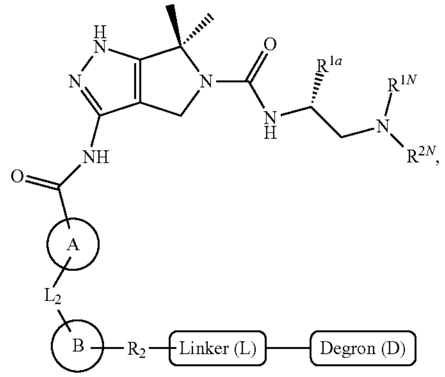
or a pharmaceutically acceptable salt or stereoisomer thereof
In some embodiments, wherein A is 6-membered carbocyclyl, $R_1$ is
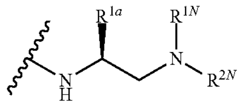
or
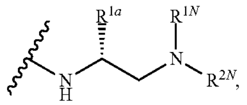
$R_3$ and $R_4$ are methyl and $R_5$ is H, the compounds of formula (I) have a structure represented by any one of formulas (I-4a) to (I-4l):
(I-4a)
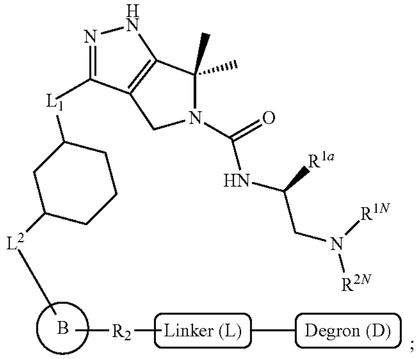
(I-4b)
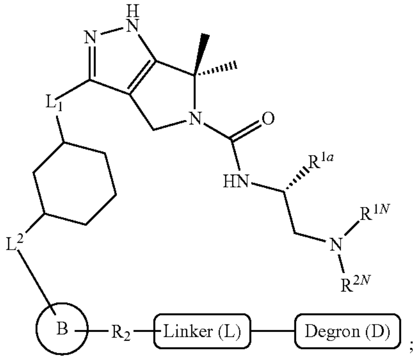
-continued
(I-4c)
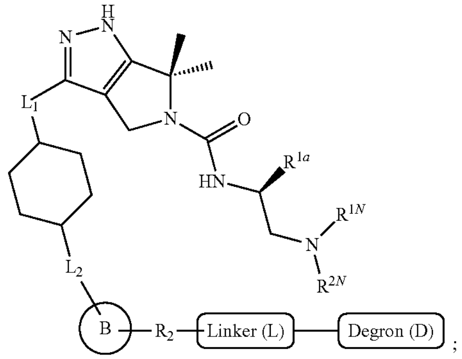
(I-4d)
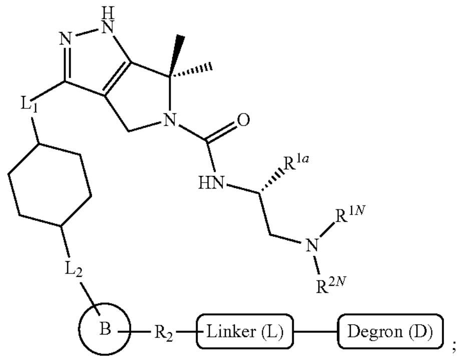
(I-4e)
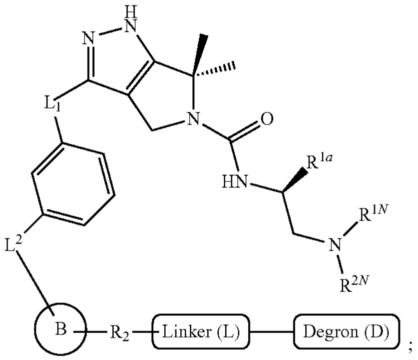
(I-4f)
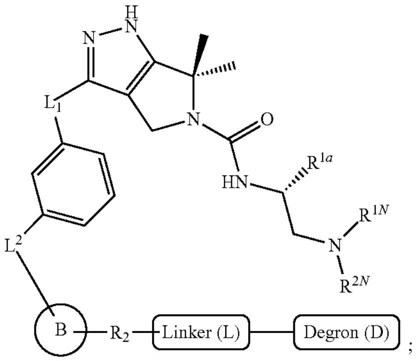

-continued
(I-4g)
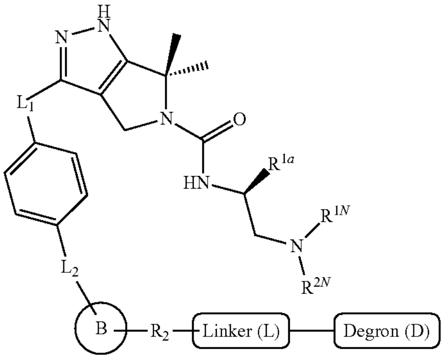
;
(I-4h)
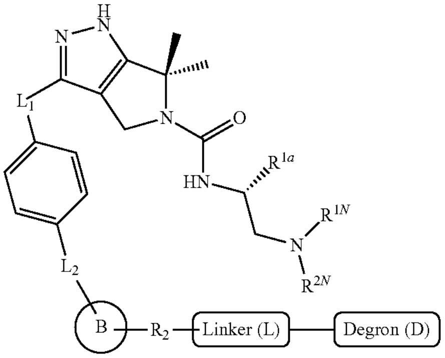
;
(I-4i)
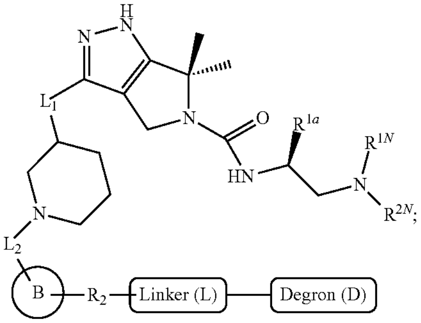
(I-4j)
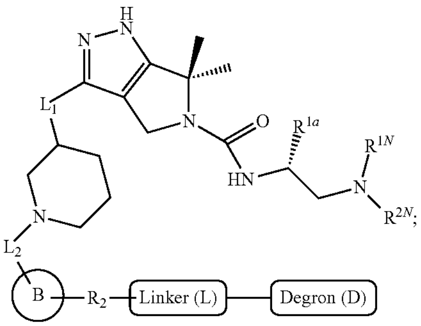
-continued
(I-4k)
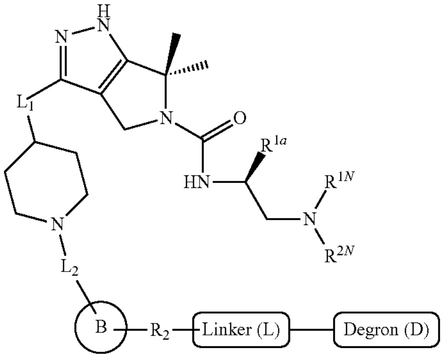
; and
(I-4l)
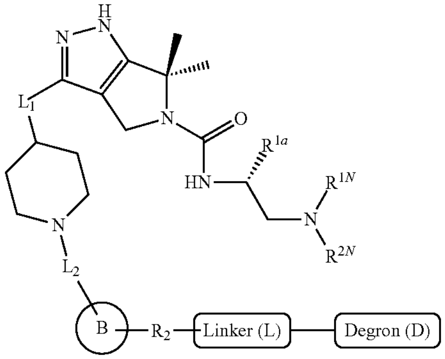
,
or a pharmaceutically acceptable salt or stereoisomer thereof.
In some embodiments, wherein $L_1$ is NH or —NHC(O)—, $R_1$ is
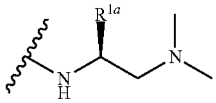
or
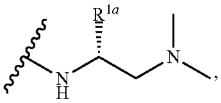
,
$R_3$ and $R_4$ are methyl and $R_5$ is H, the compounds of formula (I) have a structure represented by any one of formulas (I-5a) and (I-5b):
(I-5a)
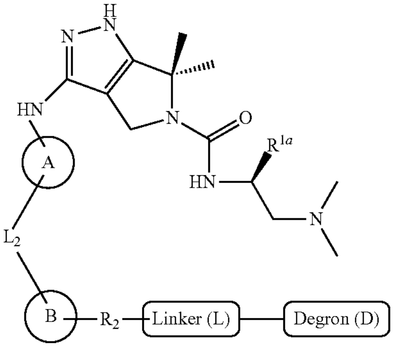
;

-continued
(I-5b)
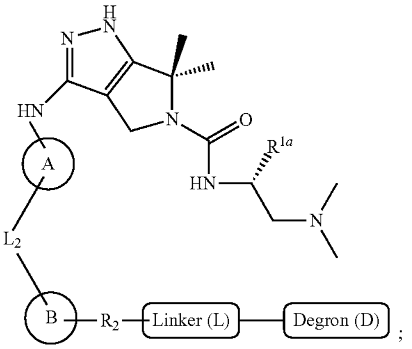
(I-5c)
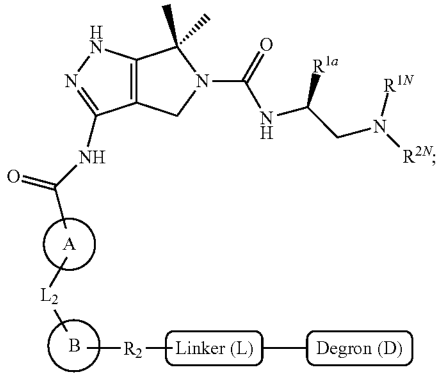
and
(I-5d)
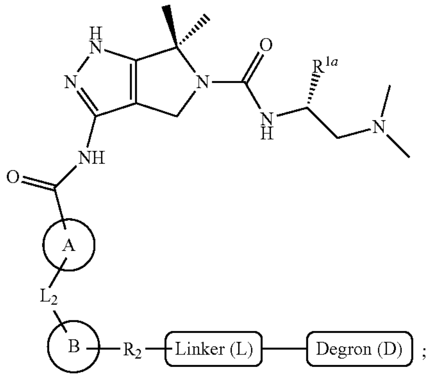
or a pharmaceutically acceptable salt or stereoisomer thereof.
In some embodiments, wherein A is 6-membered carbocyclyl, $R_1$ is
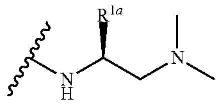
or
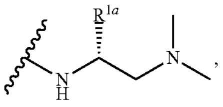
,
$R_3$ and $R_4$ are methyl and $R_5$ is H, the compounds of formula (I) have a structure represented by any one of formulas (I-6a) to (I-6l):
(I-6a)
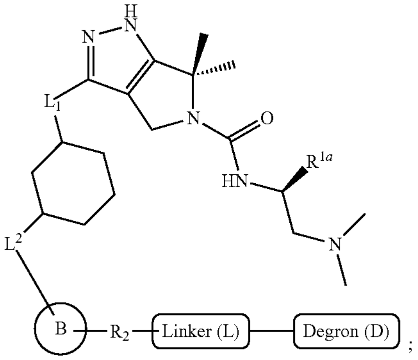
(I-6b)
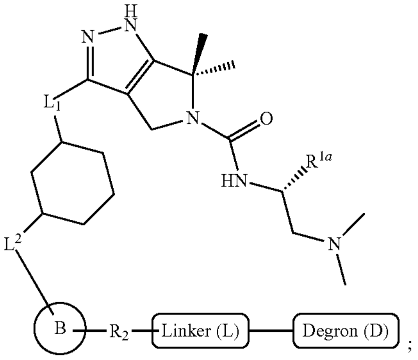
(I-6c)
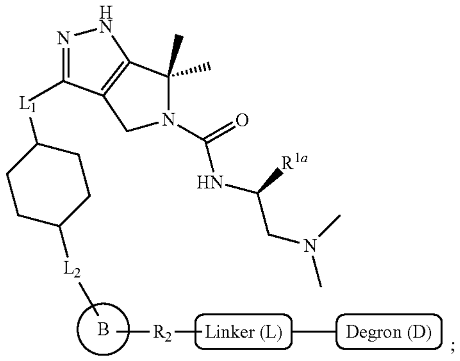
(I-6d)
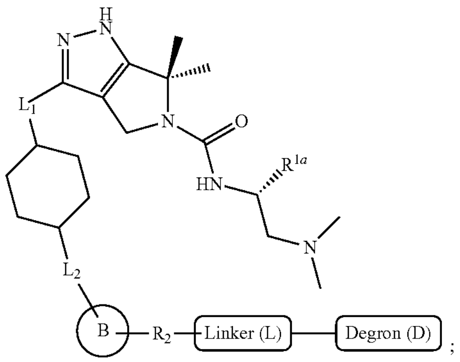

-continued
(I-6e)
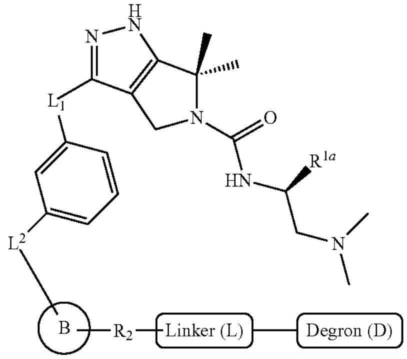
;
(I-6f)
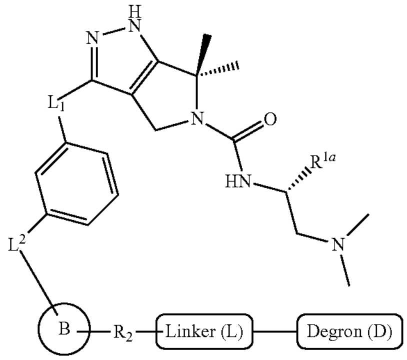
;
(I-6g)
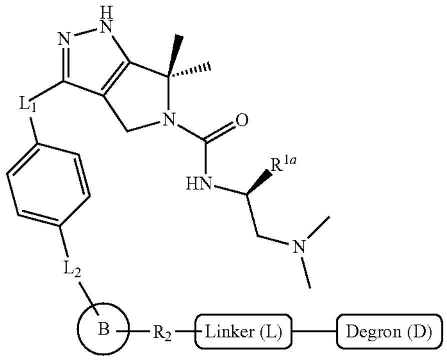
;
(I-6h)
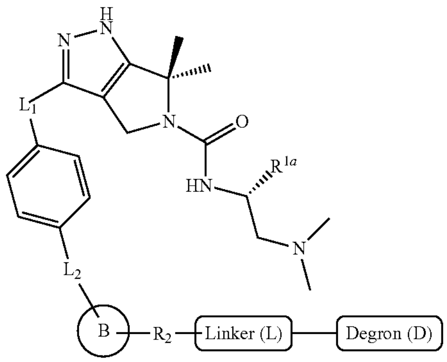
;
-continued
(I-6i)
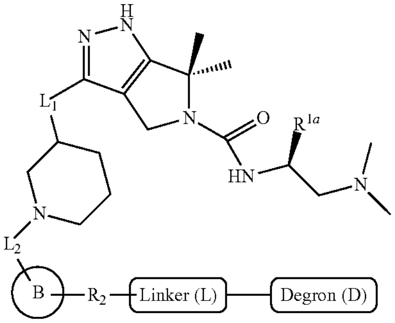
;
(I-6j)
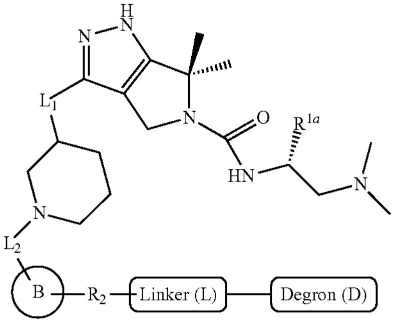
;
(I-6k)
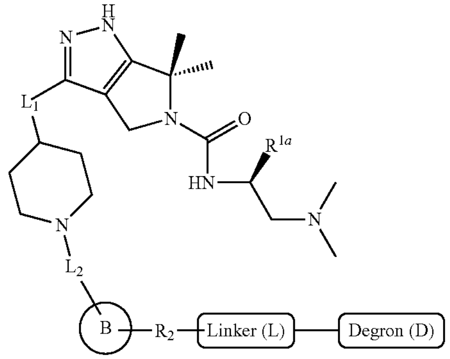
; and
(I-6l)
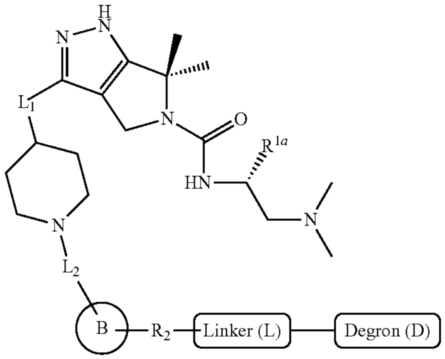
,
or a pharmaceutically acceptable salt or stereoisomer thereof.
In some embodiments, the compounds of formula (I) have a structure represented by any one of formulas (I-7) to (I-57):

(I-7)
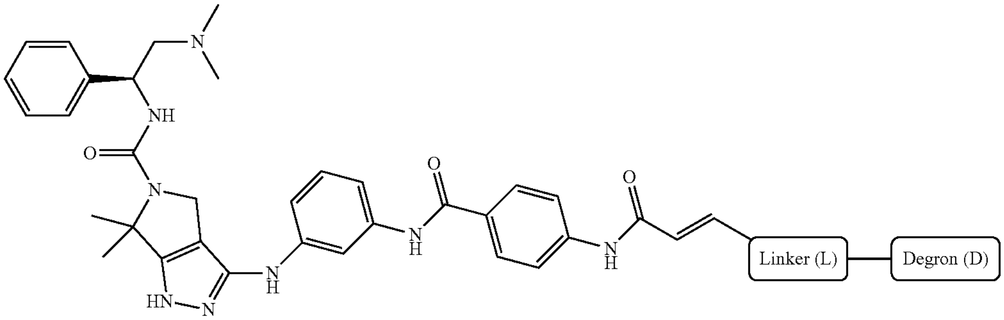
;
(I-8)
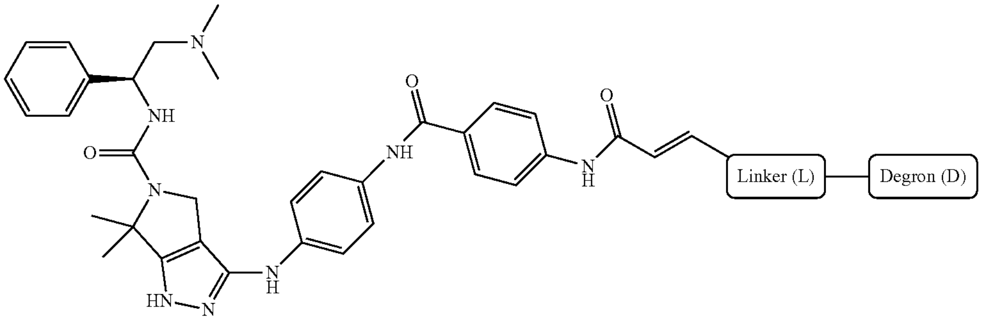
;
(I-9)
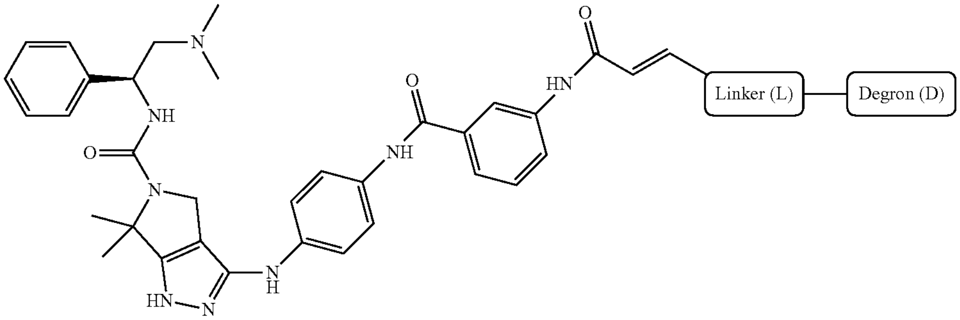
;
(I-10)
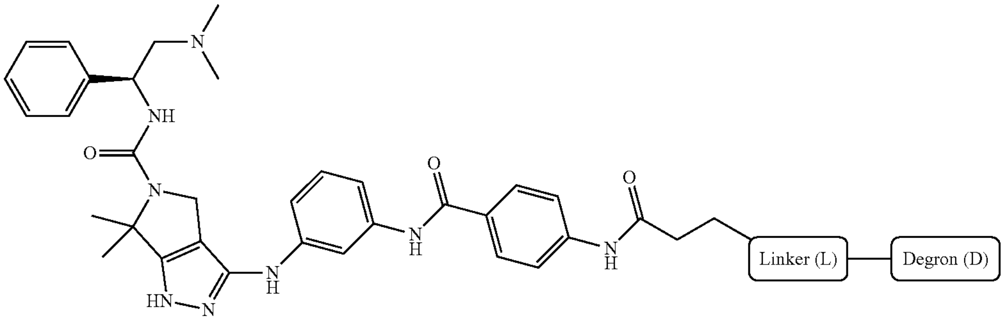
;
(I-11)
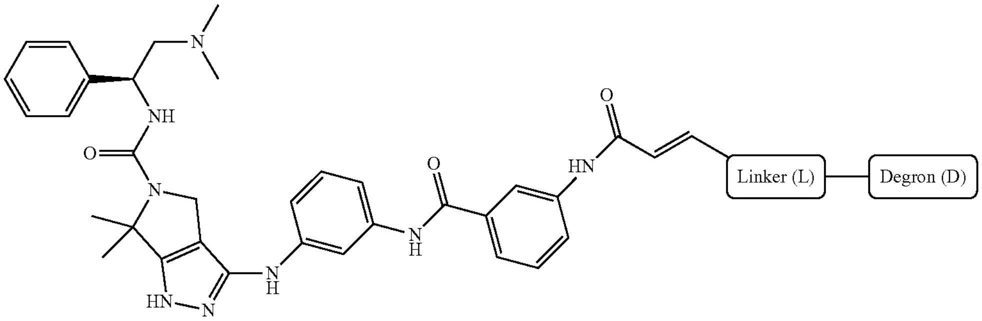
;

-continued
(I-12)
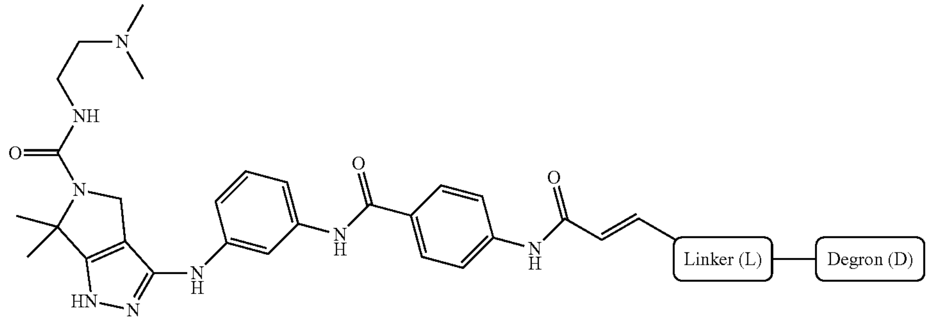
;
(I-13)
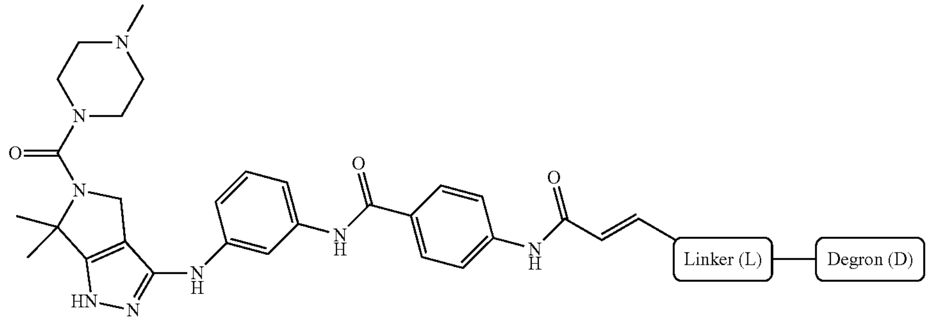
;
(I-14)
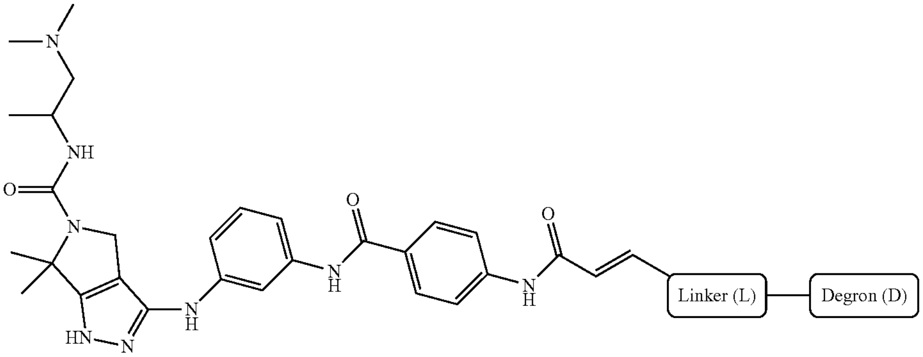
;
(I-15)
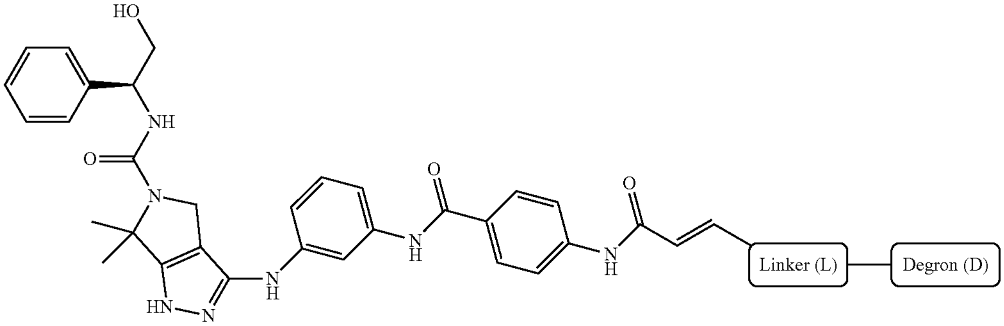
;

-continued
(I-16)
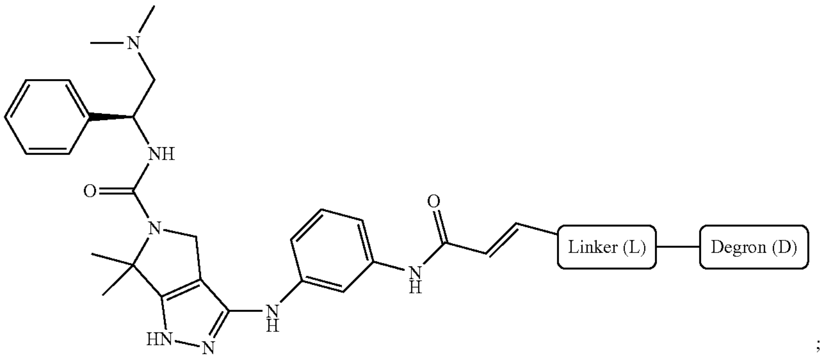
(I-17)
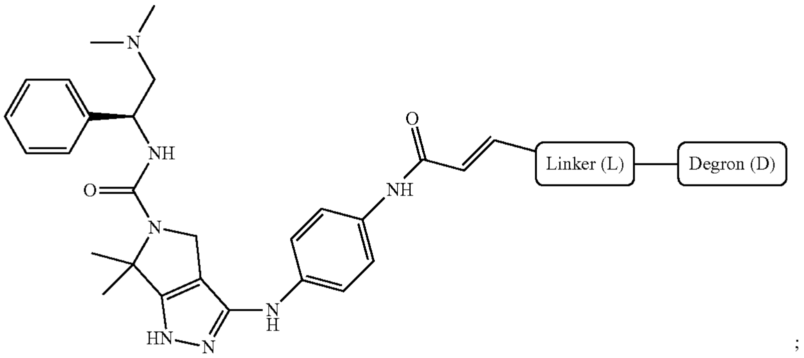
(I-18)
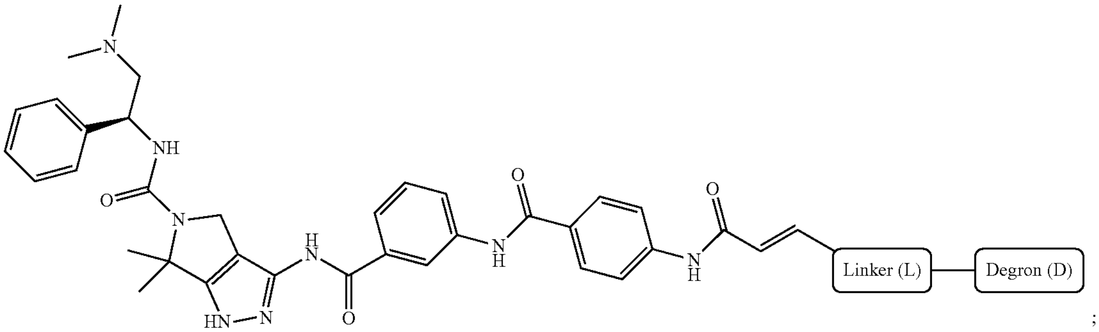
(I-19)
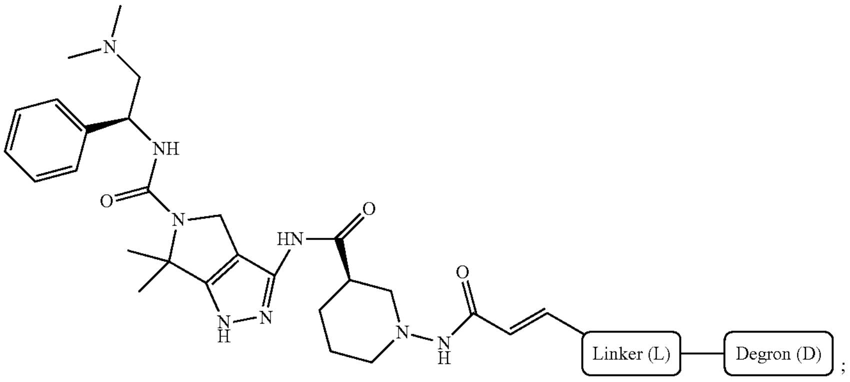

-continued
(I-20)
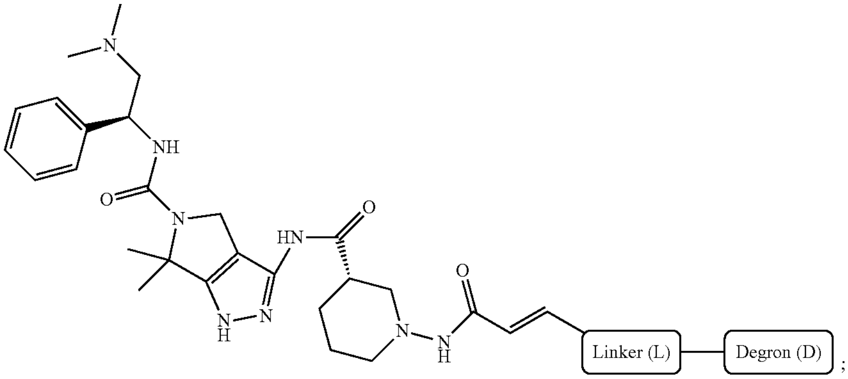
;
(I-21)
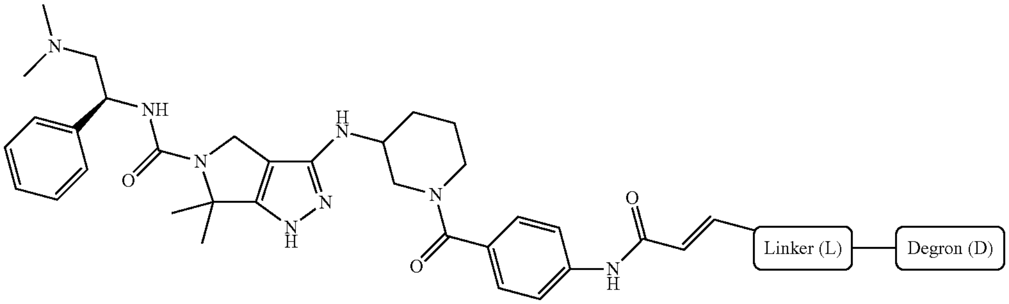
;
(I-22)
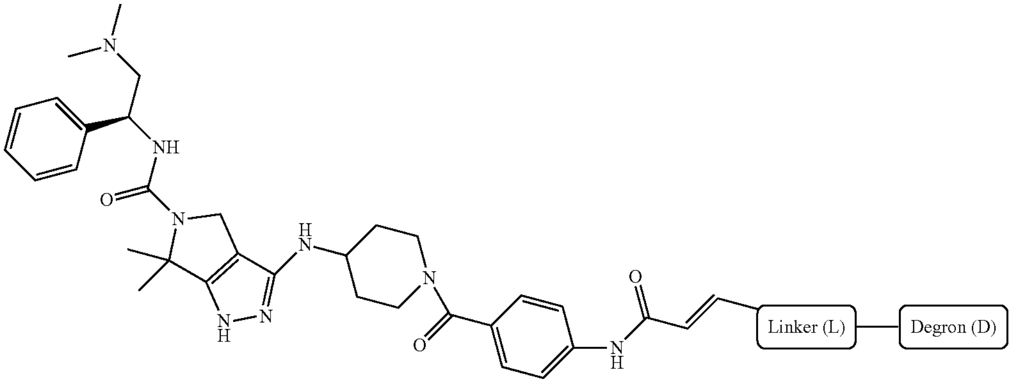
;
(I-23)
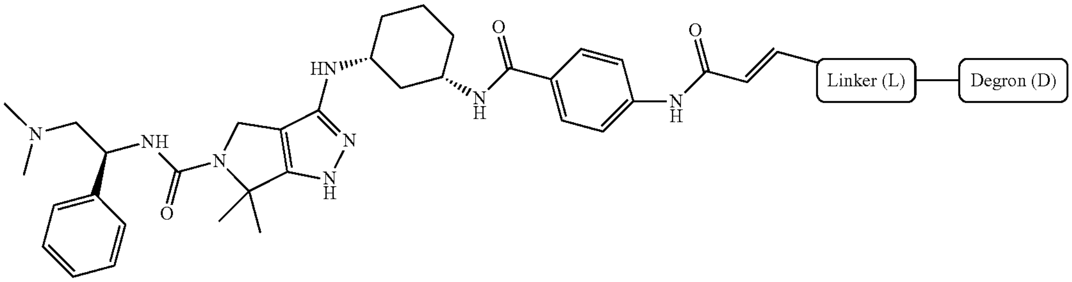
;

-continued
(I-24)
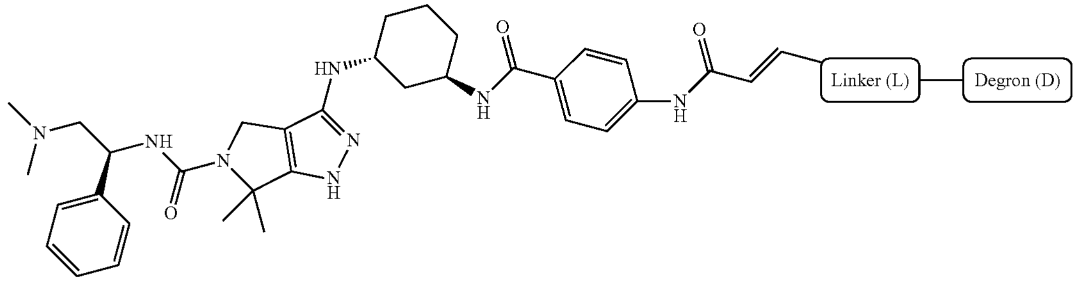
;
(I-25)
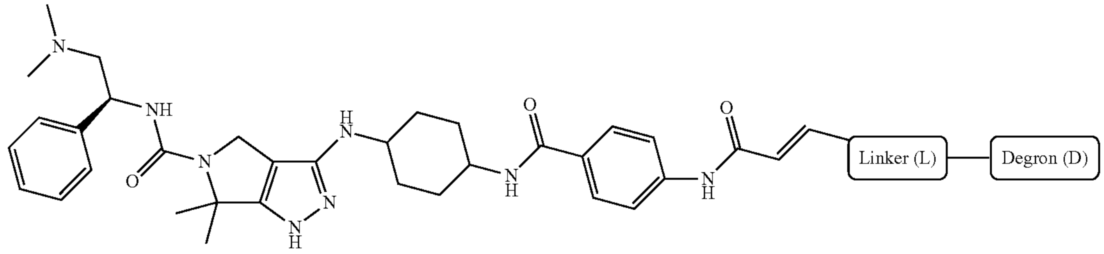
;
(I-26)
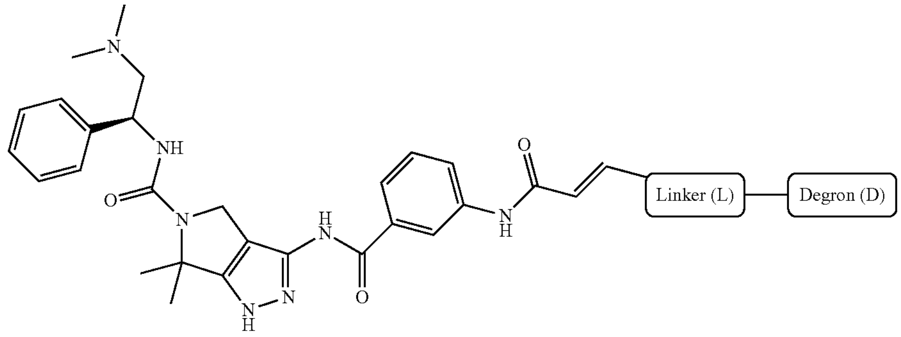
;
(I-27)
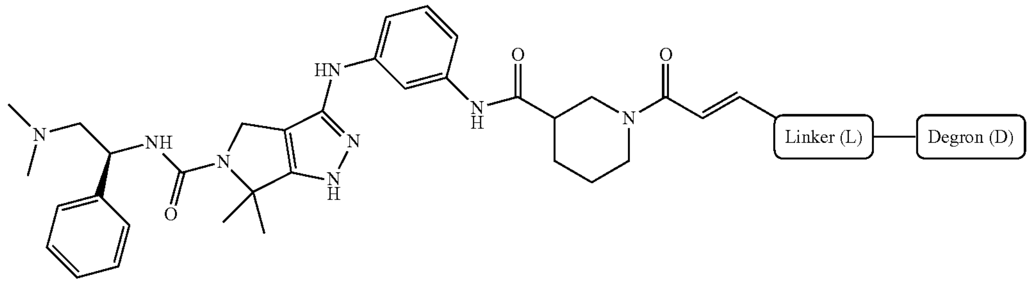
;
(I-28)
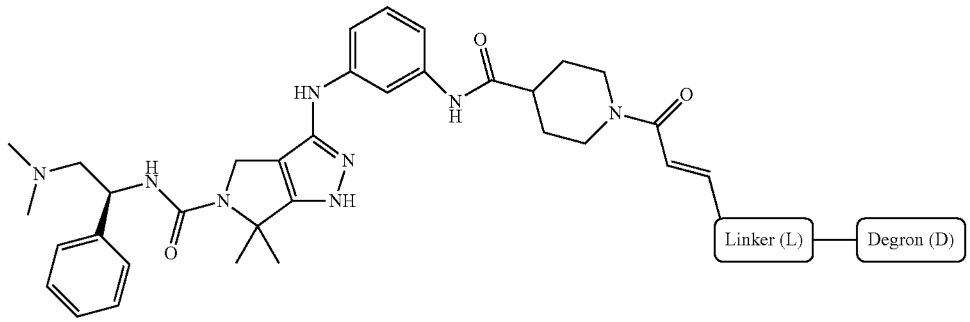
;

-continued
(I-29)
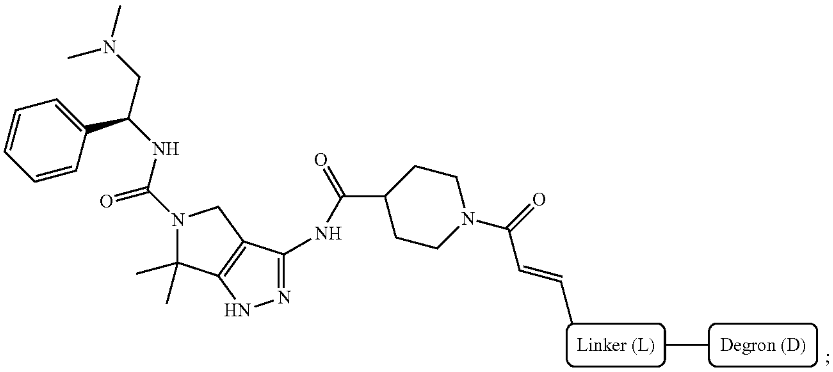
;
(I-30)
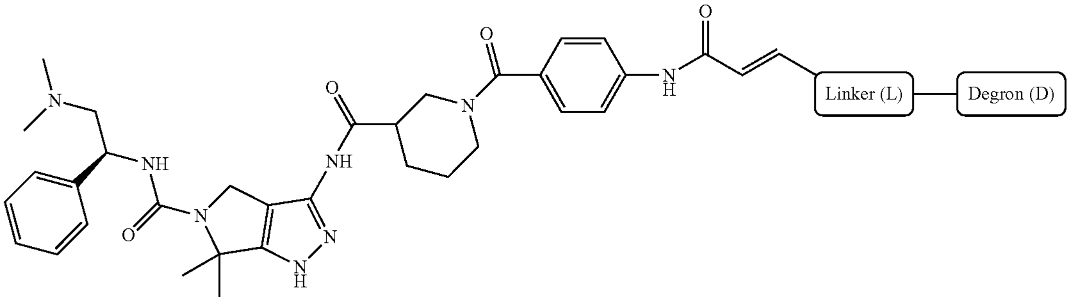
;
(I-31)
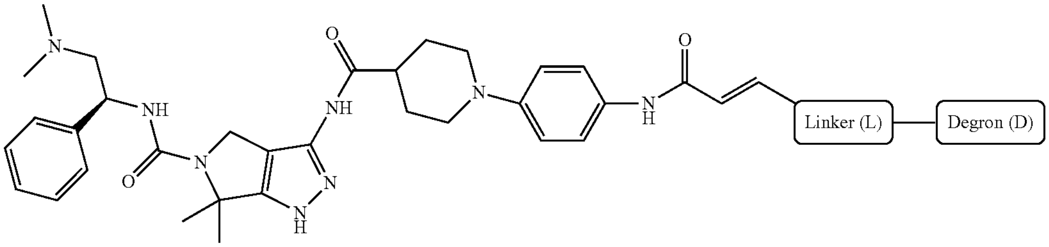
;
(I-32)
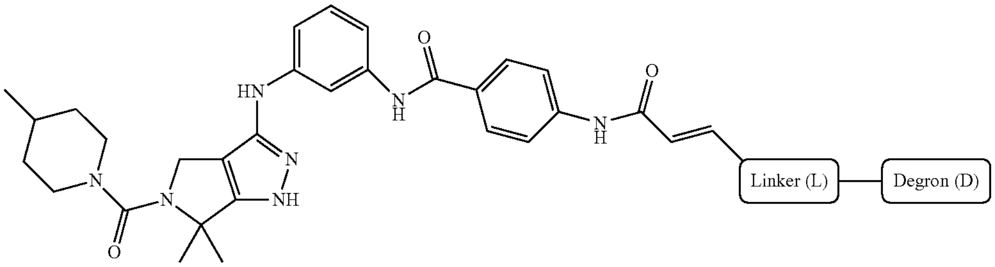
;
(I-33)
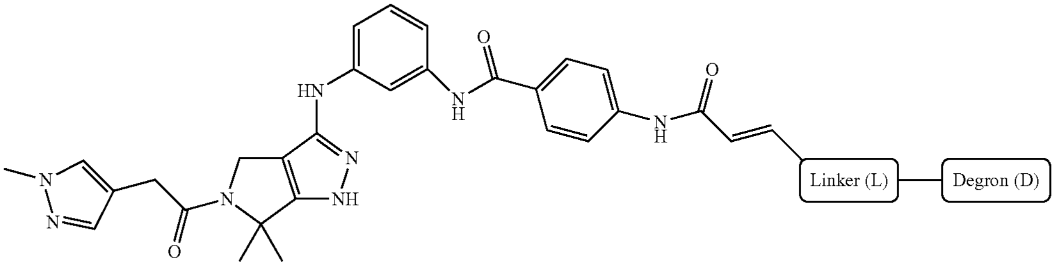
;

-continued
(I-34)
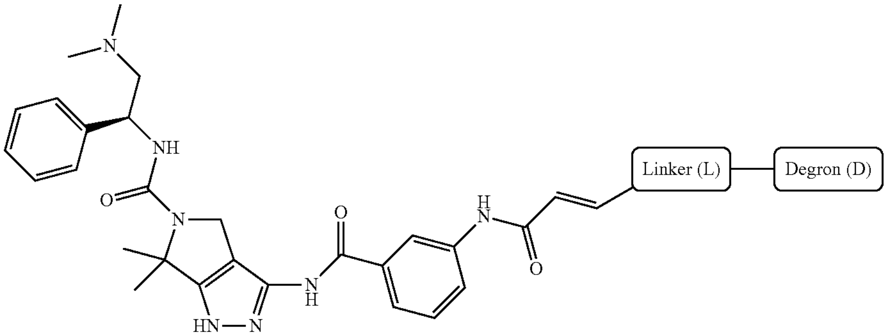
;
(I-35)
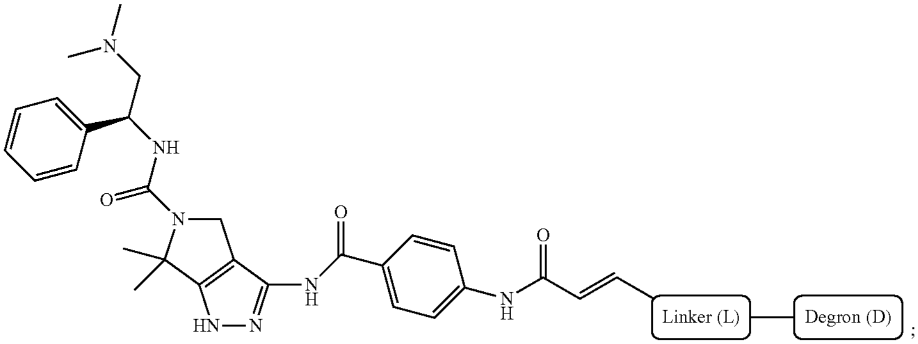
;
(I-36)
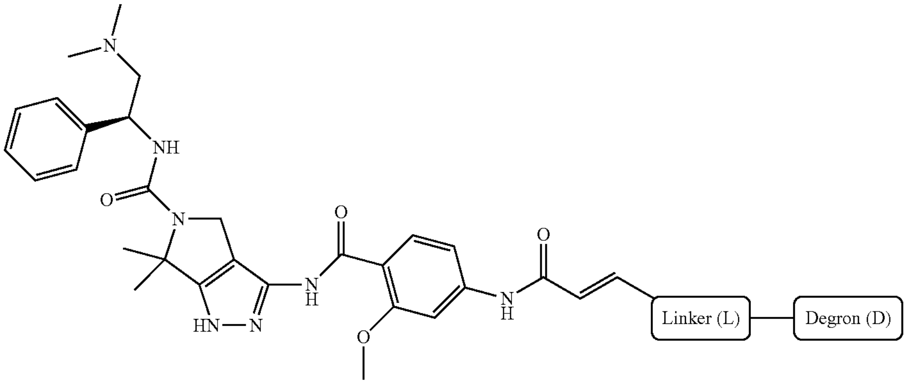
;
(I-37)
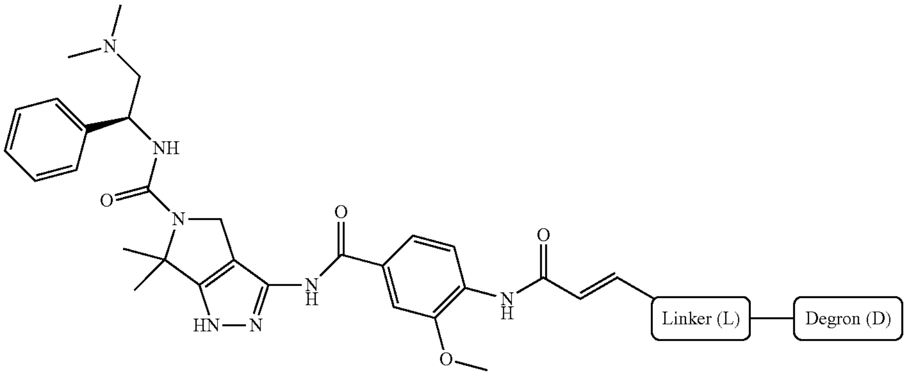
;

-continued
(I-38)
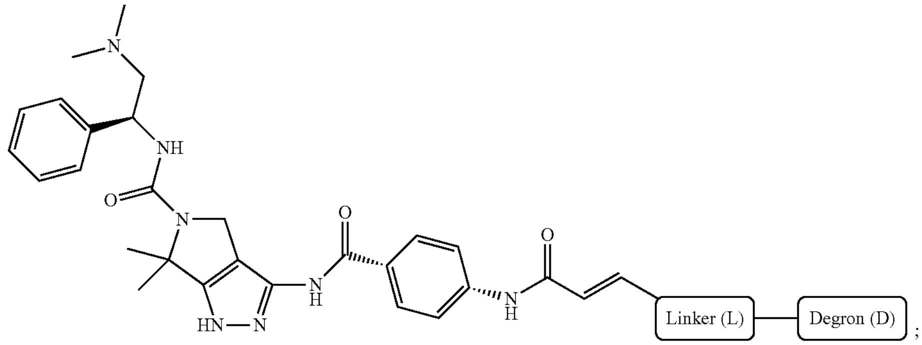
;
(I-39)
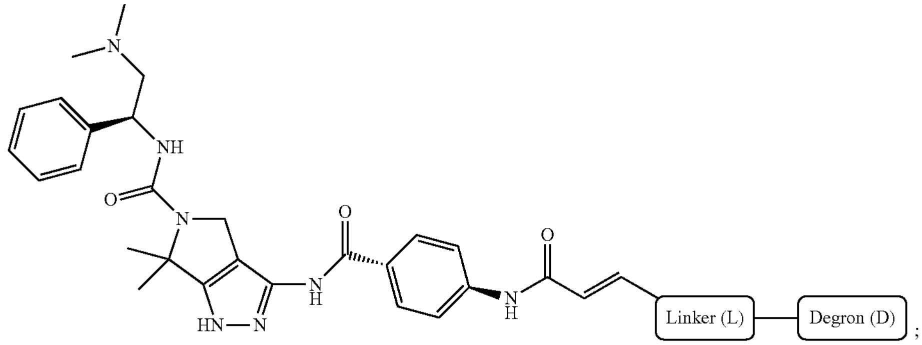
;
(I- 40)
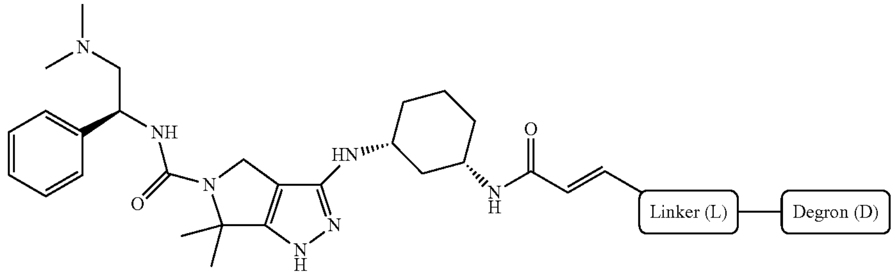
;
(I-41)
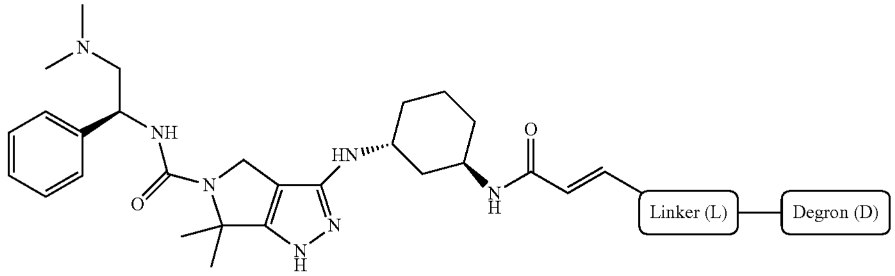
;
(I-42)
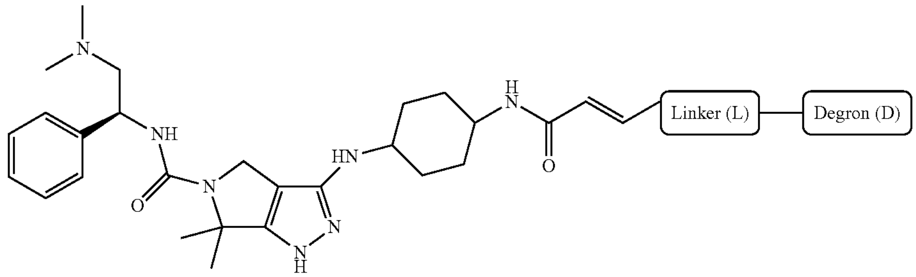
;

-continued
(I-43)
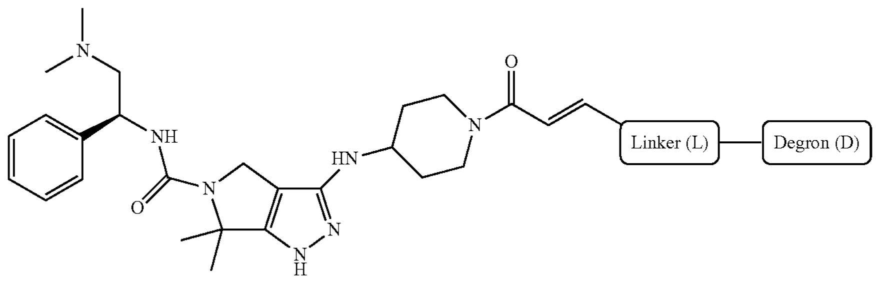
;
(I-44)
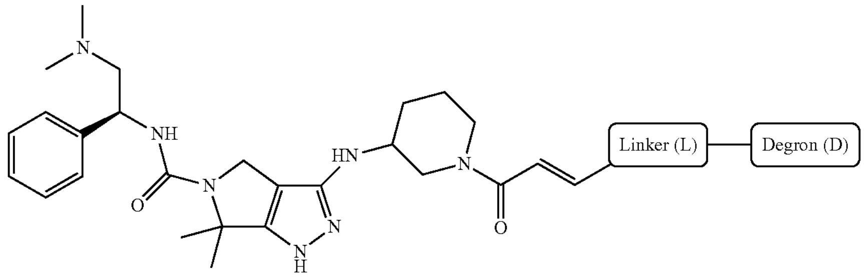
;
(I-45)
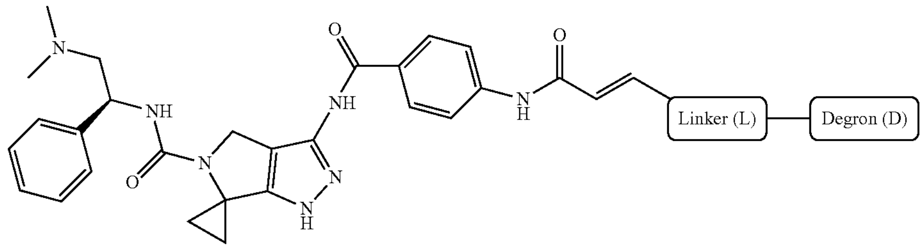
;
(I-46)
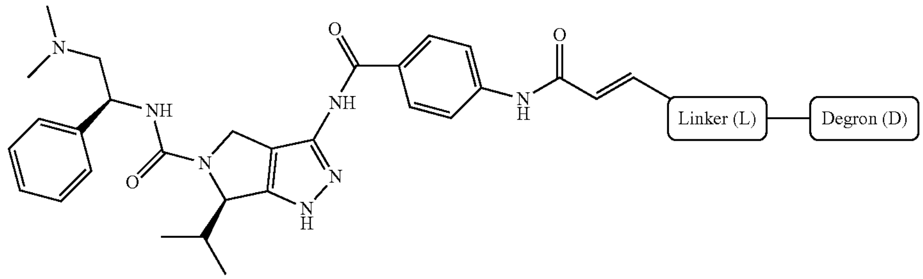
;
(I-47)
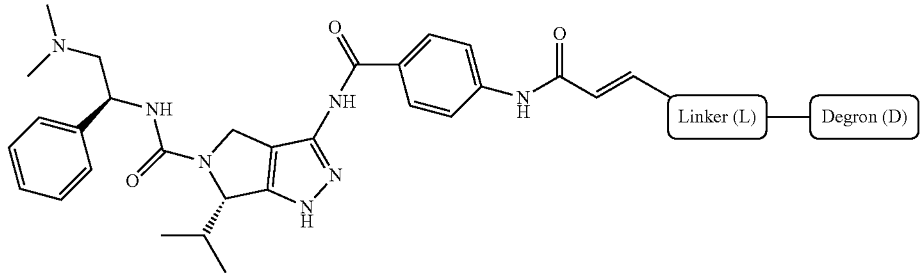
;

-continued
(I-48)
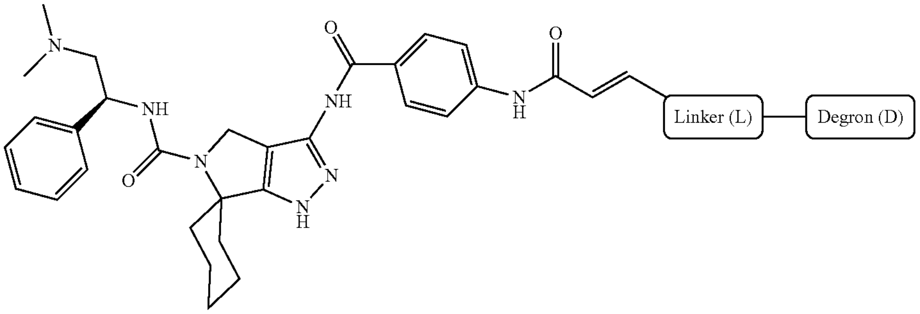
;
(I-49)
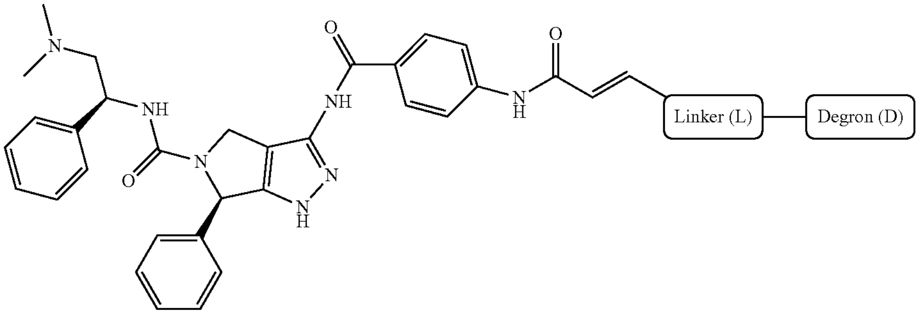
;
(I-50)
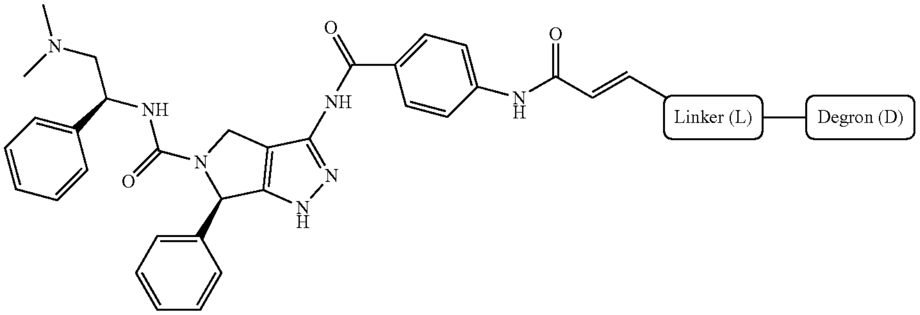
;
(I-51)
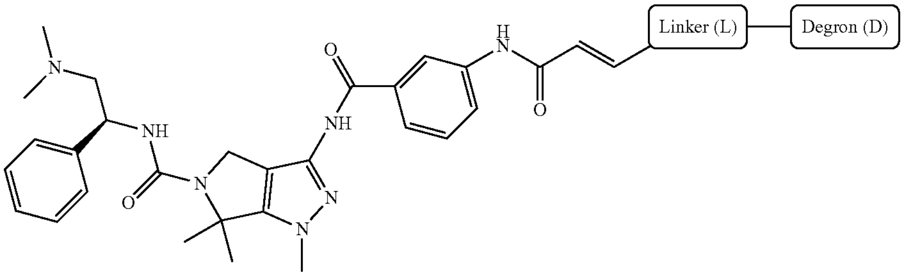
;
(I-52)
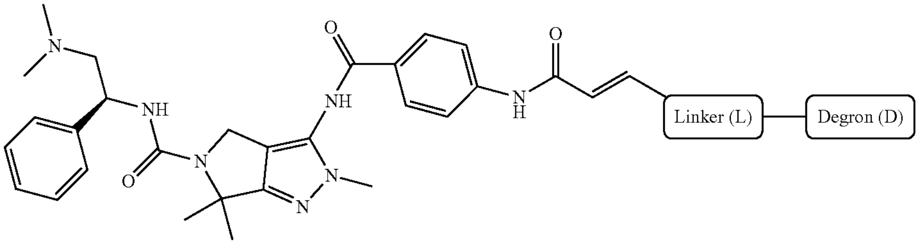
;

-continued
(I-53)
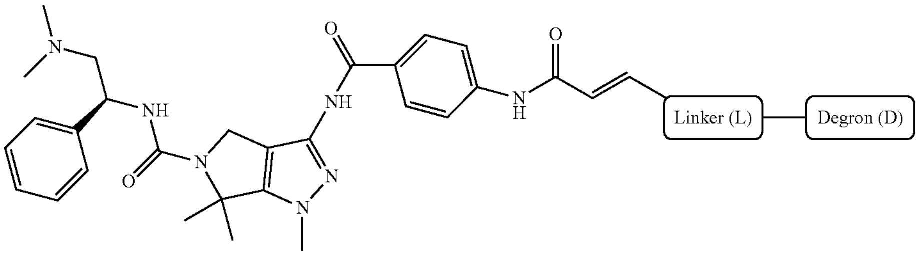
;
(I-54)
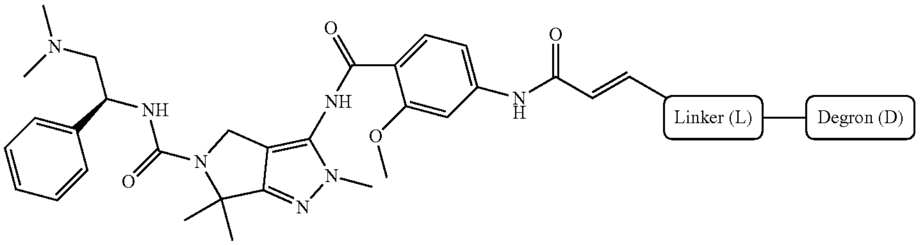
;
(I-55)
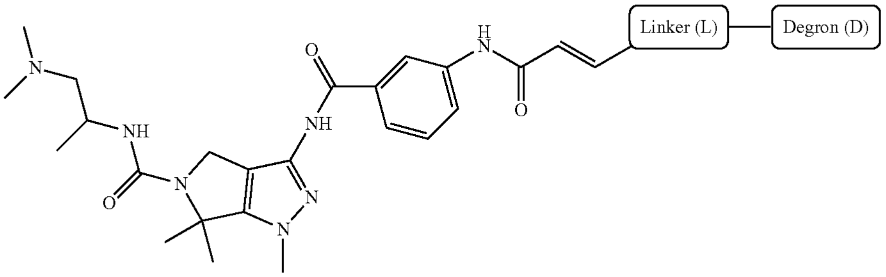
;
(I-56)
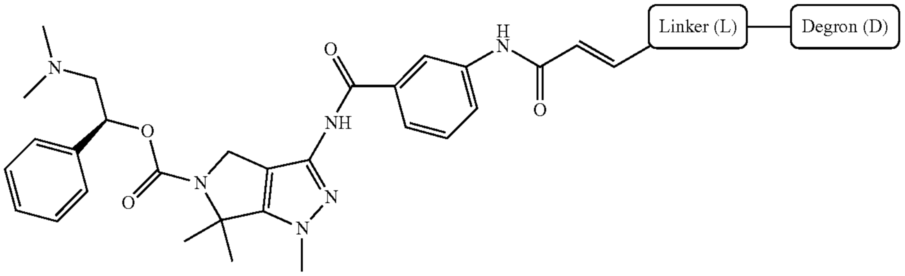
; and
(I-57)
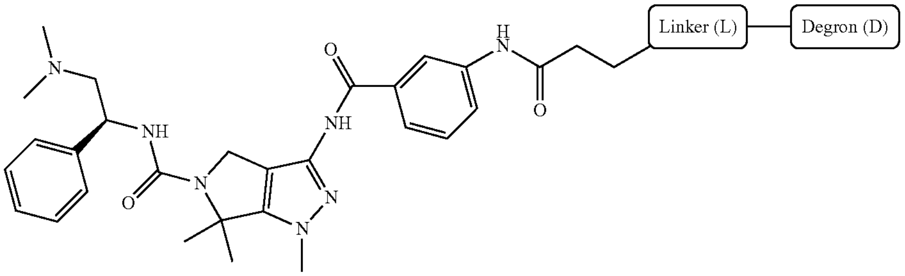
, or a pharmaceutically acceptable salt or stereoisomer thereof.

In some embodiments, wherein $L_1$ is —NHC(O)—, A is a 6-membered carbocyclyl, each of B, $L_2$, and $R_2$ is a bond (or absent), $R_1$ is

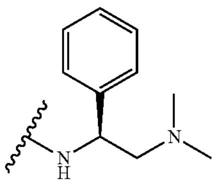 [SMILES: *N[C@H](CN(C)C)c1ccccc1]

and both $R_3$ and $R_4$ are methyl, the compounds of formula (I) have a structure represented by formula (I-58):

(I-58)

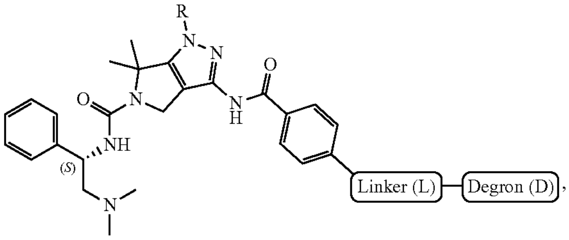

or a pharmaceutically acceptable salt or stereoisomer thereof.

Linkers

The linker ("L") provides a covalent attachment the targeting ligand and the degron. The structure of linker may not be critical, provided it does not substantially interfere with the activity of the targeting ligand or the degron. In some embodiments, the linker includes an alkylene chain (e.g., having 2-20 alkylene units). In other embodiments, the linker may include an alkylene chain or a bivalent alkylene chain, either of which may be interrupted by, and/or terminate (at either or both termini) at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —$S(O)_2$—, —OS(O)—, —S(O)O—, —S(O)—, —$OS(O)_2$—, —$S(O)_2O$—, —N(R')$S(O)_2$—, —$S(O)_2N(R')$—, —N(R')S(O)—, —S(O)N(R')—, —N(R')$S(O)_2$N(R')—, —N(R')S(O)N(R')—, $C_3$-$C_{12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different.

In some embodiments, the linker may include a $C_1$-$C_{12}$ alkylene chain terminating in NH-group wherein the nitrogen is also bound to the degron.

In some embodiments, the linker includes an alkylene chain having 1-10 alkylene units and interrupted by or terminating in

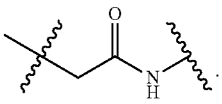 [SMILES: *CC(=O)N*]

"Carbocyclene" refers to a bivalent carbocycle radical, which is optionally substituted.

"Heterocyclene" refers to a bivalent heterocyclyl radical which may be optionally substituted.

"Heteroarylene" refers to a bivalent heteroaryl radical which may be optionally substituted.

Representative examples of alkylene linkers that may be suitable for use in the present invention include the following:

(L1)

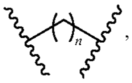, wherein n is an integer of 1-12 ("of" meaning inclusive), e.g., 1-12, 1-11, 1-10, 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10 and 1, 2, 3, 4, 5, 6, 7, 8, 9 and 10, examples of which include:

(L1-a)

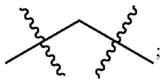;

(L1-b)

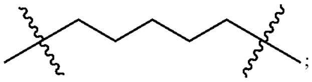;

(L1-c)

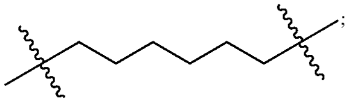;

(L1-d)

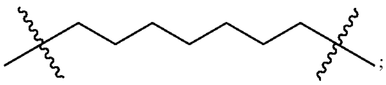; and (L1-e)

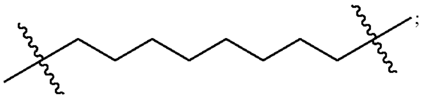;

alkylene chains terminating in various functional groups (as described above), examples of which are as follows:

(L2-a)

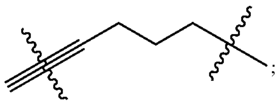;

-continued (L2-b)

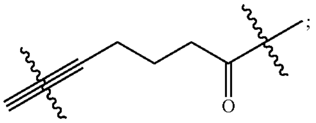

(L2-c)

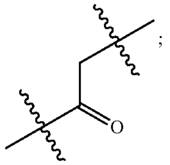

(L2-d)

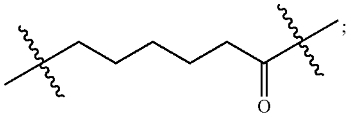

(L2-e)

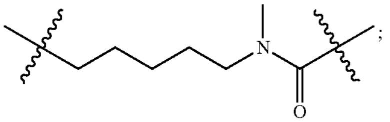

(L2-f)

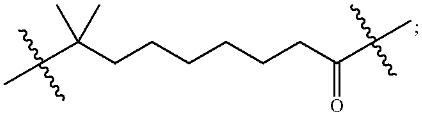

and (L2-g)

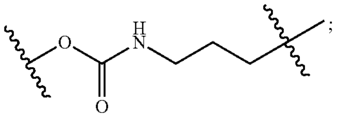

alkylene chains interrupted with various functional groups (as described above), examples of which are as follows:

(L3-a)

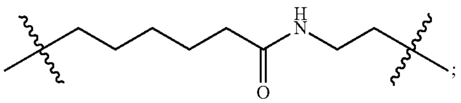

(L3-b)

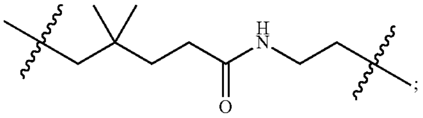

(L3-c)

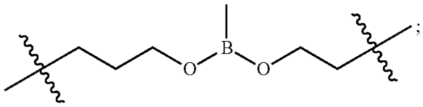

and (L3-d)

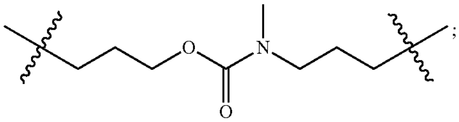

alkylene chains interrupted or terminating with heterocyclene groups, e.g., (L4)

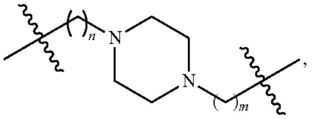

wherein m and n are independently integers of 0-10, examples of which include:

(L4-a)

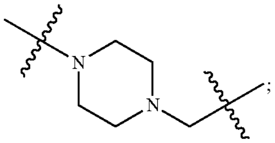

(L4-b)

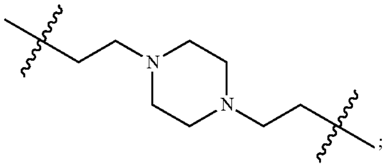

(L4-c)

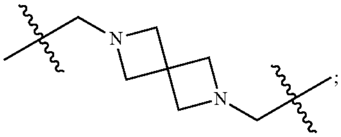

(L4-d)

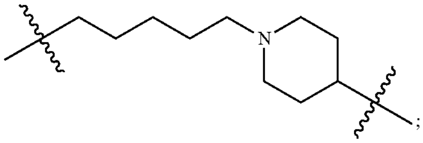

and (L4-e)

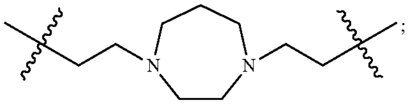

alkylene chains interrupted by amide, heterocyclene and/or aryl groups, examples of which include:

(L5-a)

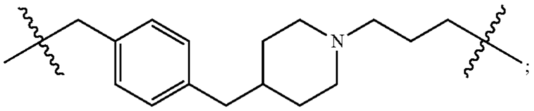

and (L5-b)

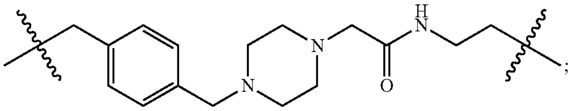

alkylene chains interrupted by heterocyclene and aryl groups, and a heteroatom, examples of which include:

(L6-a)

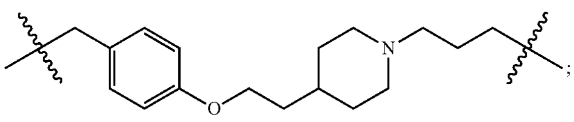

(L6-b)

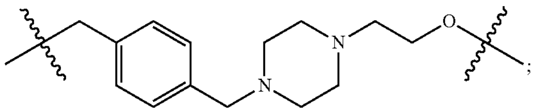

(L6-c)

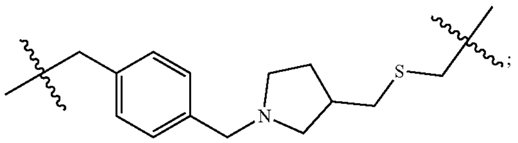

and alkylene chains interrupted by a heteroatom such as N, O or B, e.g., (L7)

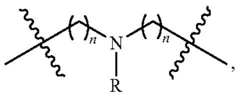

wherein each n is independently an integer of 1-10, e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10, and 1, 2, 3, 4, 5, 6, 7, 8, 9 and 10, and R is H or C1 to C4 alkyl, an example of which is (L7-a)

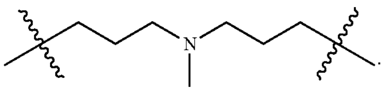

In some embodiments, the linker may include a polyethylene glycol chain which may terminate (at either or both termini) in at least one of —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, $—S(O)_2—$, —OS(O)—, —S(O)O—, —S(O)—, $—OS(O)_2—$, $—S(O)_2O—$, $—N(R')S(O)_2—$, $—S(O)_2N(R')—$, —N(R')S(O)—, —S(O)N(R')—, $—N(R')S(O)_2N(R')—$, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the one or both terminating groups may be the same or different.

In some embodiments, the linker includes a polyethylene glycol chain having 2-8 PEG units and terminating in

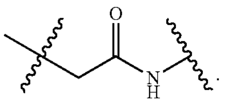 [SMILES: *CC(=O)N*]

Examples of linkers that include a polyethylene glycol chain include:

(L8)

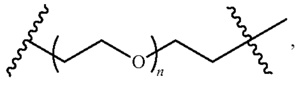

wherein n is an integer of 2-10, examples of which include:

(L8-a)

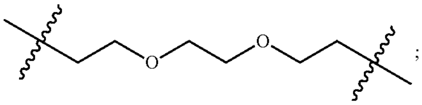

(L8-b)

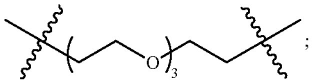

(L8-c)

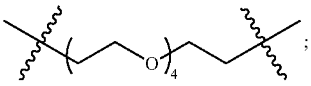

and (L8-d)

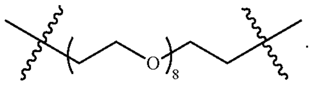

In some embodiments, the polyethylene glycol linker may terminate in a functional group, examples of which are as follows:

(L9-a)

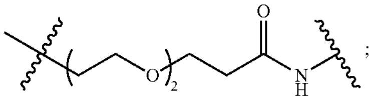

(L9-b)

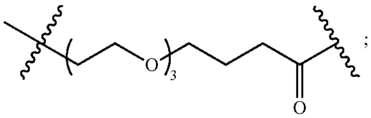

-continued
(L9-c)
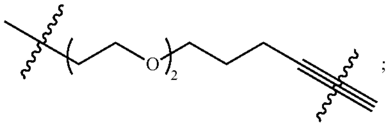
;
(L9-d)
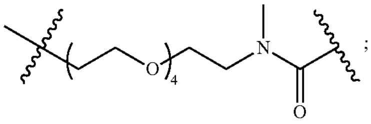
; and
(L9-e)
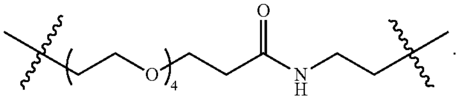
.
In some embodiments, the compounds of formula (I) include a linker that is represented by structure (L10):
(L10)
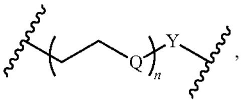
,
wherein Q is $CH_2$ or O;
Y is $CH_2$, $CH_2CH_2$, or absent, provided that when X is O, Y is $CH_2CH_2$;
and n is an integer from 0 and 6.
In some embodiments, the linker is represented by any one of structures L11-L23:
(L11)
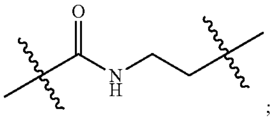
;
(L12)
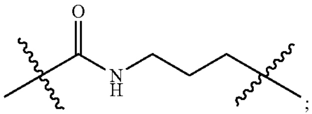
;
(L13)
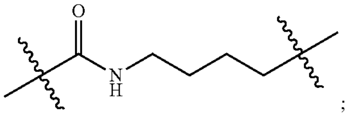
;
(L14)
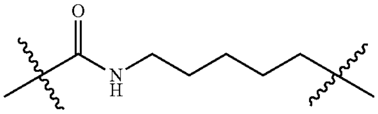
;
(L15)
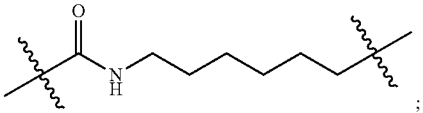
;
(L16)
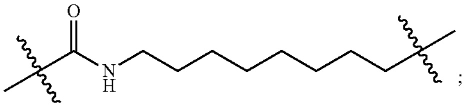
;
(L17)
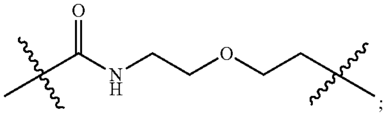
;
(L18)
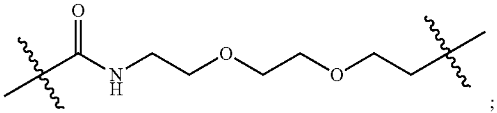
;
(L19)
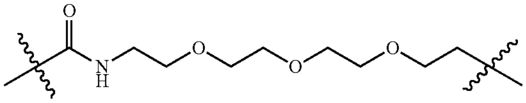
;
(L20)
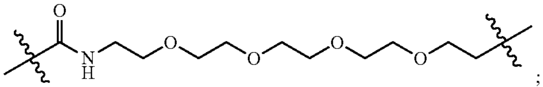
;
(L21)
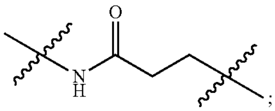
;
(L22)
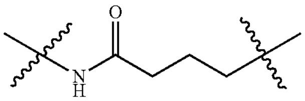
;
(L23)
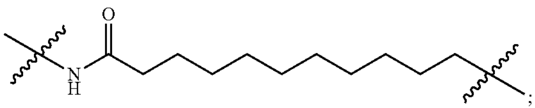
;
(L24)
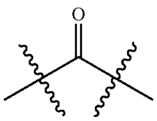
;

-continued
(L25)
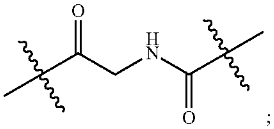
;
(L26)
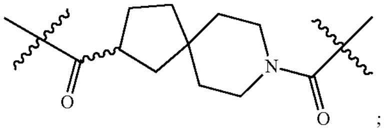
;
(L27)
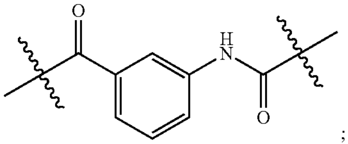
; and
(L28)
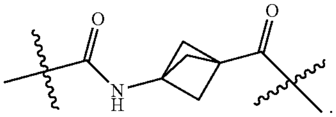
.
In some embodiments, the bispecific compounds of formula (I) have a structure represented by any one of formulas (I-59) to (I-71):
(I-59)
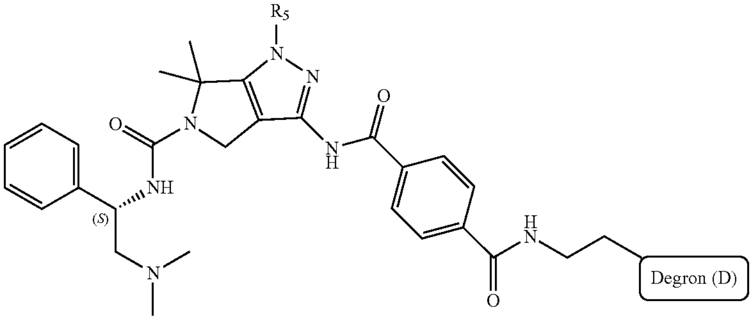
;
(I-60)
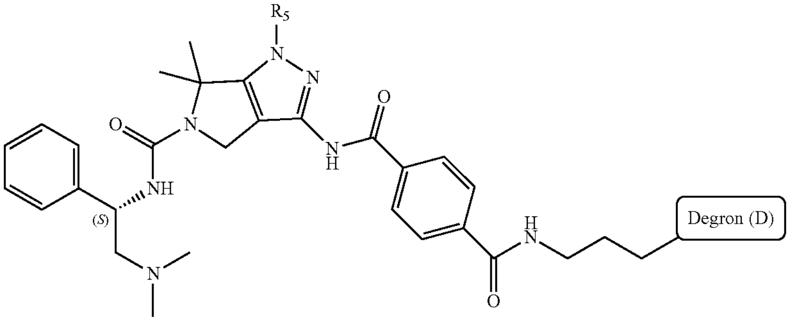
;
(I-61)
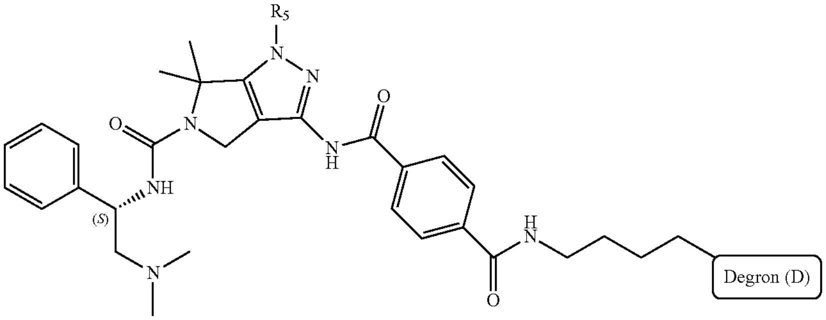
;

-continued
(I-62)
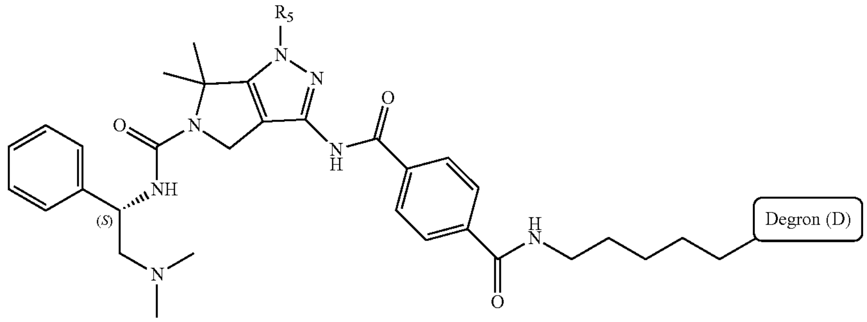
;
(I-63)
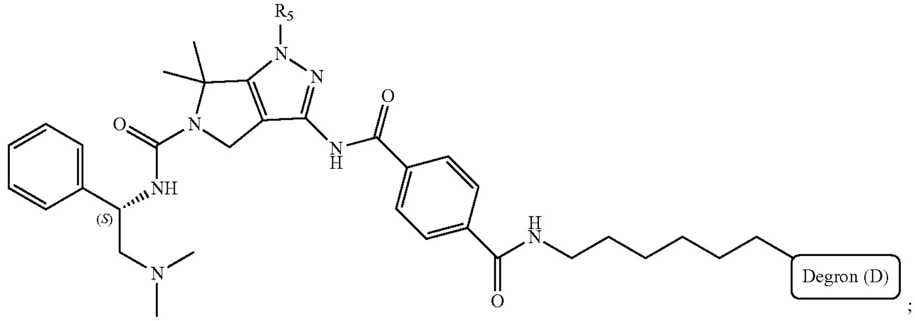
;
(I-64)
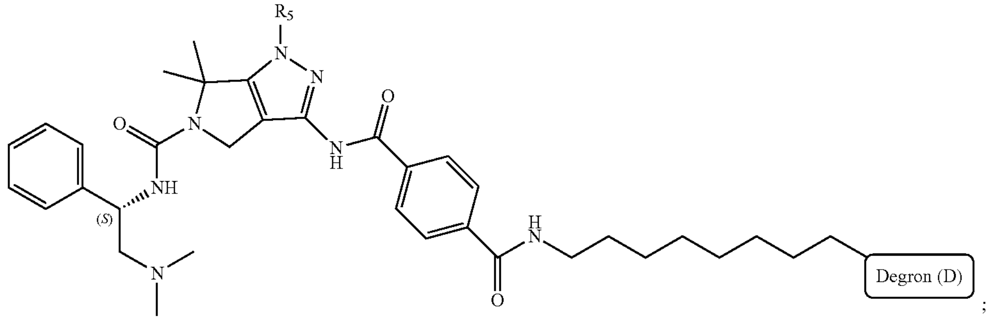
;
(I-65)
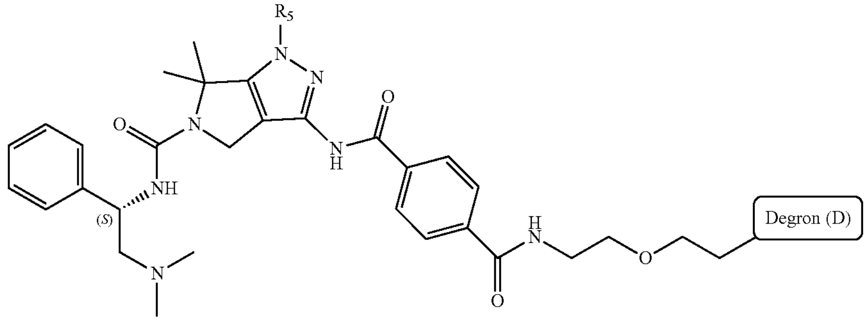
;
(I-66)
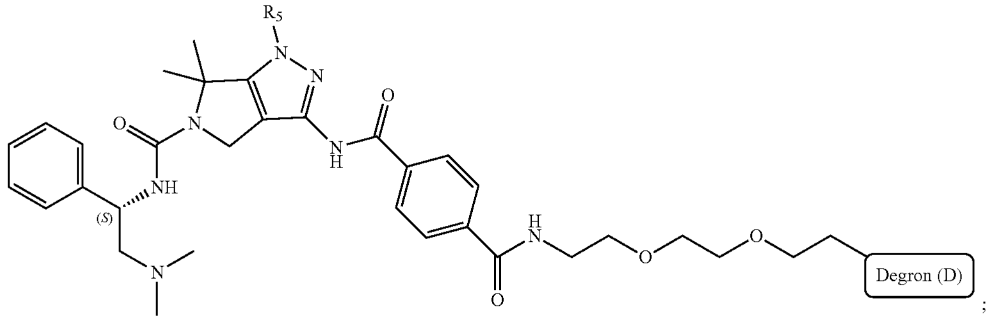
;

-continued
(I-67)
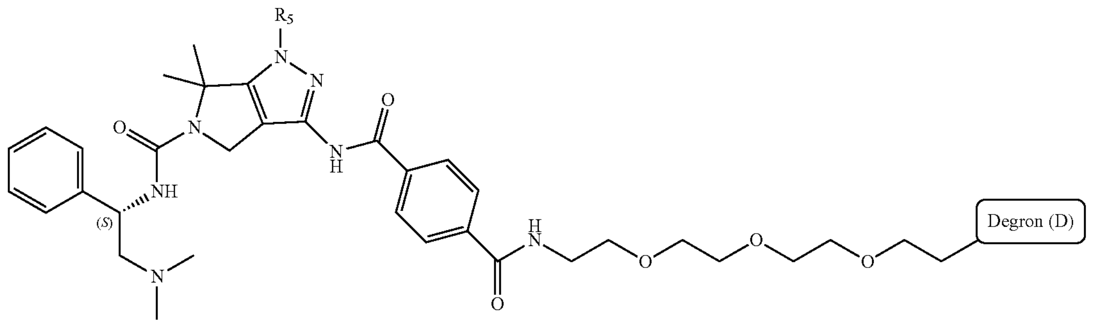
;
(I-68)
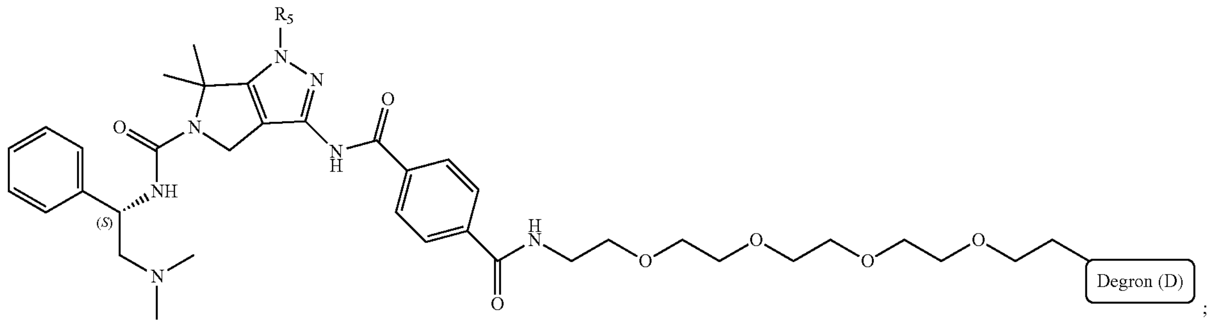
;
(I-69)
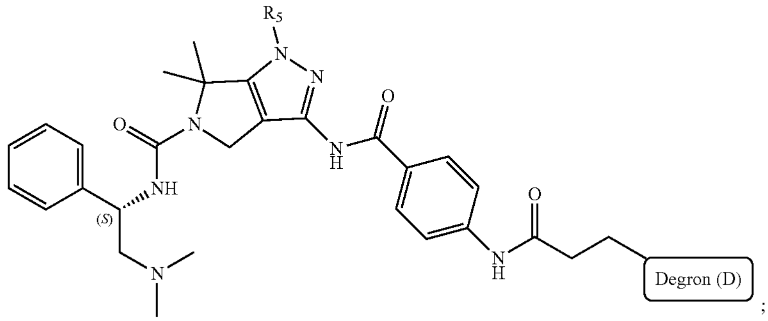
;
(I-70)
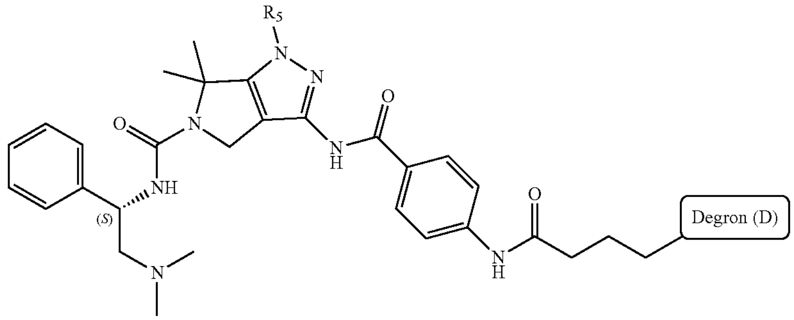
; and -continued (I-71)

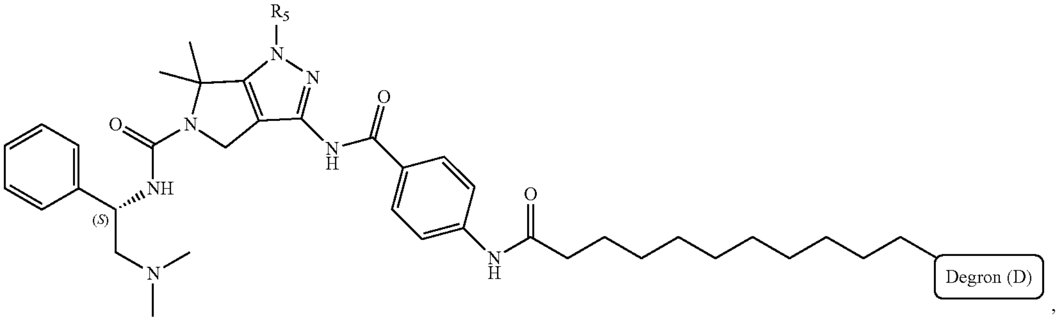

or a pharmaceutically acceptable salt or stereoisomer thereof.

Degrons

The degron ("D") is a functional moiety that binds an E3 ubiquitin ligase. In some embodiments, the Degron binds cereblon (CRBN).

Representative examples of degrons that bind cereblon and which may be suitable for use in the present invention are described in U.S. Patent Application Publication 2018/0015085 (e.g., the indolinones such as isoindolinones and isoindoline-1,3-diones embraced by formulas IA ad IA' therein, and the bridged cycloalkyl compounds embraced by formulas IB and IB' therein).

In some embodiments, the compounds of formula (I) include a cereblon-binding degron that is represented by any one of structures (D1-a) to (D1-h):

(D1-a)

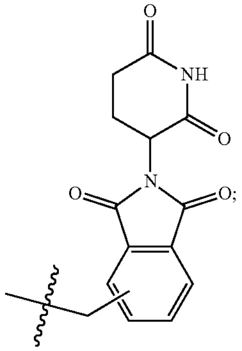

(D1-b)

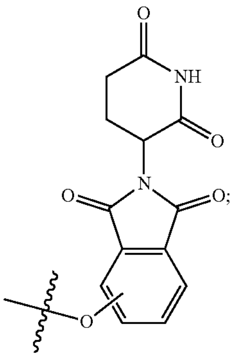

-continued (D1-c)

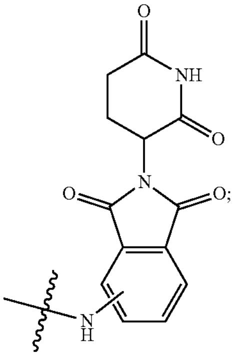

(D1-d)

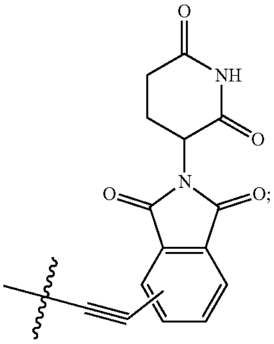

(D1-e)

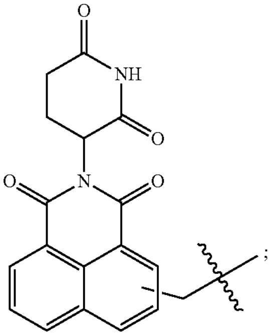

-continued
(D1-f)
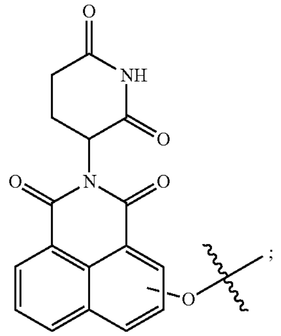
(D1-g)
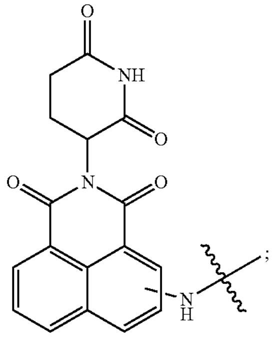
and
-continued
(D1-h)
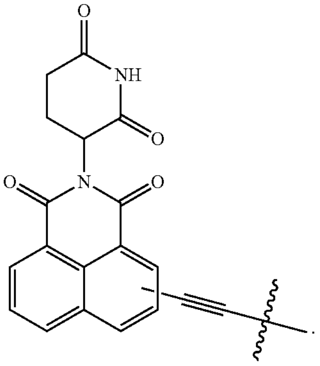
In some embodiments, the compounds of formula (I) have a structure represented by any one of formulas (I-72a) to (I-72h):
(I-72a)
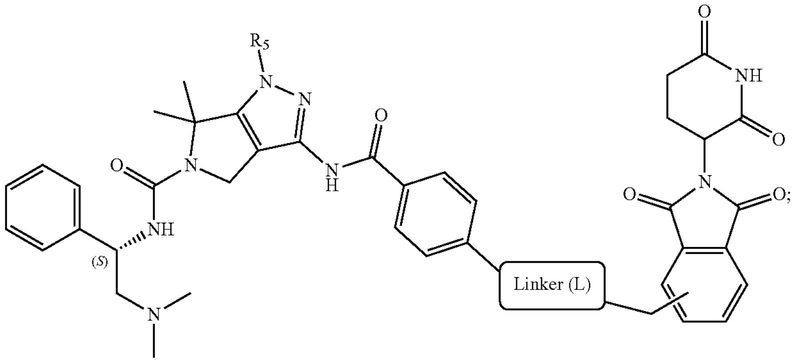
(I-72b)
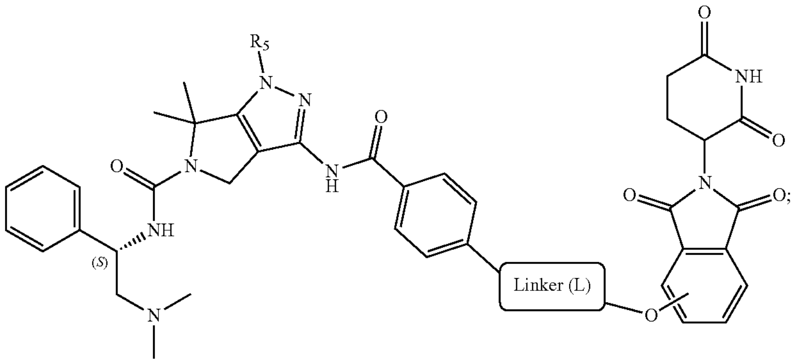

-continued
(I-72c)
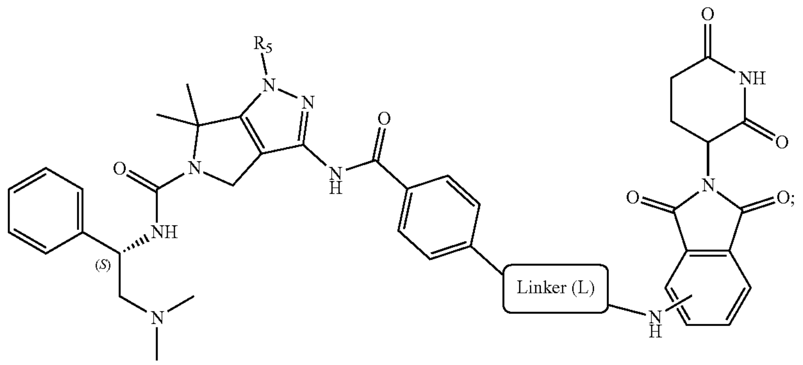
(I-72d)
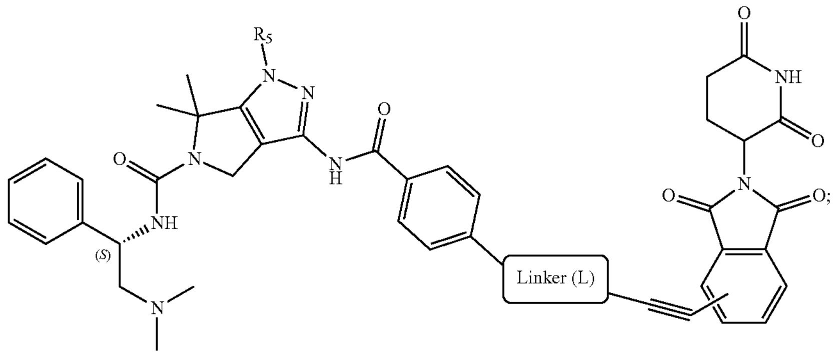
(I-72e)
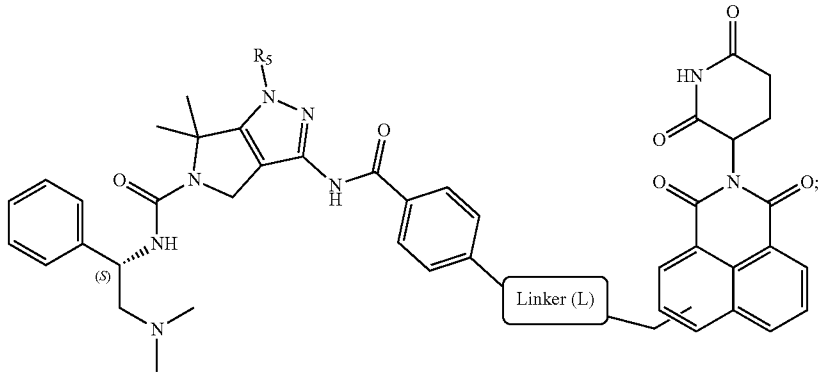
(I-72f)
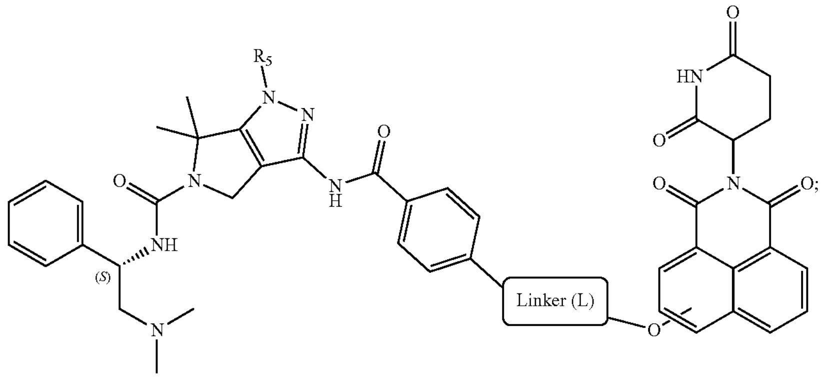

-continued
(I-72g)
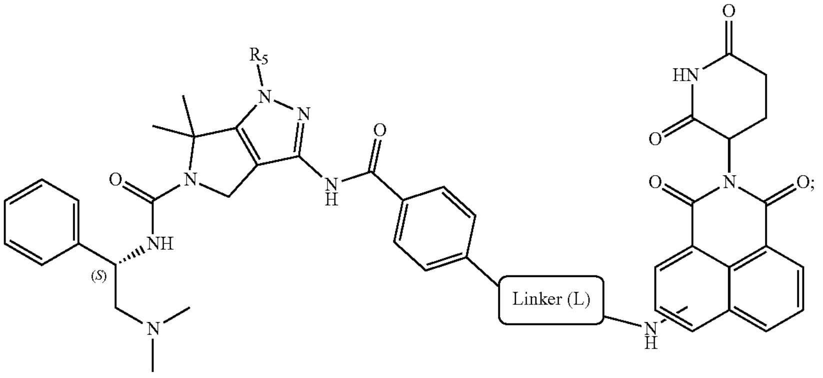
and
(I-72h)
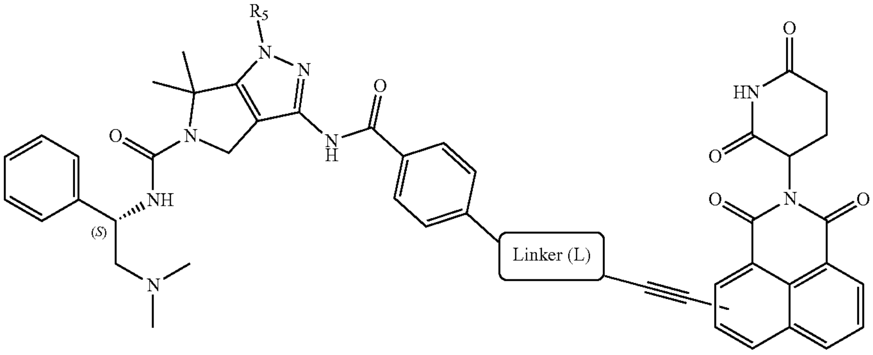
or a pharmaceutically acceptable salt or stereoisomer thereof.
In some embodiments, the degron binds a Von Hippel-Lindau (VHL) tumor suppressor. Representative examples of degrons that bind VHL are as follows:
(D2-a)
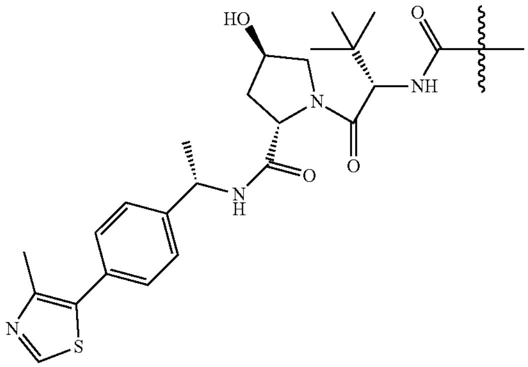
;
-continued
(D2-b)
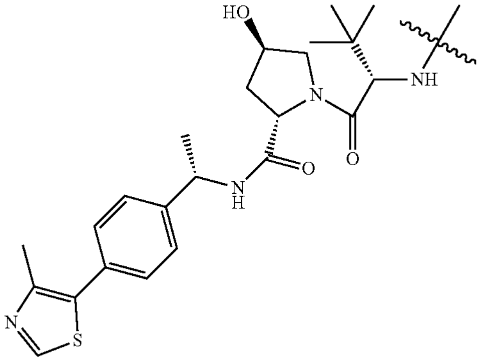
;

-continued (D2-c)

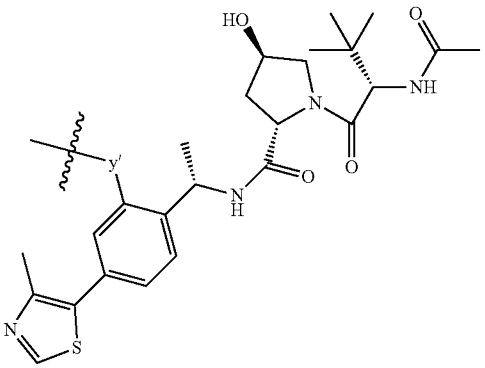

, wherein Y' is a bond, N, O or C;

(D2-d)

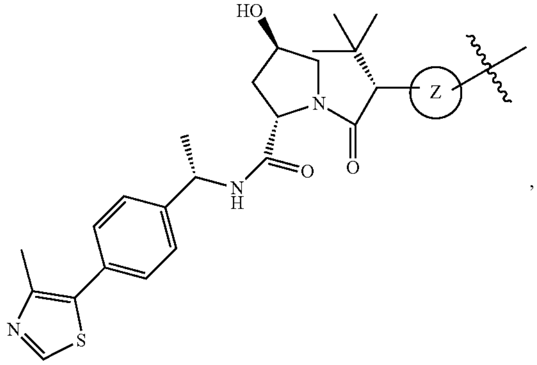

, wherein Z is a $C_5$-$C_6$ carbocyclic or $C_5$-$C_6$ heterocyclic group, and (D2-e)

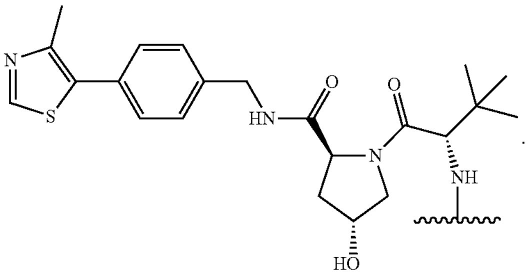

.

In some embodiments, Z is

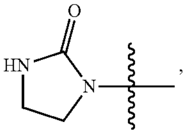
,
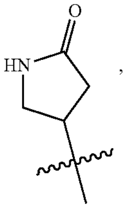
, or
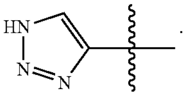
.

Yet other degrons that bind VHL and which may be suitable for use as degrons in the present invention are disclosed in U.S. Patent Application Publication 2017/0121321 A1.

In some embodiments, the compounds of formula (I) have a structure represented by any one of formulas (I-73a) to (I-73e):

(I-73a)

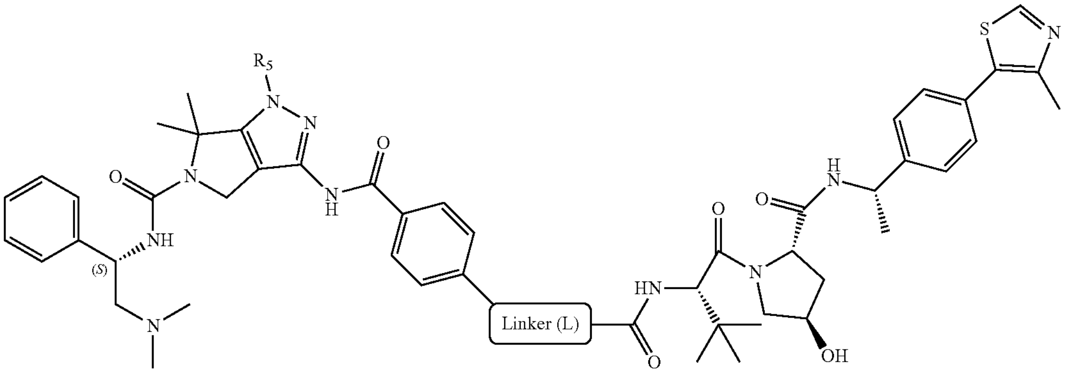

;

-continued
(I-73b)
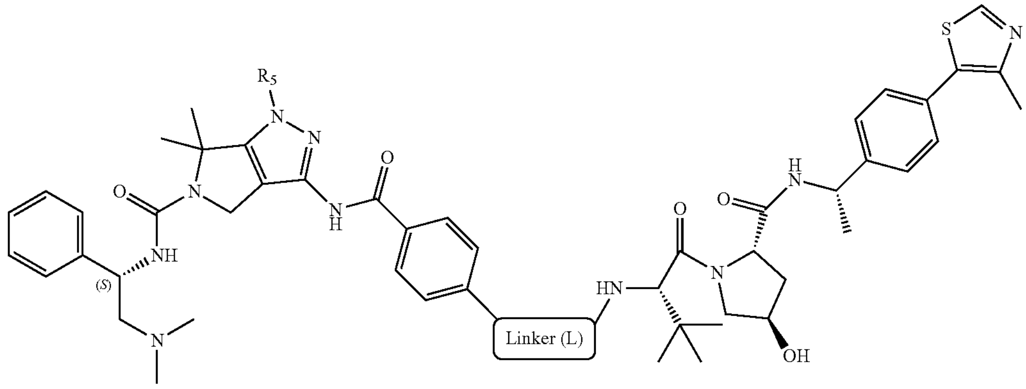
;
(I-73c)
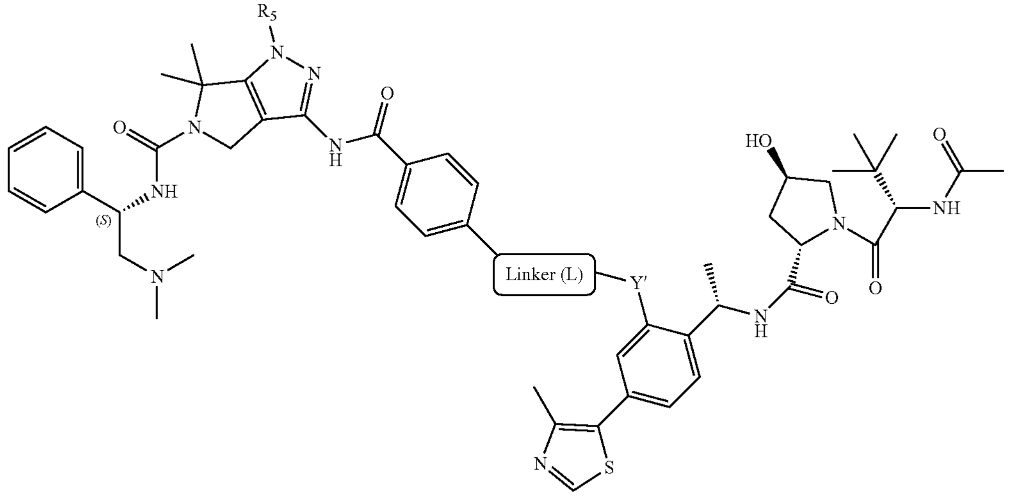
;
(I-73d)
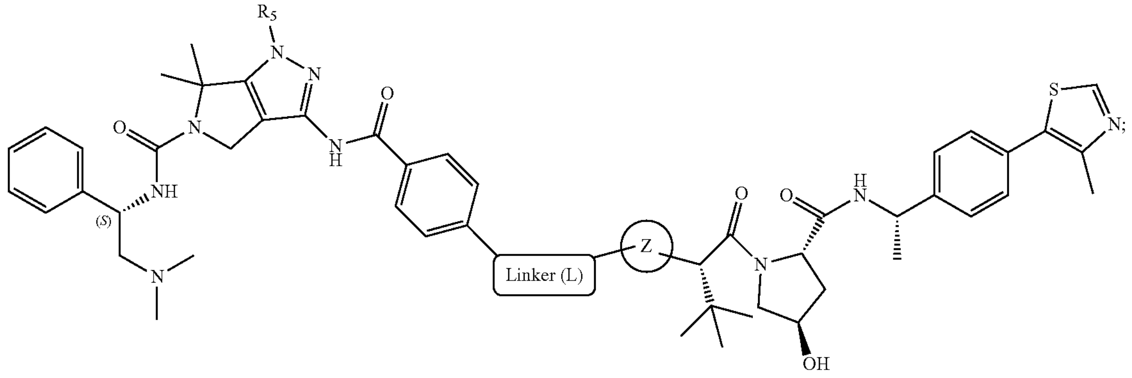
and
(I-73e)
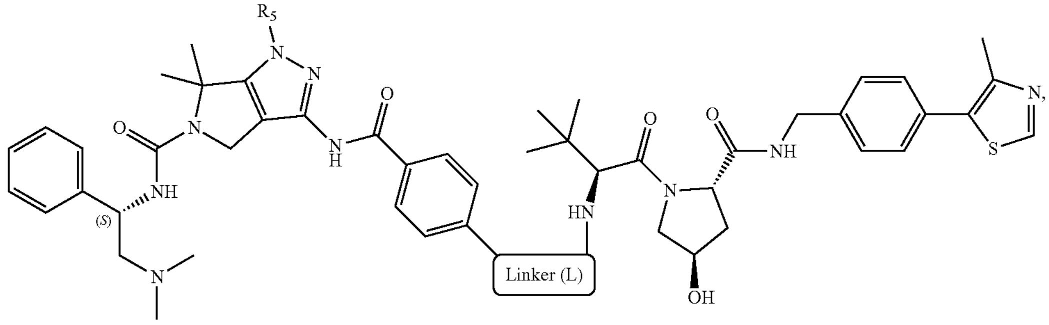

wherein R represents H, methyl, ethyl, isopropyl or $CF_3$, Y' is a bond, N, O or C; and Z is a C5-C6 carbocyclic or heterocyclic group; or a pharmaceutically acceptable salt or stereoisomer thereof
In some embodiments, the compound of formula (I) is represented by any one of structures (1) to (26):
(1)
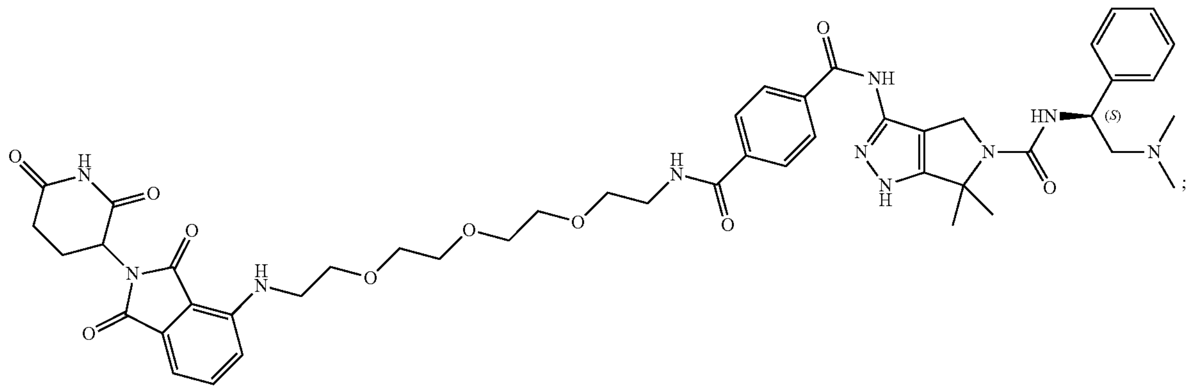
(2)
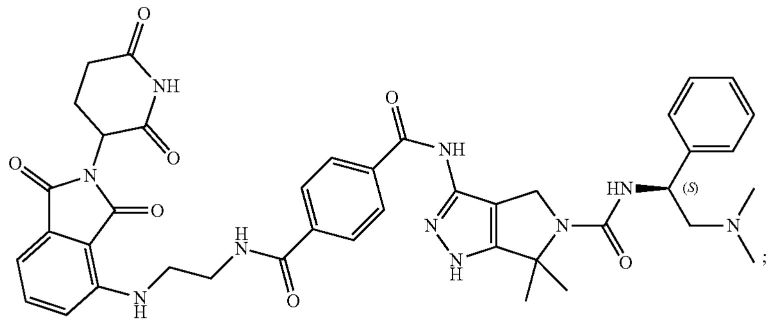
(3)
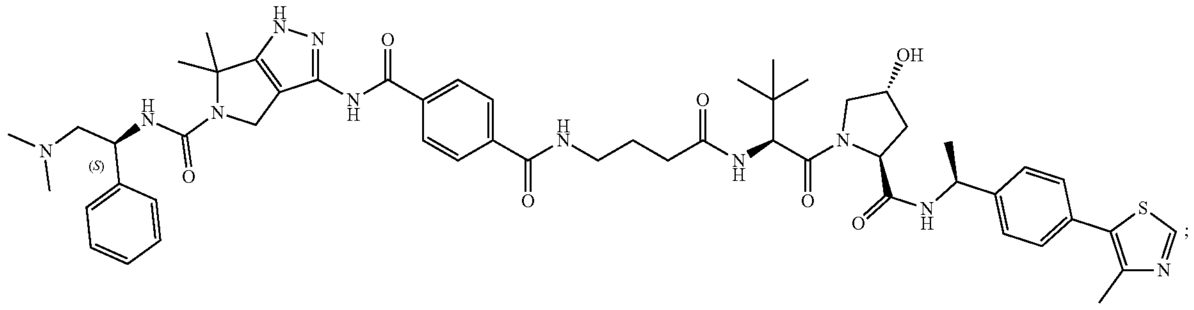
(4)
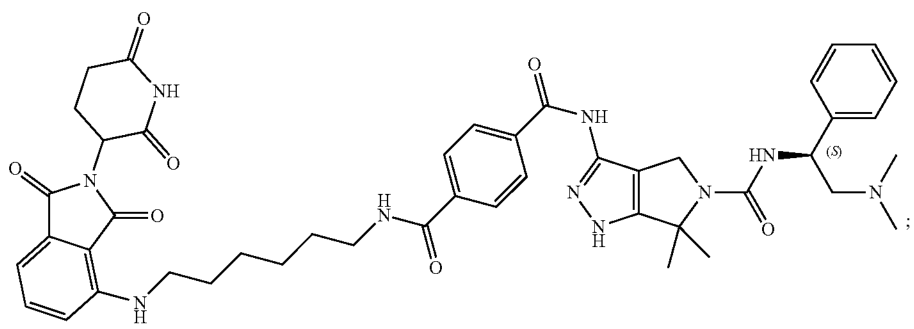

-continued
(5)
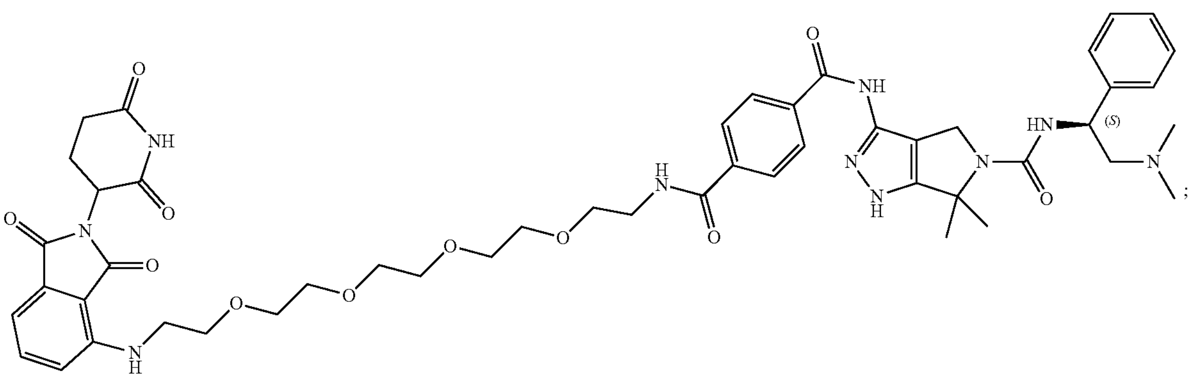
;
(6)
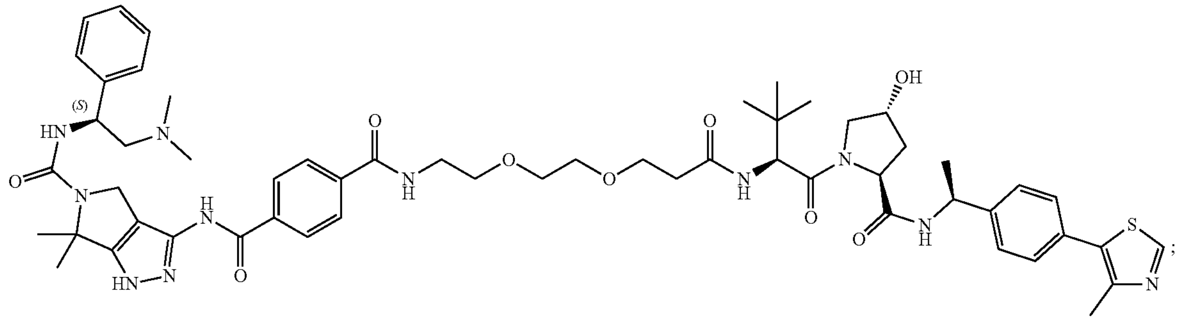
;
(7)
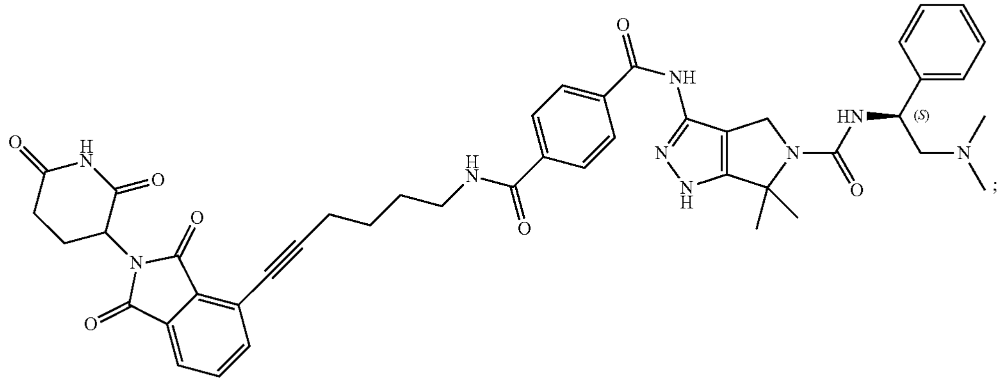
;
(8)
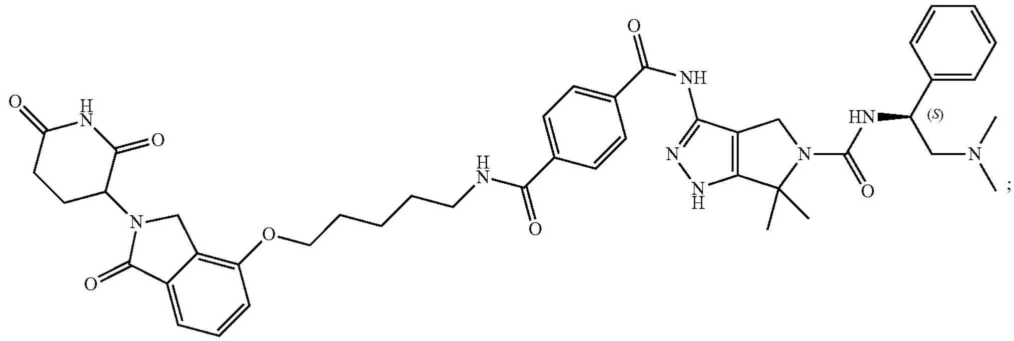
;

-continued
(9)
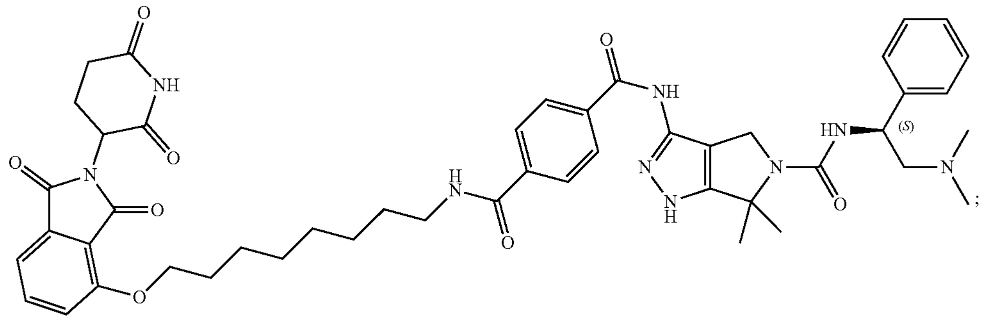
(10)
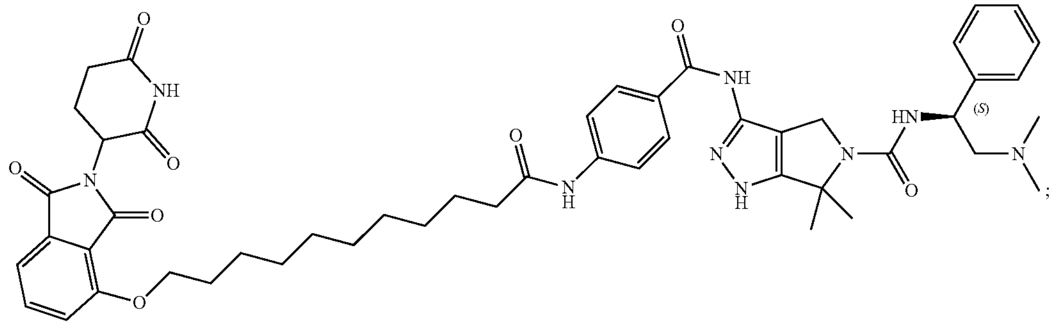
(11)
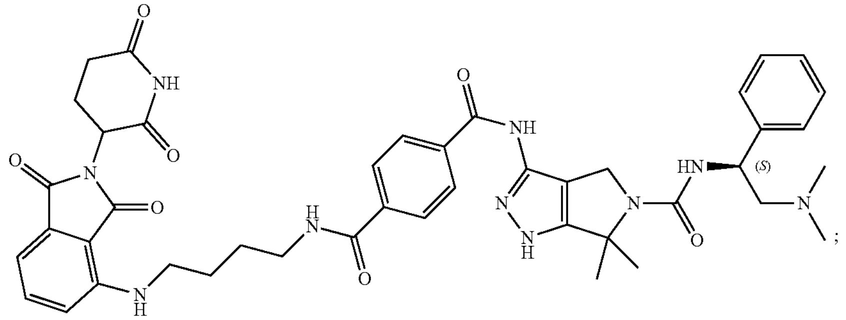
(12)
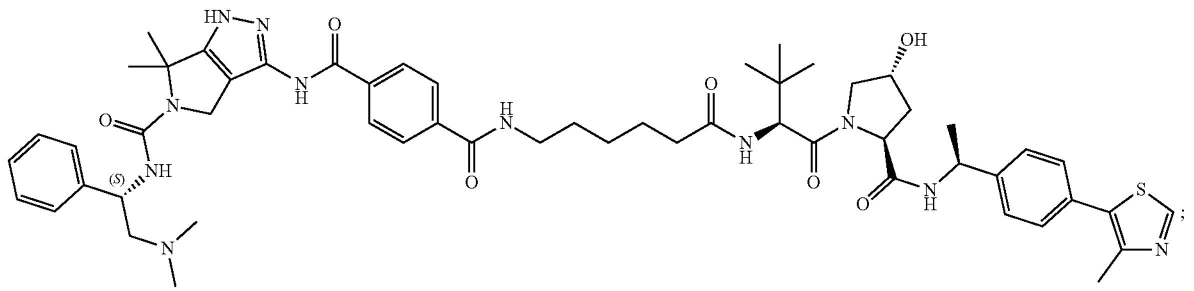
(13)
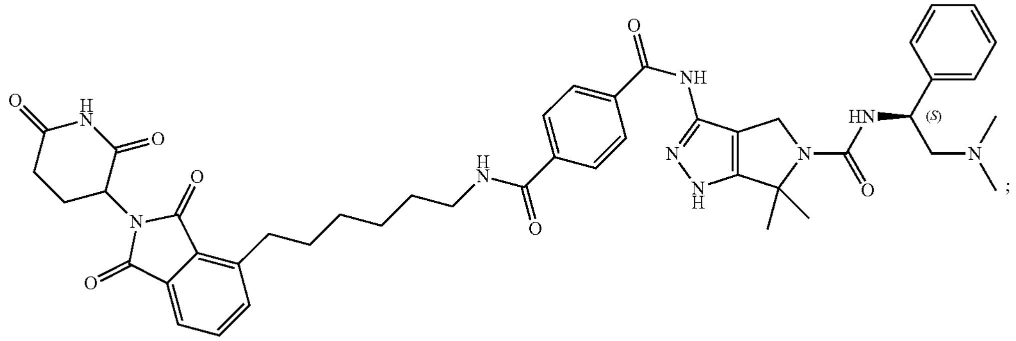

-continued
(14)
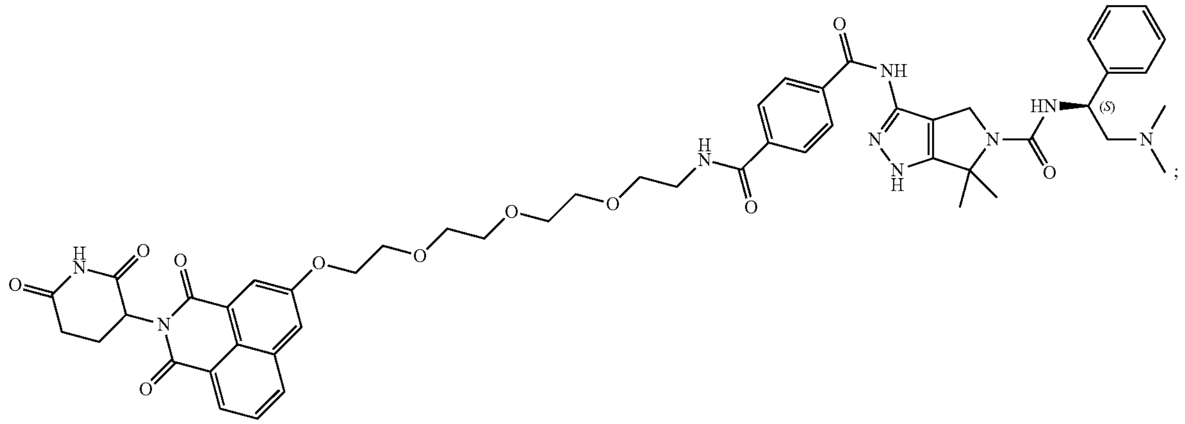
(15)
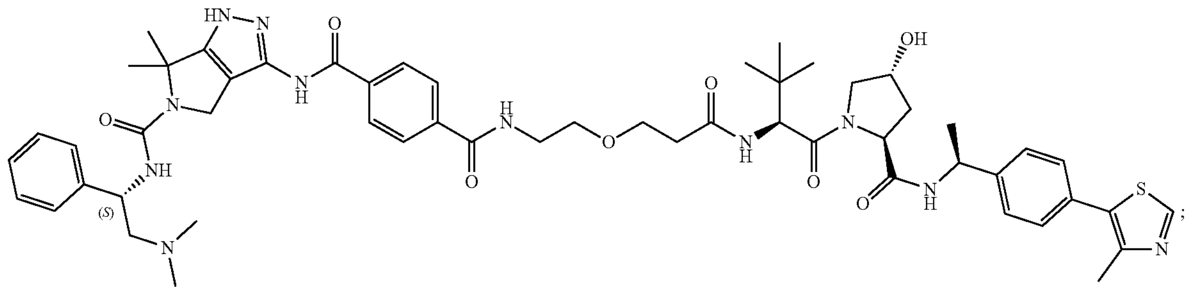
(16)
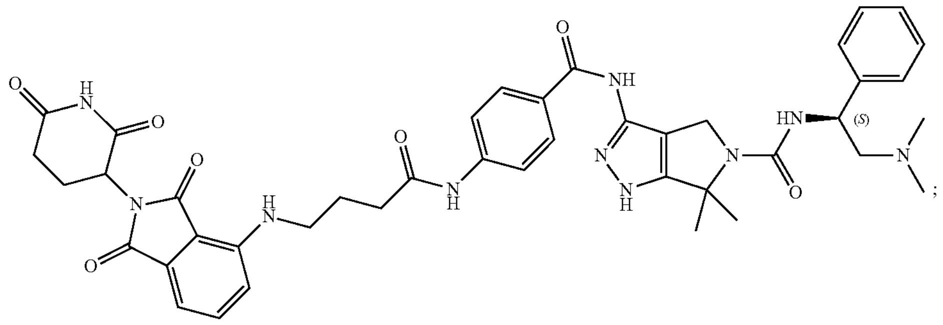
(17)
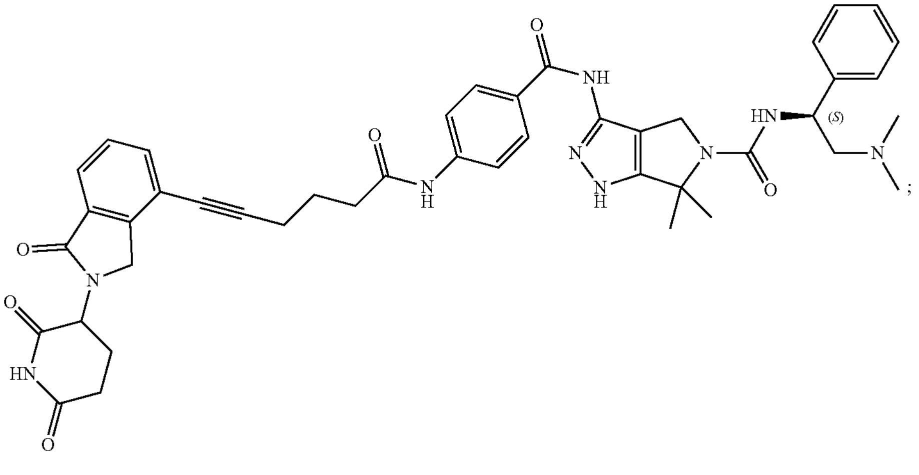

-continued
(18)
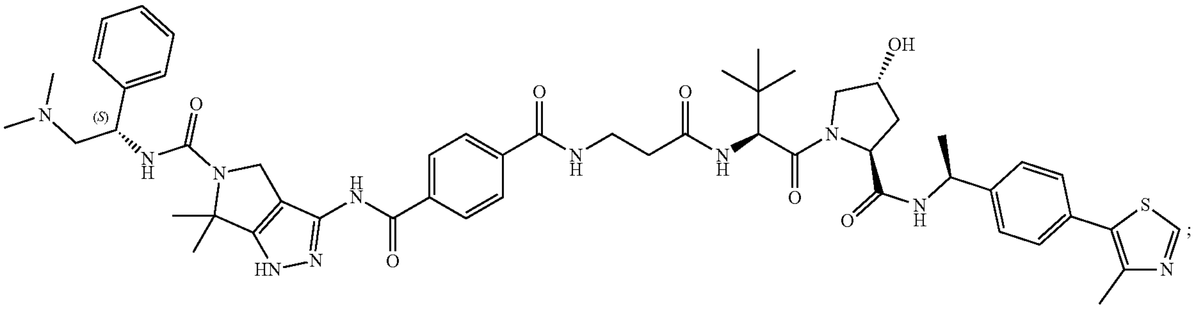
(19)
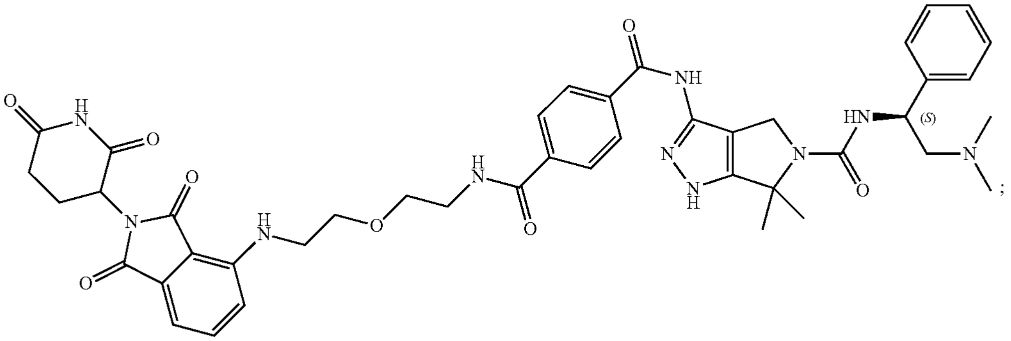
(20)
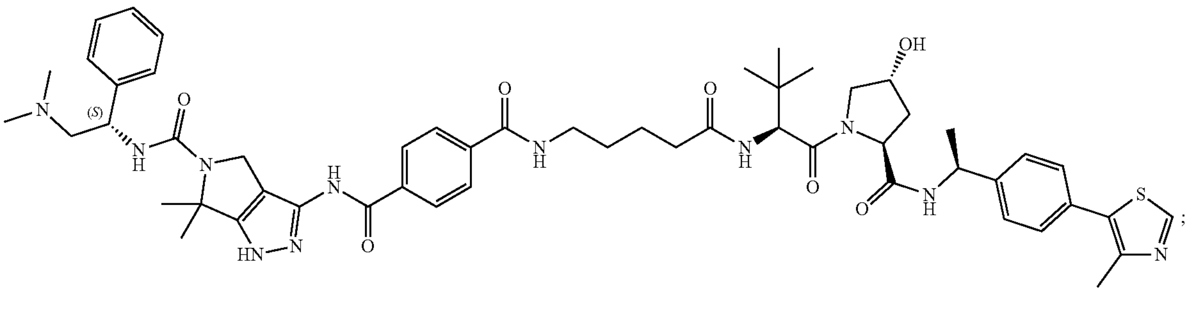
(21)
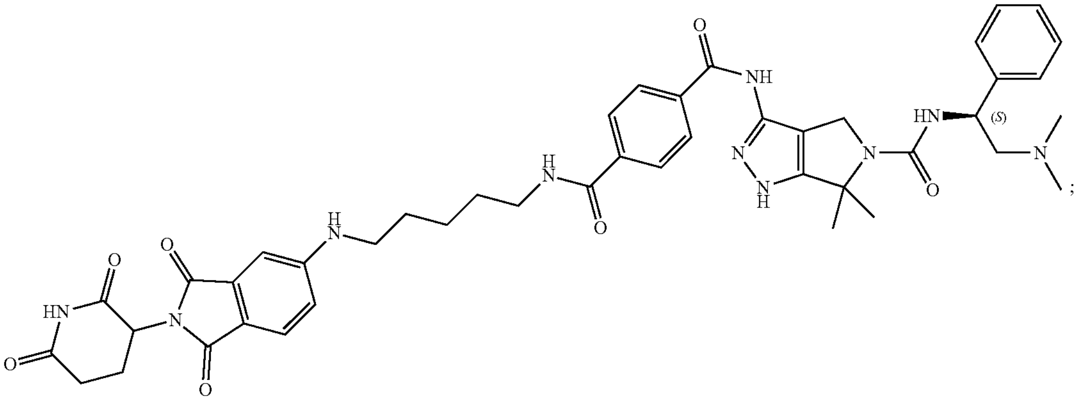

-continued
(22)
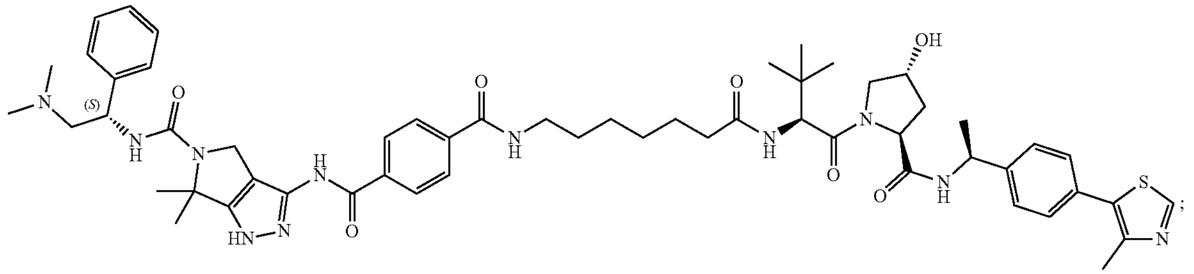
(23)
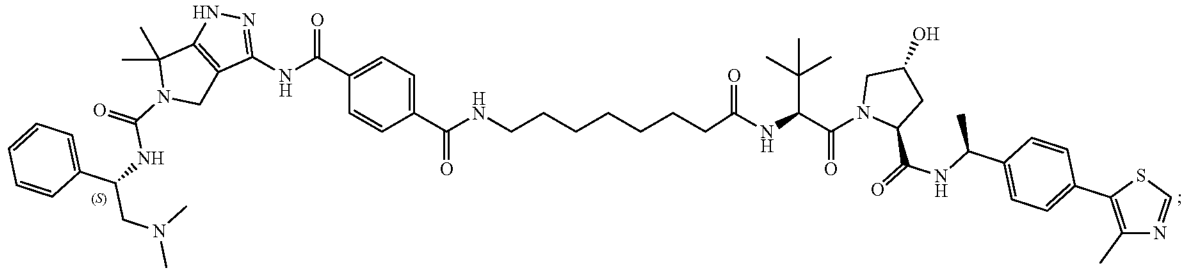
(24)
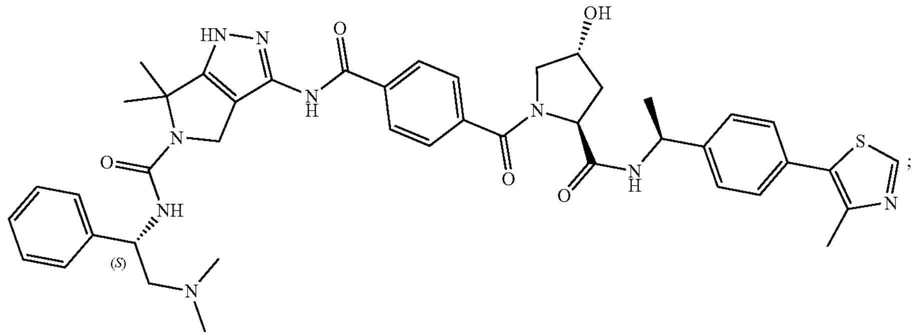
(25)
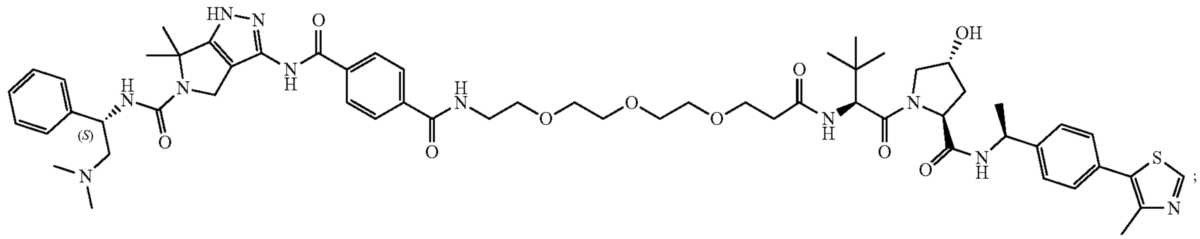
(26)
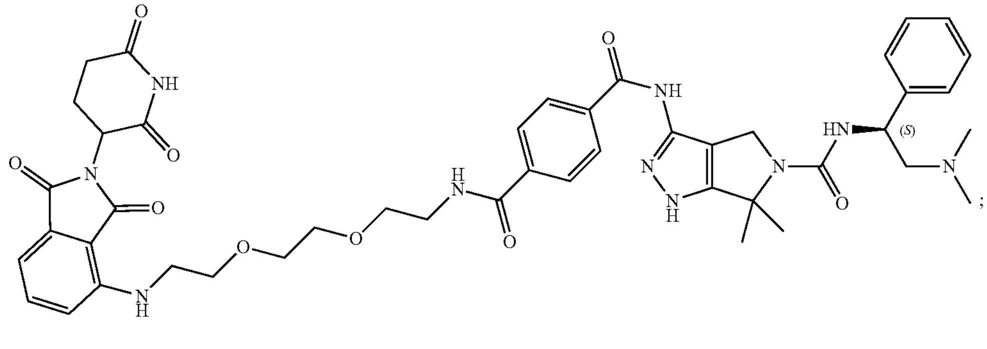

-continued
(27)
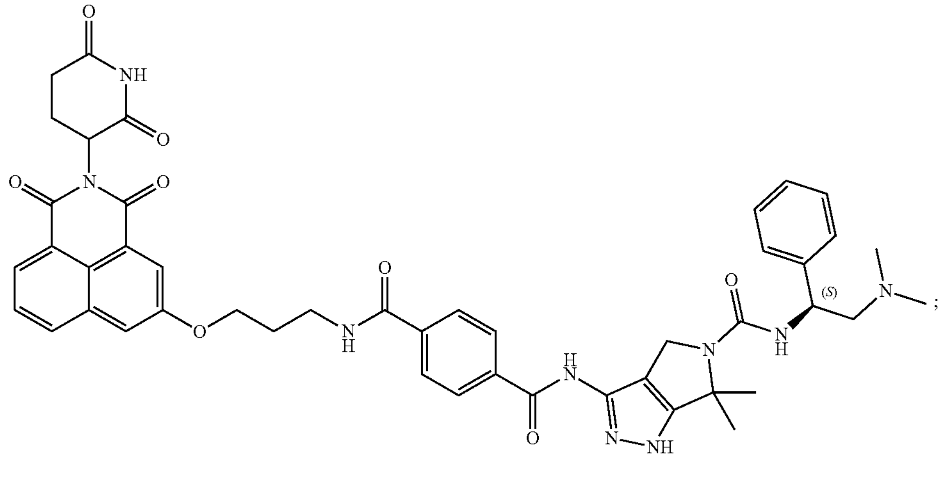
(28)
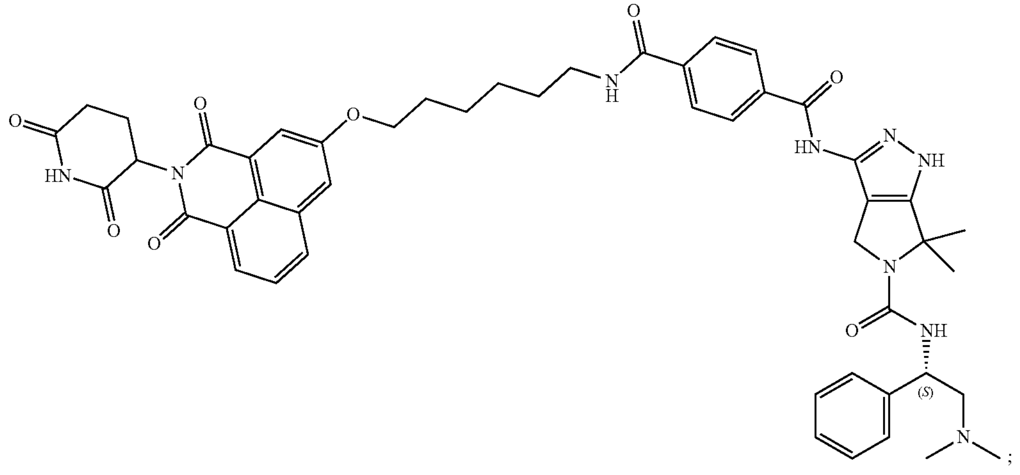
(29)
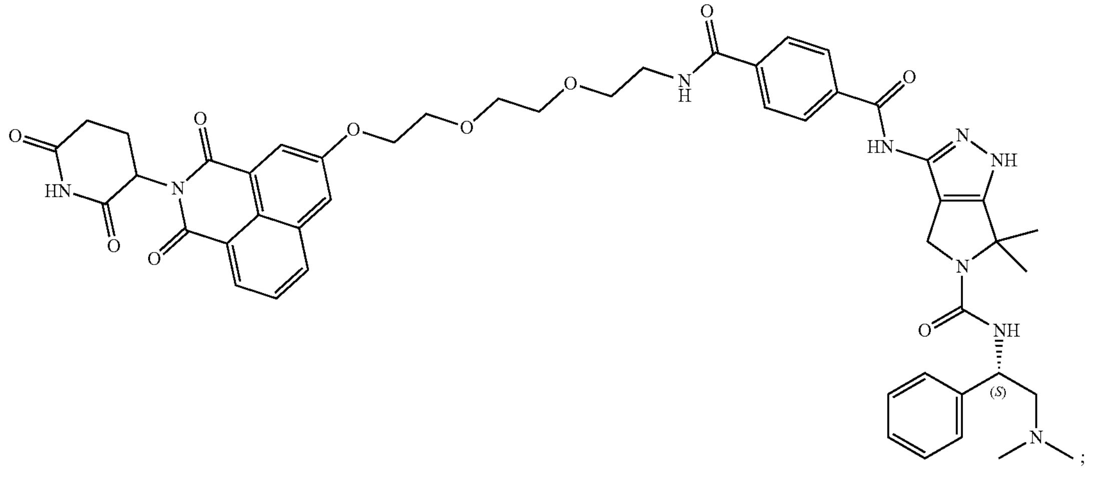

-continued
(30)
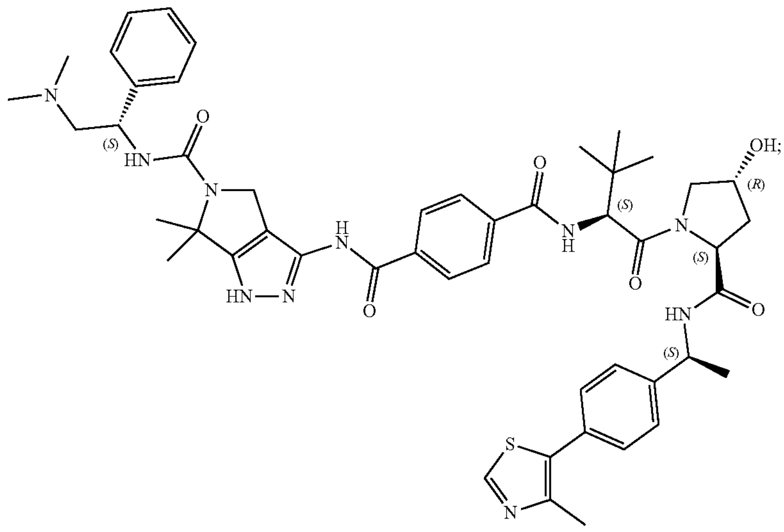
(31)
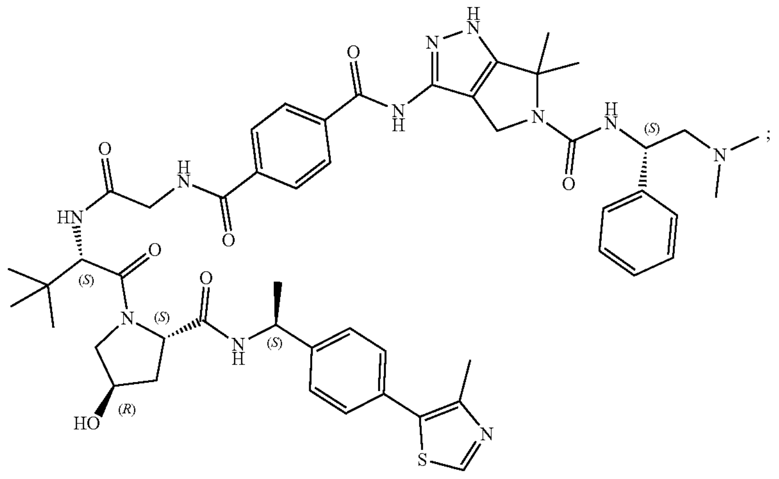
(32)
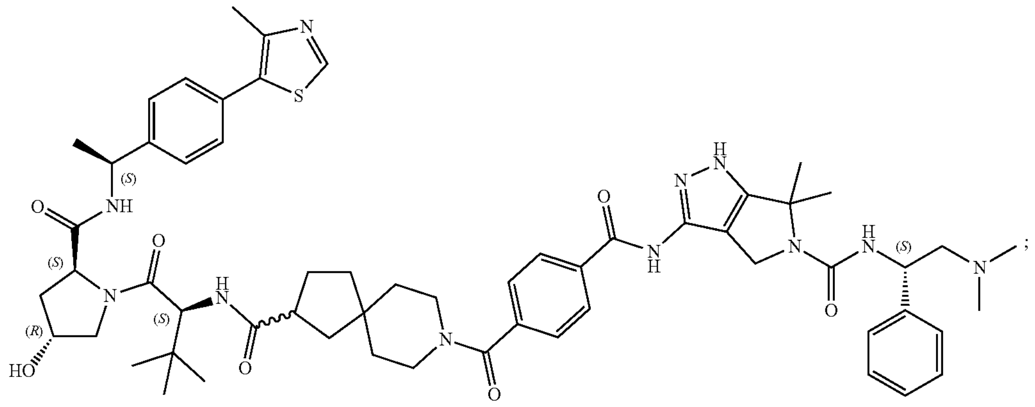

-continued (33)

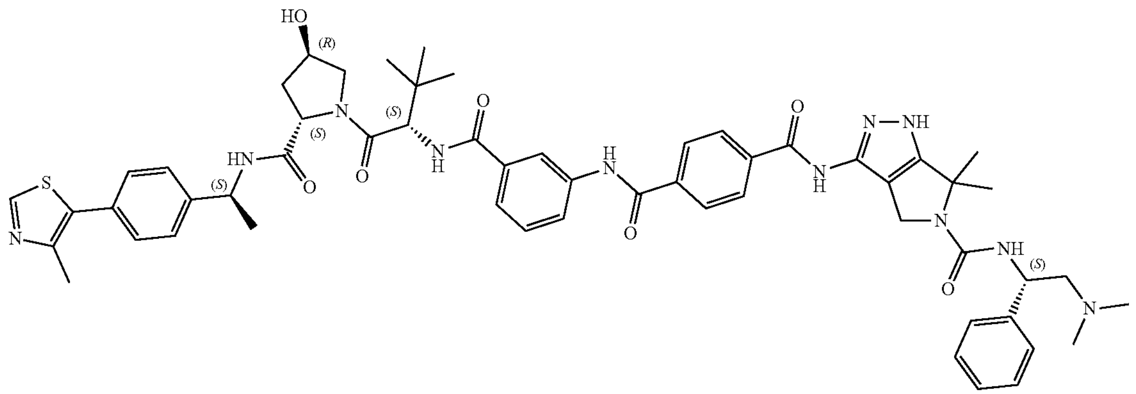

; and (34)

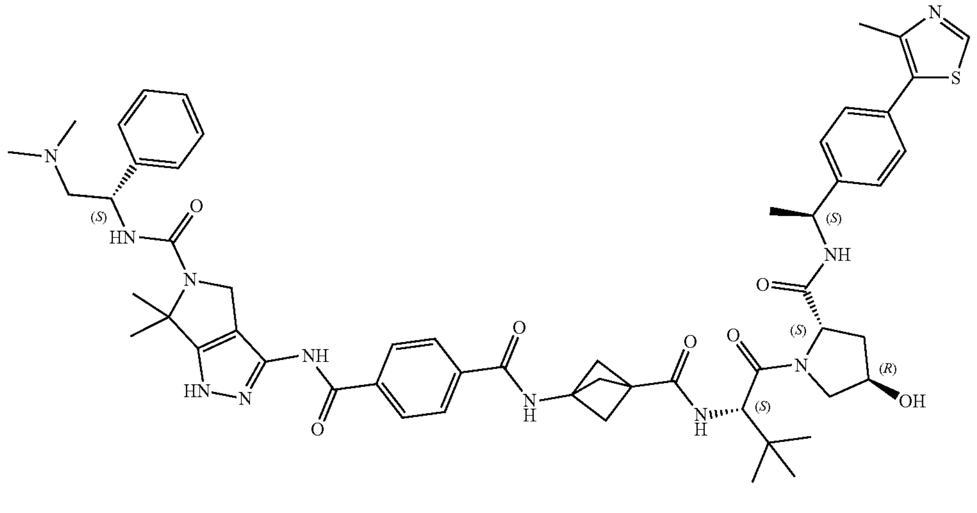

, or a pharmaceutically acceptable salt and stereoisomer thereof.

Bispecific compounds of formula (I) may be in the form of a free acid or free base, or a pharmaceutically acceptable salt. As used herein, the term "pharmaceutically acceptable" in the context of a salt refers to a salt of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt" refers to a product obtained by reaction of the compound of the present invention with a suitable acid or a base. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin.

Bispecific compounds of formula (I) may have at least one chiral center. Therefore, they may be in the form of a stereoisomer. As used herein, the term "stereoisomer" embraces all isomers of individual compounds that differ only in the orientation of their atoms in space. The term stereoisomer includes mirror image isomers (enantiomers which include the (R—) or (S—) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R—) form is considered equivalent to administration of the compound in its (S—) form. Accordingly, the compounds of the present invention may be made and used in the form of individual isomers and substantially free of other isomers, or in the form of a mixture of various isomers, e.g., racemic mixtures of stereoisomers.

In some embodiments, the bispecific compound of formula (I) is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^{2}H$, may afford certain therapeutic advantages resulting from greater metabolic stability, for example, increased in vivo half-life or reduced dosage requirements, and thus may be advantageous in some circumstances.

In addition to the isotopic derivatives, the term "bispecific compounds of formula (I)" embraces N-oxides, crystalline forms (also known as polymorphs), active metabolites of the compounds having the same type of activity, tautomers, and unsolvated as well as solvated forms with pharmaceutically acceptable solvents such as water, ethanol, and the like, of the compounds. The solvated forms of the conjugates presented herein are also considered to be disclosed herein.

Methods of Synthesis

In some embodiments, the present invention is directed to a method for making a bispecific compound of formula (I) or a pharmaceutically acceptable salt or stereoisomer thereof. Broadly, the inventive compounds or pharmaceutically-acceptable salts or stereoisomers thereof, may be prepared by any process known to be applicable to the preparation of chemically related compounds. Representative synthetic schemes are described in various working examples that illustrate non-limiting methods by which the compounds of the invention may be prepared.

Pharmaceutical Compositions

Another aspect of the present invention is directed to a pharmaceutical composition that includes a therapeutically effective amount of a bispecific compound of formula (I) or a pharmaceutically acceptable salt or stereoisomer thereof, and a pharmaceutically acceptable carrier. The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may include one or more pharmaceutically acceptable excipients.

Broadly, bispecific compounds of formula (I) and their pharmaceutically acceptable salts and stereoisomers may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and *Encyclopedia of Pharmaceutical Technology*, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, the compounds are formulated for oral or intravenous administration (e.g., systemic intravenous injection).

Accordingly, bispecific compounds of the present invention may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, bispecific compounds of the present invention may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

Injectable preparations may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, bispecific compounds of formula (I) may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The bispecific compounds may be formulated for buccal or sublingual administration, examples of which include tablets, lozenges and gels.

The bispecific compounds may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Bispecific compounds of formula (I) may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfate, butylated hydroxytoluene, butylated hydroxyanisole, tocopherols, and chelating agents like EDTA and citric acid. Suitable moisturizers include glycerin, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic Formulations Include Eye Drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a bispecific compound of formula (I) or a pharmaceutically acceptable salt or a stereoisomer thereof that is effective in producing the desired therapeutic response in a particular patient suffering from a disease or disorder characterized or mediated by aberrant CDK7 activity. The term "therapeutically effective amount" thus includes the amount of the compound of the invention or a pharmaceutically acceptable salt or a stereoisomer thereof, that when administered, induces a positive modification in the disease or disorder to be treated (e.g., to selectively inhibit/degrade CDK7), or is sufficient to prevent development or progression of the disease or disorder, or alleviate to some extent, one or more of the symptoms of the disease or disorder being treated in a subject, or which simply kills or inhibits the growth of diseased (e.g., neuroblastoma) cells, or reduces the amount of CDK7 in diseased cells.

The total daily dosage of the bispecific compounds and usage thereof may be decided in accordance with standard medical practice, e.g., by the attending physician using sound medical judgment. The specific therapeutically effective dose for any particular subject may depend upon a variety of factors including the disease or disorder being treated and the severity thereof (e.g., its present status); the age, body weight, general health, sex and diet of the subject; the time of administration, route of administration, and rate of excretion of the specific compound employed; the duration of the treatment; drugs used in combination or coincidental with the bispecific compound; and like factors well known in the medical arts (see, for example, *Goodman and Gilman's, The Pharmacological Basis of Therapeutics,* 10th Edition, A. Gilman, J. Hardman and L. Limbird, eds., McGraw-Hill Press, 155-173, 2001).

Bispecific compounds of formula (I) and their pharmaceutically acceptable salts and stereoisomers may be effective over a wide dosage range. In some embodiments, the total daily dosage (e.g., for adult humans) may range from about 0.001 to about 1600 mg, from 0.01 to about 1600 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, and in yet other embodiments from about 10 to about 30 mg per day. Individual dosages may be formulated to contain the desired dosage amount depending upon the number of times the compound is administered per day. By way of example, capsules may be formulated with from about 1 to about 200 mg of a bispecific compound of formula (I) or a pharmaceutically acceptable salt or stereoisomer thereof (e.g., 1, 2, 2.5, 3, 4, 5, 10, 15, 20, 25, 50, 100, 150, and 200 mg). In some embodiments, individual dosages may be formulated to contain the desired dosage amount depending upon the number of times the compound is administered per day.

Methods of Use

In some aspects, the present invention is directed to methods of treating diseases or disorders involving aberrant (e.g., dysfunctional or dysregulated) CDK7 activity, that entails administration of a therapeutically effective amount of a bispecific compound formula (I) or a pharmaceutically acceptable salt or stereoisomer thereof, to a subject in need thereof.

The diseases or disorders may be said to be characterized or mediated by aberrant (e.g., dysfunctional or dysregulated) CDK7 activity (e.g., elevated levels of protein or otherwise functionally abnormal relative to a non-pathological state). A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the animal's state of health.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" treatment according to the present invention may be "suffering from or suspected of suffering from" a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

Exemplary types of non-cancerous (e.g., cell proliferative) diseases or disorders that may be amenable to treatment with the compounds of the present invention include inflammatory diseases and conditions, autoimmune diseases, neurodegenerative diseases, heart diseases, viral diseases, chronic and acute kidney diseases or injuries, metabolic diseases, and allergic and genetic diseases.

Representative examples of specific non-cancerous diseases and disorders include lymphoproliferative conditions, autoimmune diseases, cholecystitis, acromegaly, rheumatoid spondylitis, osteoarthritis, gout, sepsis, septic shock, dacryoadenitis, cryopyrin associated periodic syndrome (CAPS), endotoxic shock, endometritis, gram-negative sepsis, keratoconjunctivitis sicca, toxic shock syndrome, asthma, adult respiratory distress syndrome, chronic obstructive pulmonary disease, chronic pulmonary inflammation, chronic graft rejection, hidradenitis suppurativa, inflammatory bowel disease, Crohn's disease, Behcet's syndrome, glomerulonephritis, multiple sclerosis, juvenile-onset diabetes, thyroiditis, Addison's disease, appendicitis, granulomatous orchitis, eczema, pancreatic fibrosis, hepatitis, hepatic fibrosis, CD14 mediated sepsis, non-CD14 mediated sepsis, acute and chronic renal disease, irritable bowel syndrome, pyresis, restenosis, cervicitis, stroke and ischemic injury, neural trauma, acute and chronic pain, allergic rhinitis, allergic conjunctivitis, chronic heart failure, congestive heart failure, acute coronary syndrome, cachexia, malaria, leprosy, leishmaniasis, Lyme disease, Reiter's syndrome, acute synovitis, muscle degeneration, bursitis, tendonitis, tenosynovitis, herniated, ruptured, or prolapsed intervertebral disk syndrome, osteopetrosis, rhinosinusitis, thrombosis, silicosis, pulmonary sarcosis, bone resorption diseases, such as osteoporosis, fibromyalgia, AIDS and other viral diseases such as Herpes Zoster, Herpes Simplex I or II, influenza virus and cytomegalovirus, diabetes Type I and II, obesity, insulin resistance and diabetic retinopathy, 22q11.2 deletion syndrome, Angelman syndrome, Canavan disease, Charcot-Marie-Tooth disease, color blindness, Cri du chat, Down syndrome, cystic fibrosis, Duchenne muscular dystrophy, haemophilia, Klinefleter's syndrome, neurofibromatosis, phenylketonuria, Prader-Willi syndrome, sickle cell disease, Tay-Sachs disease, Turner syndrome, urea cycle disorders, thalassemia, otitis, pancreatitis, parotitis, pericarditis, peritonitis, pharyngitis, pleuritis, phlebitis, pneumonitis, uveitis, polymyositis, proctitis, interstitial lung fibrosis, dermatomyositis, atherosclerosis, arteriosclerosis, amyotrophic lateral sclerosis, asociality, varicosis, vaginitis, depression, and Sudden Infant Death Syndrome.

Examples of autoimmune diseases include autoimmune hematological disorders (e.g., hemolytic anemia, aplastic anemia, anhidrotic ectodermal dysplasia, pure red cell anemia and idiopathic thrombocytopenia), alopecia areata, rheumatoid arthritis, scleroderma, systemic lupus erythematosus, autoimmune uveoretinitis, autoimmune vasculitis, lichen planus, bullous pemphigus, pemphigus vulgaris, pemphigus foliaceus, paraneoplastic pemphigus, myasthenia gravis, immunoglobulin A nephropathy, Hashimoto's disease, Sjogren's syndrome, vitiligo, Wegener granulomatosis, autoimmune oophoritis, sarcoidosis, rheumatic carditis, ankylosing spondylitis, Grave's disease, autoimmune thrombocytopenic purpura, psoriasis, psoriatic arthritis, dermatitis herpetiformis, ulcerative colitis, and celiac disease.

In other embodiments, the methods are directed to treating subjects having cancer. Broadly, the bispecific compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) such as leukemia, lymphoma and multiple myeloma. Adult tumors/cancers and pediatric tumors/cancers are included. The cancers may be vascularized, or not yet substantially vascularized, or non-vascularized tumors.

Representative examples of cancers includes adenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, gestational trophoblastic tumor glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), cholangiocarcinoma, germ cell tumor, ovarian germ cell tumor, head and neck cancer, neuroendocrine tumors, Hodgkin's lymphoma, Ann Arbor stage III and stage IV childhood Non-Hodgkin's lymphoma, ROS1-positive refractory Non-Hodgkin's lymphoma, leukemia, lymphoma, multiple myeloma, hypopharyngeal cancer, intraocular melanoma, ocular cancer, islet cell tumors (endocrine pancreas), renal cancer (e.g., Wilm's Tumor, renal cell carcinoma), liver cancer, lung cancer (e.g., non-small cell lung cancer and small cell lung cancer), ALK-positive anaplastic large cell lymphoma, ALK-positive advanced malignant solid neoplasm, Waldenstrom's macroglobulinema, melanoma, intraocular (eye) melanoma, merkel cell carcinoma, mesothelioma, metastatic squamous neck cancer with occult primary, multiple endocrine neoplasia (MEN), myelodysplastic syndromes, myelodyplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, metastatic anaplastic thyroid cancer, undifferentiated thyroid cancer, papillary thyroid cancer, pituitary tumor, plasma cell neoplasm/multiple myeloma, pleuropulmonary blastoma, prostate cancer, retinoblastoma, rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, juvenile xanthogranuloma, transitional cell cancer of the renal pelvis and ureter and other urinary organs, urethral cancer, gestational trophoblastic tumor, vaginal cancer, vulvar cancer, hepatoblastoma, rhabdoid tumor, and Wilms tumor.

Sarcomas that may be treatable with compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue), mesenchymous or mixed mesodermal tumor (mixed connective tissue types), and histiocytic sarcoma (immune cancer).

In some embodiments, methods of the present invention entail treatment of subjects having cell proliferative diseases or disorders of the hematological system, liver, brain, lung, colon, pancreas, prostate, ovary, breast, skin, and endometrium.

As used herein, "cell proliferative diseases or disorders of the hematological system" (also referred to as "hematologic cancers") include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, metastatic pancreatic adenocarcinoma, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, leukemia, including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the liver" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the liver may include hyperplasia, metaplasia, and dysplasia of the liver.

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, precancer and precancerous conditions of the lung, benign growths or lesions of the lung, hyperplasia, metaplasia, and dysplasia of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), squamous cell carcinoma, adenocarcinoma, small cell carcinoma, large cell carcinoma, and mesothelioma. Lung cancer can include "scar carcinoma", bronchioveolar carcinoma, giant cell carcinoma, spindle cell carcinoma, and large cell neuroendocrine carcinoma. Lung cancer also includes lung neoplasms having histologic and ultrastructural heterogeneity (e.g., mixed cell types). In some embodiments, a compound of the present invention may be used to treat non-metastatic or metastatic lung cancer (e.g., NSCLC, ALK-positive NSCLC, NSCLC harboring ROS1 rearrangement, lung adenocarcinoma, and squamous cell carcinoma).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polypopsis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting cells of the endometrium. Cell proliferative disorders of the endometrium may include a precancer or precancerous condition of the endometrium, benign growths or lesions of the endometrium, endometrial cancer, and metastatic lesions in tissue and organs in the body other than the endometrium. Cell proliferative disorders of the endometrium may include hyperplasia, metaplasia, and dysplasia of the endometrium.

In some embodiments, the bispecific compounds or pharmaceutically acceptable salts or stereoisomers of the present invention are disease or disorder is high-risk neuroblastoma. (NB).

In some embodiments, the disease or disorder treatable with the inventive bispecific compounds is acute myeloid leukemia (AML), multiple myeloma (MM), melanoma, rhabdomyosarcoma, or diffuse large B cell lymphoma. In other embodiments, the disease or disorder is small solid tumor. In other embodiments, the disease or disorder is colon cancer, rectum cancer, stomach cancer, breast cancer or pancreatic cancer.

The bispecific compounds of formula (I) may be administered to a patient, e.g., a cancer patient, as a monotherapy or by way of combination therapy. Therapy may be "front/first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which were unsuccessful or partially successful but who became unresponsive or intolerant to the particular treatment. Therapy may also be given as an adjuvant treatment, i.e., to prevent reoccurrence of cancer in patients with no currently detectable disease or after surgical removal of a tumor. Thus, in some embodiments, the compounds may be administered to a patient who has received another therapy, such as chemotherapy, radioimmunotherapy, surgical therapy, immunotherapy, radiation therapy, targeted therapy or any combination thereof.

The methods of the present invention may entail administration of bispecific compounds of formula (I) or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails a 28-day cycle which includes daily administration for 3 weeks (21 days). In other embodiments, the bispecific compound may be dosed twice a day (BID) over the course of two and a half days (for a total of 5 doses) or once a day (QD) over the course of two days (for a total of 2 doses). In other embodiments, the bispecific compound may be dosed once a day (QD) over the course of five days.

Combination Therapy

Bispecific compounds of formula (I) may be used in combination or concurrently with at least one other active agent, e.g., anti-cancer agent or regimen, in treating diseases and disorders. The terms "in combination" and "concurrently in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Thus, if given sequentially, at the onset of administration of the second compound, the first of the two compounds is in some cases still detectable at effective concentrations at the site of treatment. The sequence and time interval may be determined such that they can act together (e.g., synergistically to provide an increased benefit than if they were administered otherwise). For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the treatment regimen may include administration of a bispecific compound of formula (I) in combination with one or more additional therapeutics known for use in treating the disease or condition (e.g., cancer). The dosage of the additional anticancer therapeutic may be the same or even lower than known or recommended doses. See, Hardman et al., eds., *Goodman & Gilman's The Pharmacological Basis Of Basis Of Therapeutics,* 10th ed., McGraw-Hill, New York, 2001; Physician's Desk Reference 60th ed., 2006. For example, anti-cancer agents that may be suitable for use in combination with the inventive bispecific compounds are known in the art. See, e.g., U.S. Pat. No. 9,101,622 (Section 5.2 thereof) and U.S. Pat. No. 9,345,705 B2 (Columns 12-18 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and CAR-T therapy.

In some embodiments, the bispecific compound of formula (I) and the additional (e.g., anticancer) therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more (e.g., anticancer) therapeutics may be administered within the same patient visit.

In some embodiments involving cancer treatment, the bispecific compound of formula (I) and the additional anti-cancer agent or therapeutic are cyclically administered. Cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

Pharmaceutical Kits

The present bispecific compounds and/or compositions containing them may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain the bispecific compound of formula (I) or a pharmaceutical composition thereof. The kits or pharmaceutical systems of the invention may also include printed instructions for using the compounds and compositions.

These and other aspects of the present invention will be further appreciated upon consideration of the following Examples, which are intended to illustrate certain particular embodiments of the invention but are not intended to limit its scope, as defined by the claims.

EXAMPLES

Example 1: Synthesis of N1-(5-(((S)-2-(dimethylamino)-1-phenylethyl)carbamoyl)-6,6-dimethyl-1,4,5,6-tetrahydropyrrolo[3,4-c]pyrazol-3-yl)-N4-(2-(2-(2-(2-((2-(2,6-dioxopiperidin-3-yl)-1,3-dioxoisoindolin-4-yl)amino)ethoxy)ethoxy)ethoxy)ethyl)terephthalamide (1)

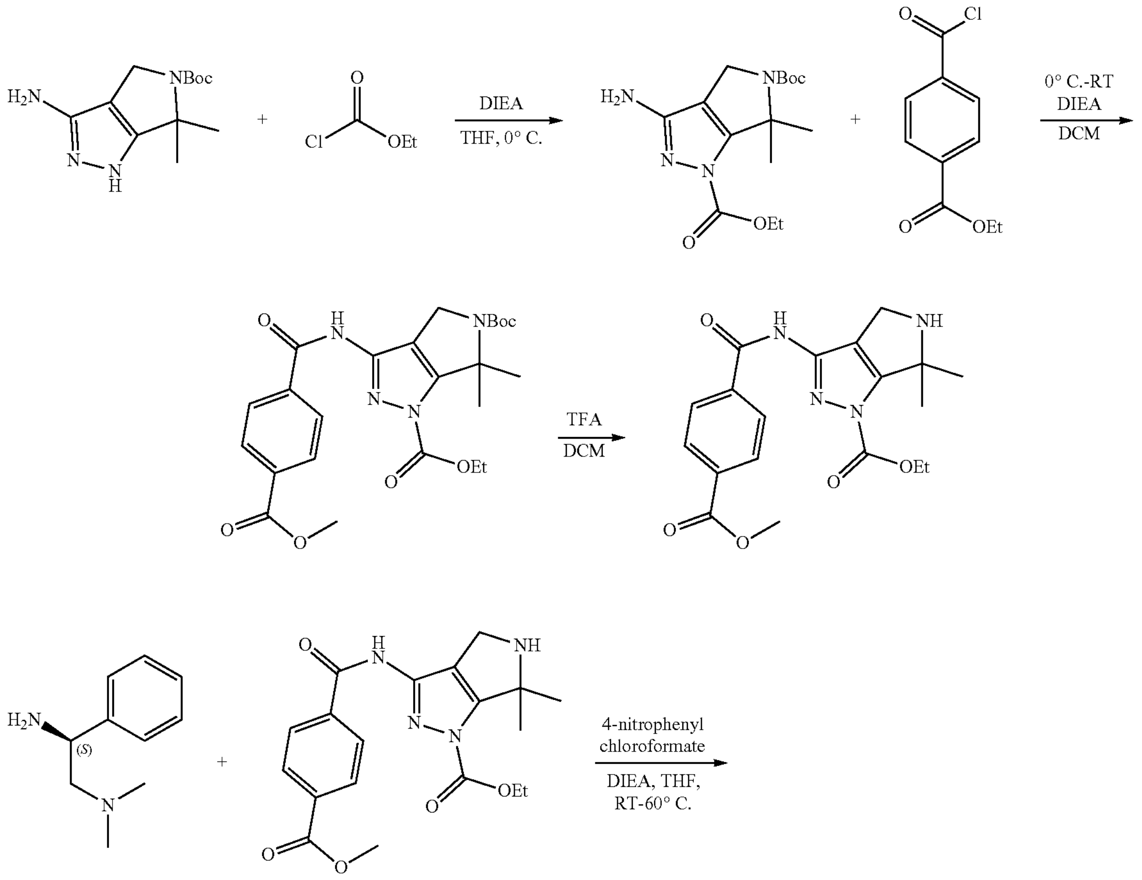

-continued

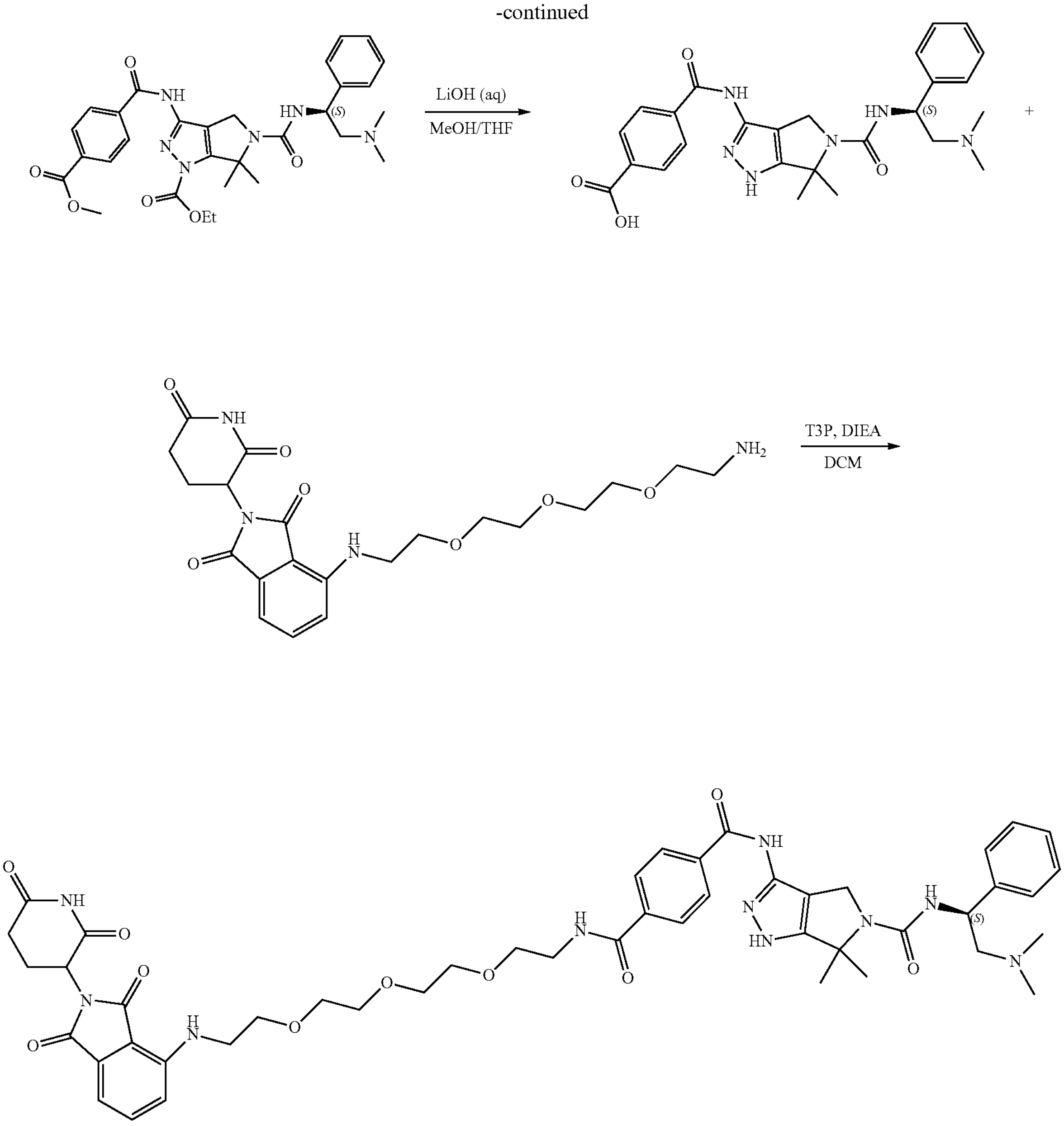

(1)

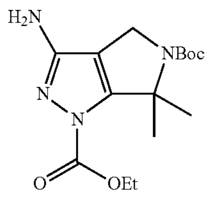 [SMILES: CCOC(=O)n1nc(N)c2c1C(C)(C)N(C(=O)OC(C)(C)C)C2]

5-(tert-Butyl) 1-ethyl 3-amino-6,6-dimethyl-4,6-dihydropyrrolo[3,4-c]pyrazole-1,5-dicarboxylate To a solution of tert-butyl 3-amino-6,6-dimethyl-4,6-dihydropyrrolo[3,4-c]pyrazole-5(1H)-carboxylate (4 g, 16 mmol) and N,N-diisopropylethylamine (DIEA) (5.2 mL, 32 mmol) in THF (160 mL) was added ethyl chloroformate (1.5 mL, 16 mmol, dissolved in 40 mL THF) dropwise at 0° C. for 30 min. The mixture was then stirred at room temperature for 1 h. After the reaction completed, the mixture was concentrated and then diluted with some water. The mixture was extracted with ethyl acetate (EA). The organic layer was concentrated in vacuo and then purified by column chromatography on silica gel (EA/hexane, 40%) to give the desired compound (1.6 g, 33%) as white solid.

LCMS: 325 $[M+H]^+$.

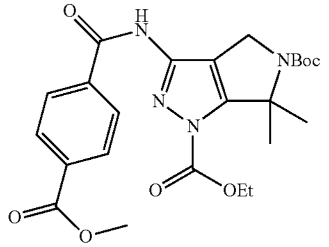 [SMILES: CCOC(=O)n1nc(NC(=O)c2ccc(C(=O)OC)cc2)c2c1C(C)(C)N(C(=O)OC(C)(C)C)C2]

5-(tert-butyl) 1-ethyl 3-(4-(methoxycarbonyl)benzamido)-6,6-dimethyl-4,6-dihydropyrrolo[3,4-c] pyrazole-1,5-dicarboxylate To a solution of 5-(tert-butyl) 1-ethyl 3-amino-6,6-dimethyl-4,6-dihydropyrrolo[3,4-c]pyrazole-1,5-dicarboxylate (972 mg, 3 mmol) and DIEA (990 μL, 6 mmol) in dry DCM (20 mL) was added methyl 4-(chlorocarbonyl)benzoate (713 mg, 3.6 mmol) at 0° C. The mixture was stirred overnight at 40° C. After the reaction completed, the mixture was concentrated in vacuo and then purified by column chromatography on silica gel (EA/hexane, 40%) to give the desired compound (1.28 g, 87%).

LCMS: 487 $[M+H]^+$.

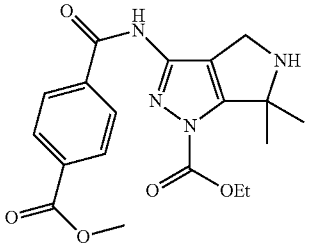 [SMILES: CCOC(=O)n1nc(NC(=O)c2ccc(C(=O)OC)cc2)c2c1C(C)(C)NC2]

Ethyl 3-(4-(methoxycarbonyl)benzamido)-6,6-dimethyl-5,6-dihydropyrrolo[3,4-c]pyrazole-1(4H)-carboxylate To a solution of 5-(tert-butyl) 1-ethyl 3-(4-(methoxycarbonyl)benzamido)-6,6-dimethyl-4,6-dihydropyrrolo[3,4-c] pyrazole-1,5-dicarboxylate (1275 mg, 2.6 mmol) in DCM (8 mL) was added TFA (2 mL) at 0° C. The mixture was then stirred at room temperature for 2 h. After the reaction completed, the mixture was diluted with some water. $Et_3N$ (2 mL) was added to the mixture before extraction with isopropanol (IPA)/chloroform (v/v=1/3). The organic layer was collected, concentrated in vacuo, and purified by column chromatography on silica gel (MeOH/DCM, 16%) to give the desired compound (940 mg, 72%).

$^1$H NMR (500 MHz, DMSO-$d_6$) δ 11.03 (s, 1H), 9.78 (s, 1H), 8.19 (d, J=8.5 Hz, 2H), 8.06 (d, J=8.5 Hz, 2H), 4.63 (s, 2H), 4.49 (q, J=7.1 Hz, 2H), 3.92 (s, 3H), 1.68 (s, 6H), 1.38 (t, J=7.1 Hz, 3H).

LCMS: 387 $[M+H]^+$.

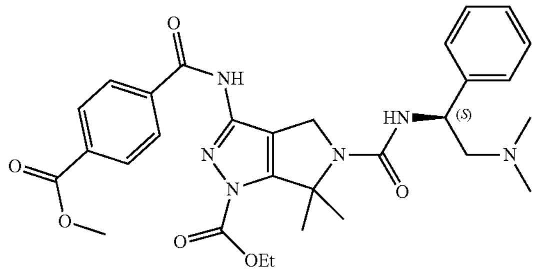

Ethyl (S)-5-((2-(dimethylamino)-1-phenylethyl)carbamoyl)-3-(4-(methoxycarbonyl)benzamido)-6,6-dimethyl-5,6-dihydropyrrolo[3,4-c]pyrazole-1(4H)-carboxylate To a solution of (S)—$N^1$,$N^1$-dimethyl-2-phenylethane-1,2-diamine (401 mg, 2.45 mmol) and DIEA (808 μL, 4.9 mmol) in dry THF (20 mL) was added 4-nitrophenyl chloroformate (542 mg, 2.69 mmol) at 0° C. The mixture was stirred at room temperature for 1 h before addition of ethyl 3-(4-(methoxycarbonyl)benzamido)-6,6-dimethyl-5,6-dihydropyrrolo[3,4-c]pyrazole-1 (4H)-carboxylate (850 mg, 2.2 mmol). The mixture was stirred overnight at 60° C. After the reaction completed, the mixture was concentrated and then purified by column chromatography on silica gel (MeOH/DCM, 5%) to give the desired compound (498 mg, 39%).

LCMS: 577 $[M+H]^+$.

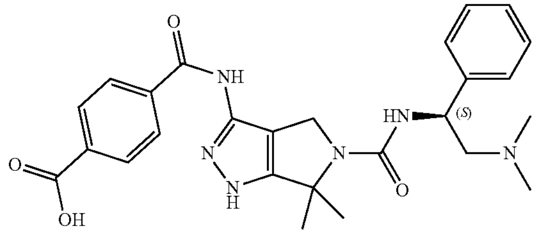

(S)-4-((5-((2-(dimethylamino)-1-phenylethyl)carbamoyl)-6,6-dimethyl-1,4,5,6-tetrahydropyrrolo[3,4-c]pyrazol-3-yl)carbamoyl)benzoic Acid To a solution of ethyl (S)-5-((2-(dimethylamino)-1-phenylethyl)carbamoyl)-3-(4-(methoxycarbonyl)benzamido)-6,6-dimethyl-5,6-dihydropyrrolo[3,4-c]pyrazole-1(4H)-carboxylate (498 mg, 0.86 mmol) in MeOH/THF (4 mL, 1:1) was added LiOH (1 M aq., 4.3 mL, 4.3 mmol). The mixture was stirred for 0.5 h. After the reaction was completed, HCl (2 M aq., 2 mL) was added and the mixture was concentrated in vacuo. The crude product was purified by column chromatography on silica gel (0.5% TFA in MeOH/DCM, 40%) to give the desired compound (407 mg, 78%) as a TFA salt.

$^1$H NMR (500 MHz, DMSO-$d_6$) δ 12.75 (s, 1H), 11.09 (s, 1H), 10.23 (s, 1H), 8.15-7.93 (m, 4H), 7.51-7.41 (m, 2H), 7.36 (t, J=7.7 Hz, 2H), 7.31-7.20 (m, 1H), 6.87 (s, 1H), 5.19-5.04 (m, 1H), 4.62 (q, J=12.1 Hz, 2H), 3.13 (d, J=14.8 Hz, 1H), 2.79 (d, J=12.0 Hz, 1H), 2.49 (s, 6H), 1.65 (s, 3H), 1.58 (s, 3H).

LCMS: 491 $[M+H]^+$.

(1)

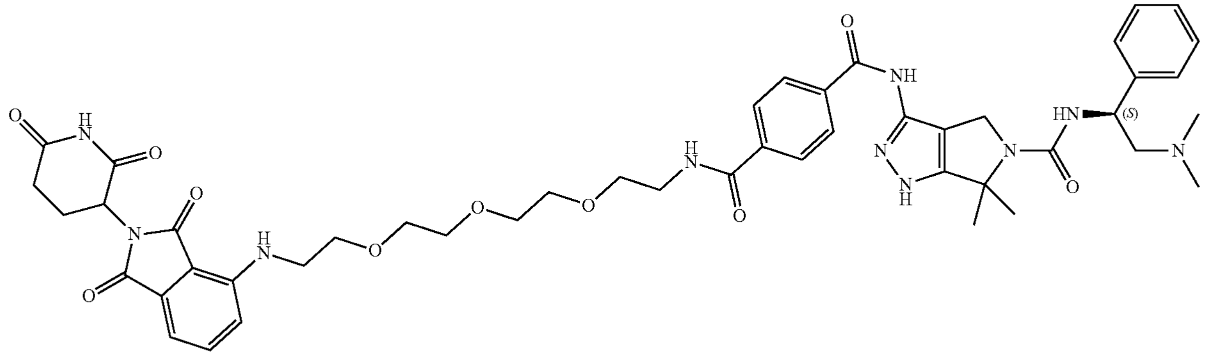

To a solution of (S)-4-((5-((2-(dimethylamino)-1-phenylethyl)carbamoyl)-6,6-dimethyl-1,4,5,6-tetrahydropyrrolo[3,4-c]pyrazol-3-yl)carbamoyl)benzoic acid (22 mg, 0.036 mmol) and DIEA (60 µL, 0.36 mmol) in dry DCM (2 mL) was added propanephosphonic acid anhydride (T3P®) (50% w.t. in EA, 115 µL, 0.18 mmol). The reaction was stirred for 10 min before addition of 4-((2-(2-(2-(2-aminoethoxy)ethoxy)ethoxy)ethyl)amino)-2-(2,6-dioxopiperidin-3-yl)isoindoline-1,3-dione (16 mg, 0.036 mmol). The mixture was stirred for 30 min and then was concentrated in vacuo. The crude product was purified by pre-HPLC to obtain compound 1 (2.6 mg, 7%) as a TFA salt.

$^1$H NMR (500 MHz, DMSO-$d_6$) δ 12.47 (s, 1H), 11.10 (s, 1H), 11.02 (s, 1H), 8.66 (s, 1H), 8.09 (d, J=8.1 Hz, 2H), 7.95 (d, J=8.1 Hz, 2H), 7.58 (dd, J=8.6, 7.1 Hz, 1H), 7.38 (d, J=7.2 Hz, 2H), 7.30 (t, J=7.5 Hz, 2H), 7.20 (t, J=7.3 Hz, 1H), 7.14 (d, J=8.6 Hz, 1H), 7.04 (d, J=7.0 Hz, 1H), 6.60 (t, J=5.8 Hz, 1H), 6.27 (s, 1H), 5.06 (dd, J=12.8, 5.4 Hz, 1H), 4.90 (s, 1H), 4.57 (s, 2H), 3.61 (t, J=5.4 Hz, 2H), 3.54 (d, J=3.5 Hz, 9H), 3.45 (dt, J=11.2, 5.6 Hz, 4H), 3.33 (s, 6H), 2.88 (ddd, J=16.7, 13.7, 5.4 Hz, 1H), 2.62-2.53 (m, 1H), 2.22 (s, 5H), 2.10-1.98 (m, 1H), 1.66 (s, 3H), 1.58 (s, 3H).

LCMS: 921 [M+H]$^+$.

Example 2: Synthesis of N1-(5-(((S)-2-(dimethylamino)-1-phenylethyl)carbamoyl)-6,6-dimethyl-1,4,5,6-tetrahydropyrrolo[3,4-c]pyrazol-3-yl)-N4-(2-((2-(2,6-dioxopiperidin-3-yl)-1,3-dioxoisoindolin-4-yl)amino)ethyl)terephthalamide (2)

(2)

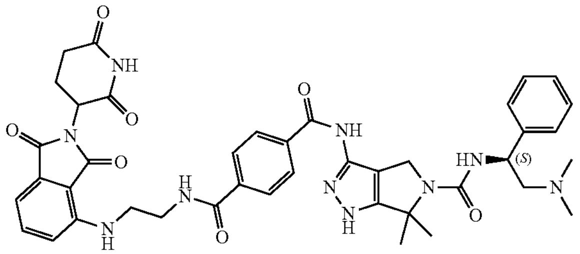

Compound 2 (20.4 mg, 65%) was obtained according to the synthetic route of compound 1 in Example 1 with 4-((2-aminoethyl)amino)-2-(2,6-dioxopiperidin-3-yl)isoindoline-1,3-dione.

$^1$H NMR (500 MHz, DMSO-$d_6$) δ 11.09 (d, J=6.4 Hz, 2H), 9.05 (s, 1H), 8.86 (t, J=5.3 Hz, 1H), 8.10 (d, J=8.5 Hz, 2H), 7.96 (d, J=8.5 Hz, 2H), 7.59 (dd, J=8.6, 7.0 Hz, 1H), 7.48-7.43 (m, 2H), 7.40 (t, J=7.7 Hz, 2H), 7.34-7.28 (m, 1H), 7.26 (d, J=8.7 Hz, 1H), 7.04 (d, J=7.0 Hz, 1H), 6.86 (s, 1H), 6.77 (d, J=9.2 Hz, 1H), 5.36 (ddd, J=12.6, 9.2, 3.9 Hz, 1H), 5.06 (dd, J=12.8, 5.5 Hz, 1H), 4.78 (d, J=11.8 Hz, 1H), 4.58 (d, J=11.9 Hz, 1H), 3.62-3.47 (m, 5H), 3.36 (ddd, 1H), 2.89 (d, J=4.7 Hz, 3H), 2.85 (d, J=4.8 Hz, 3H), 2.60 (dt, J=17.6, 3.5 Hz, 1H), 2.03 (dtd, J=11.3, 6.3, 5.6, 3.0 Hz, 1H), 1.69 (s, 3H), 1.60 (s, 3H).

LCMS: 789 [M+H]$^+$.

Example 3: Synthesis of N1-(5-(((S)-2-(dimethylamino)-1-phenylethyl)carbamoyl)-6,6-dimethyl-1,4,5,6-tetrahydropyrrolo[3,4-c]pyrazol-3-yl)-N4-(4-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-4-oxobutyl)terephthalamide (3)

(3)

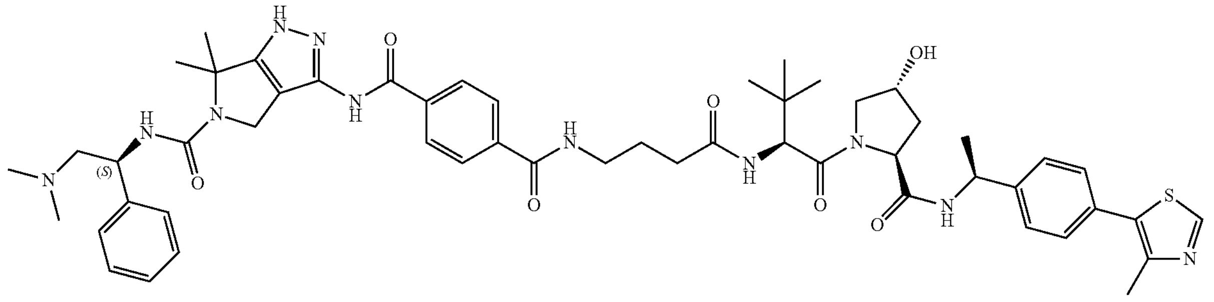

Compound 3 (13.2 mg, 35%) was obtained according to the synthetic route of compound 1 in Example 1 with (2S,4R)-1-((S)-2-(4-aminobutanamido)-3,3-dimethylbutanoyl)-4-hydroxy-N—((S)-1-(4-(4-methylthiazol-5-yl)phenyl)ethyl)pyrrolidine-2-carboxamide.

$^1$H NMR (500 MHz, DMSO-$d_6$) δ 11.08 (s, 1H), 9.00 (s, 2H), 8.64 (t, J=5.5 Hz, 1H), 8.38 (d, J=7.8 Hz, 1H), 8.22-8.05 (m, 2H), 8.04-7.94 (m, 2H), 7.90 (d, J=9.3 Hz, 1H), 7.44 (dd, J=8.5, 2.0 Hz, 4H), 7.40 (td, J=8.3, 7.9, 2.8 Hz, 4H), 7.36-7.27 (m, 1H), 6.77 (d, J=9.1 Hz, 1H), 5.40-5.31 (m, 2H), 4.93 (t, J=7.2 Hz, 1H), 4.79 (d, J=11.8 Hz, 1H), 4.56 (dd, J=17.6, 10.6 Hz, 2H), 4.44 (t, J=8.0 Hz, 1H), 4.30 (s, 1H), 3.67-3.51 (m, 4H), 3.39-3.26 (m, 4H), 2.89 (d, J=4.8 Hz, 3H), 2.85 (d, J=4.8 Hz, 3H), 2.46 (s, 3H), 2.34 (dt, J=14.8, 7.8 Hz, 1H), 2.22 (dt, J=14.5, 7.3 Hz, 1H), 2.01 (d, J=14.5 Hz, 1H), 1.79 (tdd, 3H), 1.69 (s, 3H), 1.60 (s, 3H), 1.38 (d, J=6.9 Hz, 3H), 0.96 (s, 9H).

LCMS: 1002 $[M+H]^+$.

Example 4: Synthesis of N1-(5-(((S)-2-(dimethylamino)-1-phenylethyl)carbamoyl)-6,6-dimethyl-1,4,5,6-tetrahydropyrrolo[3,4-c]pyrazol-3-yl)-N4-(6-((2-(2,6-dioxopiperidin-3-yl)-1,3-dioxoisoindolin-4-yl)amino)hexyl)terephthalamide (4)

(4)

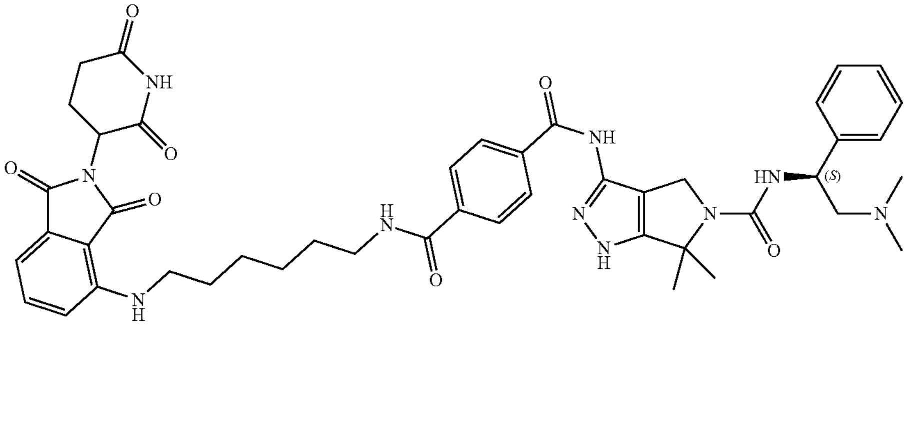

Compound 4 (11 mg, 38%) was obtained according to the synthetic route of compound 1 in Example 1 with 4-((6-aminohexyl)amino)-2-(2,6-dioxopiperidin-3-yl)isoindoline-1,3-dione.

$^1$H NMR (500 MHz, DMSO-$d_6$) δ 12.55 (s, 1H), 11.07 (d, J=21.1 Hz, 2H), 8.64 (t, J=5.6 Hz, 1H), 8.13-8.05 (m, 2H), 7.97 (d, J=8.0 Hz, 2H), 7.58 (dd, J=8.6, 7.1 Hz, 1H), 7.43 (d, J=7.2 Hz, 2H), 7.37 (t, J=7.6 Hz, 2H), 7.27 (t, J=7.3 Hz, 1H), 7.10 (d, J=8.6 Hz, 1H), 7.03 (d, J=7.0 Hz, 1H), 6.61 (s, 1H), 6.55 (t, J=5.9 Hz, 1H), 5.21 (s, 1H), 5.06 (dd, J=12.7, 5.5 Hz, 1H), 4.74 (d, J=12.0 Hz, 1H), 4.57 (d, J=11.8 Hz, 1H), 3.34 (s, 6H), 3.29 (p, J=6.6 Hz, 4H), 2.89 (ddd, J=16.8, 13.7, 5.4 Hz, 1H), 2.72-2.55 (m, 6H), 2.03 (dtd, J=13.1, 5.3, 2.2 Hz, 1H), 1.68 (s, 3H), 1.60 (s, 3H), 1.55 (m, 2H), 1.39 (dt, J=7.0, 3.7 Hz, 4H).

LCMS: 845 [M+H]$^+$.

Example 5: Synthesis of N$^1$-(5-(((S)-2-(dimethylamino)-1-phenylethyl)carbamoyl)-6,6-dimethyl-1,4,5,6-tetrahydropyrrolo[3,4-c]pyrazol-3-yl)-N$^4$-(14-((2-(2,6-dioxopiperidin-3-yl)-1,3-dioxoisoindolin-4-yl)amino)-3,6,9,12-tetraoxatetradecyl)terephthalamide (5)

(5)

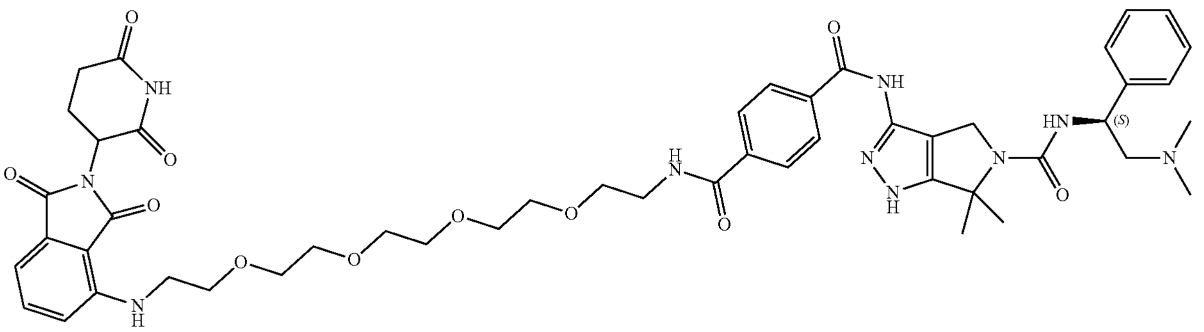

Compound 5 (5 mg, 17%) was obtained according to the synthetic route of compound 1 in Example 1 with 4-((14-amino-3,6,9,12-tetraoxatetradecyl)amino)-2-(2,6-dioxopiperidin-3-yl)isoindoline-1,3-dione.

$^1$H NMR (500 MHz, DMSO-$d_6$) δ 12.49 (s, 1H), 11.10 (s, 1H), 11.03 (s, 1H), 8.67 (s, 1H), 8.09 (d, J=8.1 Hz, 2H), 7.96 (d, J=8.1 Hz, 2H), 7.58 (dd, J=8.6, 7.0 Hz, 1H), 7.39 (d, J=7.2 Hz, 2H), 7.32 (t, J=7.5 Hz, 2H), 7.22 (t, J=7.3 Hz, 1H), 7.14 (d, J=8.6 Hz, 1H), 7.04 (d, J=7.0 Hz, 1H), 6.60 (t, J=5.8 Hz, 1H), 6.35 (s, 1H), 5.06 (dd, J=12.7, 5.4 Hz, 1H), 4.98 (s, 1H), 4.58 (s, 2H), 3.62 (t, J=5.4 Hz, 2H), 3.57-3.49 (m, 12H), 3.46 (dt, J=12.0, 5.8 Hz, 5H), 2.89 (ddd, J=16.9, 13.7, 5.4 Hz, 1H), 2.63-2.54 (m, 2H), 2.31 (s, 1H), 2.03 (ddd, J=11.7, 6.4, 3.9 Hz, 1H), 1.66 (s, 3H), 1.59 (s, 3H).

LCMS: 965 [M+H]$^+$.

Example 6: Synthesis of N$^1$-(5-(((S)-2-(dimethylamino)-1-phenylethyl)carbamoyl)-6,6-dimethyl-1,4,5,6-tetrahydropyrrolo[3,4-c]pyrazol-3-yl)-N$^4$-(2-(2-(3-(4S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-3-oxopropoxy)ethoxy)ethyl)terephthalamide (6)

(6)

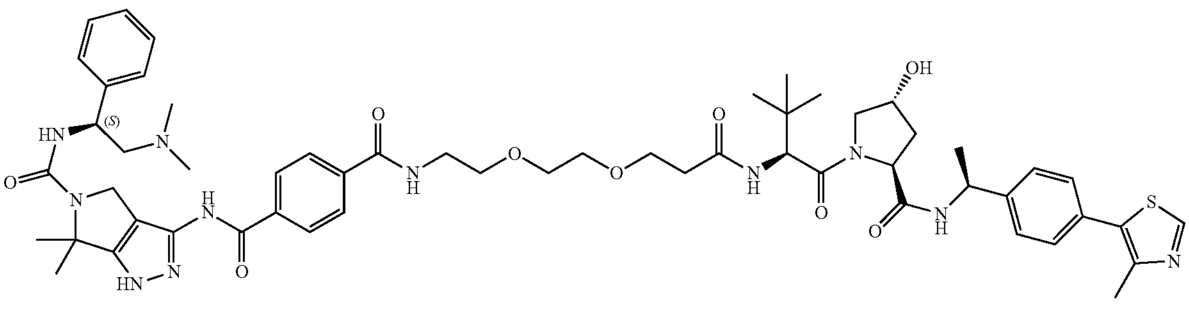

Compound 6 (6.5 mg, 20%) was obtained according to the synthetic route of compound 1 in Example 1 with (2S,4R)-1-((S)-2-(3-(2-(2-aminoethoxy)ethoxy)propanamido)-3,3-dimethylbutanoyl)-4-hydroxy-N—((S)-1-(4-(4-methylthiazol-5-yl)phenyl)ethyl)pyrrolidine-2-carboxamide.

$^1$H NMR (500 MHz, DMSO-$d_6$) δ 11.08 (s, 1H), 9.05 (s, 1H), 8.99 (s, 1H), 8.69 (t, J=5.6 Hz, 1H), 8.38 (d, J=7.8 Hz, 1H), 8.10 (d, J=8.5 Hz, 2H), 7.98 (d, J=8.5 Hz, 2H), 7.87 (d, J=9.3 Hz, 1H), 7.46-7.42 (m, 4H), 7.42-7.35 (m, 4H), 7.33-7.29 (m, 1H), 6.77 (d, J=9.1 Hz, 1H), 5.36 (ddd, J=12.4, 9.1, 4.0 Hz, 2H), 4.91 (p, J=7.3 Hz, 2H), 4.79 (d, J=11.9 Hz, 1H), 4.55 (dd, J=19.3, 10.6 Hz, 2H), 4.43 (t, J=8.1 Hz, 1H), 4.29 (dd, J=4.7, 2.4 Hz, 1H), 3.67-3.47 (m, 11H), 3.45 (q, J=6.8, 6.3 Hz, 2H), 3.36 (ddt, J=12.6, 8.9, 4.4 Hz, 1H), 2.89 (d, J=4.8 Hz, 3H), 2.84 (d, J=4.8 Hz, 3H), 2.46 (s, 3H), 2.36 (dt, J=14.6, 6.1 Hz, 1H), 2.07-1.99 (m, 1H), 1.80 (ddd, J=12.9, 8.5, 4.6 Hz, 1H), 1.69 (s, 3H), 1.60 (s, 3H), 1.37 (d, J=7.0 Hz, 3H), 0.94 (s, 9H).

LCMS: 1076 [M+H]$^+$.

Example 7: Synthesis of N$^1$-(5-(((S)-2-(dimethylamino)-1-phenylethyl)carbamoyl)-6,6-dimethyl-1,4,5,6-tetrahydropyrrolo[3,4-c]pyrazol-3-yl)-N$^4$-(6-(2-(2,6-dioxopiperidin-3-yl)-1,3-dioxoisoindolin-4-yl)hex-5-yn-1-yl)terephthalamide (7)

(7)

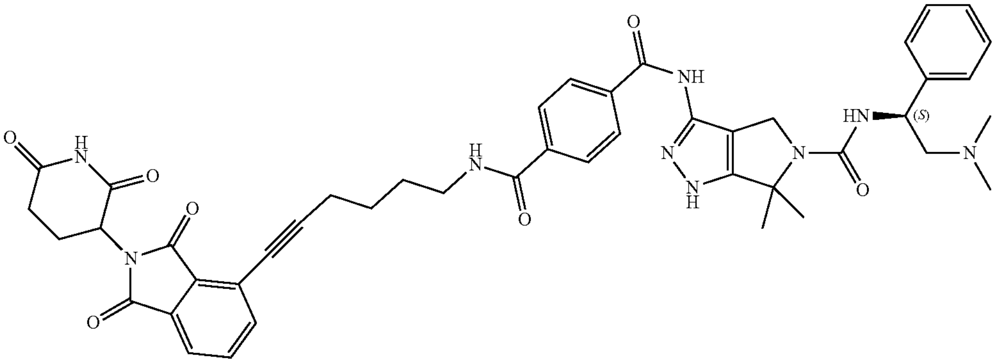

Compound 7 (3.3 mg, 12%) was obtained according to the synthetic route of compound 1 in Example 1 with 4-(6-aminohex-1-yn-1-yl)-2-(2,6-dioxopiperidin-3-yl)isoindoline-1,3-dione.

$^1$H NMR (500 MHz, DMSO-$d_6$) δ 12.61 (s, 1H), 11.13 (s, 1H), 11.04 (s, 1H), 9.71 (s, 1H), 8.73 (s, 1H), 8.11 (d, J=8.1 Hz, 2H), 7.98 (d, J=8.1 Hz, 2H), 7.90-7.85 (m, 1H), 7.84-7.81 (m, 2H), 7.45 (d, J=7.7 Hz, 2H), 7.38 (t, J=7.6 Hz, 2H), 7.29 (t, J=7.3 Hz, 1H), 6.73 (s, 1H), 5.32 (s, 1H), 5.14 (dd, J=12.8, 5.5 Hz, 1H), 4.81 (d, J=12.1 Hz, 1H), 4.57 (d, J=11.8 Hz, 1H), 2.93-2.70 (m, 4H), 2.60 (t, J=7.0 Hz, 4H), 2.09-2.00 (m, 1H), 1.76 (q, J=7.4, 6.7 Hz, 2H), 1.68 (d, J=6.3 Hz, 4H), 1.60 (s, 3H), 1.21 (d, J=29.7 Hz, 2H).

LCMS: 826 [M+H]$^+$.

Example 8: Synthesis of N$^1$-(5-(((S)-2-(dimethylamino)-1-phenylethyl)carbamoyl)-6,6-dimethyl-1,4,5,6-tetrahydropyrrolo[3,4-c]pyrazol-3-yl)-N$^4$-(5-((2-(2,6-dioxopiperidin-3-yl)-1,3-dioxoisoindolin-4-yl)oxy)pentyl)terephthalamide (8)

(8)

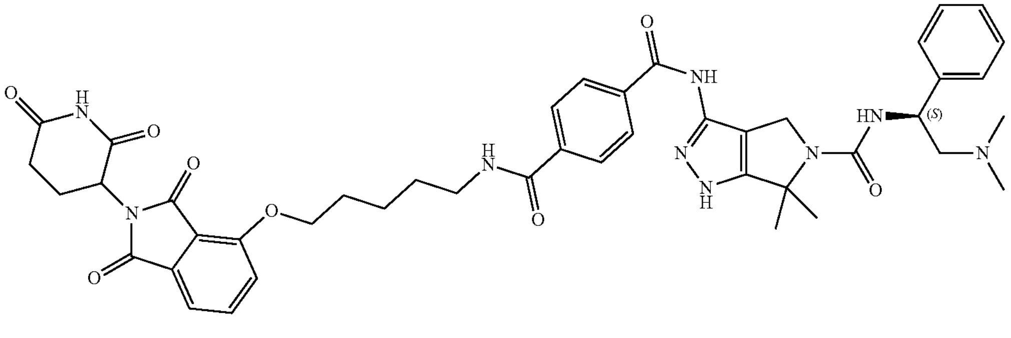

Compound 8 (7.2 mg, 29%) was obtained according to the synthetic route of compound 1 in Example 1 with 4-((5-aminopentyl)oxy)-2-(2,6-dioxopiperidin-3-yl)isoindoline-1,3-dione.

$^1$H NMR (500 MHz, DMSO-$d_6$) δ 11.04 (d, J=18.1 Hz, 2H), 8.59 (t, J=5.7 Hz, 1H), 8.04 (d, J=8.3 Hz, 2H), 7.91 (d, J=8.1 Hz, 2H), 7.76 (dd, J=8.5, 7.2 Hz, 1H), 7.48 (d, J=8.6 Hz, 1H), 7.38 (dd, J=14.5, 7.4 Hz, 3H), 7.30 (t, J=7.6 Hz, 2H), 7.21 (t, J=7.2 Hz, 1H), 6.51 (s, 1H), 5.03 (dd, J=12.8, 5.5 Hz, 1H), 4.64 (s, 1H), 4.52 (d, J=11.9 Hz, 1H), 4.18 (t, J=6.4 Hz, 1H), 3.55 (s, 1H), 3.31-3.26 (m, 6H), 3.07 (s, 1H), 3.01 (q, J=7.2 Hz, 3H), 2.83 (ddd, J=17.0, 13.8, 5.5 Hz, 2H), 2.59-2.49 (m, 3H), 2.01-1.95 (m, 1H), 1.77 (p, J=6.6 Hz, 2H), 1.62 (s, 3H), 1.58 (t, J=7.4 Hz, 2H), 1.54 (s, 3H), 1.48 (qd, J=9.9, 9.0, 6.0 Hz, 2H).

LCMS: 832 $[M+H]^+$.

Example 9: Synthesis of $N^1$-(5-(((S)-2-(dimethylamino)-1-phenylethyl)carbamoyl)-6,6-dimethyl-1,4,5,6-tetrahydropyrrolo[3,4-c]pyrazol-3-yl)-$N^4$-(8-((2-(2,6-dioxopiperidin-3-yl)-1,3-dioxoisoindolin-4-yl)oxy)octyl)terephthalamide (9)

(9)

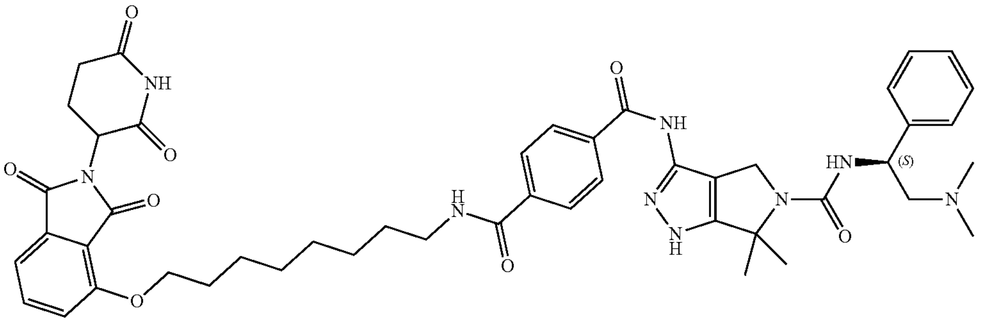

Compound 9 (15 mg, 52%) was obtained according to the synthetic route of compound 1 in Example 1 with 4-((8-aminooctyl)oxy)-2-(2,6-dioxopiperidin-3-yl)isoindoline-1,3-dione.

$^1$H NMR (500 MHz, DMSO-$d_6$) δ 12.49 (s, 1H), 11.11 (s, 1H), 11.02 (s, 1H), 8.60 (t, J=5.7 Hz, 1H), 8.09 (d, J=8.1 Hz, 2H), 7.95 (d, J=8.1 Hz, 2H), 7.81 (dd, J=8.5, 7.3 Hz, 1H), 7.52 (d, J=8.5 Hz, 1H), 7.44 (d, J=7.2 Hz, 1H), 7.32 (t, J=7.6 Hz, 2H), 7.22 (t, J=7.3 Hz, 1H), 6.33 (s, 1H), 5.09 (dd, J=12.8, 5.5 Hz, 1H), 4.95 (s, 1H), 4.59 (s, 2H), 4.21 (t, J=6.4 Hz, 2H), 3.33 (s, 6H), 2.89 (ddd, J=16.8, 13.8, 5.4 Hz, 1H), 2.64-2.54 (m, 1H), 2.33-2.18 (m, 5H), 2.03 (dtd, J=13.0, 5.3, 2.2 Hz, 1H), 1.83-1.71 (m, 2H), 1.66 (s, 3H), 1.63-1.53 (m, 5H), 1.48 (t, J=7.8 Hz, 2H), 1.35 (d, J=4.1 Hz, 6H).

LCMS: 874 $[M+H]^+$.

Example 10: Synthesis of N—((S)-2-(dimethylamino)-1-phenylethyl)-3-(4-(11-((2-(2,6-dioxopiperidin-3-yl)-1,3-dioxoisoindolin-4-yl)oxy)undecanamido)benzamido)-6,6-dimethyl-4,6-dihydropyrrolo[3,4-c]pyrazole-5(1H)-carboxamide (10)

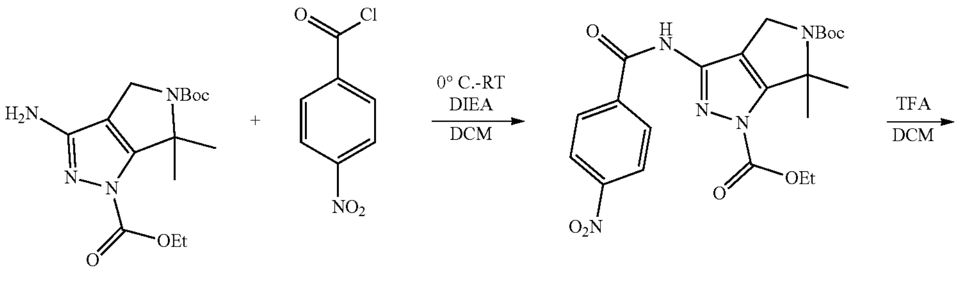

-continued
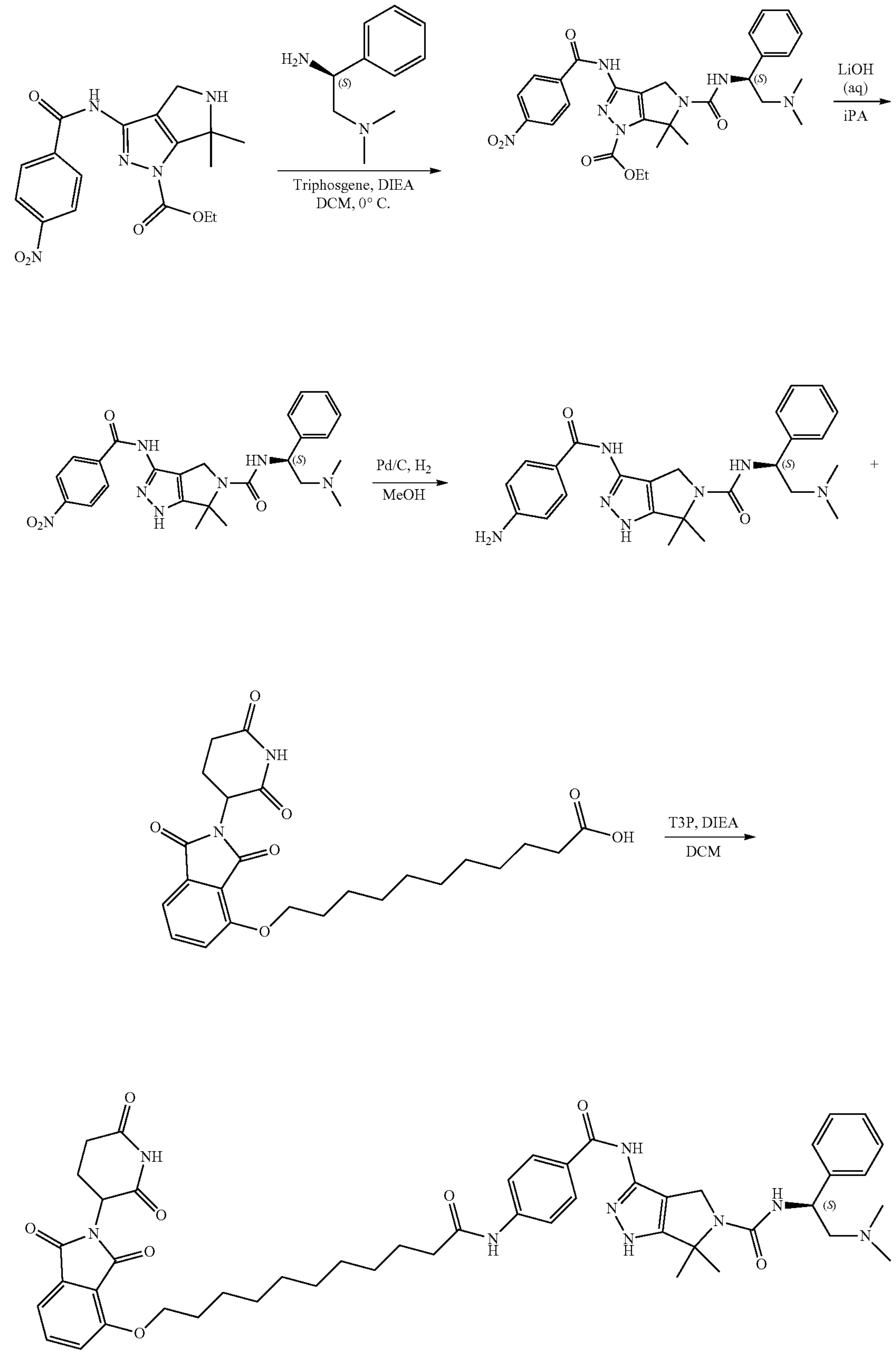
(10)

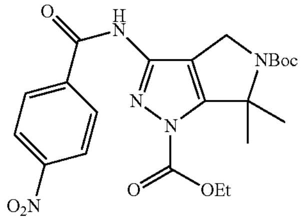 [SMILES: CCOC(=O)n1nc(NC(=O)c2ccc([N+](=O)[O-])cc2)c2c1C(C)(C)N(C(=O)OC(C)(C)C)C2]

5-(tert-Butyl) 1-ethyl 6,6-dimethyl-3-(4-nitrobenzamido)-4,6-dihydropyrrolo[3,4-c]pyrazole-1,5-dicarboxylate To a solution of 5-(tert-butyl) 1-ethyl 3-amino-6,6-dimethyl-4,6-dihydropyrrolo[3,4-c]pyrazole-1,5-dicarboxylate (875 mg, 2.7 mmol) and DIEA (1.34 mL, 8.1 mmol) in DCM (40 mL) was added 4-nitrobenzoyl chloride (600 mg, 3.24 mmol) at 0° C. The reaction was stirred overnight at room temperature. The mixture was concentrated in vacuo and then purified by column chromatography on silica gel (EA/hexane, 30%) to give the desired compound (822 mg, 64%).

LCMS: 474 $[M+H]^+$.

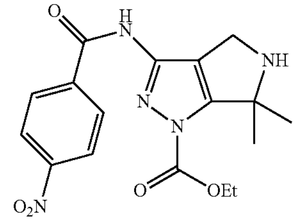 [SMILES: CCOC(=O)n1nc(NC(=O)c2ccc([N+](=O)[O-])cc2)c2c1C(C)(C)NC2]

Ethyl 6,6-dimethyl-3-(4-nitrobenzamido)-5,6-dihydropyrrolo[3,4-c]pyrazole-1(4H)-carboxylate To a solution of 5-(tert-butyl) 1-ethyl 6,6-dimethyl-3-(4-nitrobenzamido)-4,6-dihydropyrrolo[3,4-c]pyrazole-1,5-dicarboxylate (822 mg, 1.74 mmol) in DCM (8 mL) was added TFA (2 mL) at 0° C. The mixture was stirred at room temperature for 2 h and then concentrated in vacuo. The crude product was used in the next step without further purification.

LCMS: 374 $[M+H]^+$.

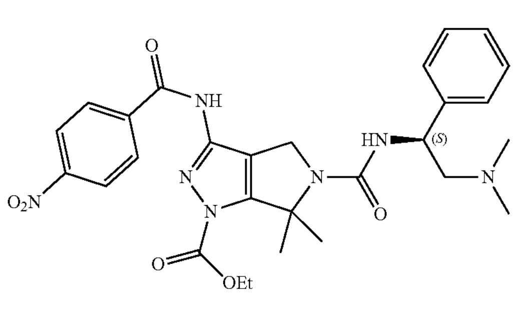

Ethyl (S)-5-((2-(dimethylamino)-1-phenylethyl)carbamoyl)-6,6-dimethyl-3-(4-nitrobenzamido)-5,6-dihydropyrrolo[3,4-c]pyrazole-1(4H)-carboxylate To a solution of ethyl 6,6-dimethyl-3-(4-nitrobenzamido)-5,6-dihydropyrrolo[3,4-c]pyrazole-1(4H)-carboxylate (633 mg, 1.3 mmol) and DIEA (130 μL, 0.78 mmol) in DCM (10 mL) was added triphosgene (194 mg, 0.65 mmol, dissolved in 2 mL DCM) dropwise at 0° C. The mixture was stirred for 30 min at 0° C. (S)—$N^1$,$N^1$-Dimethyl-2-phenylethane-1,2-diamine (256 mg, 1.56 mmol) and DIEA (320 μL, 1.95 mmol) were then added. The mixture was stirred overnight at 40° C. After the reaction completed, the mixture was concentrated in vacuo and then purified by column chromatography on silica gel (MeOH/DCM, 6%) to give the desired compound (232 mg, 32%).

LCMS: 564 $[M+H]^+$.

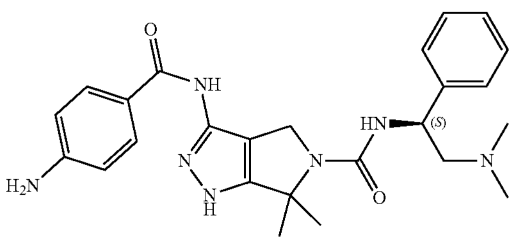

(S)-3-(4-aminobenzamido)-N-(2-(dimethylamino)-1-phenylethyl)-6,6-dimethyl-4,6-dihydropyrrolo[3,4-c]pyrazole-5(1H)-carboxamide To a solution of ethyl (S)-5-((2-(dimethylamino)-1-phenylethyl)carbamoyl)-6,6-dimethyl-3-(4-nitrobenzamido)-5,6-dihydropyrrolo[3,4-c]pyrazole-1(4H)-carboxylate (232 mg, 0.41 mmol) in isopropanol (2 mL) was added LiOH (1 N aq., 2 mL). The reaction was stirred at room temperature for 10 min and then extracted with IPA/chloroform (v/v=1/3). The pooled organic layers were concentrated in vacuo. The resulting product was then redissolved in MeOH (20 mL). Palladium (10% on activated carbon, 30 mg) was added, and the mixture was stirred for 3 h under $H_2$ atmosphere. After the reaction completed, the mixture was filtered and the filtrate was concentrated in vacuo. The crude product was purified by column chromatography on silica gel (1.75 N $NH_3$ in MeOH/DCM, 30%) to give the desired compound (153 mg, 81% for 2 steps).

$^1H$ NMR (500 MHz, DMSO-$d_6$) δ 12.33 (s, 0H), 10.33 (s, 0H), 9.19 (s, 0H), 7.77 (d, J=8.3 Hz, 1H), 7.41 (d, J=7.5 Hz, 1H), 6.57 (d, J=8.3 Hz, 1H), 5.88 (s, 0H), 5.75 (s, 1H), 4.63 (s, 1H), 4.53 (d, J=11.9 Hz, 2H), 3.17 (d, J=5.2 Hz, 1H), 2.64 (p, J=1.8 Hz, 1H), 1.66 (s, 3H), 1.58 (s, 3H).

LCMS: 462 $[M+H]^+$.

(10)

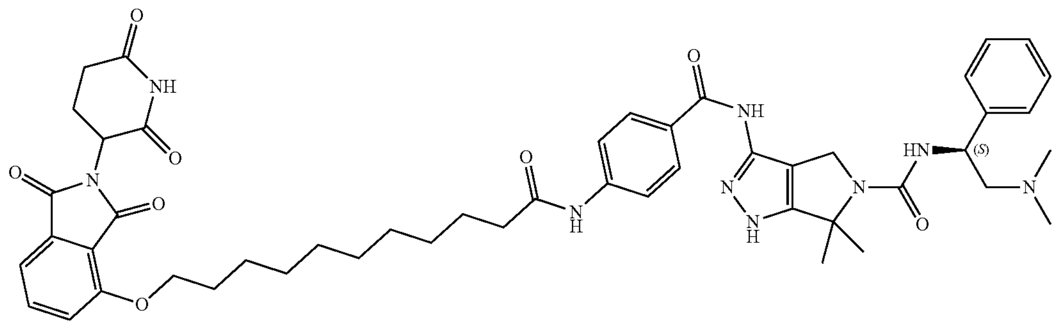

To a solution of 11-((2-(2,6-dioxopiperidin-3-yl)-1,3-dioxoisoindolin-4-yl)oxy)undecanoic acid (14 mg, 0.03 mmol) and DIEA (50 μL, 0.3 mmol) in dry DCM (2 mL) was added T3P (50% w.t. in EA, 90 μL, 0.15 mmol). The reaction was stirred for 10 min before addition of (S)-3-(4-aminobenzamido)-N-(2-(dimethylamino)-1-phenylethyl)-6,6-dimethyl-4,6-dihydropyrrolo[3,4-c]pyrazole-5(1H)-carboxamide (14 mg, 0.03 mmol). The mixture was stirred for 30 min and then concentrated in vacuo. The crude product was purified by prep-HPLC to obtain compound 10 (7.6 mg, 25%) as a TFA salt.

$^1$H NMR (500 MHz, DMSO-$d_6$) δ 11.10 (s, 1H), 10.79 (s, 1H), 10.16 (s, 1H), 9.00 (s, 1H), 7.98 (d, J=8.7 Hz, 2H), 7.81 (dd, J=8.5, 7.2 Hz, 1H), 7.72 (d, J=8.6 Hz, 2H), 7.51 (d, J=8.5 Hz, 1H), 7.44 (d, J=7.4 Hz, 3H), 7.42-7.38 (m, 2H), 7.34-7.28 (m, 1H), 6.76 (d, J=9.1 Hz, 1H), 5.35 (ddd, J=12.4, 9.0, 3.9 Hz, 1H), 5.08 (dd, J=12.8, 5.5 Hz, 1H), 4.76 (d, J=11.9 Hz, 1H), 4.55 (d, J=11.8 Hz, 1H), 4.20 (t, J=6.4 Hz, 2H), 3.59-3.51 (m, 1H), 3.35 (ddt, J=17.1, 12.3, 6.2 Hz, 1H), 3.18-3.13 (m, 1H), 2.89 (d, J=4.8 Hz, 3H), 2.84 (d, J=4.9 Hz, 3H), 2.59 (dt, J=17.4, 3.4 Hz, 1H), 2.34 (t, J=7.4 Hz, 2H), 2.03 (dtd, J=13.0, 5.2, 2.2 Hz, 1H), 1.75 (q, J=6.9, 6.4 Hz, 2H), 1.68 (s, 3H), 1.59 (s, 3H), 1.46 (dq, J=15.1, 7.3, 6.7 Hz, 2H), 1.38-1.22 (m, 12H).

LCMS: 902 $[M+H]^+$.

Example 11 Synthesis of $N^1$-(5-(((S)-2-(dimethylamino)-1-phenylethyl)carbamoyl)-6,6-dimethyl-1,4,5,6-tetrahydropyrrolo[3,4-c]pyrazol-3-yl)-$N^4$-(8-((2-(2,6-dioxopiperidin-3-yl)-1,3-dioxoisoindolin-4-yl)oxy)octyl)terephthalamide (11)

(11)

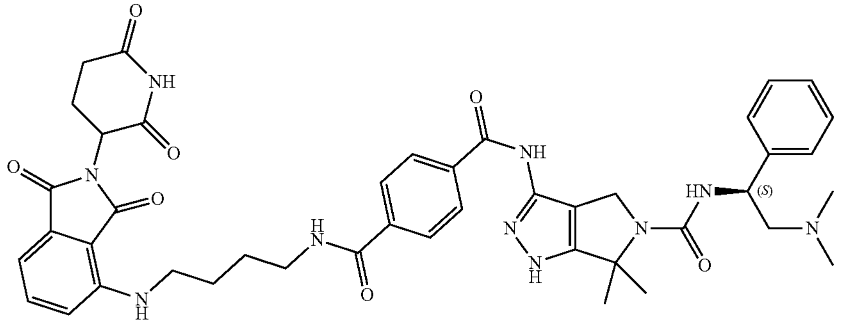

Compound 9 (15 mg, 52%) was obtained according to the synthetic route of compound 1 in Example 1 with 4-((4-aminobutyl)amino)-2-(2,6-dioxopiperidin-3-yl)isoindoline-1,3-dione.

LCMS: 817 $[M+H]^+$.

Example 12: Synthesis of N[1]-(5-(((S)-2-(dimethylamino)-1-phenylethyl)carbamoyl)-6,6-dimethyl-1,4,5,6-tetrahydropyrrolo[3,4-c]pyrazol-3-yl)-N[4]-(6-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-6-oxohexyl)terephthalamide (12)

(12)

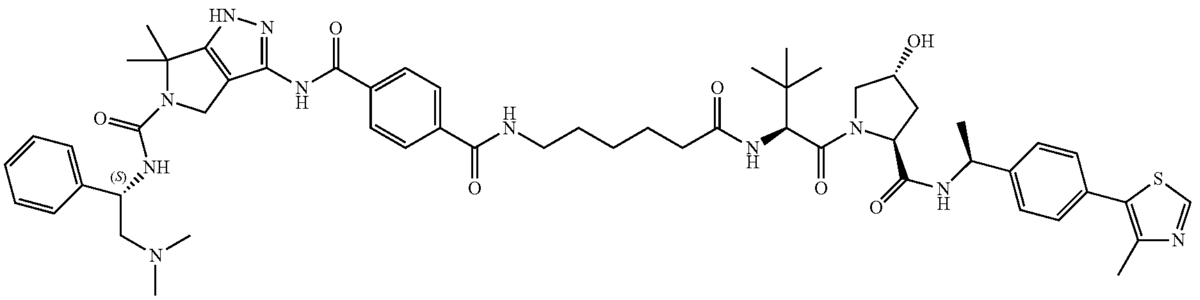

Compound 12 (8.6 mg, 28%) was obtained according to the synthetic route of compound 1 in Example 1 with (2S,4R)-1-((S)-2-(6-aminohexanamido)-3,3-dimethylbutanoyl)-4-hydroxy-N—((S)-1-(4-(4-methylthiazol-5-yl)phenyl)ethyl)pyrrolidine-2-carboxamide.

$^1$H NMR (500 MHz, DMSO-$d_6$) δ 11.08 (s, 1H), 9.00 (s, 1H), 8.60 (t, J=5.6 Hz, 1H), 8.38 (d, J=7.8 Hz, 1H), 8.09 (d, J=8.5 Hz, 2H), 7.96 (d, J=8.5 Hz, 2H), 7.80 (d, J=9.3 Hz, 1H), 7.65 (s, 1H), 7.48-7.42 (m, 4H), 7.42-7.38 (m, 4H), 7.34-7.28 (m, 1H), 6.77 (d, J=9.2 Hz, 1H), 5.36 (ddd, J=12.5, 9.1, 3.9 Hz, 2H), 4.92 (t, J=7.2 Hz, 1H), 4.78 (d, J=11.8 Hz, 1H), 4.58 (d, J=11.9 Hz, 2H), 4.53 (d, J=9.3 Hz, 1H), 4.43 (t, J=8.0 Hz, 1H), 4.29 (t, J=3.6 Hz, 1H), 3.66-3.50 (m, 5H), 3.35 (td, J=8.6, 4.2 Hz, 1H), 3.27 (q, J=6.5 Hz, 2H), 2.89 (d, J=4.8 Hz, 3H), 2.85 (d, J=4.8 Hz, 3H), 2.46 (s, 3H), 2.27 (dq, J=13.3, 6.9, 6.1 Hz, 1H), 2.15 (tdd, J=14.3, 8.2, 5.5 Hz, 2H), 2.02 (ddd, J=11.1, 7.8, 2.7 Hz, 1H), 1.80 (td, J=8.4, 4.2 Hz, 1H), 1.69 (s, 3H), 1.60 (s, 3H), 1.38 (d, J=7.0 Hz, 3H), 0.94 (s, 9H).

LCMS: 1030 $[M+H]^+$.

Example 13: Synthesis of N[1]-(5-(((S)-2-(dimethylamino)-1-phenylethyl)carbamoyl)-6,6-dimethyl-1,4,5,6-tetrahydropyrrolo[3,4-c]pyrazol-3-yl)-N[4]-(6-(2-(2,6-dioxopiperidin-3-yl)-1,3-dioxoisoindolin-4-yl)hexyl)terephthalamide (13)

(13)

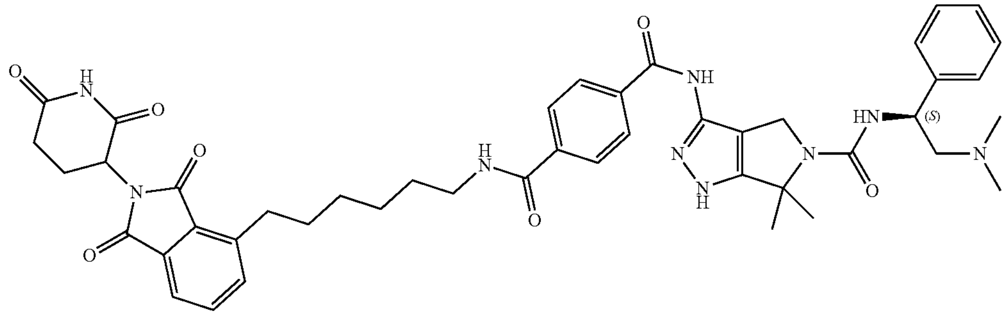

Compound 13 (12 mg, 48%) was obtained according to the synthetic route of compound 1 in Example 1 with 4-(6-aminohexyl)-2-(2,6-dioxopiperidin-3-yl)isoindoline-1,3-dione.

$^1$H NMR (500 MHz, DMSO-$d_6$) δ 11.12 (s, 1H), 11.08 (s, 1H), 9.05 (s, 1H), 8.60 (t, J=5.6 Hz, 1H), 8.09 (d, J=8.5 Hz, 2H), 7.96 (d, J=8.5 Hz, 2H), 7.80-7.74 (m, 2H), 7.71 (dd, J=6.9, 1.9 Hz, 1H), 7.45 (d, J=7.3 Hz, 2H), 7.40 (t, J=7.7 Hz, 2H), 7.35-7.29 (m, 1H), 6.77 (d, J=9.1 Hz, 1H), 5.36 (ddd, J=12.6, 9.1, 3.9 Hz, 1H), 5.13 (dd, J=12.7, 5.5 Hz, 1H), 4.78 (d, J=11.9 Hz, 1H), 4.58 (d, J=11.9 Hz, 1H), 3.56 (td, J=12.9, 2.7 Hz, 1H), 3.36 (ddd, J=12.8, 8.8, 4.0 Hz, 1H), 3.27 (q, J=6.6 Hz, 2H), 3.09-2.99 (m, 2H), 2.89 (d, J=4.7 Hz, 3H), 2.86 (s, 3H), 2.65-2.52 (m, 2H), 2.06 (dp, J=10.5, 3.3 Hz, 1H), 1.69 (s, 3H), 1.60 (s, 5H), 1.55 (t, J=7.0 Hz, 2H), 1.42-1.33 (m, 4H).

LCMS: 830 $[M+H]^+$.

Example 14: Synthesis of N[1]-(5-(((S)-2-(dimethylamino)-1-phenylethyl)carbamoyl)-6,6-dimethyl-1,4,5,6-tetrahydropyrrolo[3,4-c]pyrazol-3-yl)-N[4]-(2-(2-(2-(2-((2-(2,6-dioxopiperidin-3-yl)-1,3-dioxo-2,3-dihydro-1H-benzo[de]isoquinolin-4-yl)oxy)ethoxy)ethoxy)ethoxy)ethyl)terephthalamide (14)

(14)

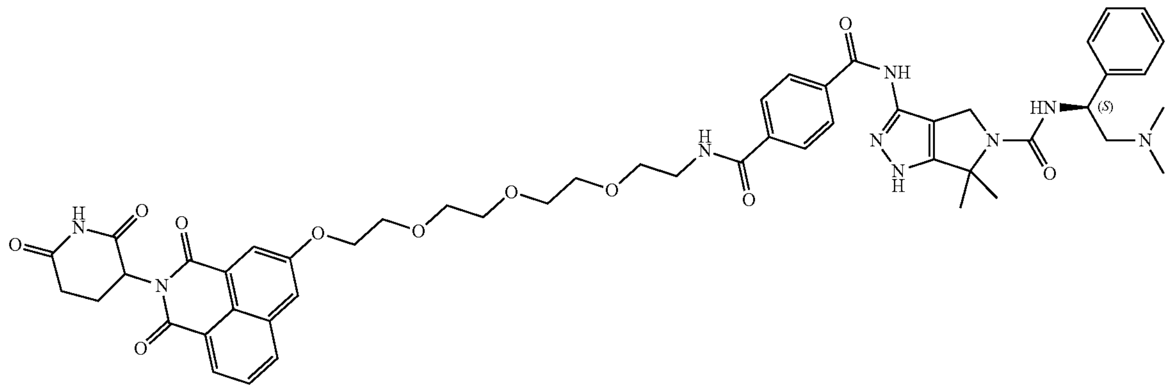

Compound 14 (5 mg, 16%) was obtained according to the synthetic route of compound 1 in Example 1 with 4-(2-(2-(2-(2-aminoethoxy)ethoxy)ethoxy)ethoxy)-2-(2,6-dioxopiperidin-3-yl)-1H-benzo[de]isoquinoline-1,3(2H)-dione.

$^1$H NMR (500 MHz, DMSO-$d_6$) δ 11.07 (s, 1H), 11.02 (s, 1H), 9.01 (s, 1H), 8.67 (t, J=5.6 Hz, 1H), 8.46-8.26 (m, 2H), 8.14-8.06 (m, 2H), 8.03-7.93 (m, 4H), 7.84 (dt, J=11.0, 7.8 Hz, 1H), 7.48-7.37 (m, 4H), 7.33-7.26 (m, 1H), 6.76 (d, J=9.2 Hz, 1H), 5.83 (dt, J=11.9, 6.0 Hz, 1H), 5.36 (td, J=10.6, 9.1, 3.9 Hz, 1H), 4.78 (d, J=11.8 Hz, 1H), 4.57 (d, J=11.8 Hz, 1H), 4.40-4.21 (m, 2H), 3.85 (d, J=4.2 Hz, 2H), 3.63 (dt, J=5.7, 2.5 Hz, 2H), 3.56 (dt, J=8.2, 5.1 Hz, 10H), 3.44 (t, J=5.8 Hz, 2H), 2.89 (d, J=4.7 Hz, 3H), 2.84 (d, J=4.7 Hz, 3H), 2.65-2.54 (m, 2H), 2.06 (d, J=19.3 Hz, 1H), 1.69 (s, 3H), 1.60 (s, 3H).

LCMS: 972 $[M+H]^+$.

Example 15: Synthesis of N[1]-(5-(((S)-2-(dimethylamino)-1-phenylethyl)carbamoyl)-6,6-dimethyl-1,4,5,6-tetrahydropyrrolo[3,4-c]pyrazol-3-yl)-N[4]-(2-(3-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-3-oxopropoxy)ethyl)terephthalamide (15)

(15)

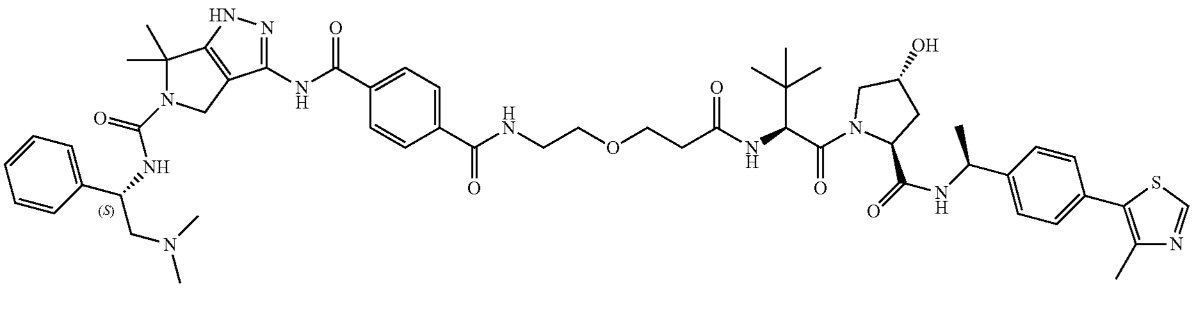

Compound 15 (11.7 mg, 33%) was obtained according to the synthetic route of compound 1 in Example 1 with (2S,4R)-1-((S)-2-(3-(2-aminoethoxy)propanamido)-3,3-dimethylbutanoyl)-4-hydroxy-N—(((S)-1-(4-(4-methylthiazol-5-yl)phenyl)ethyl)pyrrolidine-2-carboxamide.

$^1$H NMR (500 MHz, DMSO-$d_6$) δ 11.09 (s, 1H), 8.99 (s, 2H), 8.66 (t, J=5.7 Hz, 1H), 8.39 (d, J=7.8 Hz, 1H), 8.10 (d, J=8.5 Hz, 2H), 7.99 (d, J=8.5 Hz, 2H), 7.90 (d, J=9.3 Hz, 1H), 7.47-7.42 (m, 4H), 7.42-7.35 (m, 4H), 7.32-7.27 (m, 1H), 6.77 (d, J=9.1 Hz, 1H), 5.36 (ddd, J=12.6, 9.1, 3.9 Hz, 1H), 4.91 (p, J=7.0 Hz, 1H), 4.78 (d, J=11.9 Hz, 1H), 4.56 (dd, J=19.3, 10.6 Hz, 2H), 4.44 (t, J=8.1 Hz, 1H), 4.29 (dd, J=4.7, 2.4 Hz, 1H), 3.72-3.50 (m, 8H), 3.45 (q, J=5.5 Hz, 2H), 2.89 (d, J=4.8 Hz, 3H), 2.84 (d, J=4.8 Hz, 3H), 2.61-2.53 (m, 1H), 2.46 (s, 3H), 2.42-2.35 (m, 1H), 2.11-1.99 (m, 1H), 1.79 (ddd, J=13.0, 8.6, 4.5 Hz, 1H), 1.69 (s, 3H), 1.60 (s, 3H), 1.36 (d, J=7.0 Hz, 3H), 0.93 (s, 9H).

LCMS: 1032 $[M+H]^+$.

Example 16: Synthesis of N—((S)-2-(dimethylamino)-1-phenylethyl)-3-(4-(4-((2-(2,6-dioxopiperidin-3-yl)-1,3-dioxoisoindolin-4-yl)amino)butanamido)benzamido)-6,6-dimethyl-4,6-dihydropyrrolo[3,4-c]pyrazole-5(1H)-carboxamide (16)

(16)

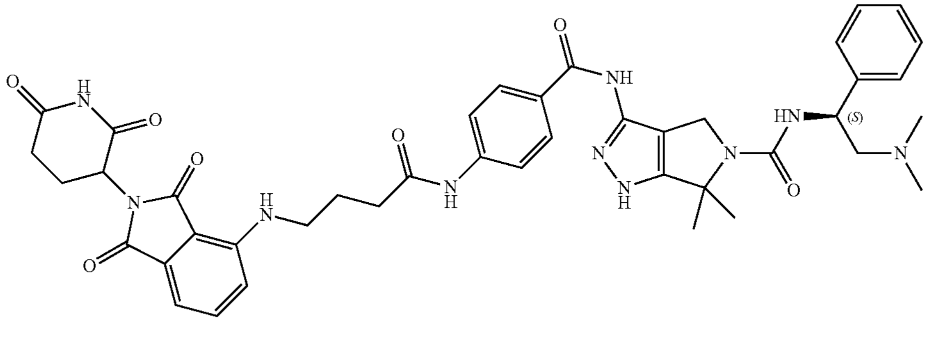

Compound 16 (9.5 mg, 35%) was obtained according to the synthetic route of compound 10 in Example 10 with 4-42-(2,6-dioxopiperidin-3-yl)-1,3-dioxoisoindolin-4-yl)amino)butanoic acid.

LCMS: 803 $[M+H]^+$.

Example 17: Synthesis of N—((S)-2-(dimethylamino)-1-phenylethyl)-3-(4-(6-(2-(2,6-dioxopiperidin-3-yl)-1-oxoisoindolin-4-yl)hex-5-ynamido)benzamido)-6,6-dimethyl-4,6-dihydropyrrolo[3,4-c]pyrazole-5(1H)-carboxamide (17)

(17)

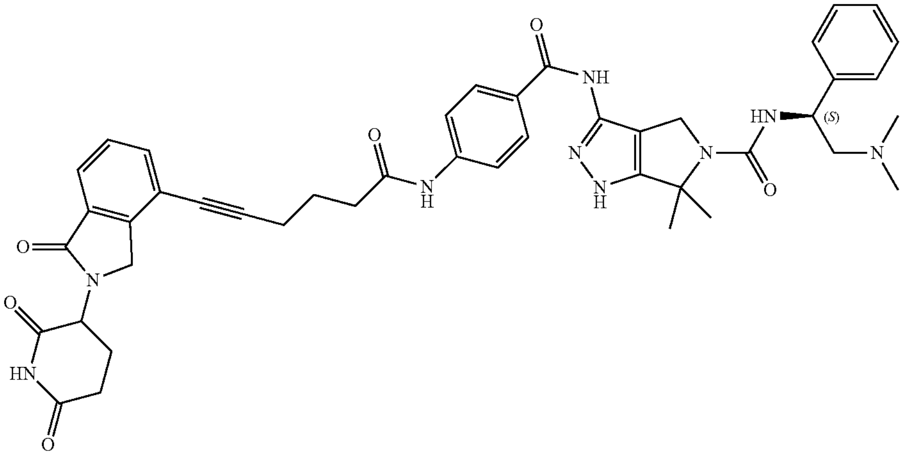

Compound 17 (5.2 mg, 19%) was obtained according to the synthetic route of compound 10 in Example 10 with 6-(2-(2,6-dioxopiperidin-3-yl)-1-oxoisoindolin-4-yl)hex-5-ynoic acid.

$^1$H NMR (500 MHz, DMSO-$d_6$) δ 12.42 (s, 1H), 11.00 (s, 1H), 10.76 (s, 1H), 10.26 (s, 1H), 7.98 (d, J=8.4 Hz, 2H), 7.72 (dd, J=7.9, 3.5 Hz, 3H), 7.65 (t, J=9.1 Hz, 2H), 7.53 (t, J=7.6 Hz, 1H), 7.40 (d, J=7.6 Hz, 2H), 7.33 (t, J=7.5 Hz, 2H), 7.24 (d, J=8.3 Hz, 1H), 5.14 (dd, J=13.3, 5.1 Hz, 1H), 5.01 (s, 1H), 4.63-4.53 (m, 1H), 4.49 (d, J=17.9 Hz, 1H), 4.35 (d, J=7.7 Hz, 1H), 2.92 (ddd, J=17.3, 13.6, 5.4 Hz, 1H), 2.58 (q, J=7.3 Hz, 7H), 2.04-1.98 (m, 1H), 1.93 (td, J=8.4, 7.2, 4.9 Hz, 3H), 1.66 (s, 3H), 1.58 (s, 3H).

LCMS: 798 $[M+H]^+$.

Example 18: Synthesis of $N^1$-(5-(((S)-2-(dimethylamino)-1-phenylethyl)carbamoyl)-6,6-dimethyl-1,4,5,6-tetrahydropyrrolo[3,4-c]pyrazol-3-yl)-$N^4$-(3-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-3-oxopropyl)terephthalamide (18)

(18)

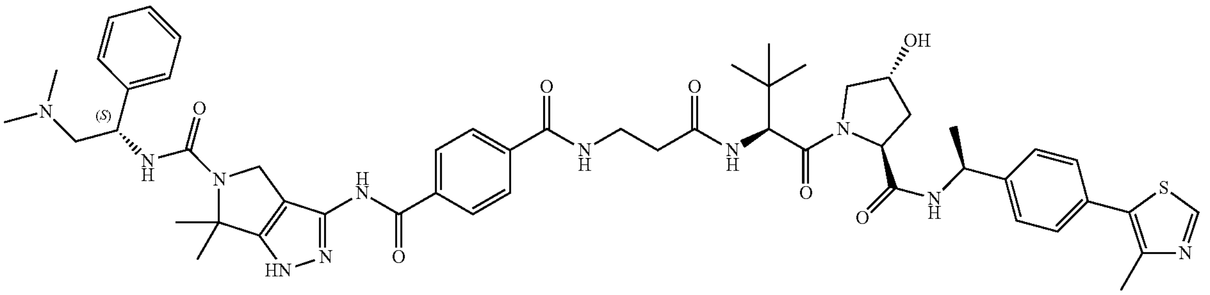

Compound 18 (3.6 mg) was obtained according to the synthetic route of compound 1 in Example 1 with (2S,4R)-1-((S)-2-(3-aminopropanamido)-3,3-dimethylbutanoyl)-4-hydroxy-N—((S)-1-(4-(4-methylthiazol-5-yl)phenyl)ethyl) pyrrolidine-2-carboxamide.

$^1$H NMR (500 MHz, DMSO-$d_6$) δ 12.61 (s, 1H), 11.05 (s, 1H), 8.99 (s, 1H), 8.68 (s, 1H), 8.42 (d, J=7.8 Hz, 1H), 8.11 (d, J=7.9 Hz, 2H), 7.98 (d, J=8.7 Hz, 2H), 7.50-7.20 (m, 9H), 6.75 (s, 1H), 5.33 (s, 1H), 5.17 (s, 1H), 4.91 (q, J=7.4 Hz, 1H), 4.82 (d, J=11.8 Hz, 1H), 4.55 (dd, J=14.4, 10.4 Hz, 2H), 4.45 (t, J=8.0 Hz, 1H), 4.29 (s, 1H), 3.63 (d, J=4.4 Hz, 2H), 3.50 (ddd, J=29.3, 13.5, 6.6 Hz, 2H), 2.79 (s, 6H), 2.59 (dt, J=14.7, 7.4 Hz, 1H), 2.46 (s, 3H), 2.09-1.98 (m, 1H), 1.80 (ddd, J=12.9, 8.5, 4.7 Hz, 1H), 1.69 (s, 3H), 1.61 (s, 3H), 1.38 (d, J=7.0 Hz, 3H), 0.94 (s, 9H).

LCMS: 988 [M+H]$^+$.

Example 19: Synthesis of N$^1$-(5-(((S)-2-(dimethylamino)-1-phenylethyl)carbamoyl)-6,6-dimethyl-1,4,5,6-tetrahydropyrrolo[3,4-c]pyrazol-3-yl)-N$^4$-(2-(2-((2-(2,6-dioxopiperdin-3-yl)-1,3-dioxoisoindolin-4-yl)amino)ethoxy)ethyl)terephthalamide (19)

(19)

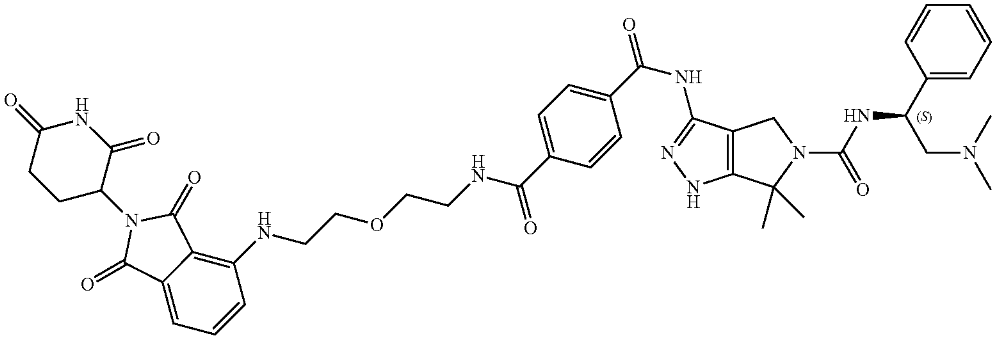

Compound 19 (5.9 mg, 21%) was obtained according to the synthetic route of compound 1 in Example 1 with 4-((2-(2-aminoethoxy)ethyl)amino)-2-(2,6-dioxopiperidin-3-yl)isoindoline-1,3-dione.

$^1$H NMR (500 MHz, DMSO-$d_6$) δ 12.52 (s, 1H), 11.09 (d, J=20.2 Hz, 2H), 9.12 (s, 1H), 8.69 (t, J=5.6 Hz, 1H), 8.47 (s, 1H), 8.08 (d, J=8.3 Hz, 2H), 7.96 (d, J=8.0 Hz, 2H), 7.57 (dd, J=8.6, 7.1 Hz, 1H), 7.43 (d, J=7.5 Hz, 2H), 7.37 (t, J=7.6 Hz, 2H), 7.29 (d, J=7.4 Hz, 1H), 7.17 (d, J=8.6 Hz, 1H), 7.03 (d, J=7.0 Hz, 1H), 6.64 (t, J=5.8 Hz, 1H), 5.24 (s, 1H), 5.05 (dd, J=12.8, 5.5 Hz, 1H), 4.72 (s, 1H), 4.58 (d, J=11.8 Hz, 1H), 3.64 (dt, J=26.2, 5.6 Hz, 4H), 3.49 (dq, J=12.0, 5.7 Hz, 4H), 3.16 (d, J=16.7 Hz, 2H), 2.89 (ddd, J=17.0, 13.9, 5.4 Hz, 2H), 2.65-2.53 (m, 1H), 2.02 (dtd, J=12.6, 5.2, 2.2 Hz, 1H), 1.68 (s, 3H), 1.60 (s, 3H).

LCMS: 833 [M+H]$^+$.

Example 20: Synthesis of N$^1$-(5-(((S)-2-(dimethylamino)-1-phenylethyl)carbamoyl)-6,6-dimethyl-1,4,5,6-tetrahydropyrrolo[3,4-c]pyrazol-3-yl)-N$^4$-(5-(((S)-1-((2S,4R)-4-hydroxy-2-(((S)-1-(4-(4-methylthiazol-5-yl)phenyl)ethyl)carbamoyl) pyrrolidin-1-yl)-3,3-dimethyl-1-oxobutan-2-yl) amino)-5-oxopentyl)terephthalamide (20)

(20)

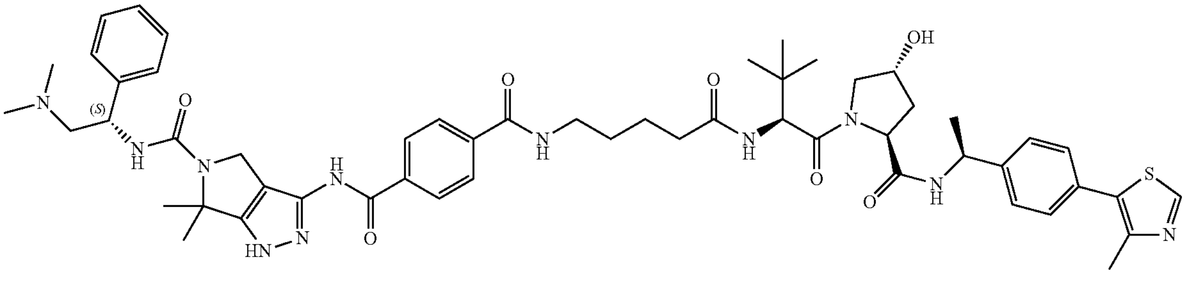

Compound 20 (9.1 mg, 28%) was obtained according to the synthetic route of compound 1 in Example 1 with (2S,4R)-1-((S)-2-(5-aminopentanamido)-3,3-dimethylbutanoyl)-4-hydroxy-N—((S)-1-(4-(4-methylthiazol-5-yl)phenyl)ethyl)pyrrolidine-2-carboxamide.

$^1$H NMR (500 MHz, DMSO-$d_6$) δ 12.49 (s, 1H), 11.03 (s, 1H), 8.99 (s, 1H), 8.62 (s, OH), 8.38 (d, J=7.8 Hz, 1H), 8.10 (d, J=8.1 Hz, 2H), 7.95 (d, J=8.0 Hz, 2H), 7.82 (d, J=9.3 Hz, 1H), 7.46-7.42 (m, 2H), 7.41-7.36 (m, 4H), 7.32 (t, J=7.7 Hz, 2H), 7.22 (t, J=7.3 Hz, 1H), 6.34 (s, 1H), 5.11 (d, J=3.6 Hz, 1H), 4.93 (q, J=7.2 Hz, 1H), 4.59 (s, 2H), 4.53 (d, J=9.3 Hz, 1H), 4.43 (t, J=8.0 Hz, 1H), 4.29 (s, 1H), 3.70-3.54 (m, 2H), 2.46 (s, 3H), 2.30 (q, J=14.3, 7.8 Hz, 4H), 2.17 (dd, J=14.0, 7.5 Hz, 2H), 2.02 (td, J=8.9, 4.4 Hz, 1H), 1.81 (td, J=8.4, 4.2 Hz, 1H), 1.66 (s, 3H), 1.60-1.48 (m, 7H), 1.38 (d, J=7.0 Hz, 3H), 0.95 (s, 9H).

LCMS: 1016 $[M+H]^+$.

Example 21: Synthesis of $N^1$-(5-(((S)-2-(dimethylamino)-1-phenylethyl)carbamoyl)-6,6-dimethyl-1,4,5,6-tetrahydropyrrolo[3,4-c]pyrazol-3-yl)-$N^4$-(5-((2-(2,6-dioxopiperidin-3-yl)-1,3-dioxoisoindolin-5-yl)amino)pentyl)terephthalamide (21)

(21)

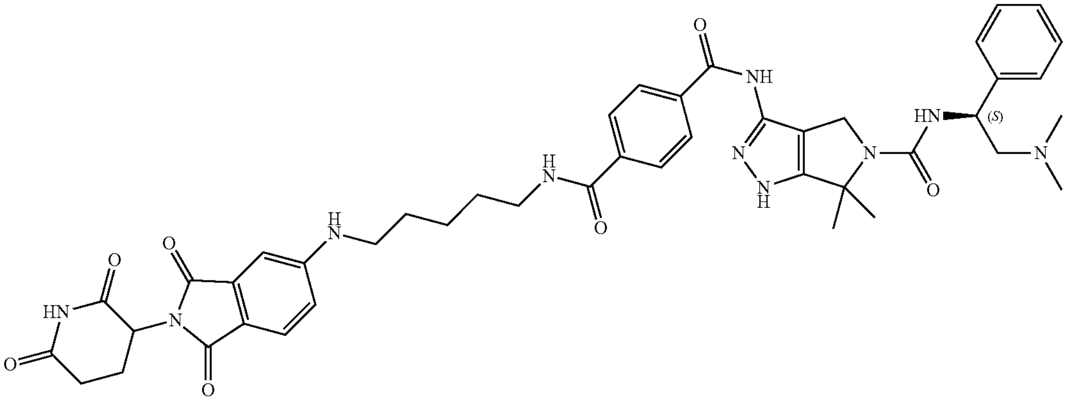

Compound 21 (8.5 mg, 30%) was obtained according to the synthetic route of compound 1 in Example 1 with 5-((5-aminopentyl)amino)-2-(2,6-dioxopiperidin-3-yl)isoindoline-1,3-dione.

$^1$H NMR (500 MHz, DMSO-$d_6$) δ 11.07 (d, J=3.8 Hz, 2H), 9.01 (s, 1H), 8.63 (t, J=5.7 Hz, 1H), 8.09 (d, J=8.2 Hz, 2H), 7.96 (d, J=8.5 Hz, 2H), 7.57 (d, J=8.4 Hz, 1H), 7.45 (d, J=7.4 Hz, 2H), 7.40 (t, J=7.7 Hz, 2H), 7.34-7.27 (m, 1H), 6.96 (d, J=2.1 Hz, 1H), 6.86 (dd, J=8.4, 2.2 Hz, 1H), 6.77 (d, J=9.2 Hz, 1H), 5.36 (ddd, J=12.5, 9.1, 3.9 Hz, 1H), 5.03 (dd, J=12.7, 5.5 Hz, 1H), 4.78 (d, J=11.9 Hz, 1H), 4.58 (d, J=11.9 Hz, 1H), 3.64-3.42 (m, 10H), 3.21-3.15 (m, 2H), 2.89 (d, J=4.9 Hz, 3H), 2.85 (d, J=4.8 Hz, 3H), 2.58 (dt, J=20.4, 4.2 Hz, 1H), 2.06-1.95 (m, 1H), 1.69 (s, 3H), 1.60 (s, 3H), 1.45 (td, J=8.4, 4.2 Hz, 2H).

LCMS: 831 $[M+H]^+$.

Example 22: Synthesis of N1-(5-(((S)-2-(dimethylamino)-1-phenylethyl)carbamoyl)-6,6-dimethyl-1,4,5,6-tetrahydropyrrolo[3,4-c]pyrazol-3-yl)-N4-(7-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-7-oxoheptyl)terephthalamide (22)

(22)

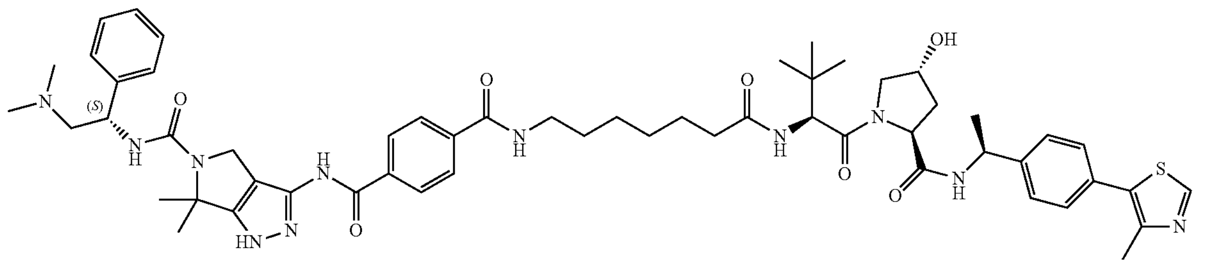

Compound 22 (6.9 mg, 20%) was obtained according to the synthetic route of compound 1 in Example 1 with (2S,4R)-1-((S)-2-(7-aminoheptanamido)-3,3-dimethylbutanoyl)-4-hydroxy-N—((S)-1-(4-(4-methylthiazol-5-yl)phenyl)ethyl)pyrrolidine-2-carboxamide.

$^1$H NMR (500 MHz, DMSO-$d_6$) δ 12.47 (s, 1H), 11.02 (s, 1H), 8.99 (s, 1H), 8.59 (s, 1H), 8.37 (d, J=7.8 Hz, 1H), 8.09 (d, J=8.0 Hz, 2H), 7.95 (d, J=8.0 Hz, 2H), 7.80 (d, J=9.3 Hz, 1H), 7.46-7.42 (m, 2H), 7.38 (d, J=8.1 Hz, 4H), 7.30 (t, J=7.6 Hz, 2H), 7.20 (t, J=7.3 Hz, 1H), 6.27 (s, 1H), 5.10 (d, J=3.5 Hz, 1H), 4.92 (p, J=8.9, 8.1 Hz, 2H), 4.57 (s, 1H), 4.53 (d, J=9.3 Hz, 1H), 4.43 (t, J=8.0 Hz, 1H), 4.29 (s, 1H), 3.62 (d, J=4.1 Hz, 2H), 3.27 (d, J=6.9 Hz, 2H), 2.46 (s, 3H), 2.27 (dd, J=14.3, 7.5 Hz, 1H), 2.16-2.11 (m, 1H), 2.05-1.96 (m, 1H), 1.80 (ddd, J=12.8, 8.5, 4.6 Hz, 1H), 1.66 (s, 3H), 1.58 (s, 3H), 1.51 (tt, J=14.5, 7.2 Hz, 4H), 1.37 (d, J=7.0 Hz, 3H), 1.31 (s, 4H), 0.94 (s, 9H).

LCMS: 1044 $[M+H]^+$.

Example 23: Synthesis of N1-(5-(((S)-2-(dimethylamino)-1-phenylethyl)carbamoyl)-6,6-dimethyl-1,4,5,6-tetrahydropyrrolo[3,4-c]pyrazol-3-yl)-N4-(8-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-8-oxooctyl)terephthalamide (23)

Compound 23 (12.3 mg, 36%) was obtained according to the synthetic route of compound 1 in Example 1 with (2S,4R)-1-((S)-2-(8-aminooctanamido)-3,3-dimethylbutanoyl)-4-hydroxy-N—((S)-1-(4-(4-methylthiazol-5-yl)phenyl)ethyl)pyrrolidine-2-carboxamide.

$^1$H NMR (500 MHz, DMSO-$d_6$) δ 12.53 (s, 1H), 11.09 (s, 1H), 9.20 (s, 1H), 8.99 (s, 1H), 8.62 (t, J=5.7 Hz, 1H), 8.38 (d, J=7.8 Hz, 1H), 8.10 (d, J=8.4 Hz, 2H), 7.96 (d, J=8.1 Hz, 2H), 7.79 (d, J=9.3 Hz, 1H), 7.44 (dd, J=7.8, 5.7 Hz, 4H), 7.42-7.36 (m, 4H), 7.33-7.27 (m, 1H), 6.77 (d, J=9.1 Hz, 1H), 5.36 (ddd, J=12.5, 9.1, 3.9 Hz, 1H), 5.11 (d, J=3.6 Hz, 1H), 4.98-4.88 (m, 1H), 4.80 (d, J=11.8 Hz, 1H), 4.57 (d, J=11.9 Hz, 1H), 4.52 (d, J=9.3 Hz, 1H), 4.43 (t, J=8.0 Hz, 1H), 4.31-4.24 (m, 1H), 3.61 (t, J=3.9 Hz, 2H), 3.55 (t, J=12.5 Hz, 1H), 3.27 (q, J=6.7 Hz, 2H), 2.86 (d, J=19.3 Hz, 6H), 2.46 (s, 3H), 2.27 (dd, J=14.3, 7.4 Hz, 1H), 2.12 (ddd, J=14.0, 7.9, 6.1 Hz, 1H), 2.02 (ddd, J=10.8, 7.4, 2.7 Hz, 1H), 1.80 (ddd, J=12.9, 8.4, 4.6 Hz, 1H), 1.69 (s, 3H), 1.60 (s, 3H), 1.57-1.45 (m, 4H), 1.38 (d, J=7.0 Hz, 3H), 1.34-1.23 (m, 4H), 0.94 (s, 9H).

LCMS: 1058 $[M+H]^+$.

(23)

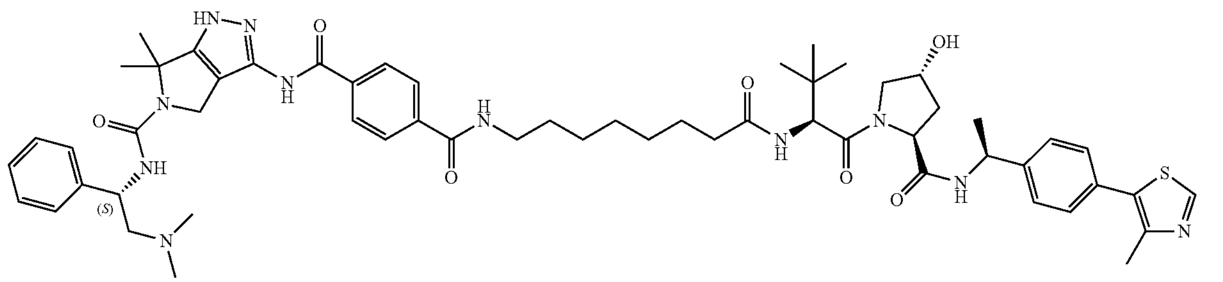

Example 24: Synthesis of N—((S)-2-(dimethylamino)-1-phenylethyl)-3-(4-((2S,4R)-4-hydroxy-2-(((S)-1-(4-(4-methylthiazol-5-yl)phenyl)ethyl)carbamoyl)pyrrolidine-1-carbonyl)benzamido)-6,6-dimethyl-4,6-dihydropyrrolo[3,4-c]pyrazole-5(1H)-carboxamide (24)

(24)

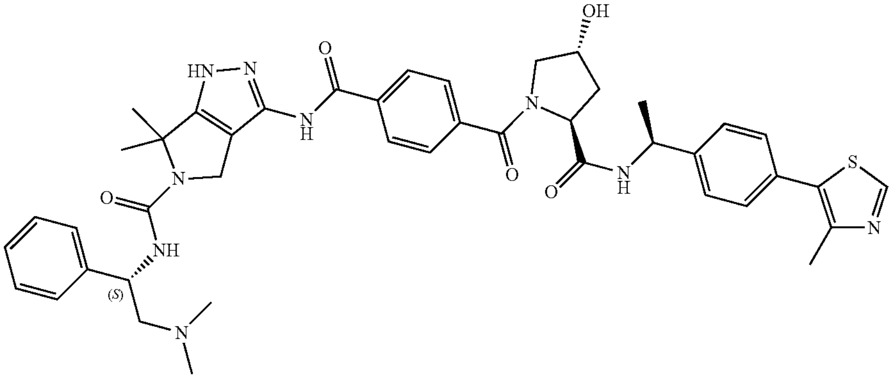

Compound 24 (3.6 mg) was obtained according to the synthetic route of compound 1 in Example 1 with (2S,4R)-4-hydroxy-N—((S)-1-(4-(4-methylthiazol-5-yl)phenyl)ethyl)pyrrolidine-2-carboxamide.

$^1$H NMR (500 MHz, DMSO-$d_6$) δ 12.49 (s, 1H), 11.05 (s, 1H), 8.99 (s, 1H), 8.51 (d, J=7.8 Hz, 1H), 8.10 (d, J=8.0 Hz, 2H), 7.68 (d, J=7.7 Hz, 2H), 7.45 (d, J=8.3 Hz, 2H), 7.43-7.37 (m, 4H), 7.33 (t, J=7.2 Hz, 2H), 7.29-7.20 (m, 1H), 5.05 (s, 1H), 4.99 (q, J=7.2 Hz, 1H), 4.68-4.48 (m, 2H), 4.26 (s, 1H), 3.73 (dd, J=10.9, 3.7 Hz, 1H), 3.27 (d, J=11.0 Hz, 1H), 2.46 (s, 3H), 2.44 (s, 1H), 2.22-2.15 (m, 1H), 1.93-1.81 (m, 1H), 1.67 (s, 3H), 1.59 (s, 3H), 1.43 (d, J=7.0 Hz, 3H).

LCMS: 804 $[M+H]^+$.

Example 25: Synthesis of N$^1$-(5-(((S)-2-(dimethylamino)-1-phenylethyl)carbamoyl)-6,6-dimethyl-1,4,5,6-tetrahydropyrrolo[3,4-c]pyrazol-3-yl)-N$^4$—((S)-14-((2S,4R)-4-hydroxy-2-(((S)-1-(4-(4-methylthiazol-5-yl)phenyl)ethyl)carbamoyl)pyrrolidine-1-carbonyl)-15,15-dimethyl-12-oxo-3,6,9-trioxa-13-azahexadecyl)terephthalamide (25)

(25)

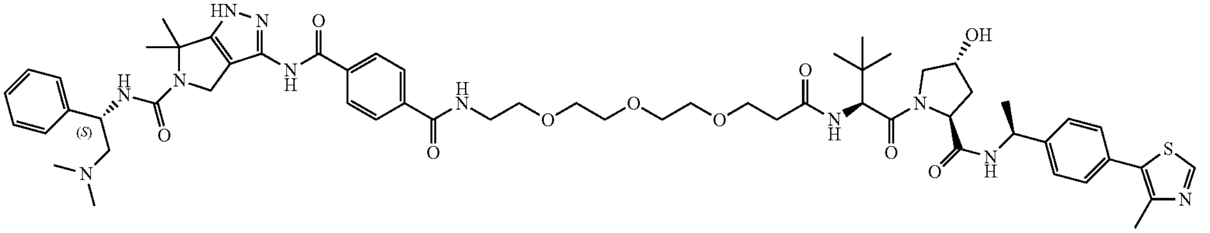

Compound 25 (7.2 mg, 19%) was obtained according to the synthetic route of compound 1 in Example 1 with (2S,4R)-1-((S)-1-amino-14-(tert-butyl)-12-oxo-3,6,9-trioxa-13-azapentadecan-15-oyl)-4-hydroxy-N—((S)-1-(4-(4-methylthiazol-5-yl)phenyl)ethyl)pyrrolidine-2-carboxamide.

$^1$H NMR (500 MHz, DMSO-$d_6$) δ 11.08 (s, 1H), 9.13-8.92 (m, 2H), 8.69 (t, J=5.6 Hz, 1H), 8.38 (d, J=7.8 Hz, 1H), 8.21-8.06 (m, 3H), 8.00-7.96 (m, 2H), 7.86 (d, J=9.3 Hz, 1H), 7.49-7.36 (m, 9H), 7.30 (td, J=6.8, 6.4, 1.5 Hz, 1H), 6.77 (d, J=9.2 Hz, 1H), 5.41-5.29 (m, 2H), 4.92 (t, J=7.3 Hz, 1H), 4.78 (d, J=11.9 Hz, 1H), 4.63-4.48 (m, 2H), 4.43 (t, J=8.0 Hz, 1H), 4.28 (s, 1H), 3.69-3.41 (m, 16H), 3.38-3.32 (m, 1H), 2.89 (d, J=4.8 Hz, 3H), 2.85 (d, J=4.8 Hz, 3H), 2.46 (s, 3H), 2.35 (dt, J=14.5, 6.1 Hz, 1H), 2.02 (dd, J=12.1, 8.7 Hz, 1H), 1.80 (td, J=8.4, 4.3 Hz, 1H), 1.69 (s, 3H), 1.60 (s, 3H), 1.38 (d, J=7.0 Hz, 3H), 0.94 (s, 9H).

LCMS: 1120 $[M+H]^+$.

Example 26: Synthesis of N[1]-(5-(((S)-2-(dimethylamino)-1-phenylethyl)carbamoyl)-6,6-dimethyl-1,4,5,6-tetrahydropyrrolo[3,4-c]pyrazol-3-yl)-N[4]-(2-(2-(2-((2-(2,6-dioxopiperidin-3-yl)-1,3-dioxoisoindolin-4-yl)amino)ethoxy)ethoxy)ethyl)terephthalamide (26)

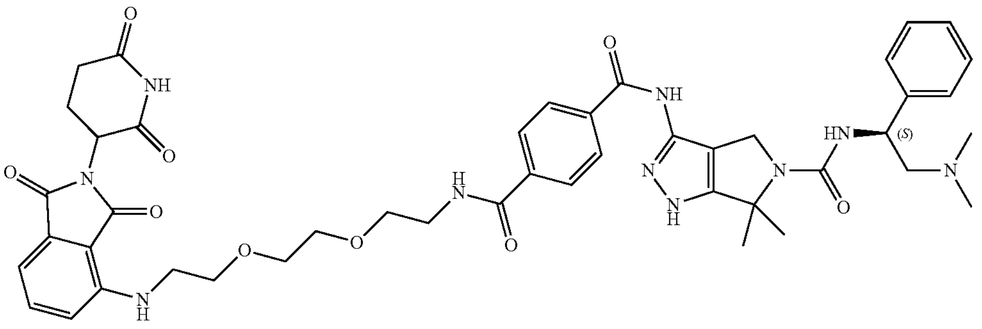

(26)

Compound 26 (14.7 mg, 49%) was obtained according to the synthetic route of compound 1 in Example 1 with 4-((2-(2-(2-aminoethoxy)ethoxy)ethyl)amino)-2-(2,6-dioxopiperidin-3-yl)isoindoline-1,3-dione.

$^1$H NMR (500 MHz, DMSO-$d_6$) δ 11.09 (d, J=9.6 Hz, 2H), 9.04 (s, 1H), 8.66 (t, J=5.6 Hz, 1H), 8.09 (d, J=8.5 Hz, 2H), 7.97 (d, J=8.5 Hz, 2H), 7.58 (dd, J=8.6, 7.0 Hz, 1H), 7.47-7.43 (m, 2H), 7.40 (dd, J=8.5, 6.8 Hz, 2H), 7.34-7.29 (m, 1H), 7.13 (d, J=8.6 Hz, 1H), 7.04 (d, J=7.0 Hz, 1H), 6.77 (d, J=9.2 Hz, 1H), 6.61 (t, J=5.9 Hz, 1H), 5.36 (ddd, J=12.5, 9.2, 3.8 Hz, 1H), 5.06 (dd, J=12.9, 5.4 Hz, 1H), 4.78 (d, J=11.9 Hz, 1H), 4.57 (d, J=11.9 Hz, 1H), 3.66-3.51 (m, 10H), 3.48-3.37 (m, 4H), 3.36 (ddd, J=12.6, 8.6, 4.0 Hz, 1H), 2.89 (d, J=4.6 Hz, 3H), 2.85 (d, J=4.7 Hz, 3H), 2.63-2.53 (m, 2H), 2.03 (ddd, J=10.6, 5.5, 3.0 Hz, 1H), 1.69 (s, 3H), 1.60 (s, 3H).

LCMS: 877 $[M+H]^+$.

Example 27: Synthesis of N[1]-(5-(((S)-2-(dimethylamino)-1-phenylethyl)carbamoyl)-6,6-dimethyl-1,4,5,6-tetrahydropyrrolo[3,4-c]pyrazol-3-yl)-N[4]-(3-((2-(2,6-dioxopiperidin-3-yl)-1,3-dioxo-2,3-dihydro-1H-benzo[de]isoquinolin-5-yl)oxy)propyl) terephthalamide (27)

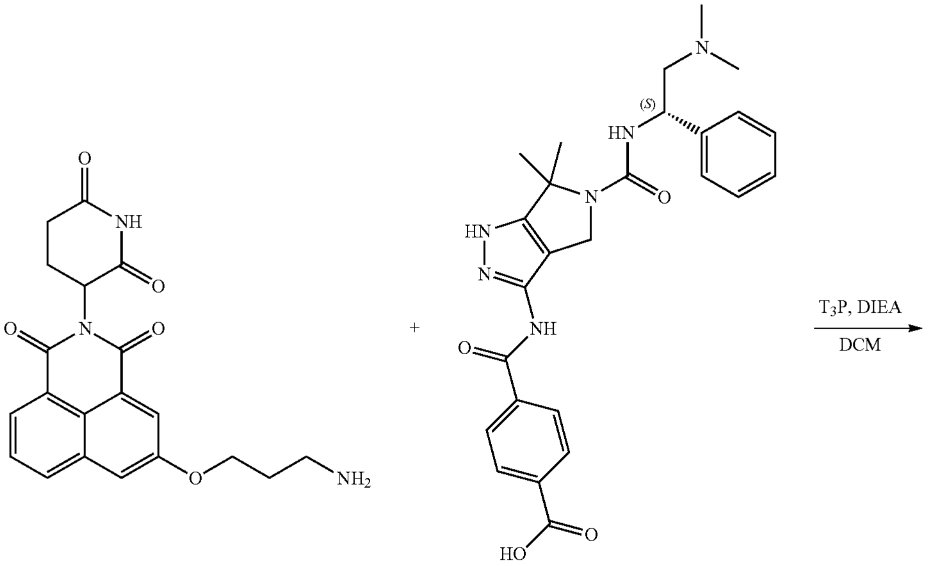

-continued

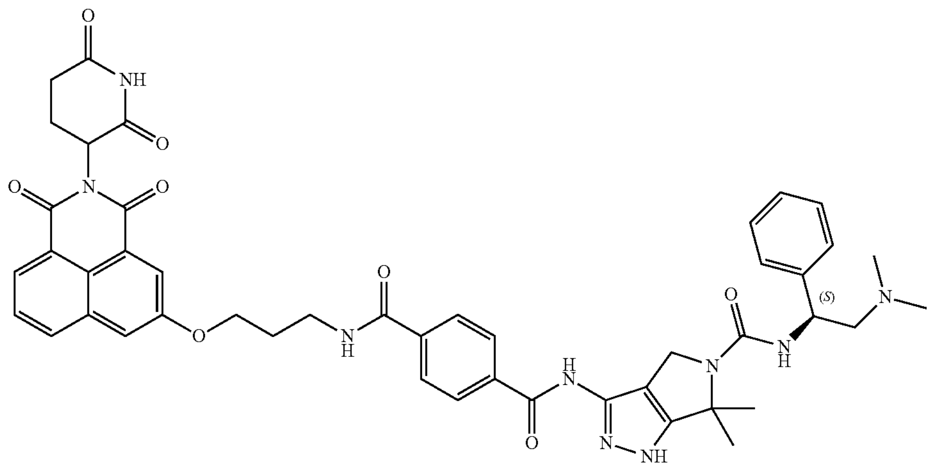

(27)

Compound 27 (7.5 mg) was obtained according to the synthetic route of compound 1 in Example 1 with 5-(3-aminopropoxy)-2-(2,6-dioxopiperidin-3-yl)-1H-benzo[de] isoquinoline-1,3(2H)-dione.

$^1$H NMR (500 MHz, DMSO-$d_6$) δ 11.00 (s, 1H), 10.95 (s, 1H), 8.96 (s, 1H), 8.70 (q, J=5.5 Hz, 1H), 8.36-8.20 (m, 2H), 8.07-7.99 (m, 3H), 7.97-7.88 (m, 4H), 7.78 (dt, J=10.3, 7.8 Hz, 1H), 7.39-7.29 (m, 4H), 7.27-7.20 (m, 1H), 6.69 (d, J=9.2 Hz, 1H), 5.76 (dt, J=12.2, 6.0 Hz, 1H), 5.28 (ddd, J=12.6, 9.1, 3.9 Hz, 1H), 4.71 (d, J=11.9 Hz, 1H), 4.50 (d, J=11.9 Hz, 1H), 4.25 (q, J=5.8 Hz, 2H), 3.51-3.44 (m, 4H), 3.31-3.22 (m, 1H), 2.81 (d, J=4.8 Hz, 3H), 2.77 (d, J=4.8 Hz, 3H), 2.57-2.47 (m, 2H), 2.05 (q, J=6.3 Hz, 2H), 1.98 (td, J=9.4, 4.1 Hz, 1H), 1.61 (s, 3H), 1.53 (s, 3H).

LCMS: 854 $[M+H]^+$.

Example 28: Synthesis of N$^1$-(5-(((S)-2-(dimethylamino)-1-phenylethyl)carbamoyl)-6,6-dimethyl-1,4,5,6-tetrahydropyrrolo[3,4-c]pyrazol-3-yl)-N$^4$-(6-((2-(2,6-dioxopiperidin-3-yl)-1,3-dioxo-2,3-dihydro-1H-benzo[de]isoquinolin-5-yl)oxy)hexyl) terephthalamide (28)

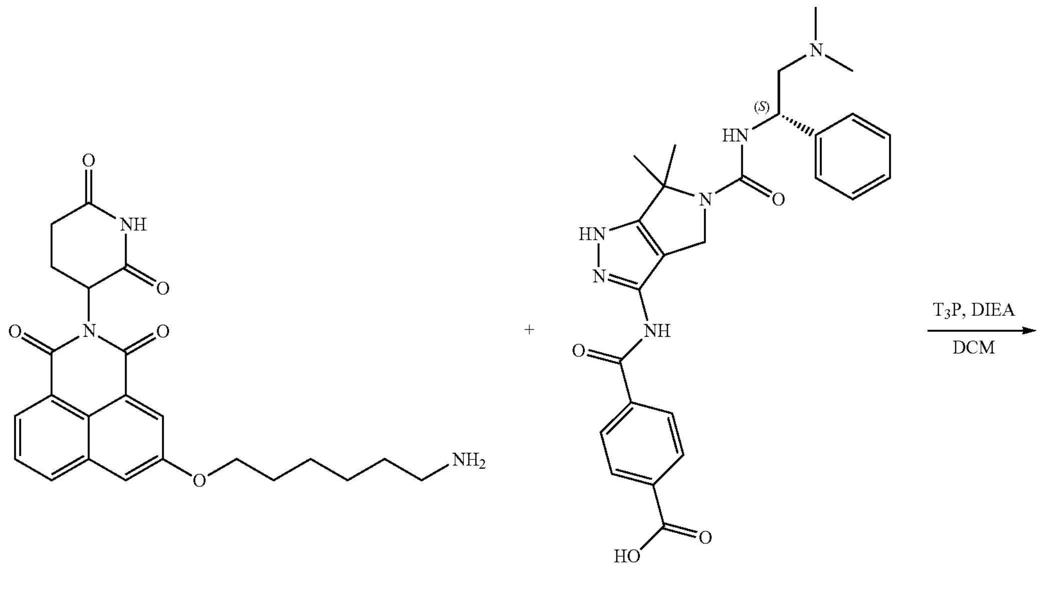

-continued

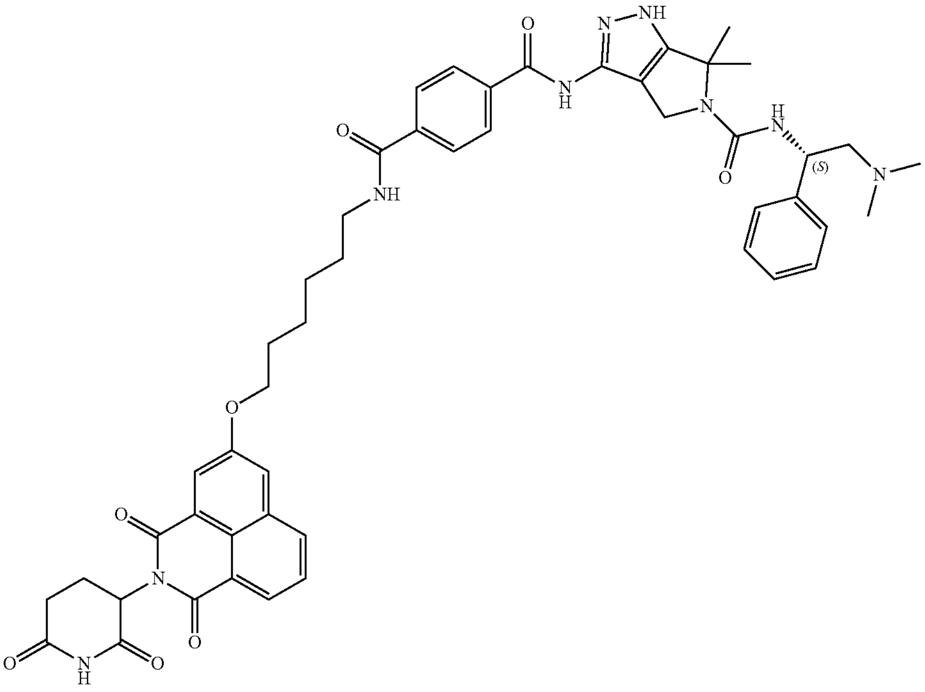

(28)

Compound 28 (6.9 mg) was obtained according to the synthetic route of compound 1 in Example 1 with 5-((6-aminohexyl)oxy)-2-(2,6-dioxopiperidin-3-yl)-1H-benzo[de]isoquinoline-1,3(2H)-dione.

$^1$H NMR (500 MHz, DMSO-$d_6$) δ 10.99 (s, 1H), 10.94 (s, 1H), 8.96 (s, 1H), 8.55 (s, 1H), 8.37-8.20 (m, 2H), 8.06-7.98 (m, 3H), 7.97-7.83 (m, 4H), 7.77 (q, J=8.5 Hz, 1H), 7.41-7.29 (m, 4H), 7.28-7.19 (m, 1H), 6.69 (d, J=9.1 Hz, 1H), 5.75 (dt, J=11.7, 5.9 Hz, 1H), 5.28 (ddd, J=12.6, 9.1, 3.9 Hz, 1H), 4.71 (d, J=11.9 Hz, 1H), 4.50 (d, J=11.9 Hz, 1H), 4.16 (q, J=6.4 Hz, 2H), 3.52-3.45 (m, 1H), 3.26 (d, J=22.8 Hz, 5H), 2.82 (d, J=4.7 Hz, 3H), 2.77 (d, J=4.8 Hz, 3H), 2.59-2.47 (m, 2H), 2.03-1.90 (m, 1H), 1.84-1.71 (m, 2H), 1.61 (s, 3H), 1.56-1.42 (m, 5H), 1.37 (s, 2H).

LCMS: 896 $[M+H]^+$.

Example 29: Synthesis of $N^1$-(5-(((S)-2-(dimethylamino)-1-phenylethyl)carbamoyl)-6,6-dimethyl-1,4,5,6-tetrahydropyrrolo[3,4-c]pyrazol-3-yl)-$N^4$-(2-(2-(2-((2-(2,6-dioxopiperidin-3-yl)-1,3-dioxo-2,3-dihydro-1H-benzo[de]isoquinolin-5-yl)oxy)ethoxy)ethoxy)ethyl)terephthalamide (29)

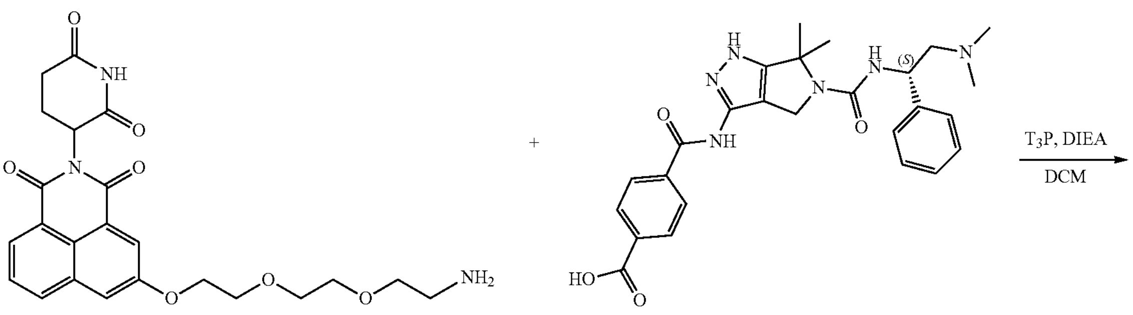

-continued

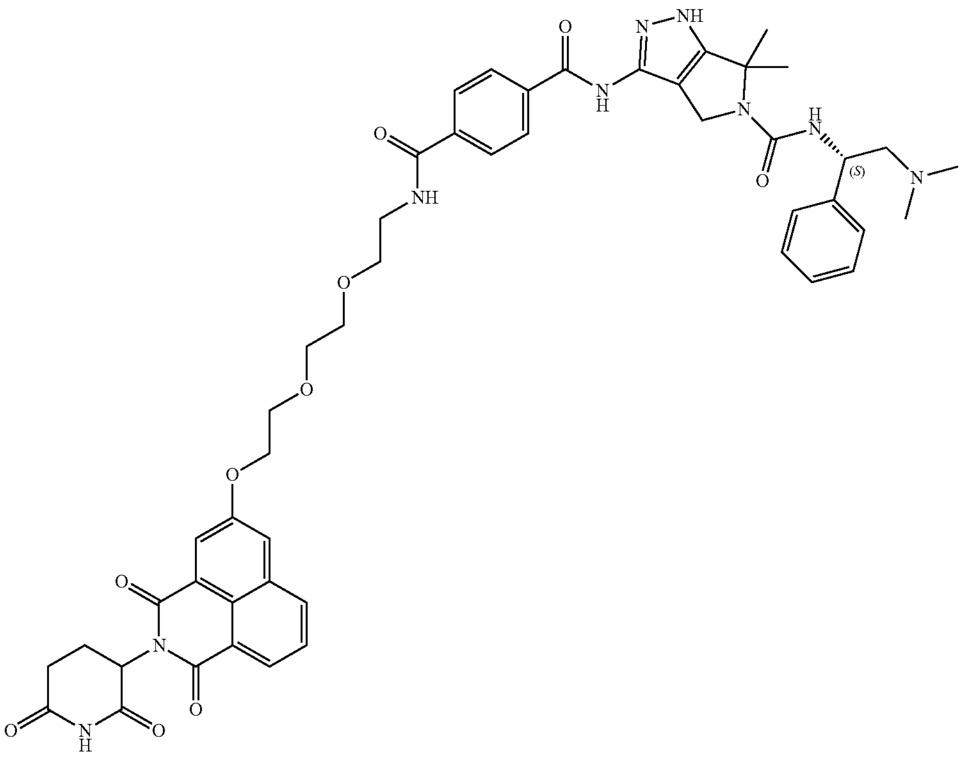

(29)

Compound 29 (4.5 mg) was obtained according to the synthetic route of compound 1 in Example 1 with 5-(2-(2-(2-aminoethoxy)ethoxy)ethoxy)-2-(2,6-dioxopiperidin-3-yl)-1H-benzo[de]isoquinoline-1,3(2H)-dione.

$^1$H NMR (500 MHz, DMSO-$d_6$) δ 10.98 (s, 1H), 10.94 (s, 1H), 8.98 (s, 1H), 8.61 (t, J=5.6 Hz, 1H), 8.38-8.16 (m, 2H), 8.08-7.86 (m, 7H), 7.75 (dt, J=10.5, 7.8 Hz, 1H), 7.45-7.28 (m, 4H), 7.23 (t, J=7.2 Hz, 1H), 6.68 (d, J=9.2 Hz, 1H), 5.75 (dt, J=11.7, 5.9 Hz, 1H), 5.28 (ddd, J=12.2, 9.2, 3.9 Hz, 1H), 4.69 (d, J=11.8 Hz, 1H), 4.54-4.40 (m, 1H), 4.27 (q, J=5.5 Hz, 2H), 3.79 (q, J=5.2 Hz, 2H), 3.64-3.43 (m, 9H), 3.41-3.35 (m, 2H), 2.79 (dd, J=22.8, 4.7 Hz, 6H), 2.61-2.46 (m, 2H), 1.97 (dd, J=11.9, 6.2 Hz, 1H), 1.61 (s, 3H), 1.53 (s, 3H).

LCMS: 928 $[M+H]^+$.

Example 30: Synthesis of N[1]-(5-(((S)-2-(dimethylamino)-1-phenylethyl)carbamoyl)-6,6-dimethyl-1,4,5,6-tetrahydropyrrolo[3,4-c]pyrazol-3-yl)-N4-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)terephthalamide (30)

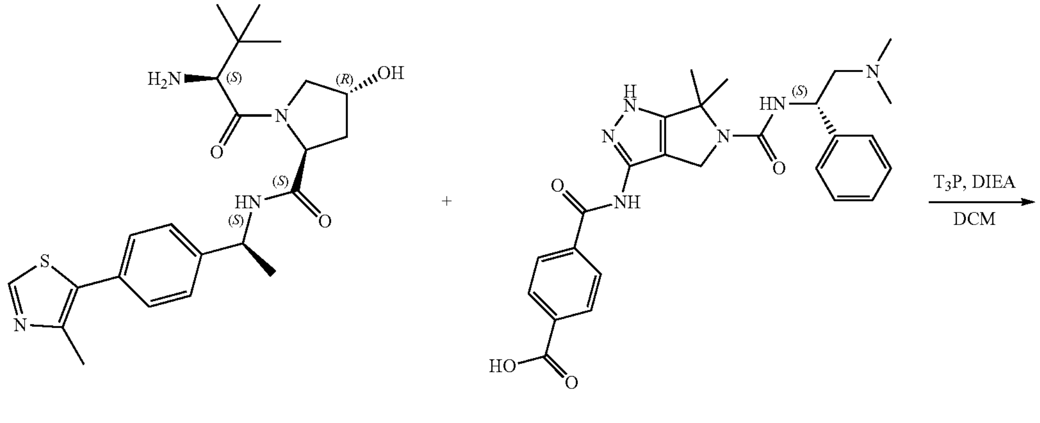

-continued

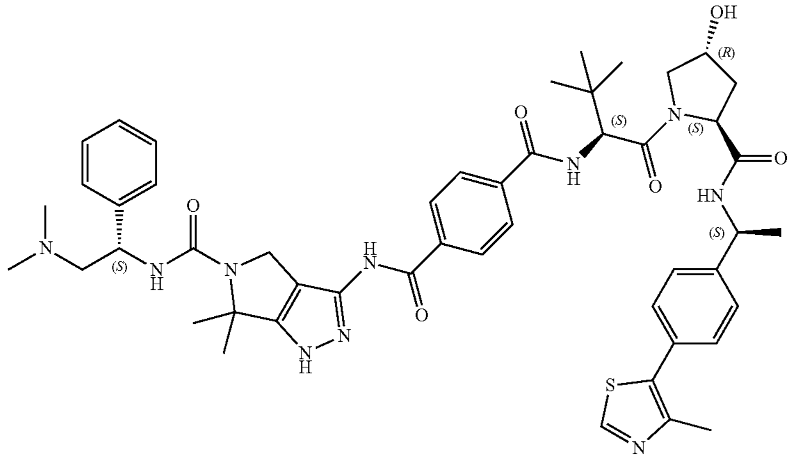

(30)

Compound 30 (7.1 mg) was obtained according to the synthetic route of compound 1 in Example 1 with (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide.

$^{1}$H NMR (500 MHz, DMSO-d$_6$) δ 12.50 (s, 1H), 11.07 (s, 1H), 8.99 (s, 1H), 8.42 (d, J=7.8 Hz, 1H), 8.20-8.14 (m, 1H), 8.10 (d, J=8.2 Hz, 2H), 8.00 (d, J=8.1 Hz, 2H), 7.48-7.43 (m, 2H), 7.42-7.38 (m, 4H), 7.33 (t, J=7.6 Hz, 2H), 7.23 (t, J=7.3 Hz, 1H), 6.38 (s, 1H), 5.15 (d, J=3.5 Hz, 1H), 5.06-4.90 (m, 2H), 4.79 (d, J=9.1 Hz, 1H), 4.58 (t, J=12.1 Hz, 2H), 4.47 (t, J=8.1 Hz, 1H), 4.33 (s, 1H), 3.69 (d, J=3.1 Hz, 2H), 2.86 (d, J=19.3 Hz, 6H), 2.47 (s, 3H), 2.42-2.27 (m, 1H), 2.05 (ddd, J=12.6, 7.6, 2.7 Hz, 1H), 1.82 (ddd, J=12.9, 8.6, 4.5 Hz, 1H), 1.66 (s, 3H), 1.59 (s, 3H), 1.39 (d, J=7.0 Hz, 3H), 1.06 (s, 9H).

LCMS: 917 [M+H]$^{+}$.

Example 31: Synthesis of N$^{1}$-(5-(((S)-2-(dimethylamino)-1-phenylethyl)carbamoyl)-6,6-dimethyl-1,4,5,6-tetrahydropyrrolo[3,4-c]pyrazol-3-yl)-N$^{4}$-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)terephthalamide (31)

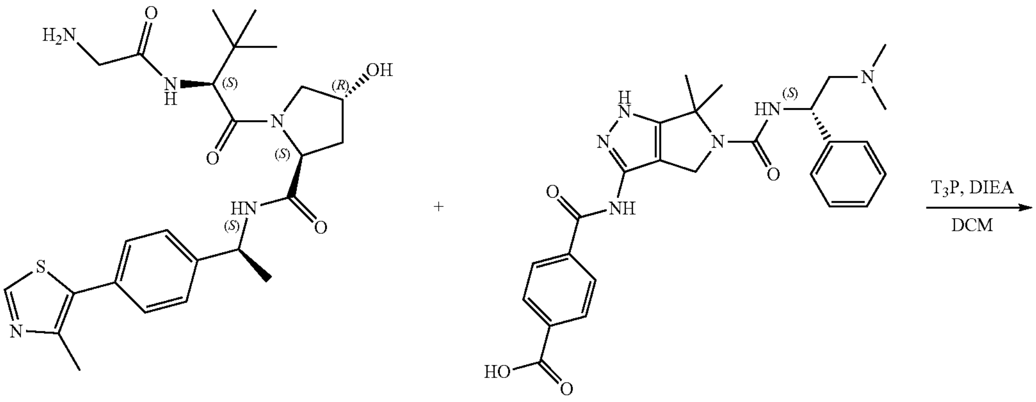

-continued

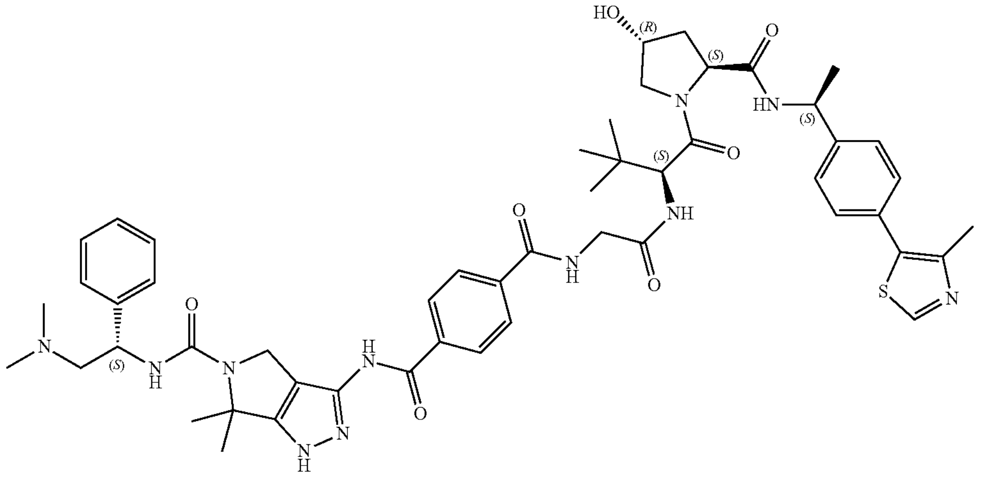

(31)

Compound 31 was obtained according to the synthetic route of compound 1 in Example 1 with (2S,4R)-1-((S)-2-(2-aminoacetamido)-3,3-dimethylbutanoyl)-4-hydroxy-N—((S)-1-(4-(4-methylthiazol-5-yl)phenyl)ethyl)pyrrolidine-2-carboxamide.

LCMS: 974 $[M+H]^+$.

Example 32: Synthesis of 8-(4-((5-(((S)-2-(dimethylamino)-1-phenylethyl)carbamoyl)-6,6-dimethyl-1,4,5,6-tetrahydropyrrolo[3,4-c]pyrazol-3-yl)carbamoyl)benzoyl)-N—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)-8-azaspiro[4.5]decane-2-carboxamide (32)

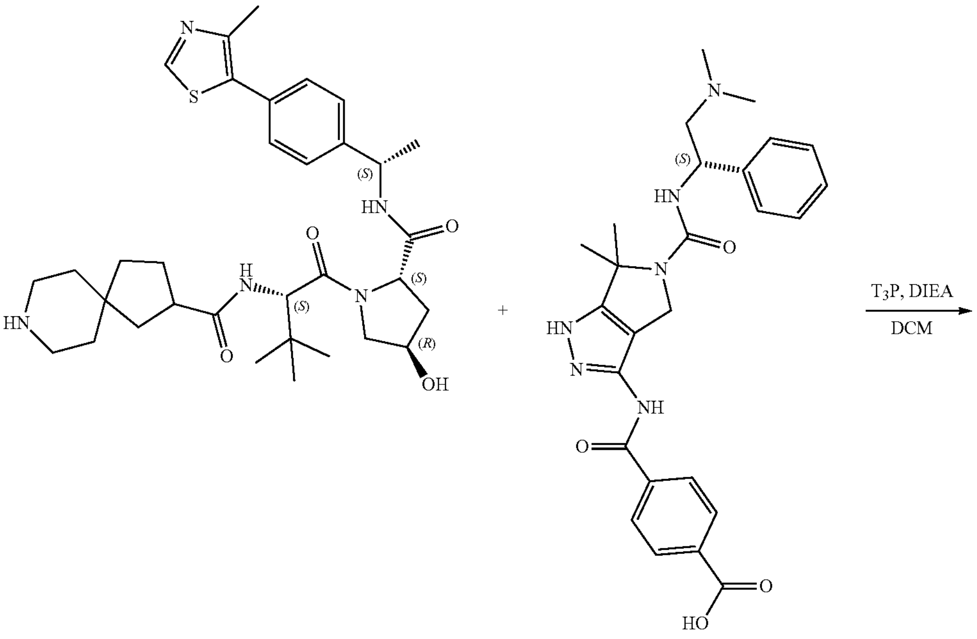

-continued

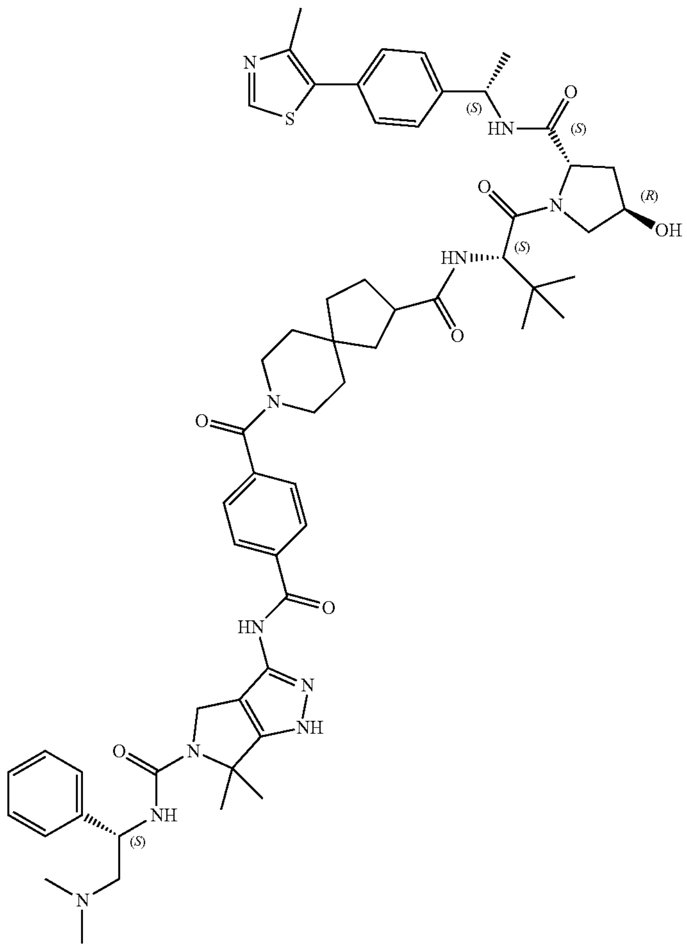

(32)

Compound 32 (11.3 mg) was obtained according to the synthetic route of compound 1 in Example 1 with N—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)-8-azaspiro[4.5]decane-2-carboxamide.

$^1$H NMR (500 MHz, DMSO-$d_6$) δ 12.51 (s, 1H), 11.02 (s, 1H), 8.99 (s, 1H), 8.39 (d, J=7.8 Hz, 1H), 8.07 (d, J=7.9 Hz, 2H), 7.74 (s, 1H), 7.51 (d, J=7.8 Hz, 2H), 7.47-7.31 (m, 9H), 7.25 (t, J=7.3 Hz, 1H), 6.48 (s, 1H), 5.12 (s, 2H), 4.92 (p, J=7.1 Hz, 1H), 4.65 (s, 1H), 4.54 (dd, J=24.8, 10.4 Hz, 2H), 4.43 (t, J=8.1 Hz, 1H), 4.29 (s, 1H), 3.60 (s, 4H), 3.29 (s, 2H), 2.99 (d, J=14.4 Hz, 6H), 2.46 (s, 3H), 2.02 (t, J=10.4 Hz, 1H), 1.84-1.75 (m, 4H), 1.67 (s, 3H), 1.59 (s, 3H), 1.55-1.44 (m, 8H), 1.38 (d, J=7.0 Hz, 3H), 0.94 (s, 9H), 0.89-0.79 (m, 1H).

LCMS: 1082 $[M+H]^+$.

Example 33: Synthesis of N[1]-(5-(((S)-2-(dimethylamino)-1-phenylethyl)carbamoyl)-6,6-dimethyl-1,4,5,6-tetrahydropyrrolo[3,4-c]pyrazol-3-yl)-N[4]-(3-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamoyl)phenyl)terephthalamide (33)
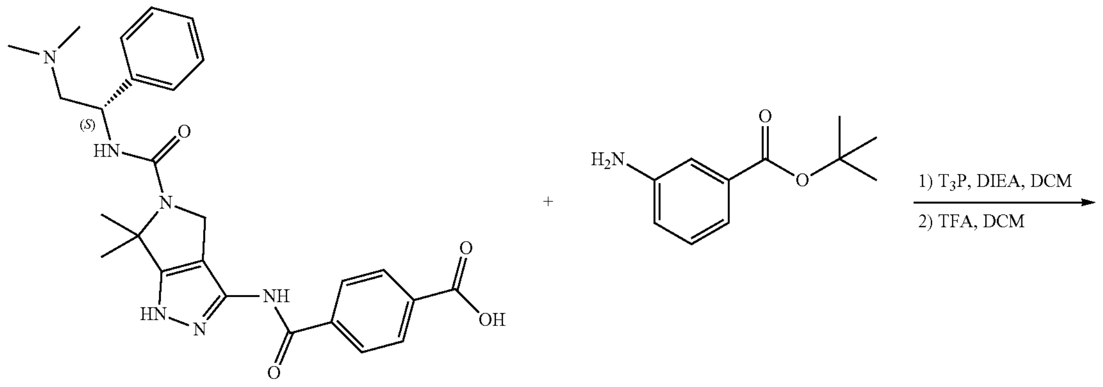
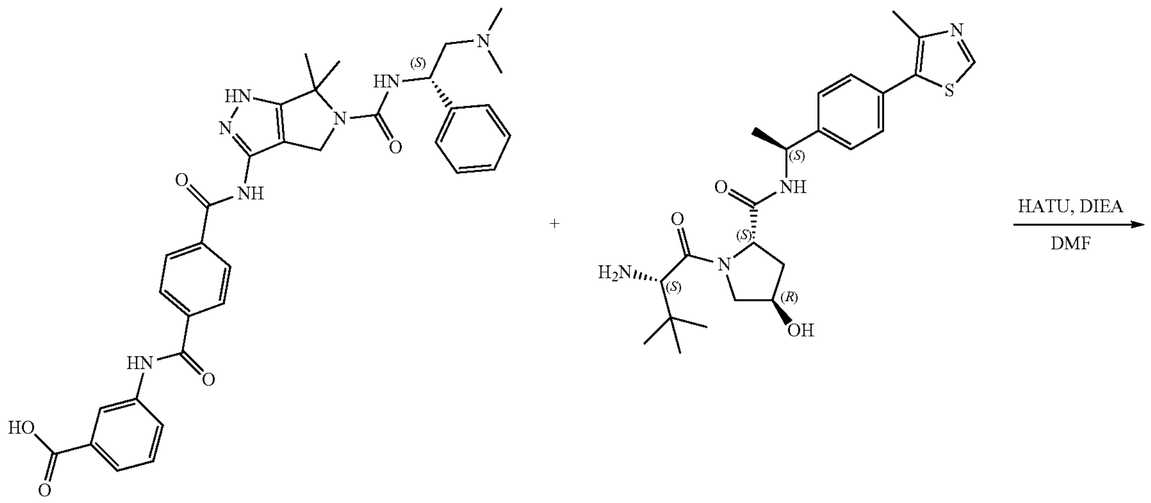

-continued

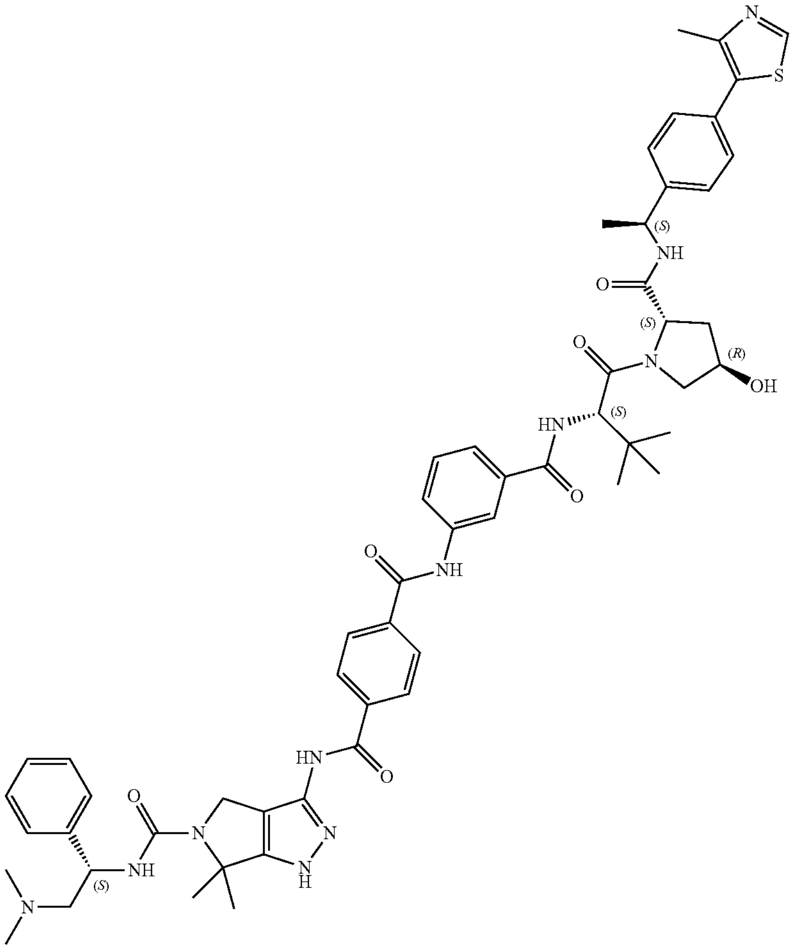

(33)

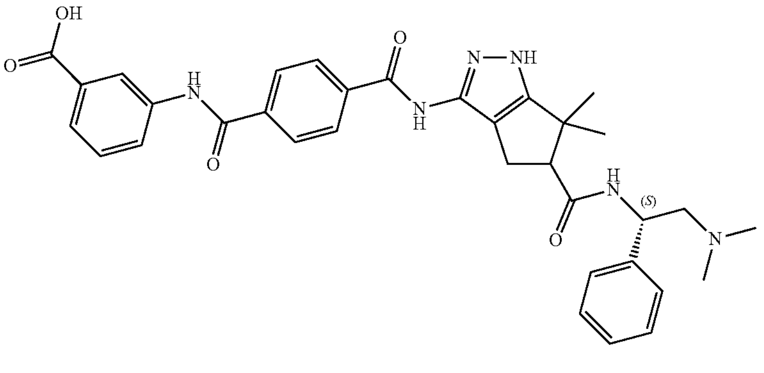

(S)-3-(4-((5-((2-(Dimethylamino)-1-phenylethyl)carbamoyl)-6,6-dimethyl-1,4,5,6-tetrahydropyrrolo[3,4-c]pyrazol-3-yl)carbamoyl)benzamido)benzoic acid To a solution of (S)-4-((5-((2-(dimethylamino)-1-phenylethyl)carbamoyl)-6,6-dimethyl-1,4,5,6-tetrahydropyrrolo[3,4-c]pyrazol-3-yl)carbamoyl)benzoic acid (15 mg, 0.025 mmol) and DIEA (12.9 mg, 0.1 mmol) in dry DCM (1 mL) was added propanephosphonic acid anhydride (T3P®) (50% w.t. in EA, 32 μl, 0.05 mmol). The reaction was stirred for 10 min before addition of tert-butyl 3-aminobenzoate (4.8 mg, 0.025 mmol). The mixture was stirred for 30 min and then was concentrated in vacuo. The crude product was dissolved in DCM (1 mL) before addition of TFA (0.5 mL). After 1 hour, the solvent was removed in vacuo to get crude product without further purification.

LCMS: 666 [M+H]+.

(33)

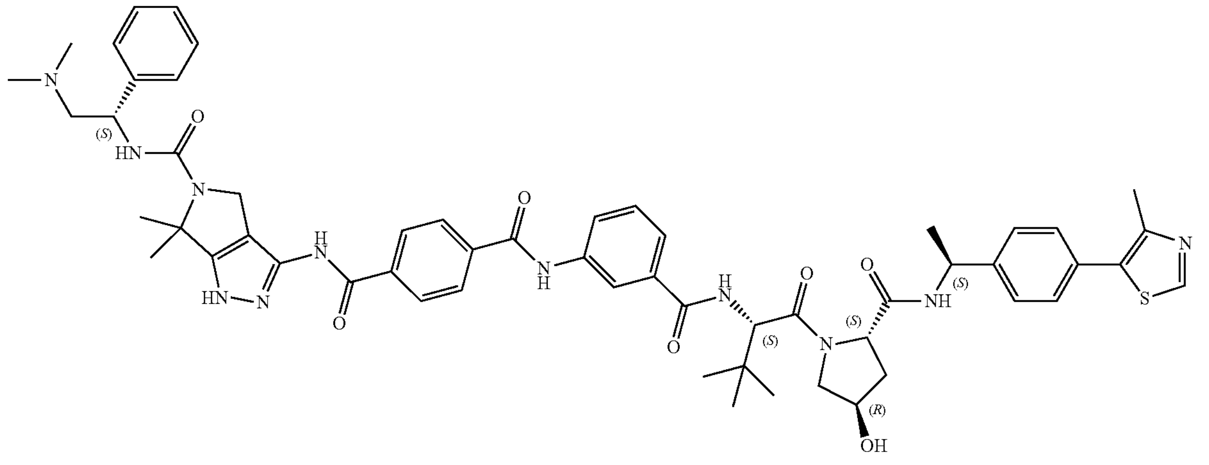

To a solution of (S)-3-(4-((5-((2-(dimethylamino)-1-phenylethyl)carbamoyl)-6,6-dimethyl-1,4,5,6-tetrahydropyrrolo[3,4-c]pyrazol-3-yl)carbamoyl)benzamido)benzoic acid (15 mg, 0.025 mmol) and (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide HCl salt (13 mg, 0.025 mmol) and DIEA (13 mg, 0.098 mmol) in DMF (1 mL) was added HATU (18 mg, 0.049 mmol). The mixture was stirred at room temperature for 10 min before purification by reversed HPLC to get compound 33 as TFA salt (1.8 mg, 6%).

LCMS: 1036 $[M+H]^+$.

Example 34: Synthesis of $N^1$-(5-(((S)-2-(dimethylamino)-1-phenylethyl)carbamoyl)-6,6-dimethyl-1,4,5,6-tetrahydropyrrolo[3,4-c]pyrazol-3-yl)-N4-(3-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamoyl)bicyclo[1.1.1]pentan-1-yl)terephthalamide (34)

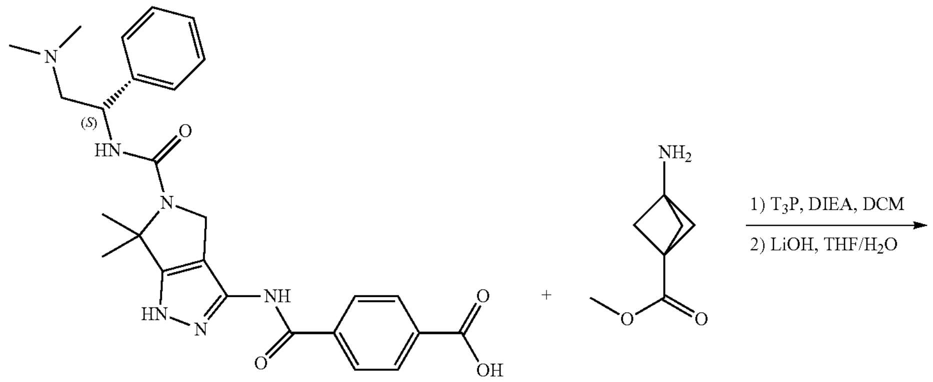

-continued
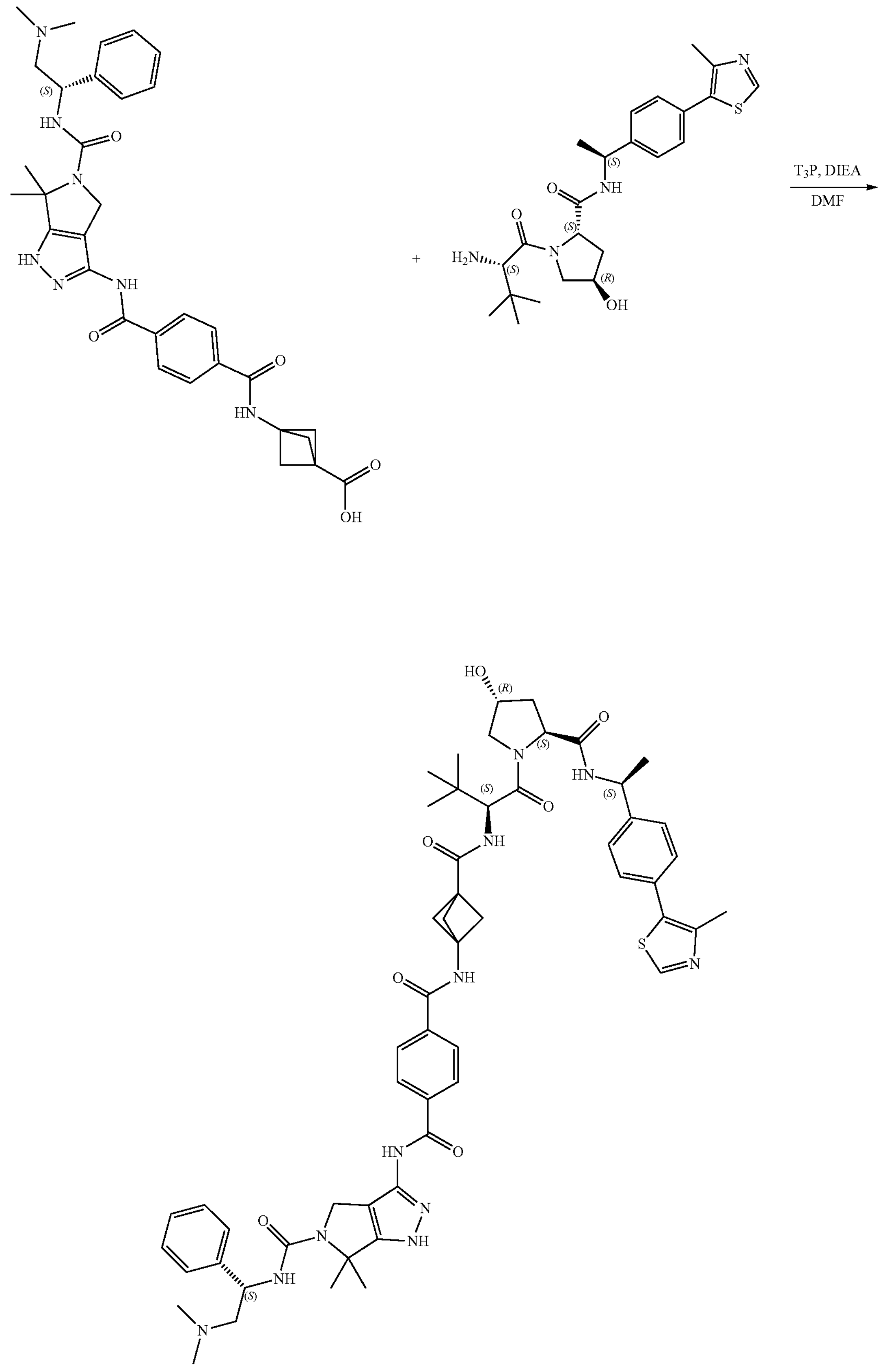
(34)

-continued

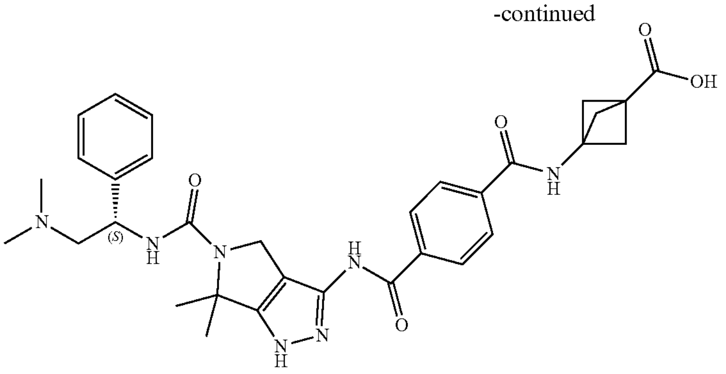

(S)-3-(4-((5-((2-(Dimethylamino)-1-phenylethyl)carbamoyl)-6,6-dimethyl-1,4,5,6-tetrahydropyrrolo[3,4-c]pyrazol-3-yl)carbamoyl)benzamido)bicyclo[1.1.1]pentane-1-carboxylic acid To a solution of (S)-4-((5-((2-(dimethylamino)-1-phenylethyl)carbamoyl)-6,6-dimethyl-1,4,5,6-tetrahydropyrrolo[3,4-c]pyrazol-3-yl)carbamoyl)benzoic acid (20 mg, 0.040 mmol) and DIEA (21 mg, 0.16 mmol) in dry DCM (1 mL) was added propanephosphonic acid anhydride (T3P®) (50% w.t. in EA, 52 μL, 0.08 mmol). The reaction was stirred for 10 min before addition of methyl 3-aminobicyclo[1.1.1]pentane-1-carboxylate (8.4 mg, 0.060 mmol). The mixture was stirred for 30 min and then was concentrated in vacuo. The crude product was dissolved in THF (1 mL) before addition of LiOH (0.5 mL, 1M aq.). After 1 hour, the reaction was acidified with HCl aq. The mixture was extracted with EA. The organic layer was collected and concentrated in vacuo. The resulting residue was purified by reversed HPLC to get title compound (29.8 mg, 0.04 mmol).

LCMS: 600 $[M+H]^+$.

(34)

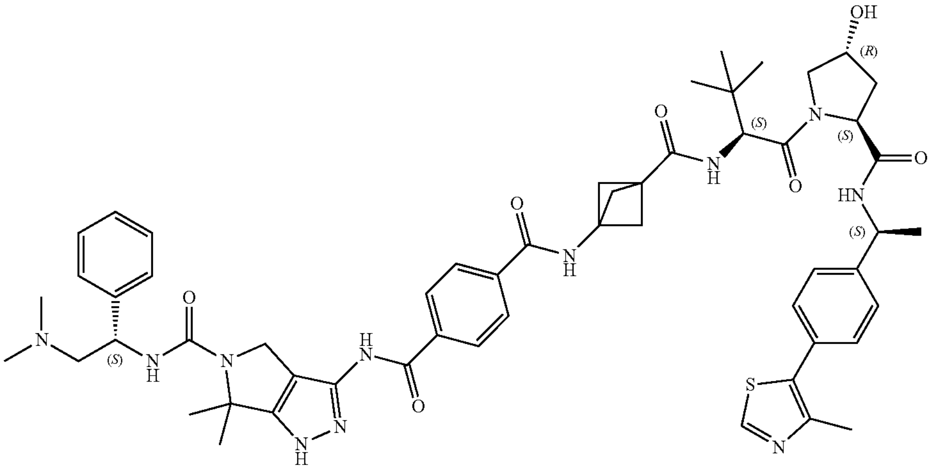

To a solution of (S)-3-(4-((5-((2-(dimethylamino)-1-phenylethyl)carbamoyl)-6,6-dimethyl-1,4,5,6-tetrahydropyrrolo[3,4-c]pyrazol-3-yl)carbamoyl)benzamido)bicyclo[1.1.1]pentane-1-carboxylic acid (29 mg, 0.04 mmol) and DIEA (31 mg, 0.24 mmol) in dry DCM (1 mL) was added propanephosphonic acid anhydride (T3P®) (50% w.t. in EA, 62 μL, 0.096 mmol). The reaction was stirred for 10 min before addition of (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide HCl salt (25 mg, 0.048 mmol). The mixture was stirred for 30 min and then was concentrated in vacuo. The residue was purified with reversed HPLC to get compound 34 as TFA salt (11 mg, 0.0096 mmol, 24%).

$^1$H NMR (500 MHz, DMSO-$d_6$) δ 12.57 (s, 1H), 11.09 (s, 1H), 9.30 (s, 1H), 9.23 (s, 1H), 8.99 (s, 1H), 8.43 (dd, J=7.8, 1.7 Hz, 1H), 8.10 (dd, J=8.5, 6.1 Hz, 2H), 7.99 (t, J=10.9 Hz, 2H), 7.45 (dq, J=8.3, 1.7 Hz, 4H), 7.42-7.37 (m, 4H), 7.33-7.26 (m, 2H), 6.77 (d, J=8.9 Hz, 1H), 5.37 (d, J=11.2 Hz, 1H), 5.17 (d, J=3.5 Hz, 1H), 4.97-4.89 (m, 1H), 4.80 (dd, J=11.2, 7.9 Hz, 1H), 4.62-4.54 (m, 2H), 4.46 (q, J=8.5 Hz, 1H), 4.30 (s, 1H), 3.69 (s, 1H), 3.65-3.52 (m, 2H), 2.86 (d, J=19.5 Hz, 6H), 2.46 (s, 3H), 2.33 (s, 4H), 2.10-2.01 (m, 1H), 1.86-1.76 (m, 1H), 1.69 (s, 3H), 1.60 (s, 3H), 1.39 (dd, J=7.0, 1.7 Hz, 3H), 1.32-1.23 (m, 1H), 1.19 (t, J=7.3 Hz, 1H), 0.96 (s, 9H).

LCMS: 1026 $[M+H]^+$.

Example 35: CDK7 Degradation with Inventive Bispecific Compounds 1-26

Jurkat cells were treated with DMSO or 1 μM of compounds 1-26 for 6 hours. Cells were then lysed in radioimmunoprecipitation assay (RIPA) buffer (Sigma® Life Science) containing protease/phosphatase inhibitor cocktail (Roche). The protein concentrations were measured by bicinchoninic acid assay (BCA) analysis (Pierce™). Equal amounts of protein were resolved by 4-12% Tris-Base gels (Invitrogen™), and then transferred to the immunoblot polyvinylidene difluoride (PVDF) membrane (BioRad), and immunoblotted with primary antibodies against CDK7 (cell signaling) and glyceraldehyde 3-phosphate dehydrogenase (GAPDH) (Cell Signaling Technology®), and then immunoblotted with IRDye®800-labeled goat anti-rabbit immunoglobulin G (IgG) and IRDye®680-labeled goat anti-mouse IgG (LI-COR®) secondary antibodies. The membranes were detected on an Odyssey® CLx system.

The results illustrated in FIG. 1A show that bispecific compounds 1, 3, 6, 7, 8, 9 and 10 induced the degradation of CDK7 after 6 hours.

Figure 2A:
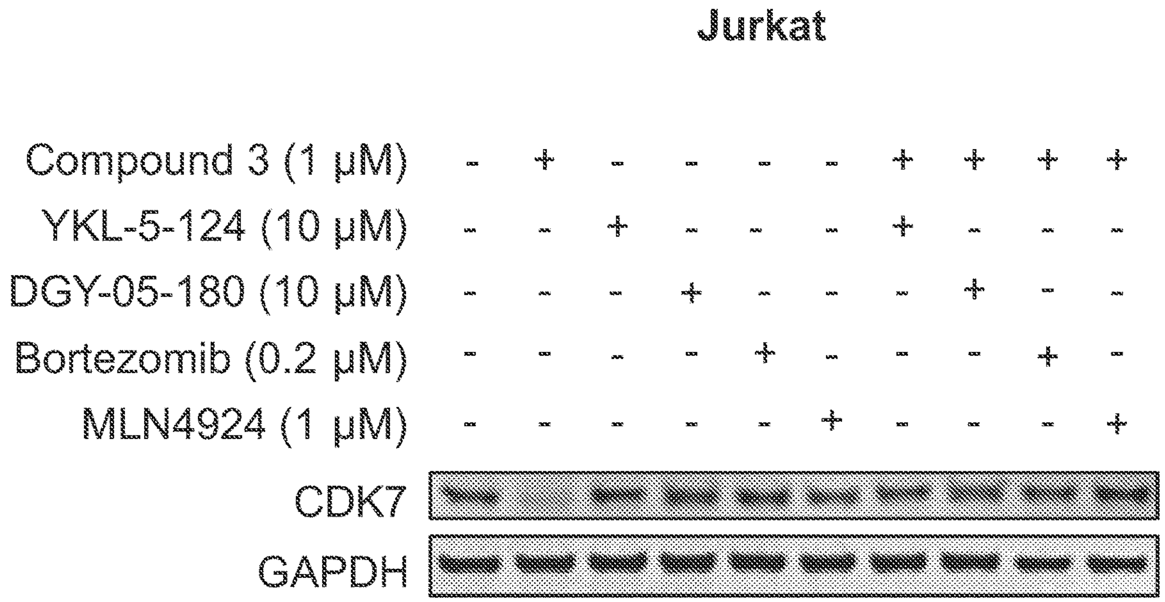
FIG. 2A is an immunoblot that shows CDK7 degradation after treating Jurkat cells with selective CDK7 inhibitor YKL-5-124, compound DGY-05-180, proteasome inhibitor bortezomib or neddylation inhibitor MLN4924 for 2 h prior to the addition of bispecific compound 3 for 4 h.

The results illustrated in FIG. 2A show that bispecific compounds 3, 11, 12, 13, 15, 16 and 20 induced the degradation of CDK7 after 6 hours.

Figure 1C:
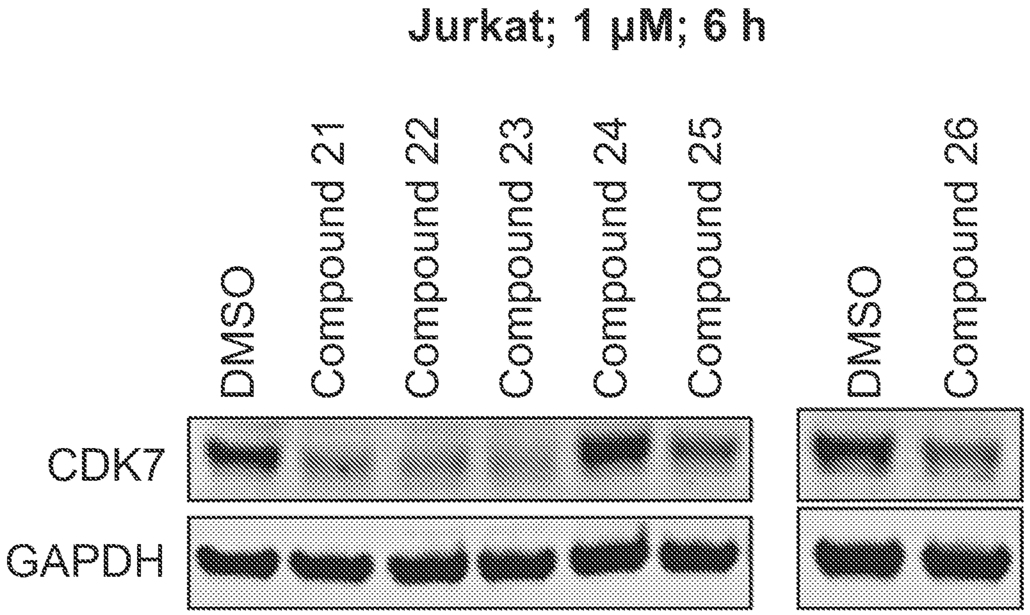
FIG. 1C is an immunoblot that shows CDK7 degradation after treating Jurkat cells with inventive bispecific compounds 21-26 and DMSO (negative control) at 6 hours.

The results illustrated in FIG. 1C show that bispecific compounds 21, 22, 23, 25 and 26 induced the degradation of CDK7 after 6 hours.

Example 36: CDK7 Degradation is Both Ligand and Proteasome Dependent

Jurkat cells were pretreated with 10 μM YKL-5-124 (the parental compound and known CDK7 inhibitor), 10 μM DGY-05-180 (VHL ligand), 0.2 μM Bortezomib (a proteasome inhibitor available from, e.g., Millipore Sigma, Cat. No. 179324-69-7, Burlington, MA), and 1 μM MLN4924 (a neddylation inhibitor available from, e.g., MedChemExpress (MCE®), Cat. No. HY-70062, Monmouth Junction, NJ), for 2 h, and then treated with 1 μM compound 3 or 20 for 4 h. Cells were lysed and immunoblotted as described in Example 27 with antibodies to CDK7 and GAPDH. The structures of YKL-5-124, DGY-05-180, Bortezomib and MLN4924 are set forth below.

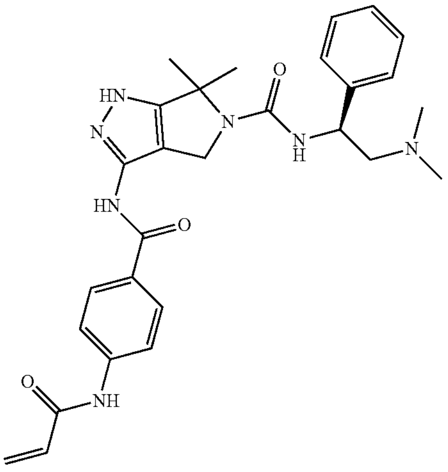

YKL-5-124

-continued

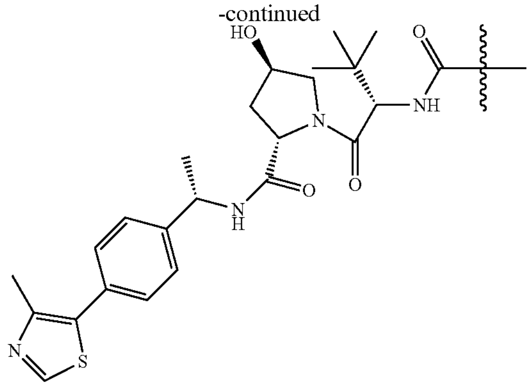

DGY-05-180

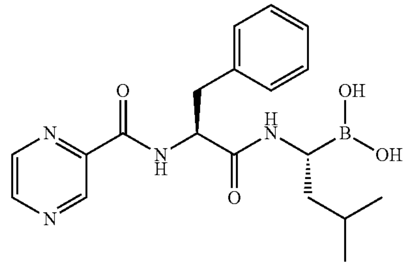

Bortezomib (VELCADE®)

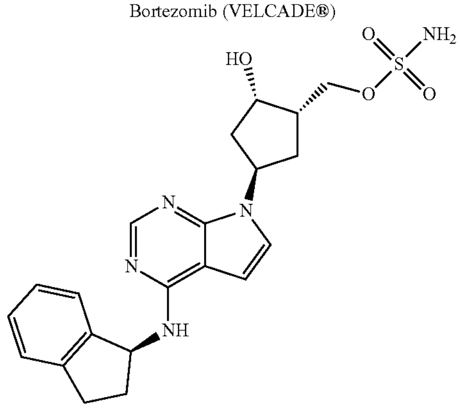

MLN4924 (Pevonedistat)

Figure 2B:
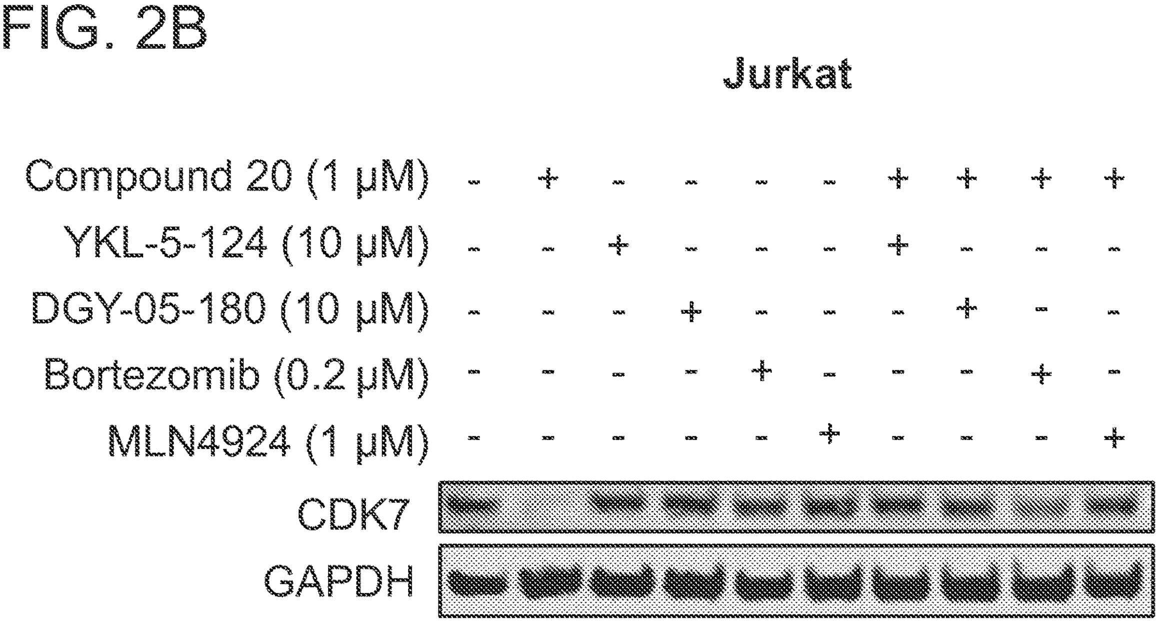
FIG. 2B is an immunoblot that shows CDK7 degradation after treating Jurkat cells with YKL-5-124, compound DGY- 05-180, bortezomib or MLN4924 for 2 h prior to the addition of bispecific compound 20 for 4 h.

The results are illustrated in FIG. 2A and FIG. 2B. They show that YKL-5-124, DGY-05-180, Bortezomib, and MLN4924 rescued the CDK7 degradation induced by bispecific compounds 3 and 20. The results indicate that the CDK7 degradation is both ligand- and proteasome-dependent.

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A bispecific compound, comprising a moiety that binds cyclin-dependent kinase 7 (CDK7) and a degron covalently attached to each other by a linker, wherein the compound has a structure represented by formula (I):

(I)

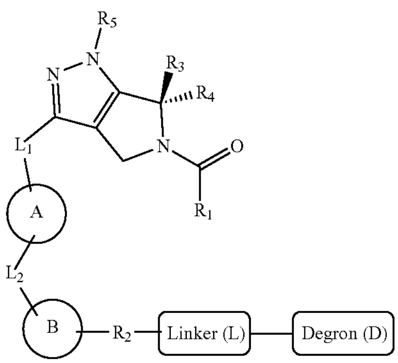

or a pharmaceutically acceptable salt or stereoisomer thereof, wherein $R_1$ represents —$NR^aR^b$, wherein each of $R^a$ and $R^b$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, or an oxygen protecting group when attached to an oxygen atom, or $R^a$ and $R^b$ together with the atoms to which they are bound form an optionally substituted carbocyclic, optionally substituted heterocyclic, optionally substituted aryl, or optionally substituted heteroaryl ring;

each of $R_3$ and $R_4$ independently represents hydrogen, halogen, optionally substituted $C_1$-$C_6$ alkyl, or optionally substituted aryl, or $R_3$ and $R_4$ together with the atoms to which they are bound form an optionally substituted $C_3$-$C_6$ carbocyclyl ring;

$R_5$ independently represents hydrogen, optionally substituted $C_1$-$C_6$ alkyl, or a nitrogen protecting group;

$L_1$ represents NH or —NHC(O)—;

A represents optionally substituted carbocyclyl, optionally substituted heterocyclyl, optionally substituted aryl, or optionally substituted heteroaryl;

$L_2$ represents a bond or absent, —C(═O)—, —C(═O)$NR^{L2}$—, —$NR^{L2}$C(═O)—, —O—, or —S—, wherein $R^{L2}$ is hydrogen, optionally substituted $C_1$-$C_6$ alkyl, or a nitrogen protecting group;

B represents a bond or absent, optionally substituted carbocyclyl, optionally substituted heterocyclyl, optionally substituted aryl, or optionally substituted heteroaryl; and $R_2$ is absent;

wherein the linker is an alkylene chain or polyethylene glycol chain, either of which may be interrupted by, and/or terminate (at either or both termini) at least one of —O—, —S—, —N(R')—, —C≡C—, —C(O)—, —C(O)O—, —OC(O)—, —OC(O)O—, —C(NOR')—, —C(O) N(R')—, —C(O)N(R')C(O)—C(O)N(R')C(O)N(R')—, —N(R')C(O)—, —N(R')C(O)N(R')—N(R')C(O)—, —OC(O)N(R')—, —C(NR)—, —N(R')C(NR)—, —C(NR')N(R')—, —N(R')C(NR')N(R')—, —OB(Me)O—, —$S(O)_2$—, —OS(O)—, —S(O)O—, —S(O)—, —$OS(O)_2$—, —$S(O)_2O$—, —N(R')$S(O)_2$—, —$S(O)_2$N(R')—, —N(R')S(O)—, —S(O) N(R')—, —N(R')$S(O)_2$N(R')—, —N(R')S(O)N(R')—, $C_3$-$C_{12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different; and wherein the degron is represented by any one of structures (D1-a) to (D1-h) and (D2-a) to (D2-e):

(D1-a)

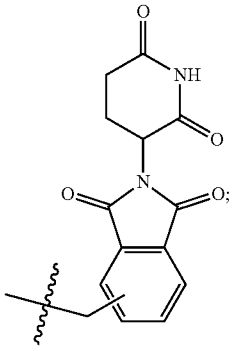

(D1-b)

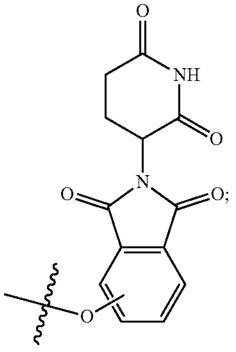

(D1-c)

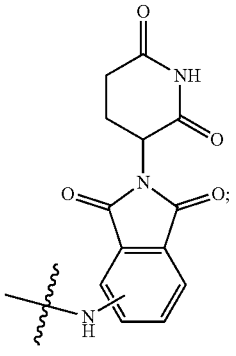

-continued
(D1-d)
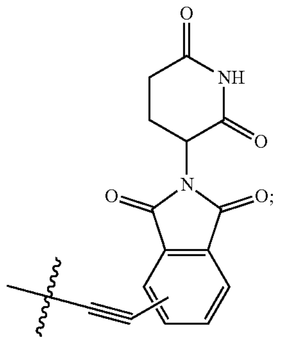
(D1-e)
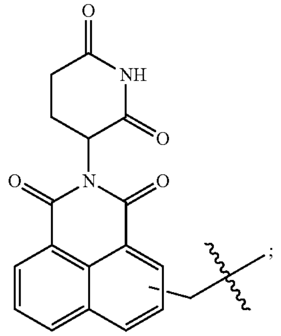
(D1-f)
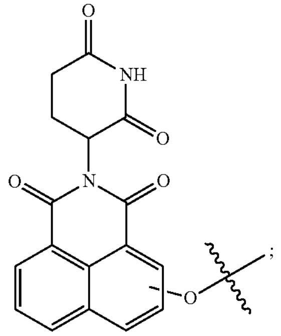
(D1-g)
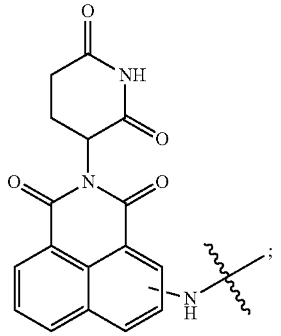
-continued
(D1-h)
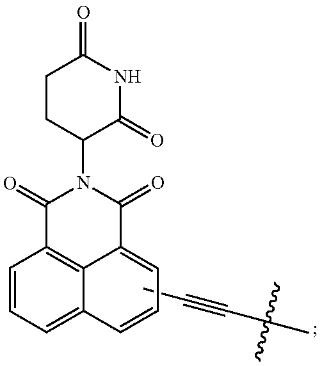
(D2-a)
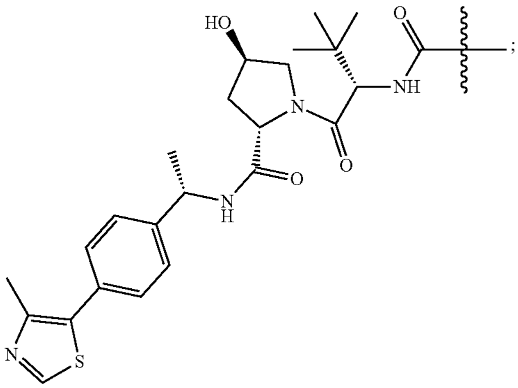
(D2-b)
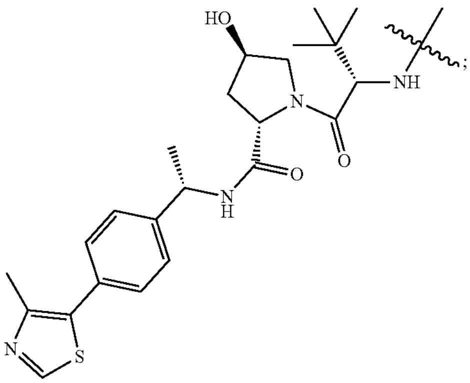

(D2-c)

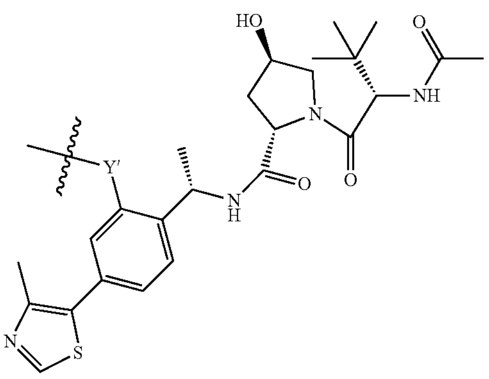

, wherein Y' is a bond, N, O or C;

(D2-d)

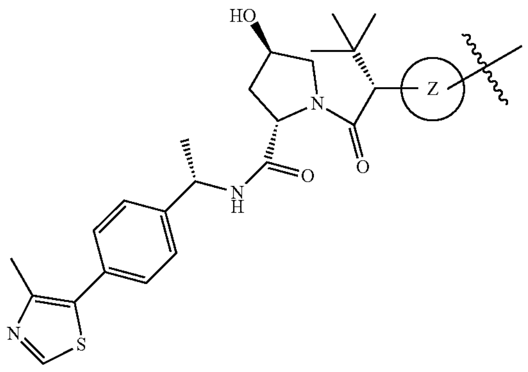

, wherein Z is a $C_5$-$C_6$ carbocyclic or $C_5$-$C_6$ heterocyclic group; and (D2-e)

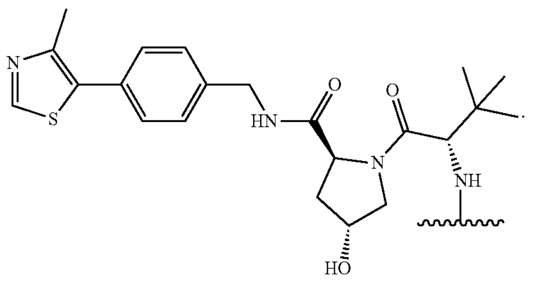

2. The bispecific compound of claim 1, wherein $R_1$ is

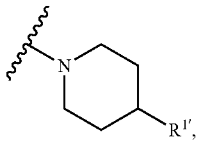

-continued

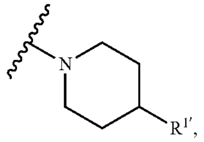

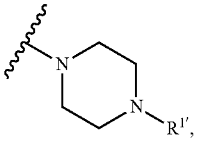

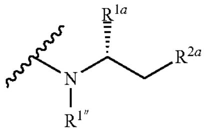

or

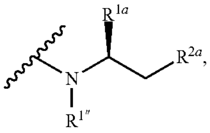

wherein each of $R^{1'}$ and $R^{1''}$ is independently hydrogen, optionally substituted $C_1$-$C_6$ alkyl, or a nitrogen protecting group, $R^{1a}$ is hydrogen, $C_1$-$C_6$ alkyl, or optionally substituted aryl, and $R^{2a}$ is hydrogen, —$OR^{1N}$, or —$NR^{1N}R^{2N}$, wherein each of $R^{1N}$ and $R^{2N}$ is independently hydrogen, $C_1$-$C_6$ alkyl or a nitrogen protecting group when attached to a nitrogen or an oxygen protecting group when attached to an oxygen atom.

3. The bispecific compound of claim 2, wherein $R^{1''}$ is hydrogen, Bn, BOC, Cbz, Fmoc, trifluoroacetyl, triphenylmethyl, acetyl, or Ts; or wherein $R_1$ is

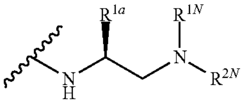

or

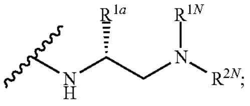

or wherein $R^{1a}$ is hydrogen, methyl, ethyl, propyl or phenyl.

4. The bispecific compound of claim 3, wherein $R_1$ is

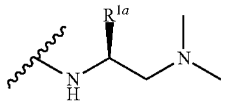

or

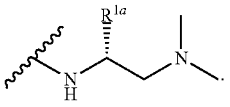

5. The bispecific compound of claim 1, wherein $R_1$ is

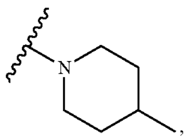

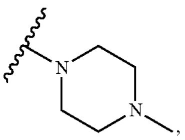

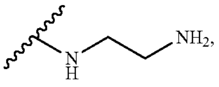

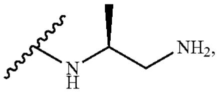

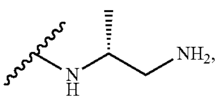

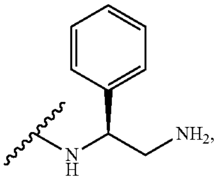

-continued

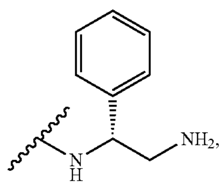, 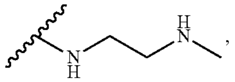, 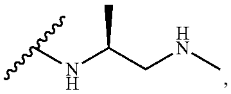, 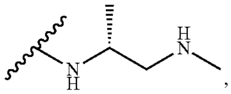, 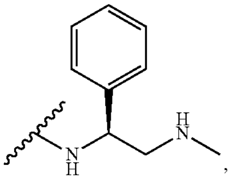, 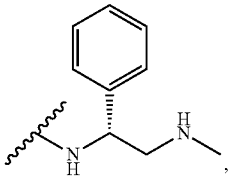, 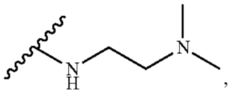, 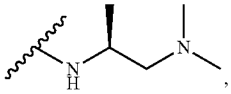, 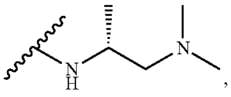, 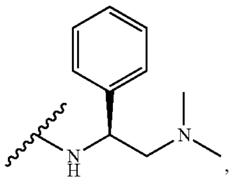, 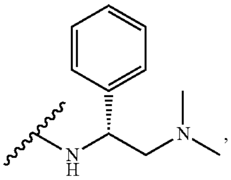, 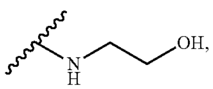, 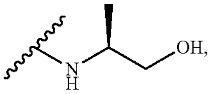, 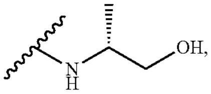, 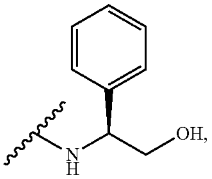, 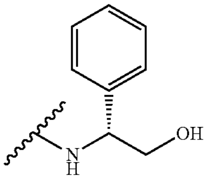 or 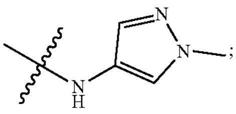;

or wherein $R_3$ and $R_4$ are independently methyl, isopropyl, or phenyl, or $R_3$ and $R_4$ together with the atoms to which they are bound form an optionally substituted $C_3$-$C_6$ carbocyclyl ring; or wherein both $R_3$ and $R_4$ are methyl; or wherein $R_5$ is hydrogen or methyl; or wherein A is 6-membered carbocyclyl or 6-membered heterocyclyl; or wherein B is a bond, 6-membered carbocyclyl or 6-membered heterocyclyl; or wherein $L_2$ is a bond, NH or —NHC(O)—.

6. The bispecific compound of claim 1, wherein Li is NH or —NHC(O)—, $R_3$ and $R_4$ are methyl and $R_5$ is H, and which has a structure represented by any one of formulas (I-1a) and (I-1b):

(I-1a)

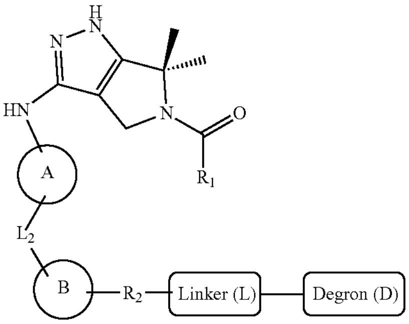

and (I-1b)

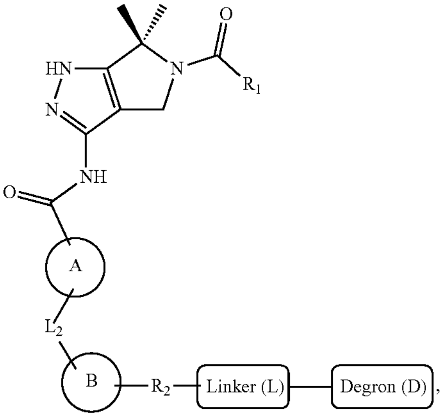, or a pharmaceutically acceptable salt or stereoisomer thereof.

7. The bispecific compound of claim 1, wherein A is 6-membered carbocyclyl, $R_3$ and $R_4$ are methyl and $R_5$ is H, and which has a structure represented by any one of formulas (I-2a) to (I-2f):

(I-2a)

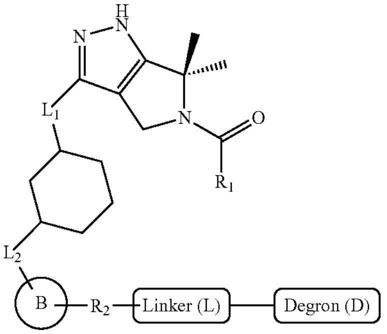;

-continued
(I-2b)
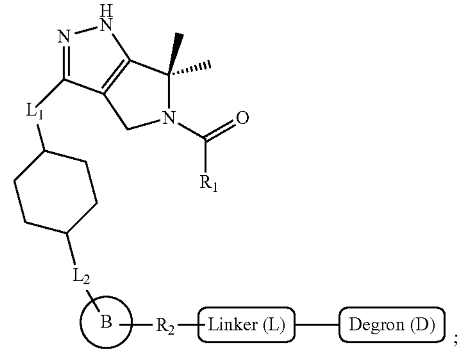
(I-2c)
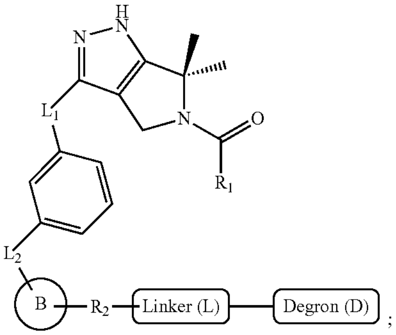
(I-2d)
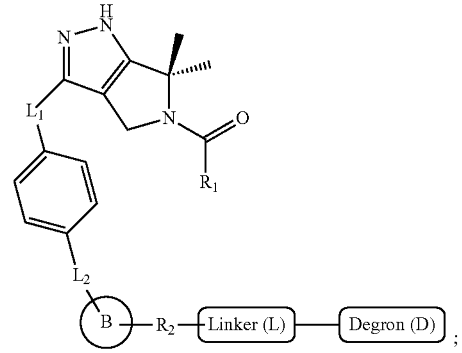
(I-2e)
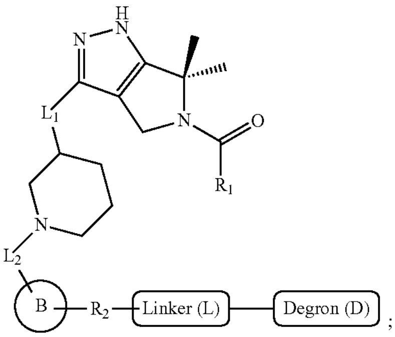
and
-continued
(I-2f)
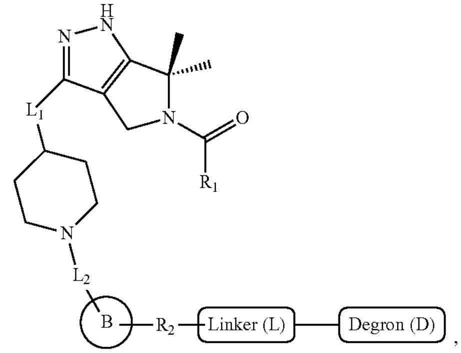
or a pharmaceutically acceptable salt or stereoisomer thereof.
8. The bispecific compound of claim 1, wherein $L_1$ is NH or —NHC(O)—, $R_1$ is
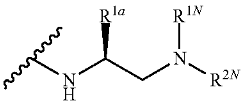
or
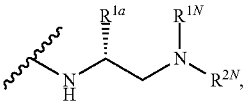
$R_3$ and $R_4$ are methyl and $R_5$ is H, and which has a structure represented by any one of formulas (I-3a) to (I-3d):
(I-3a)
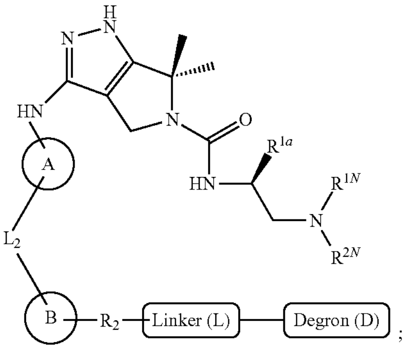
(I-3b)
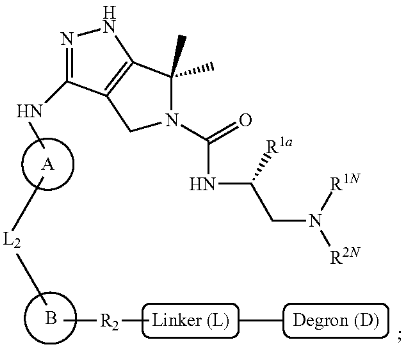

-continued
(I-3c)
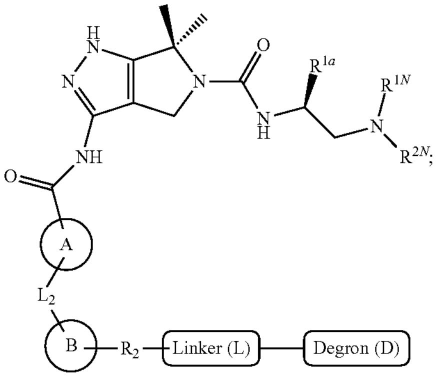
and
(I-3d)
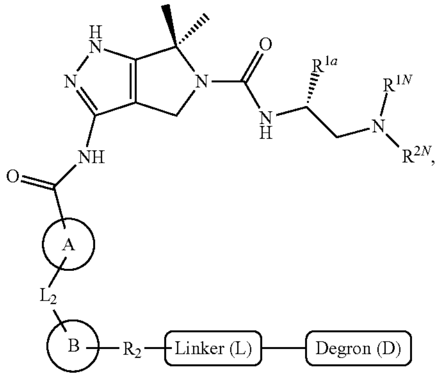
or a pharmaceutically acceptable salt or stereoisomer thereof.
9. The bispecific compound of claim 1, wherein A is 6-membered carbocyclyl, $R_1$ is
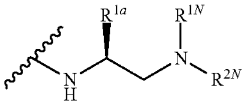
or
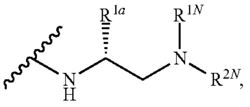
$R_3$ and $R_4$ are methyl and $R_5$ is H, and which has a structure represented by any one of formulas (I-4a) to (I-41):
(I-4a)
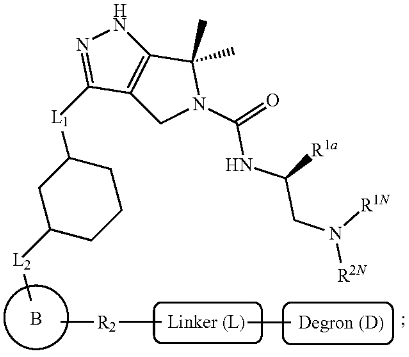
-continued
(I-4b)
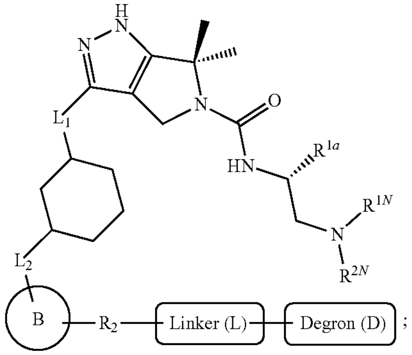
(I-4c)
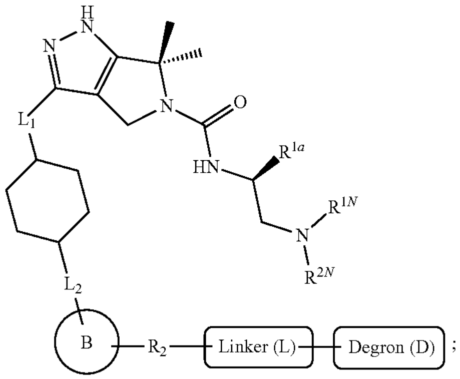
(I-4d)
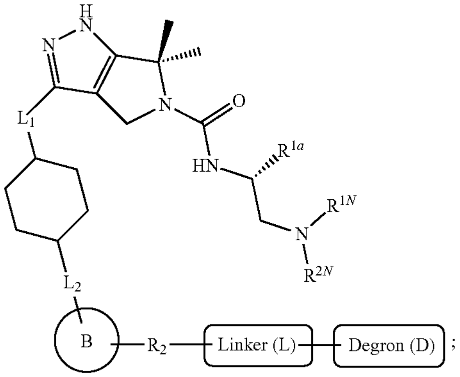
(I-4e)
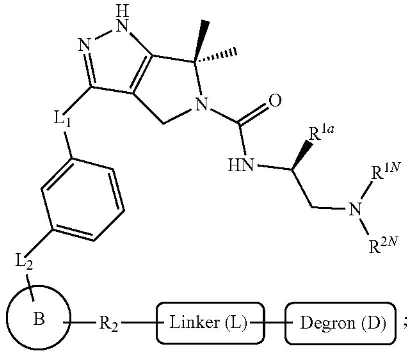

-continued
(I-4f)
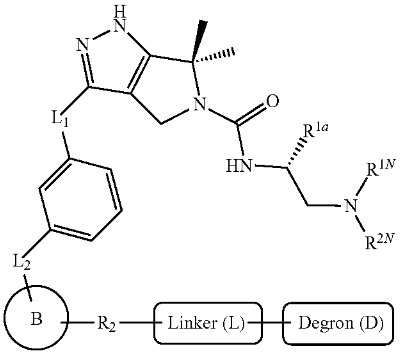
;
(I-4g)
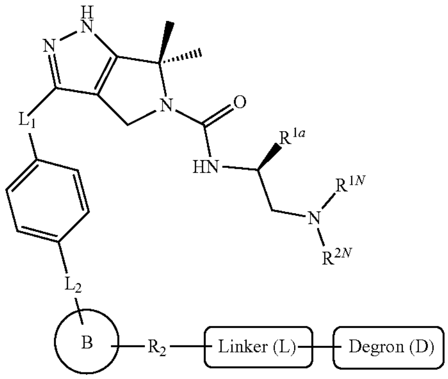
;
(I-4h)
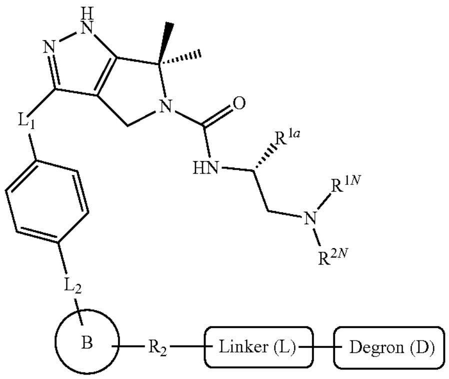
;
(I-4i)
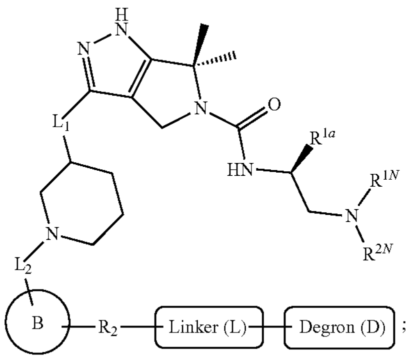
;
-continued
(I-4j)
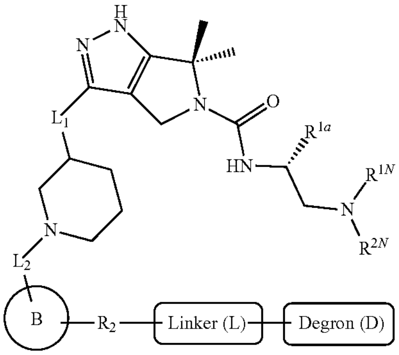
;
(I-4k)
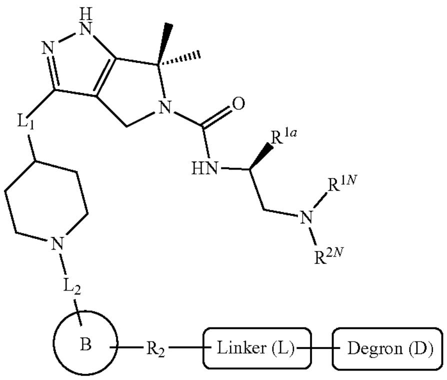
; and
(I-4l)
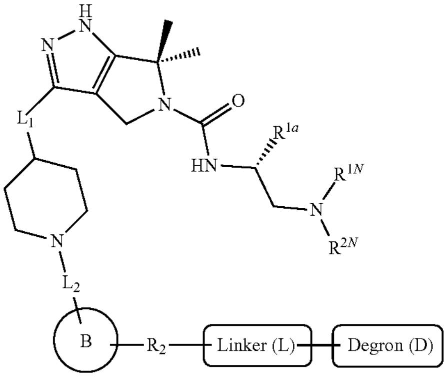
,
or a pharmaceutically acceptable salt or stereoisomer thereof.
10. The bispecific compound of claim 1, wherein Li is NH or —NHC(O)—, $R_1$ is
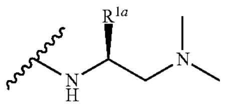 or 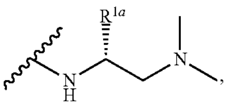, $R_3$ and $R_4$ are methyl and $R_5$ is H, and which has a structure represented by any one of formulas (I-5a) to (I-5d):
(I-5a)
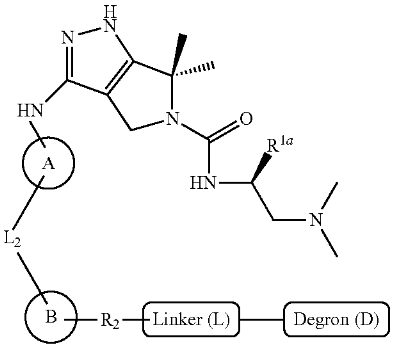
;
(I-5b)
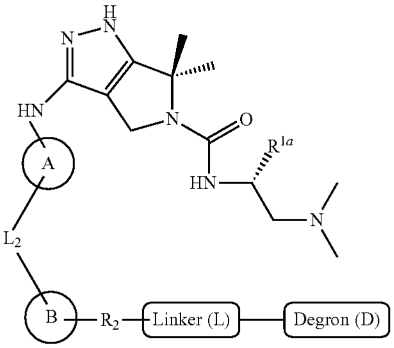
;
(I-5c)
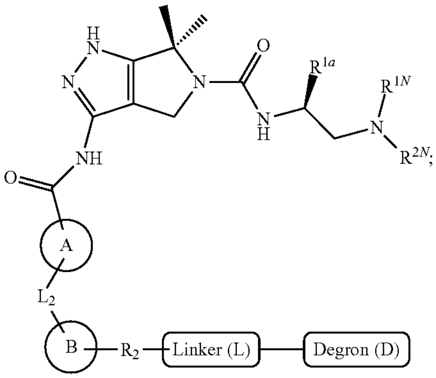
and
(I-5d)
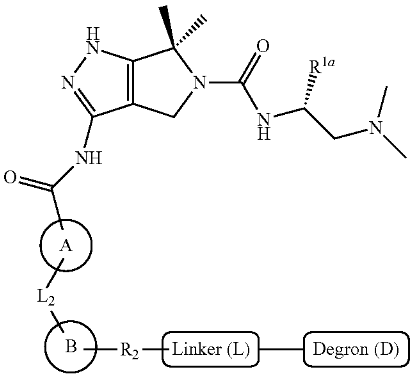
;
or a pharmaceutically acceptable salt or stereoisomer thereof.
11. The bispecific compound of claim 1, wherein $R_1$ is
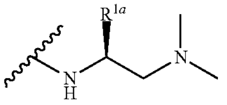
or
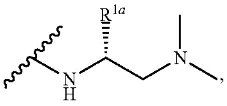
,
$R_3$ and $R_4$ are methyl and $R_5$ is H, and which has a structure represented by any one of formulas (I-6a) to (I-61):
(I-6a)
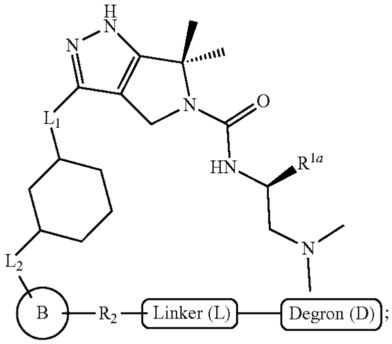
(1-6b)
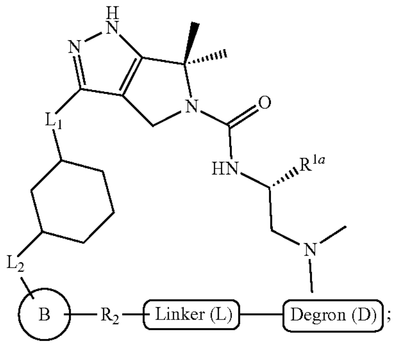
(I-6c)
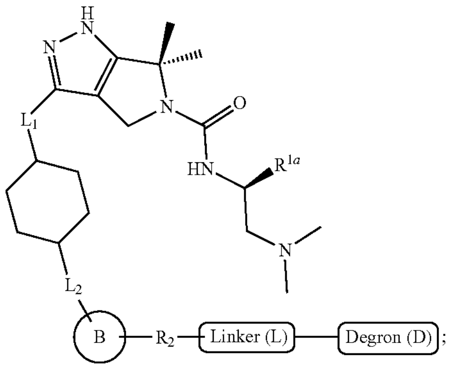

-continued
(1-6d)
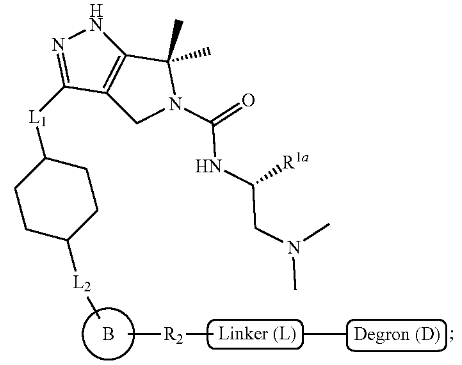
(I-6e)
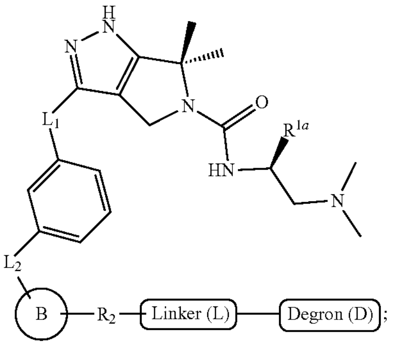
(I-6f)
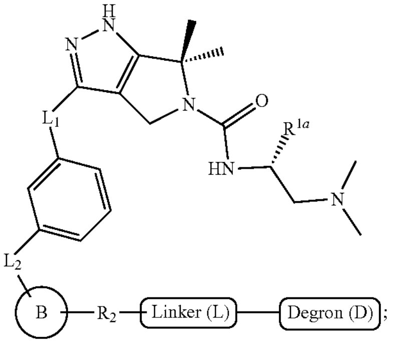
(I-6g)
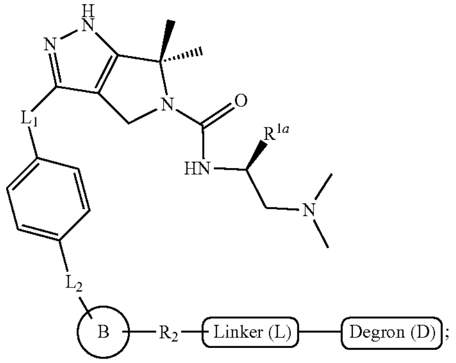
-continued
(I-6h)
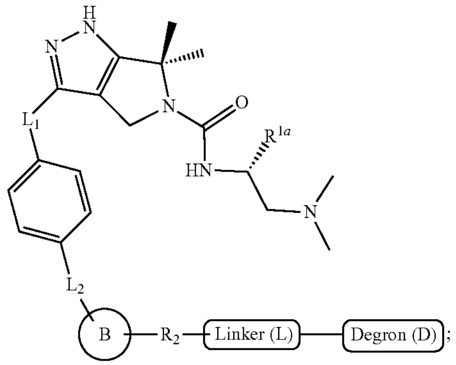
(I-6i)
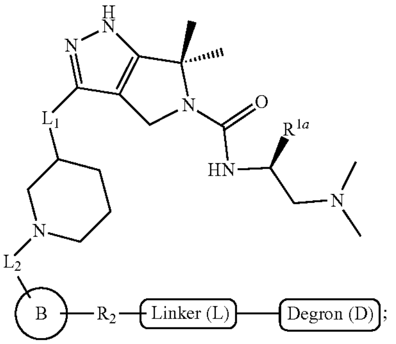
(I-6j)
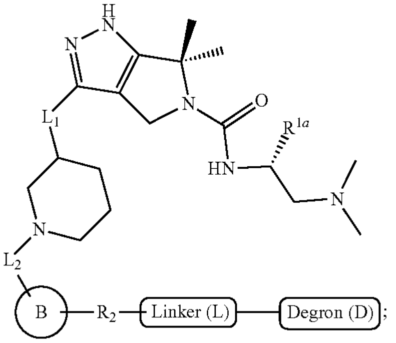
(I-6k)
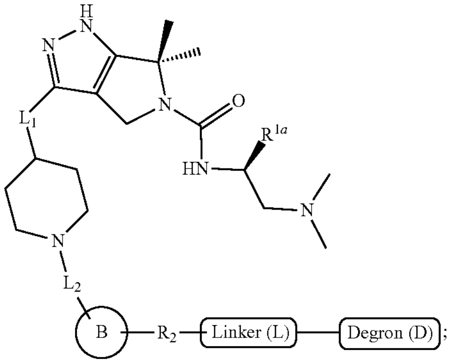
and -continued (I-61)

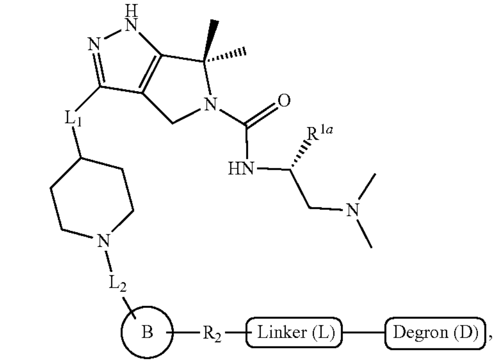

or a pharmaceutically acceptable salt or stereoisomer thereof.

12. The bispecific compound of claim 1, wherein $L_1$ is —NHC(O)—, A is 6-membered carbocyclyl, each of B, $L_2$, and $R_2$ is a bond or absent, $R_1$ is

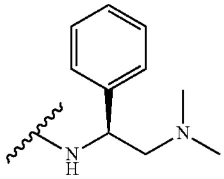 [SMILES: *N[C@H](CN(C)C)c1ccccc1]

and both $R_3$ and $R_4$ are methyl, and which has a structure represented by formula (I-58):

(I-58)

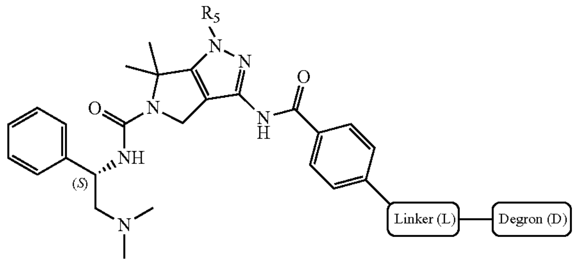

or a pharmaceutically acceptable salt or stereoisomer thereof.

13. The bispecific compound of claim 12, wherein $R_5$ is H.

14. The bispecific compound of claim 1, wherein the linker is represented by any one of structures (L11) to (L28):

(L11)

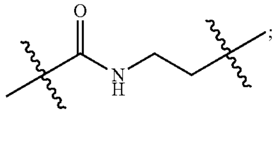

-continued (L12)

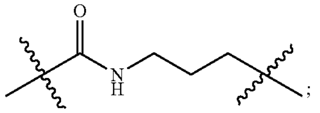

(L13)

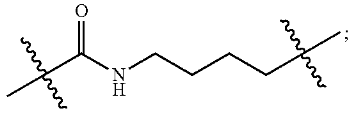

(L14)

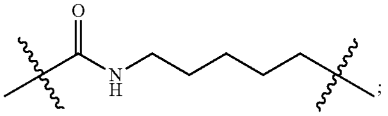

(L15)

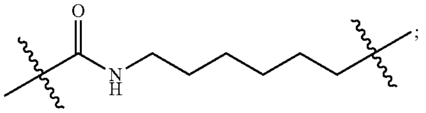

(L16)

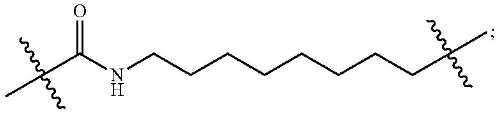

(L17)

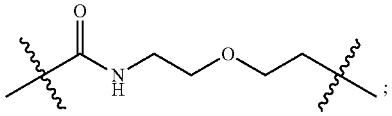

(L18)

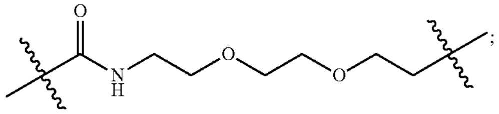

(L19)

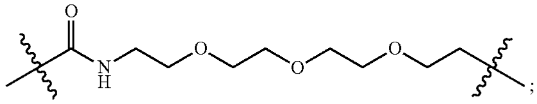

(L20)

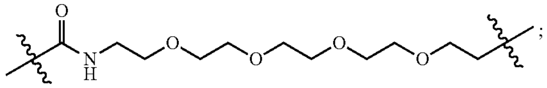

(L21)

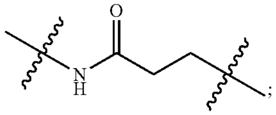

(L22)

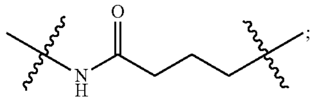

(L23)

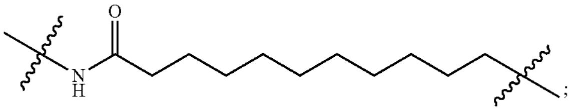

-continued
(L24)
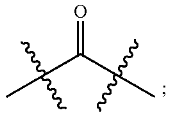
(L25)
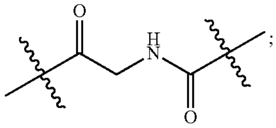
(L26)
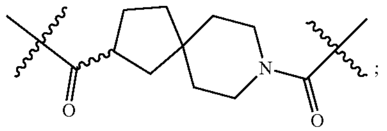
-continued
(L27)
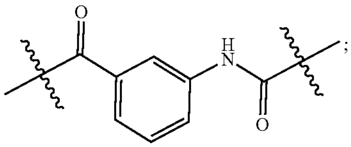
and
(L28)
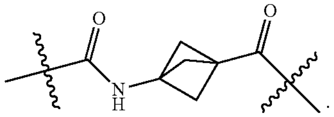
15. The bispecific compound of claim 1, which is represented by any one of formulas (I-59) to (I-71):
(I-59)
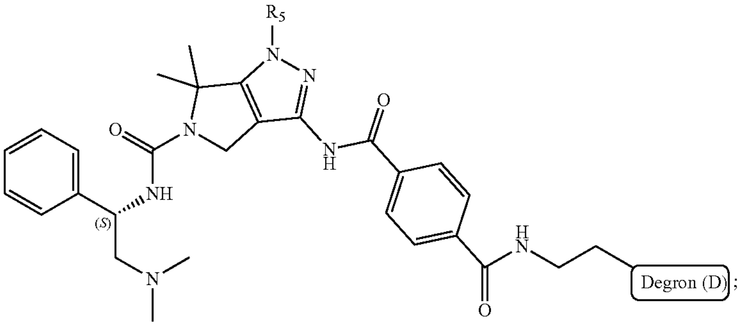
(I-60)
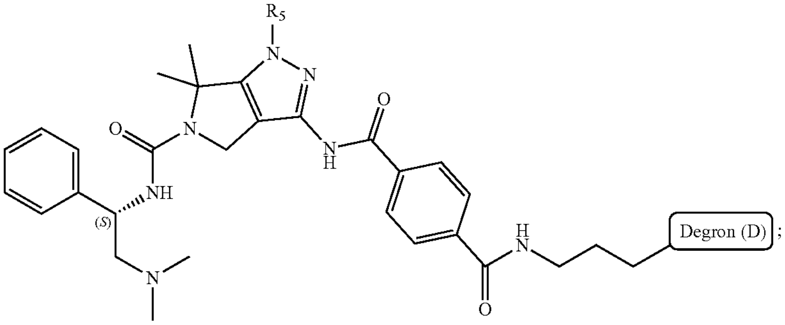
(I-61)
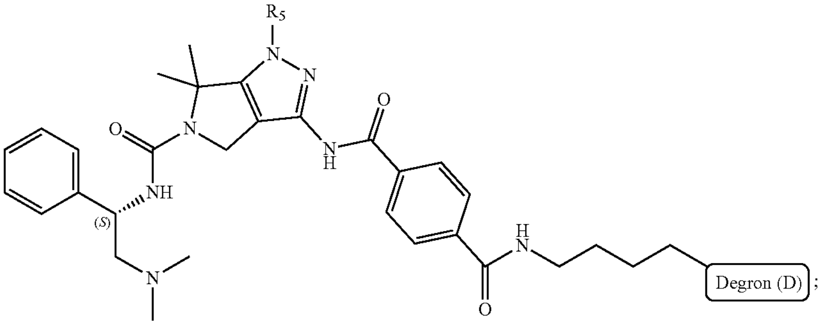

-continued
(I-62)
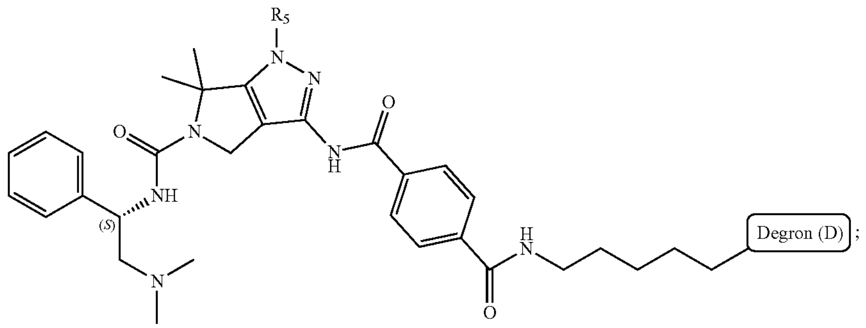
(I-63)
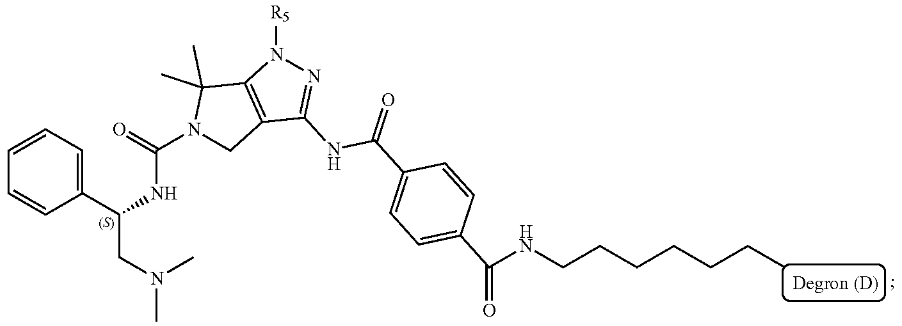
(I-64)
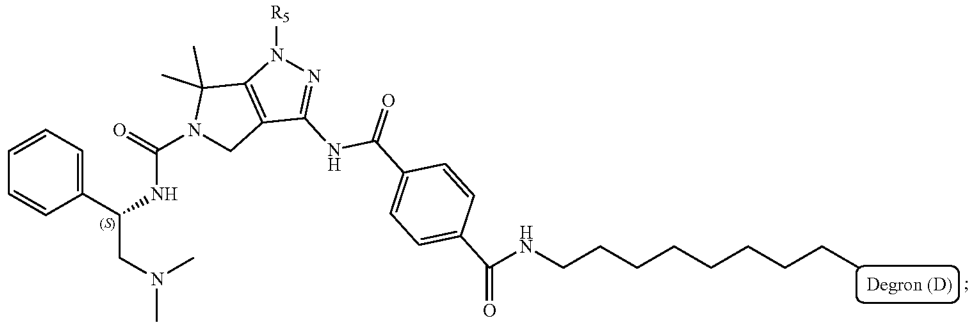
(I-65)
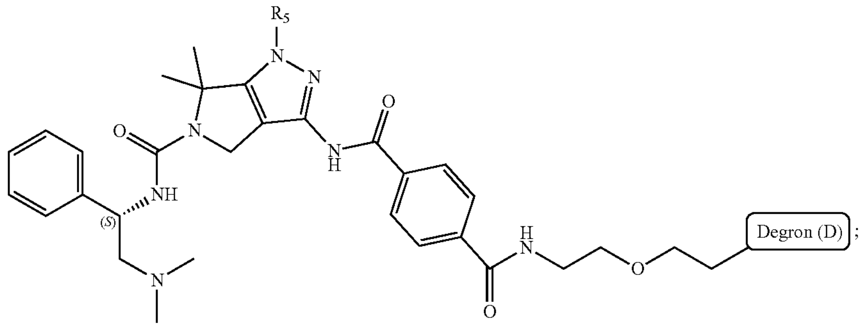
(I-66)
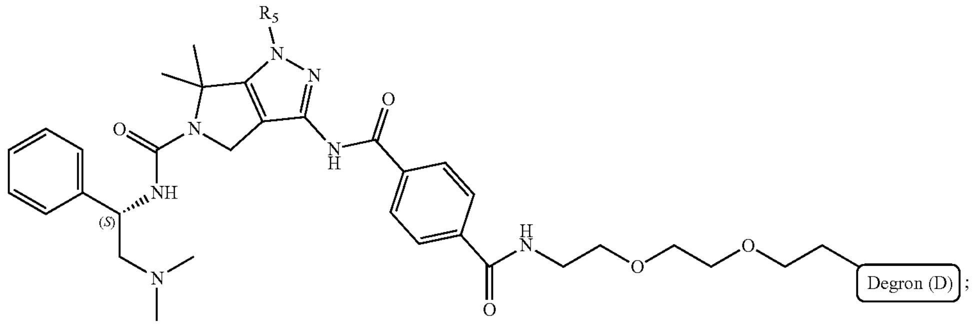

-continued
(I-67)
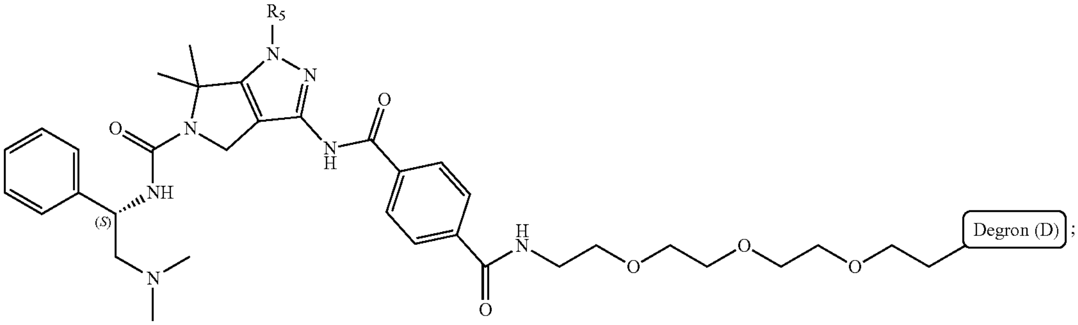
;
(I-68)
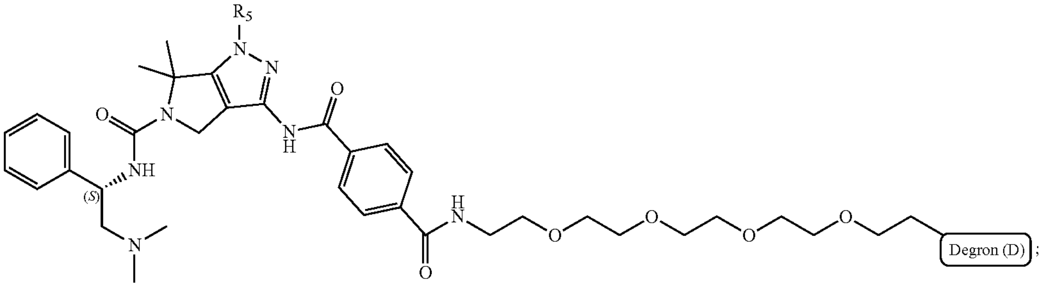
;
(I-69)
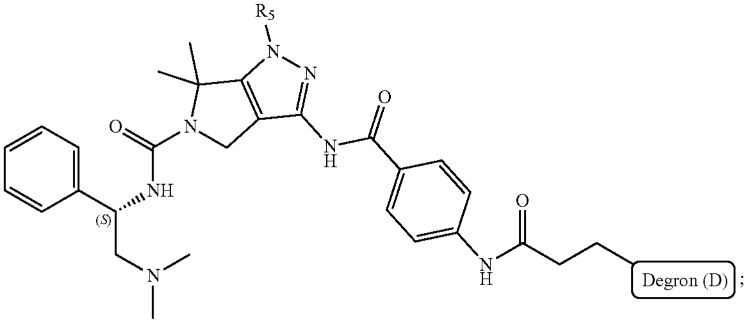
;
(I-70)
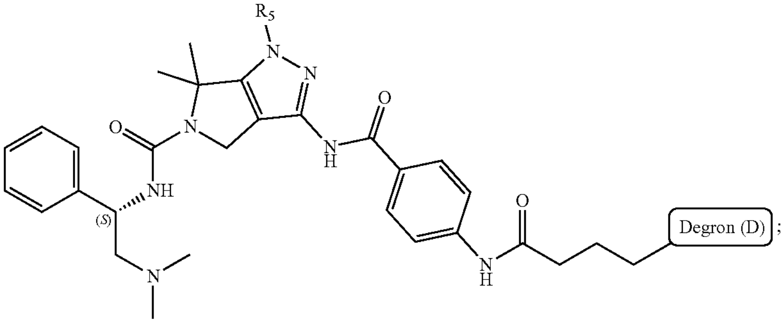
; and
(I-71)
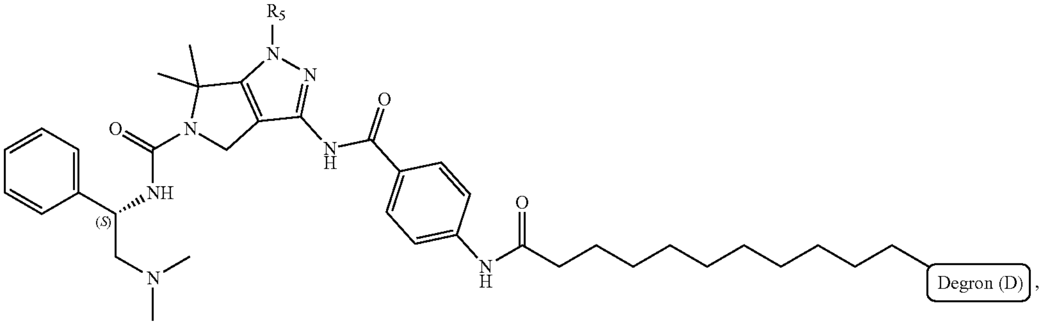
, or a pharmaceutically acceptable salt or stereoisomer thereof.
16. The bispecific compound of claim 1, wherein the degron binds the E3 ubiquitin ligase which is cereblon and is represented by any one of structures (D1-a) to (D1-h):
(D1-a)
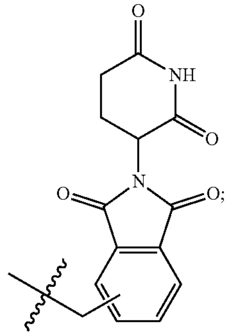
(D1-b)
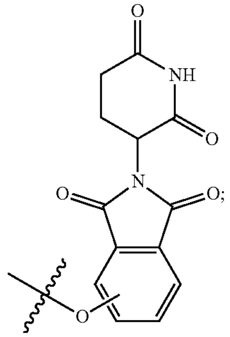
(D1-c)
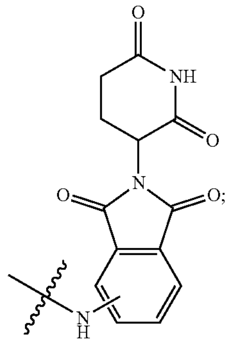
(D1-d)
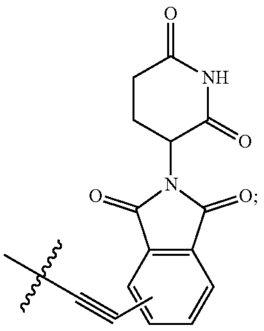
-continued
(D1-e)
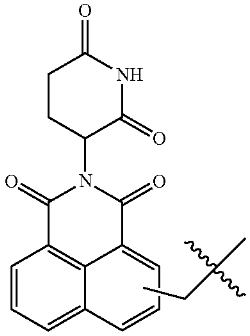
;
(D1-f)
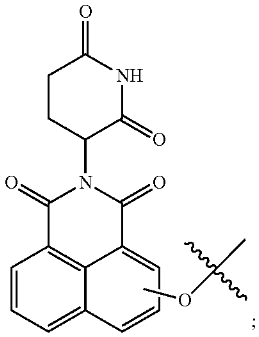
;
(D1-g)
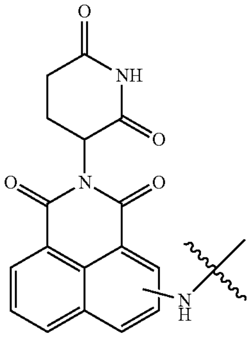
; and
(D1-h)
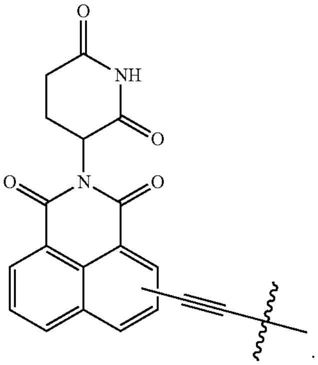
.

17. The bispecific compound of claim 1, which is represented by any one of formulas (I-72a) to (I-72h):
(I-72a)
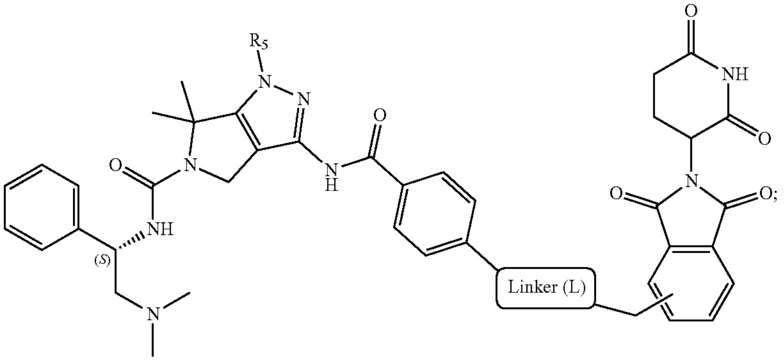
(I-72b)
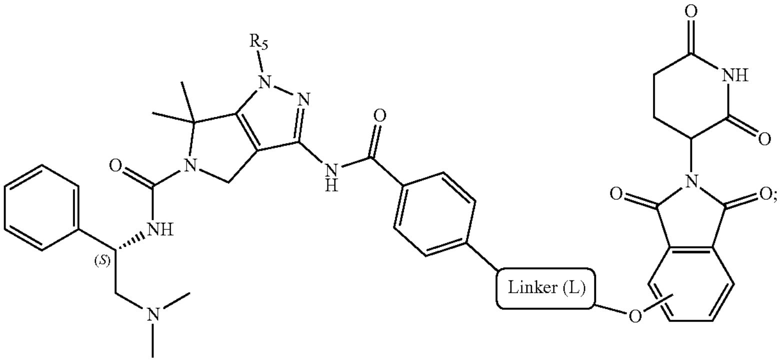
(I-72c)
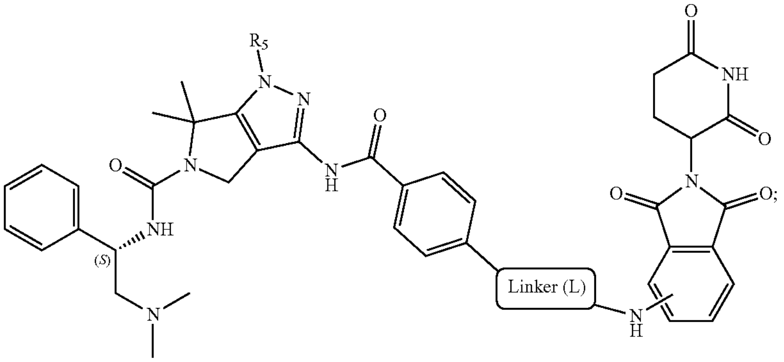
(I-72d)
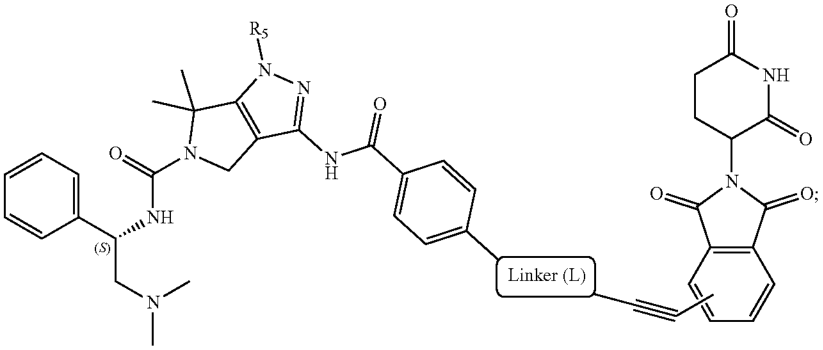

-continued
(I-72e)
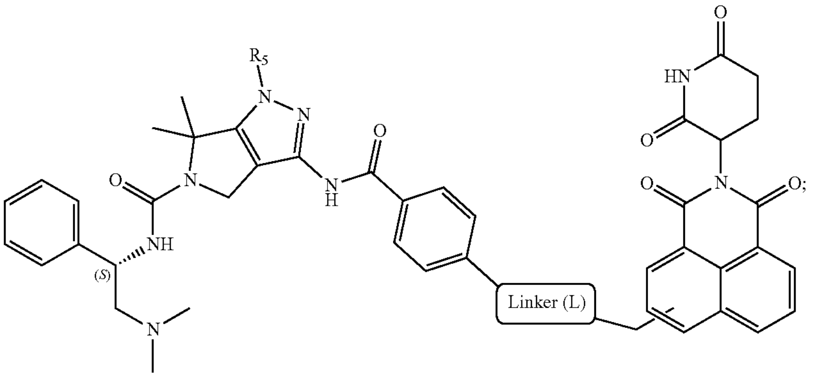
(I-72f)
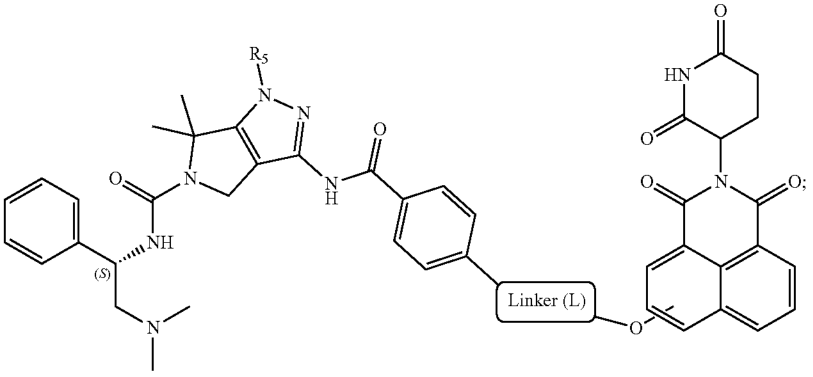
(I-72g)
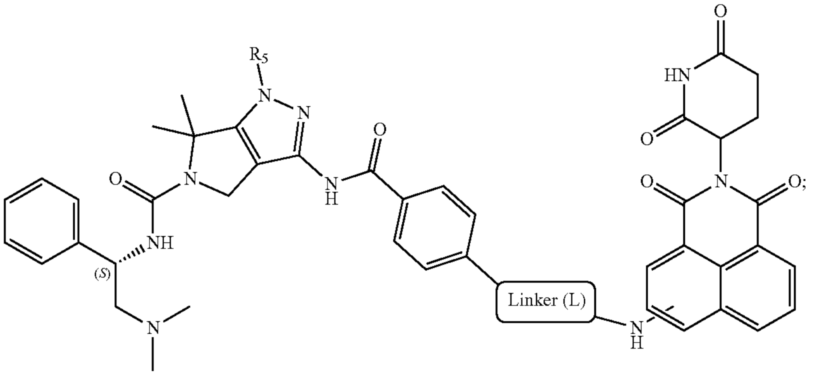
and
(I-72h)
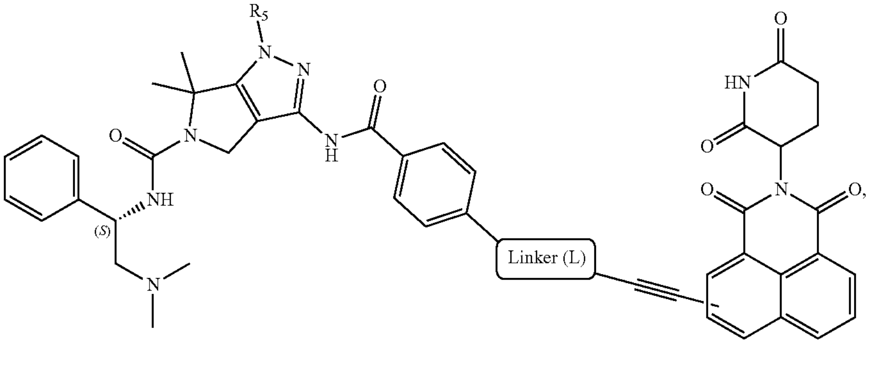
, or a pharmaceutically acceptable salt or stereoisomer thereof.

18. The bispecific compound of claim 1, wherein the degron binds the E3 ubiquitin ligase which is von Hippel-Landau tumor suppressor and is represented by any one of structures (D2-a) to (D2-e):

(D2-a)

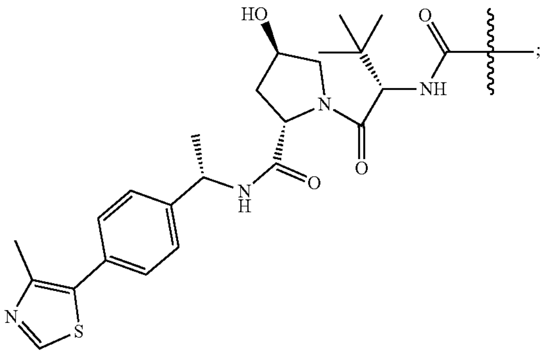

(D2-b)

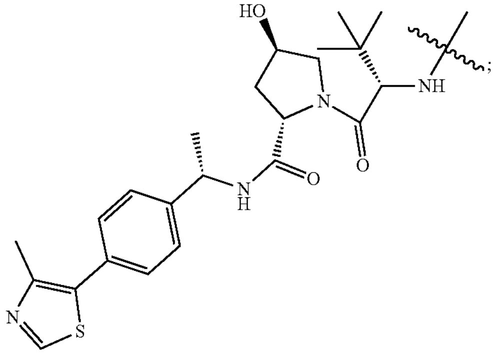

(D2-c)

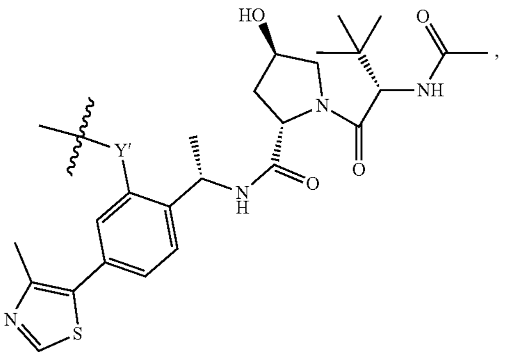

-continued (D2-d)

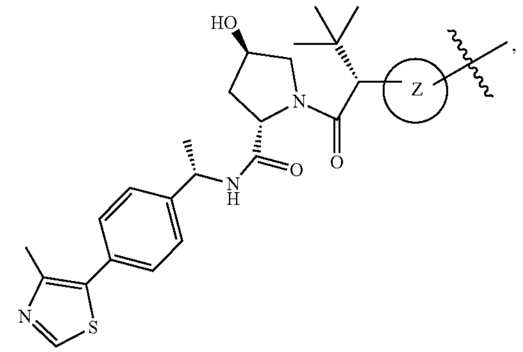

wherein Y' is a bond, N, O or C;

wherein Z is a $C_5$-$C_6$ carbocyclic or $C_5$-$C_6$ heterocyclic group; and (D2-e)

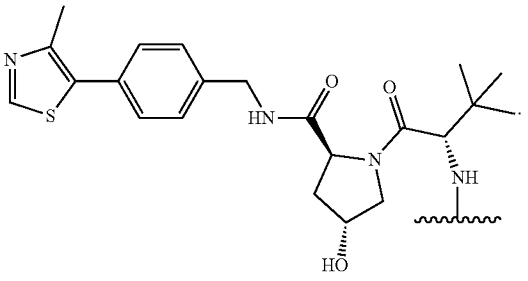

19. The bispecific compound of claim 18, wherein Z is

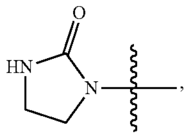

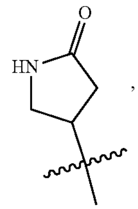

, or

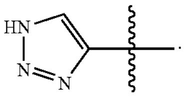

20. The bispecific compound of claim 1, which is represented by any one of formulas (I-73a) to (I-73e):
(I-73a)
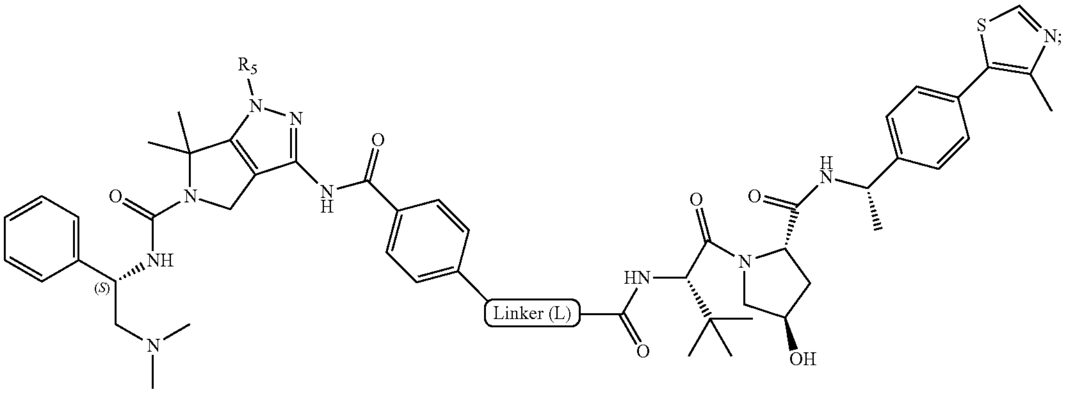
(I-73b)
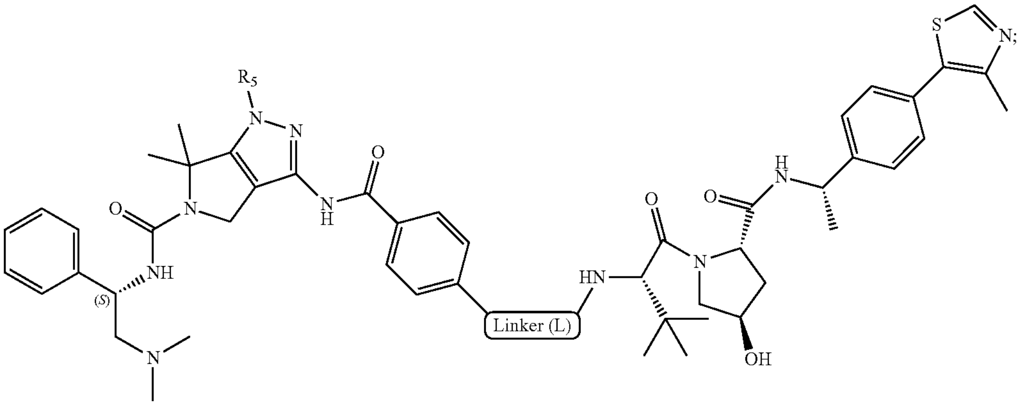
(I-73c)
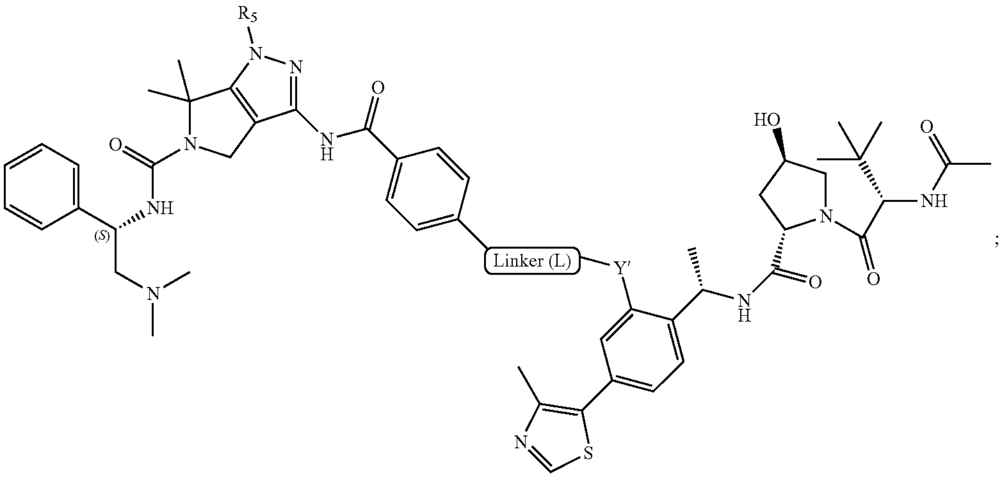
;

-continued
(I-73d)
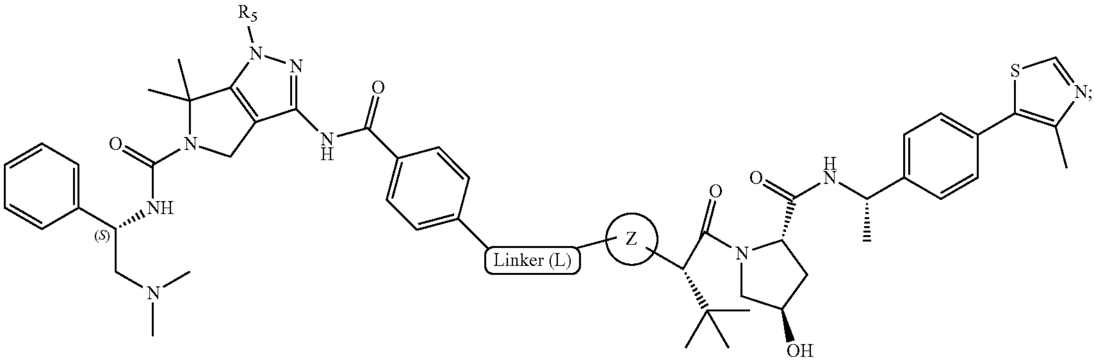
; and
(I-73e)
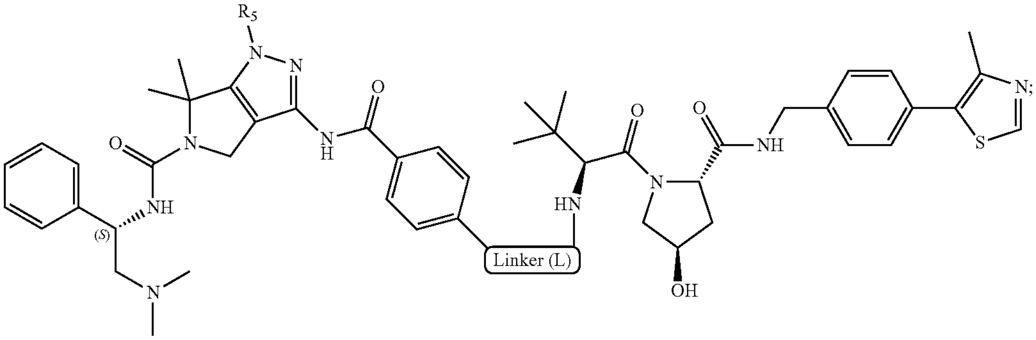
;
wherein Y' is a bond, N, O or C; and Z is a C5-C6 carbocyclic or heterocyclic group, or a pharmaceutically acceptable salt or stereoisomer thereof.
21. The bispecific compound of claim 1, which is represented by any one of structures (1) to (34):
(1)
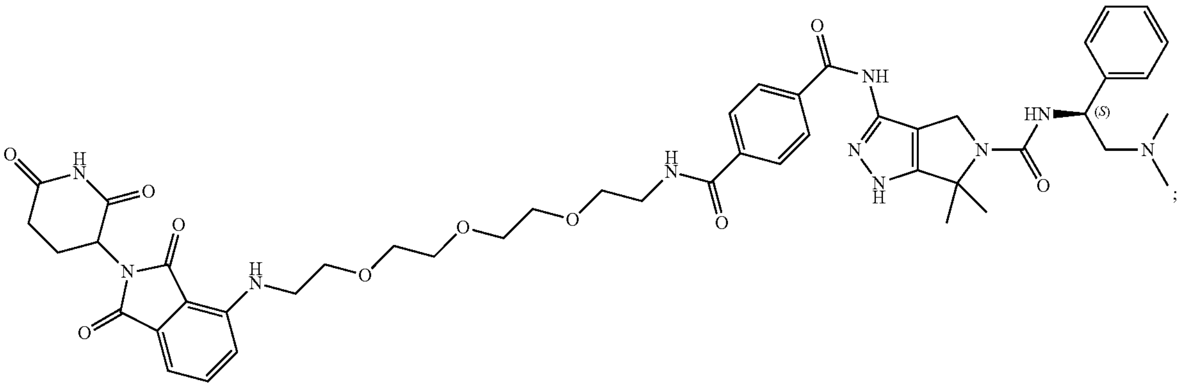
;

-continued
(2)
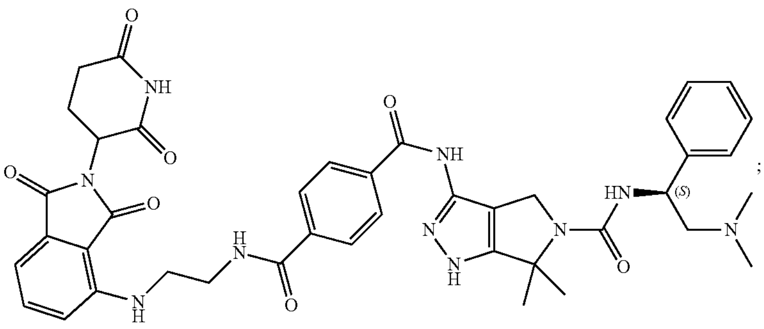
;
(3)
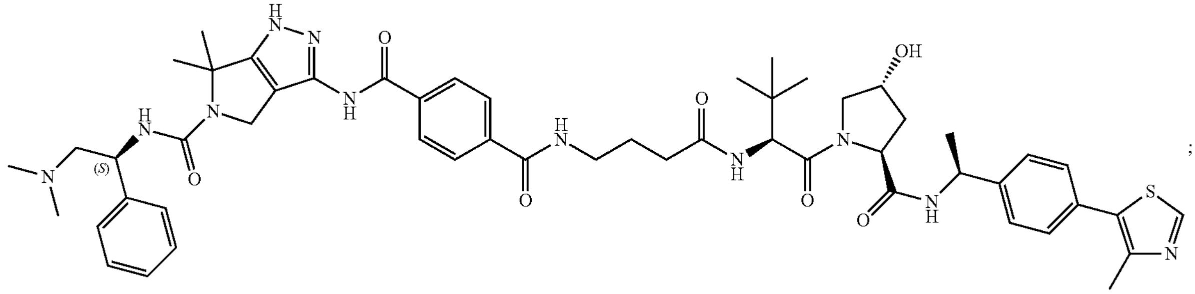
;
(4)
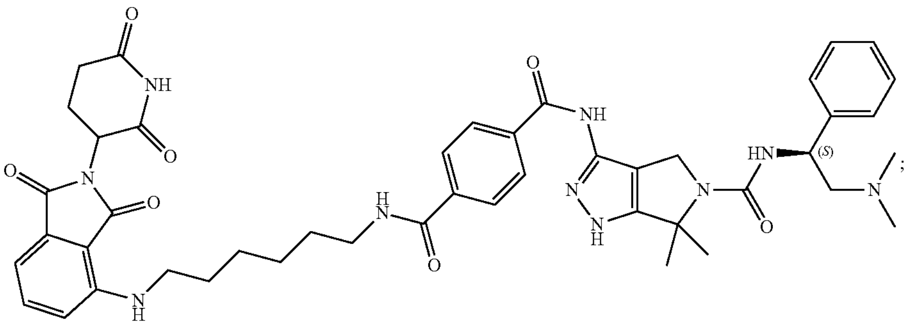
;
(5)
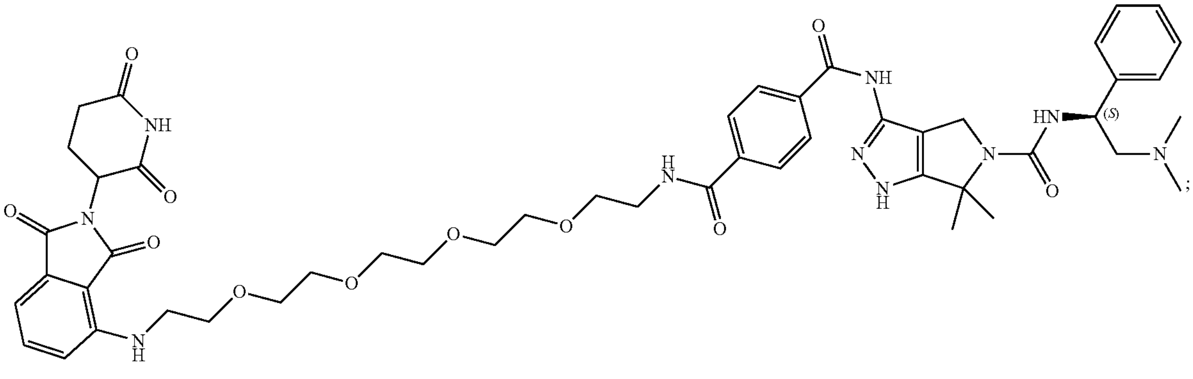
;

-continued
(6)
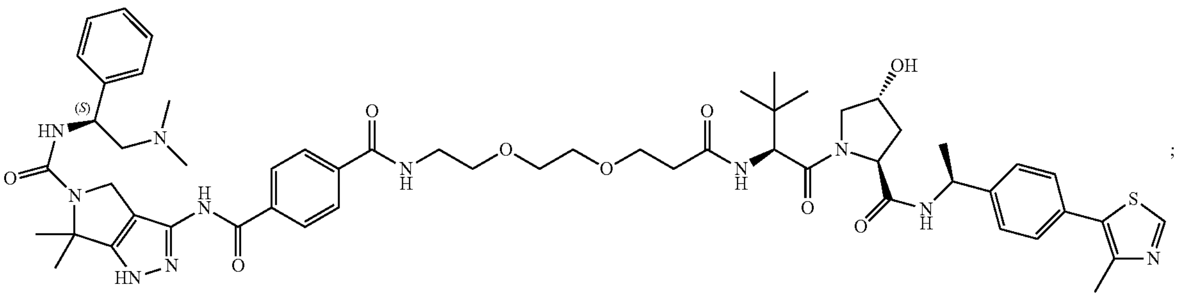
(7)
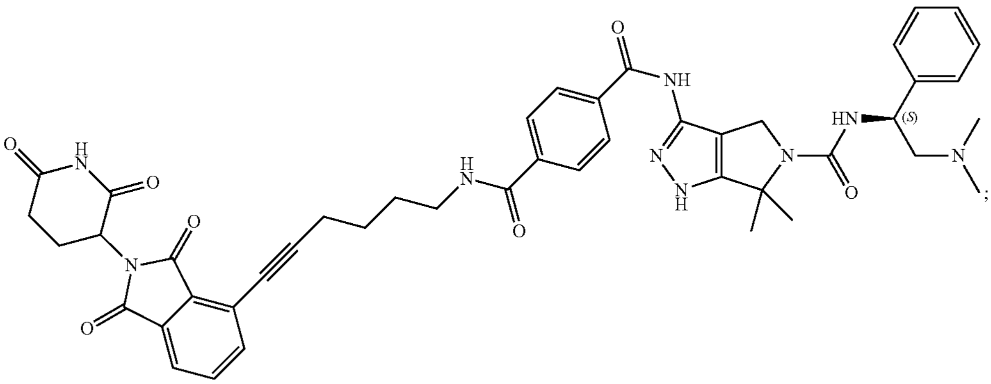
(8)
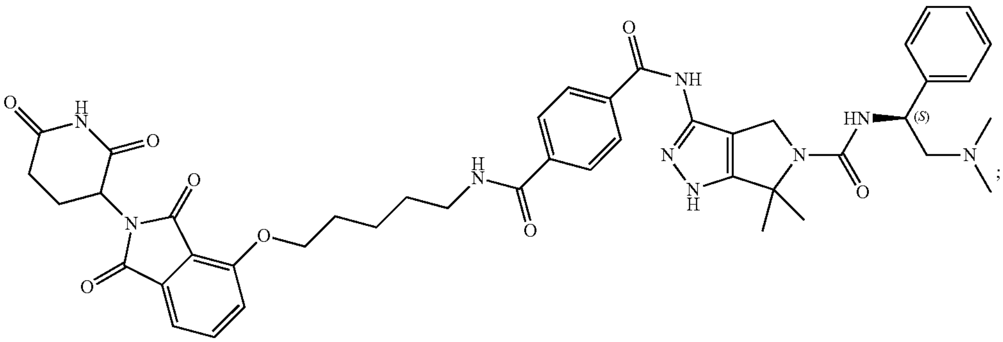
(9)
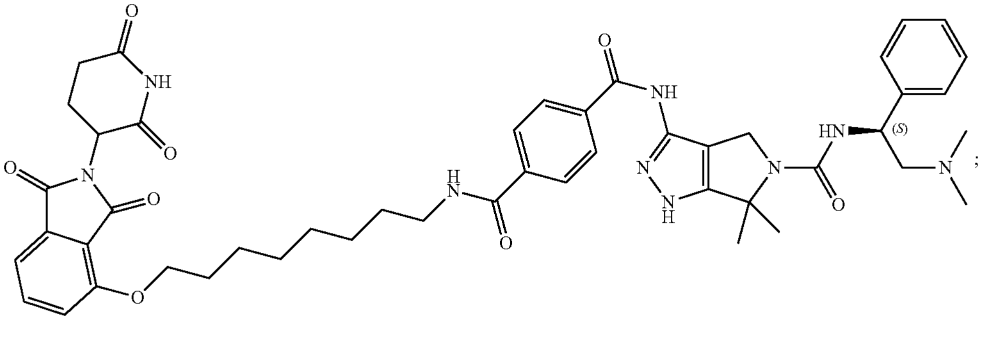

-continued
(10)
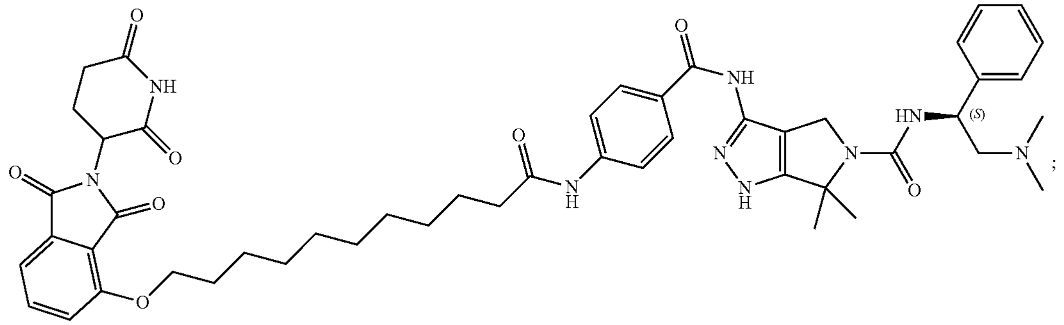
(11)
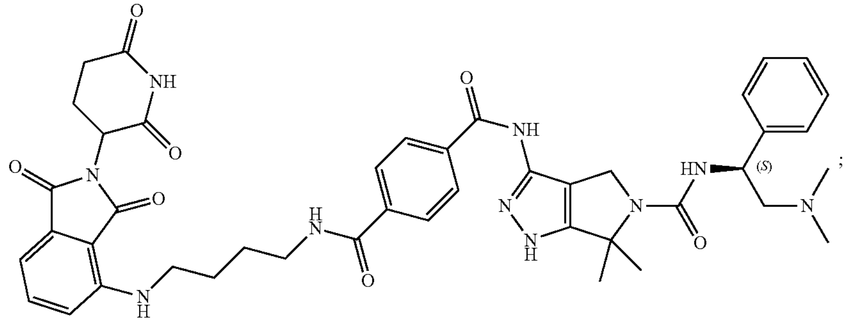
(12)
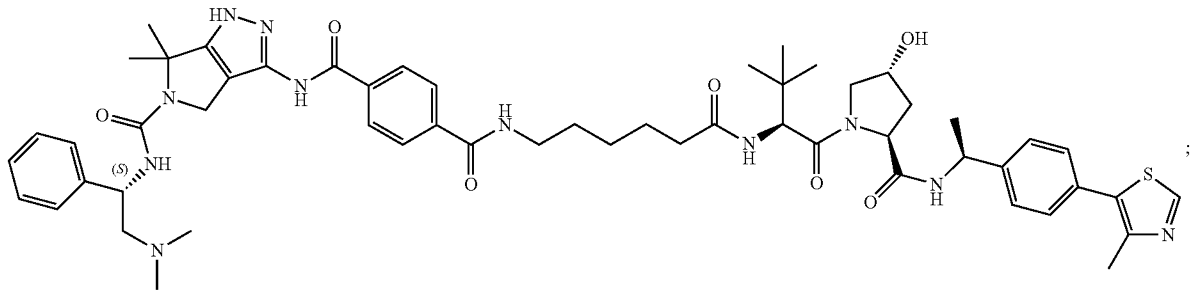
(13)
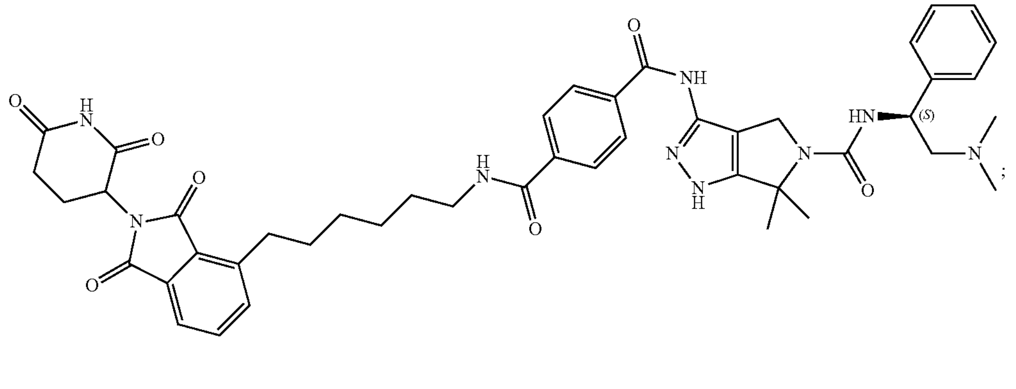

-continued
(14)
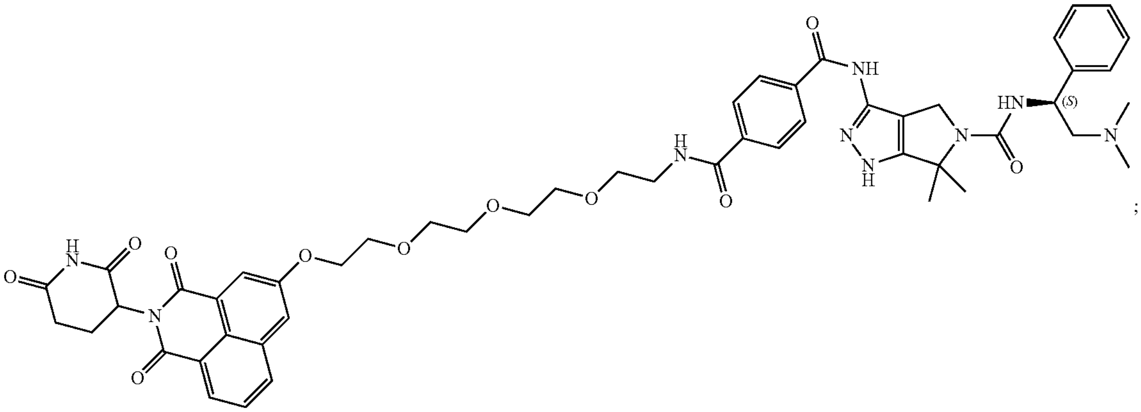
;
(15)
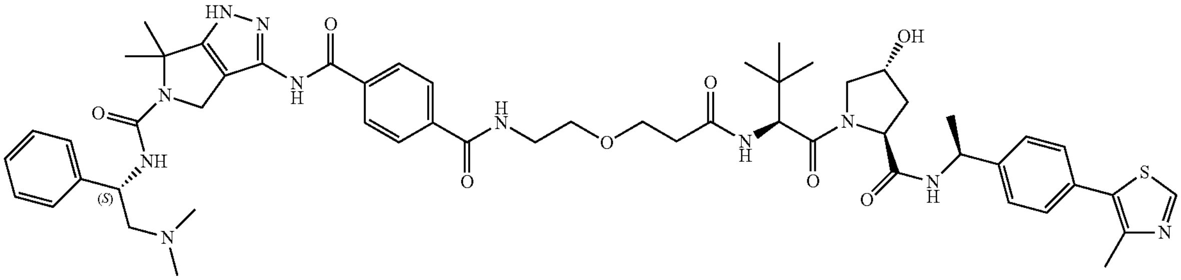
;
(16)
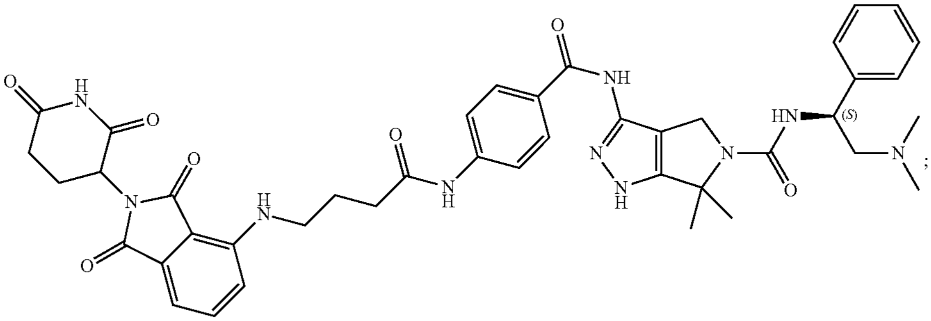
;
(17)
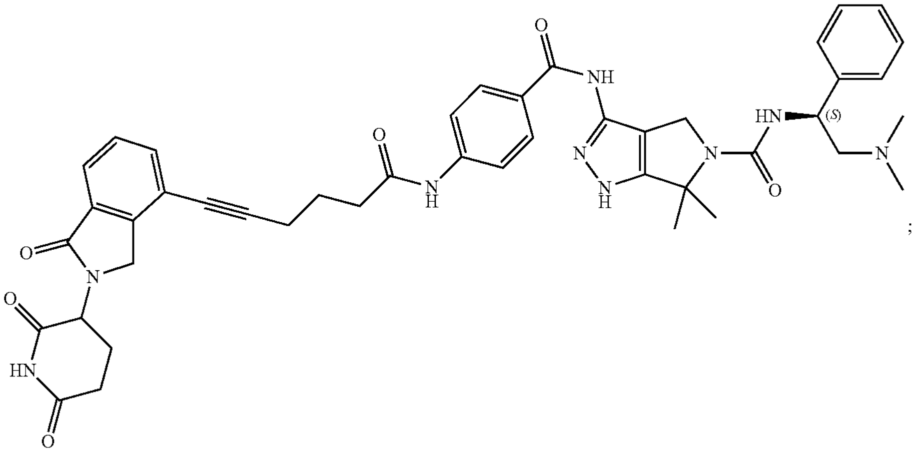
;

-continued
(18)
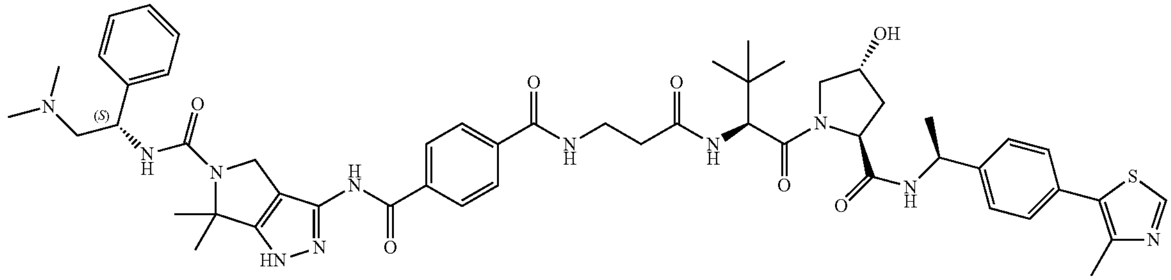
;
(19)
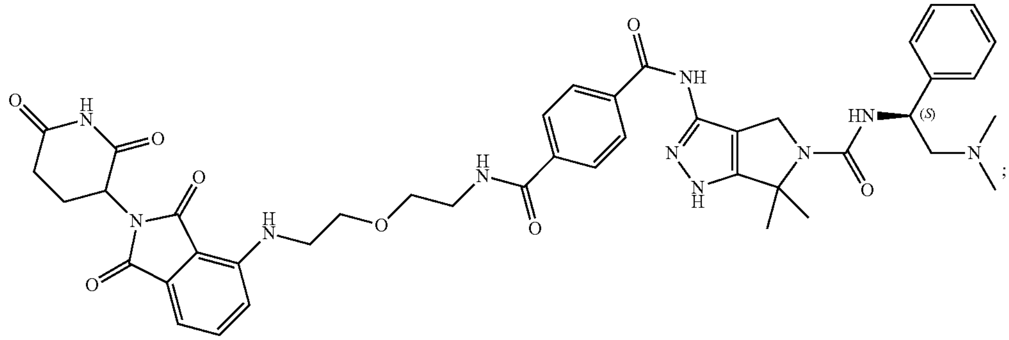
;
(20)
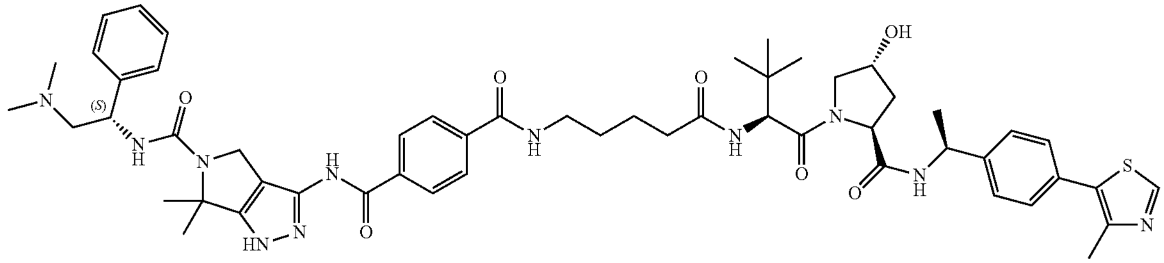
;
(21)
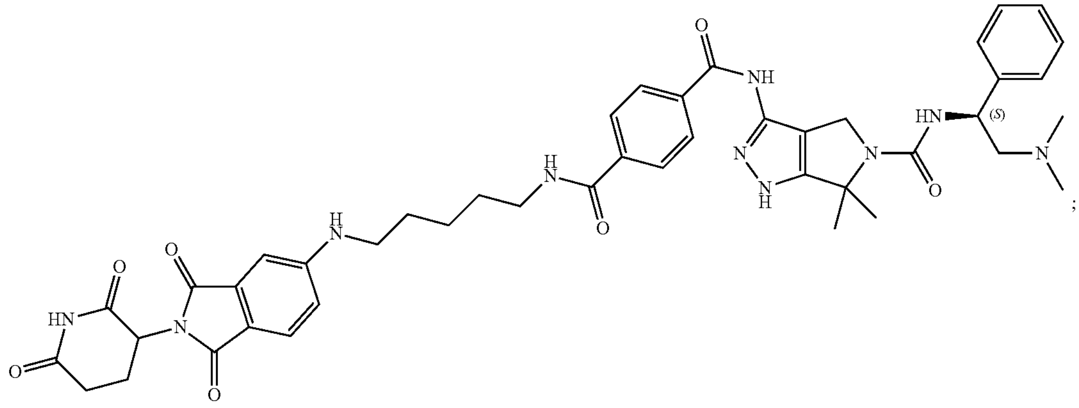
;
(22)
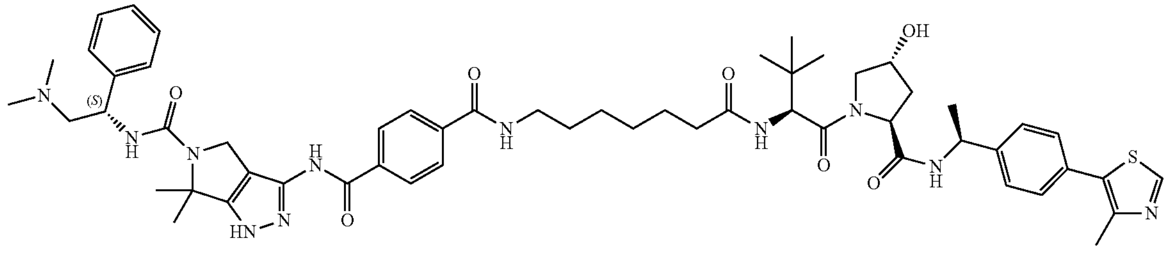
;

-continued
(23)
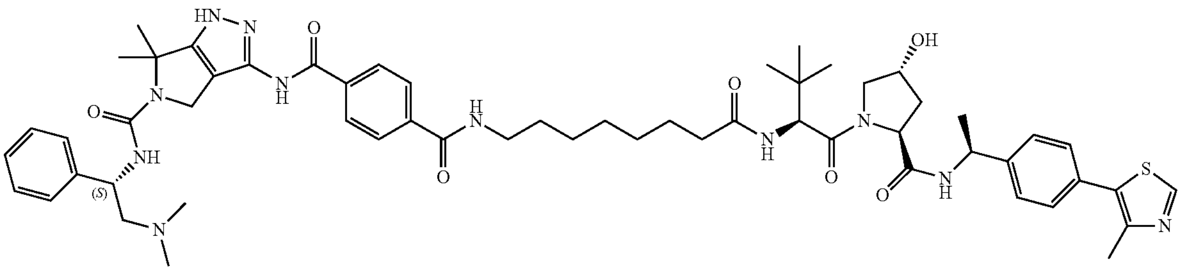
;
(24)
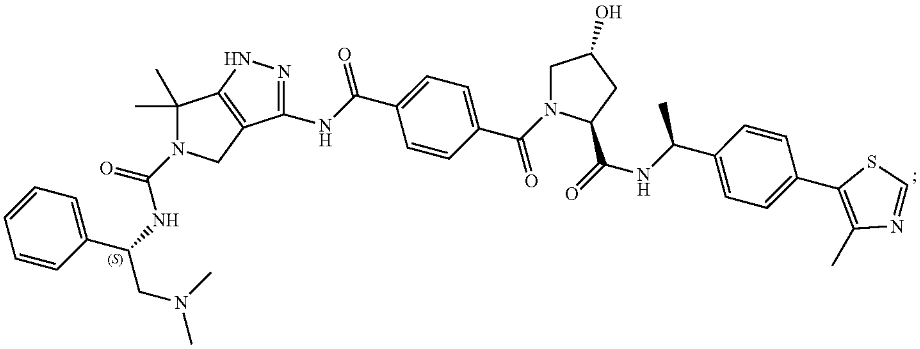
;
(25)
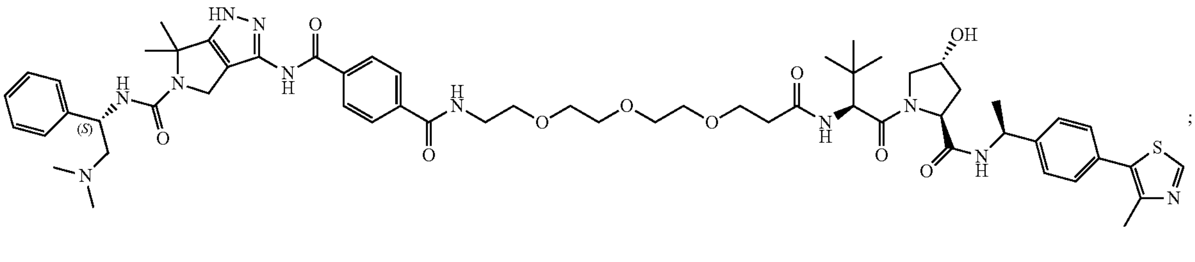
;
(26)
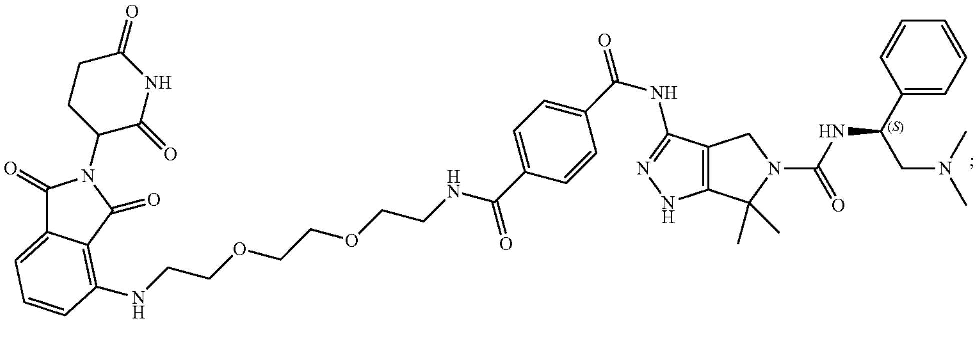
;

-continued
(27)
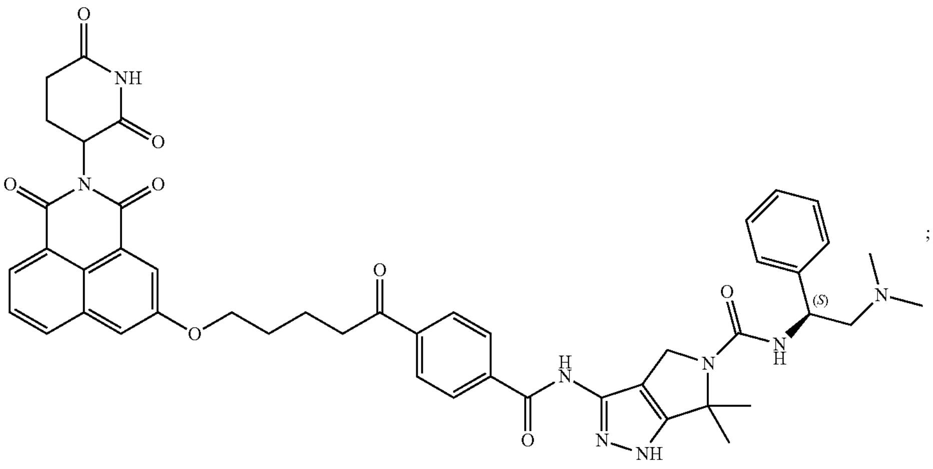
;
(28)
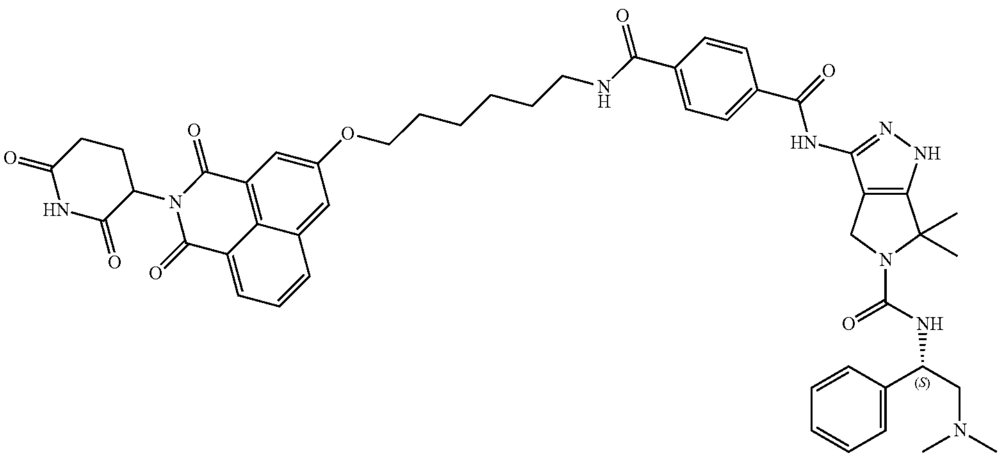
;
(29)
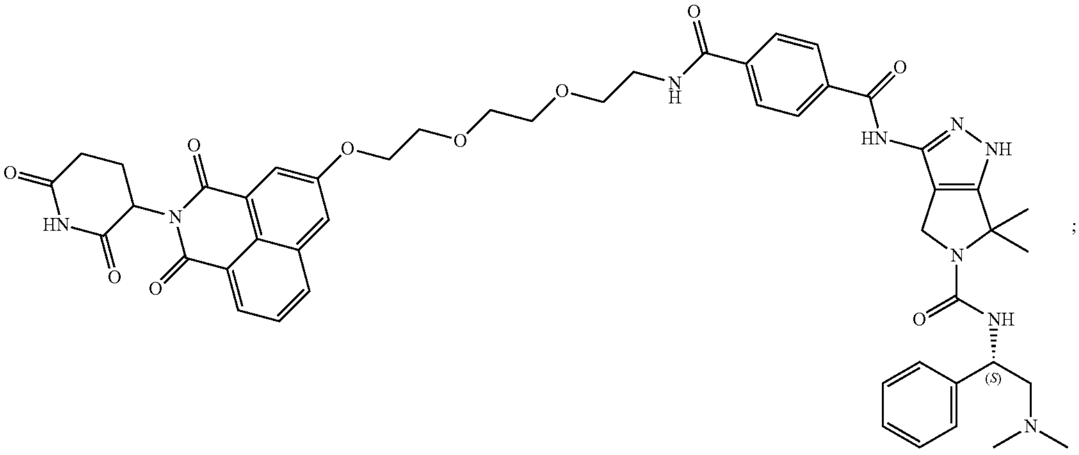
;

-continued
(30)
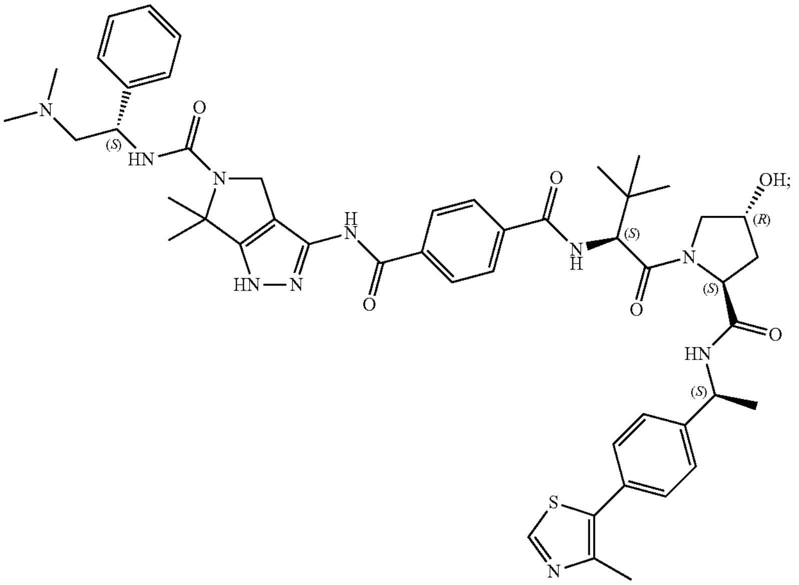
(31)
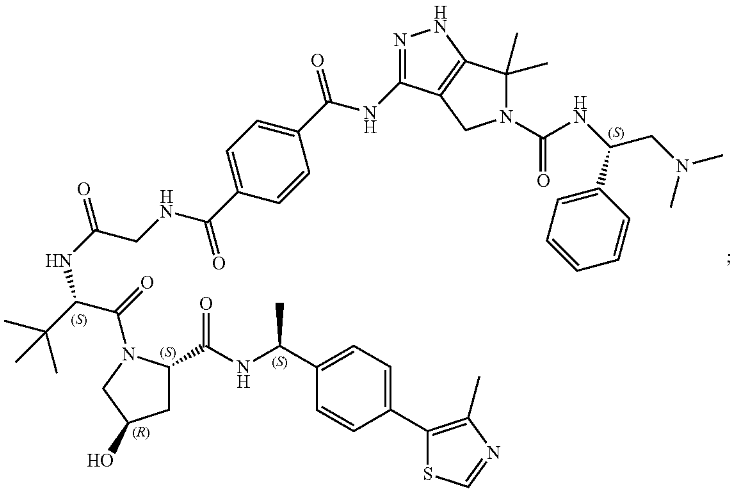
;
(32)
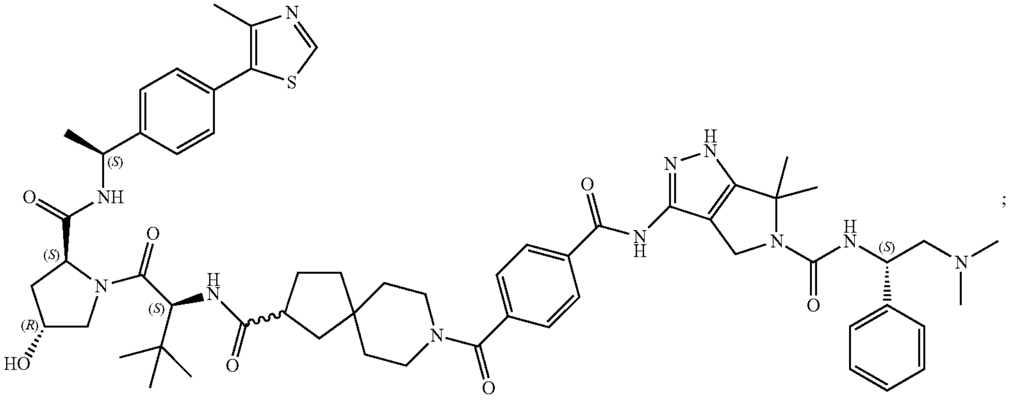
;

-continued (33)

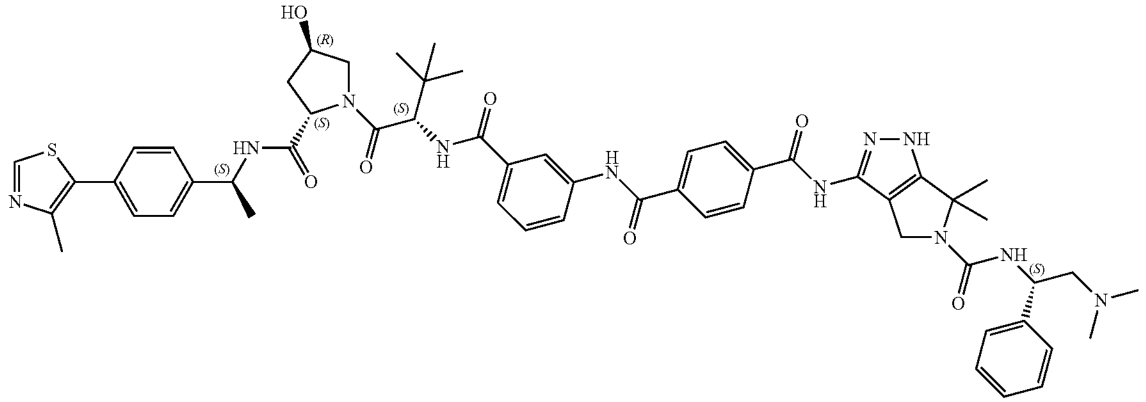

; and (34)

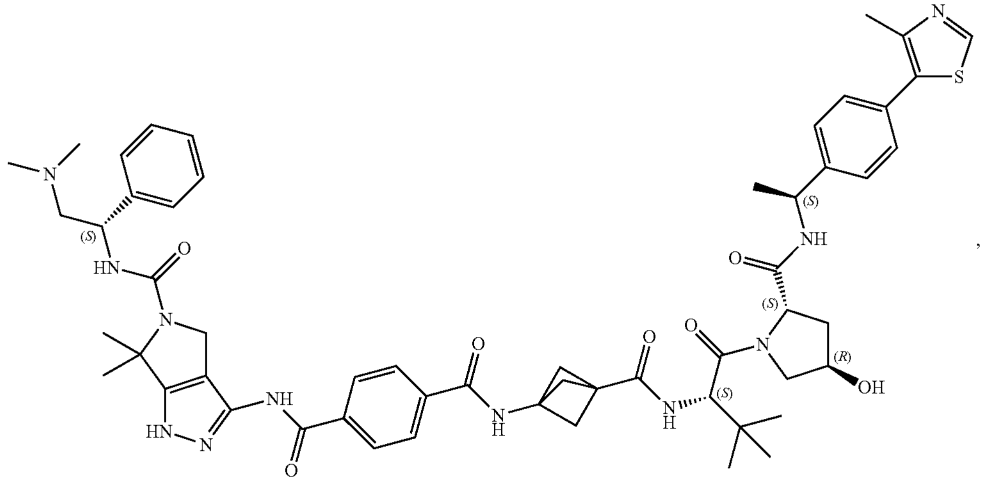

, or a pharmaceutically acceptable salt and stereoisomer thereof.

22. A pharmaceutical composition, comprising a therapeutically effective amount of the bispecific compound or a pharmaceutically acceptable salt or stereoisomer thereof of claim 1, and a pharmaceutically acceptable carrier.

23. A method of treating a disease or disorder mediated by aberrant CDK7 activity, comprising administering to a patient in need thereof a therapeutically effective amount of the bispecific compound or a pharmaceutically acceptable salt or stereoisomer thereof of claim 1, wherein the disease is a cancer or an autoimmune disease.

24. The method of claim 23, wherein the cancer is a solid tumor or a hematologic cancer.

25. The method of claim 24, wherein the solid tumor is breast cancer, brain cancer, lung cancer, colorectal cancer, neuroblastoma, or osteosarcoma, or wherein the hematologic cancer is leukemia, lymphoma or multiple myeloma.

* * * * *